(12) United States Patent
Kroetsch et al.

(10) Patent No.: US 12,403,164 B2
(45) Date of Patent: Sep. 2, 2025

(54) LENTIVIRAL VECTOR FORMULATIONS

(71) Applicants: BIOVERATIV THERAPEUTICS INC., Waltham, MA (US); FONDAZIONE TELETHON, Rome (IT); OSPEDALE SAN RAFFAELE S.R.L., Milan (IT)

(72) Inventors: Andrew Kroetsch, Waltham, MA (US); Isidro Zarraga, Waltham, MA (US)

(73) Assignees: BIOVERATIV THERAPEUTICS INC., Waltham, MA (US); FONDAZIONE TELETHON, Rome (IT); OSPEDALE SAN RAFFAELE S.R.L., Milan (IT)

( * ) Notice: Subject to any disclaimer, the term of this patent is extended or adjusted under 35 U.S.C. 154(b) by 0 days.

(21) Appl. No.: 17/038,031

(22) Filed: Sep. 30, 2020

(65) Prior Publication Data
US 2021/0113634 A1     Apr. 22, 2021

Related U.S. Application Data

(60) Provisional application No. 62/908,390, filed on Sep. 30, 2019.

(51) Int. Cl.
| | |
|---|---|
| *A61K 39/205* | (2006.01) |
| *A61K 35/76* | (2015.01) |
| *A61K 47/26* | (2006.01) |
| *A61P 7/04* | (2006.01) |
| *C12N 15/86* | (2006.01) |

(52) U.S. Cl.
CPC .............. *A61K 35/76* (2013.01); *A61K 47/26* (2013.01); *A61P 7/04* (2018.01); *C12N 15/86* (2013.01)

(58) Field of Classification Search
None
See application file for complete search history.

(56) References Cited

U.S. PATENT DOCUMENTS

| | | | |
|---|---|---|---|
| 4,683,195 | A | 7/1987 | INC |
| 4,683,202 | A | 7/1987 | INC |
| 4,704,362 | A | 11/1987 | Itakura et al. |

(Continued)

FOREIGN PATENT DOCUMENTS

| | | |
|---|---|---|
| CN | 104371982 A | 2/2015 |
| CN | 104427995 A | 3/2015 |

(Continued)

OTHER PUBLICATIONS

Akkina, et al., High-efficiency Gene Transfer into CD34+ Cells with a Human Immunodeficiency Virus Type 1-based Retroviral Vector Pseudotyped With Vesicular Stomatitis Virus Envelope Glycoprotein G, Journal of Virology, vol. 70, No. 4, pp. 2581-2585, Apr. 1996.

(Continued)

*Primary Examiner* — M Franco G Salvoza
(74) *Attorney, Agent, or Firm* — LATHROP GPM LLP; James H. Velema, Esq.; James V. DeGiulio

(57) ABSTRACT

Lentiviral vector (LV) formulations, and pharmaceutical compositions comprising such LV formulations, with improved stability and suitable for systemic administration are provided. Methods for treating disorders, especially blood disorders, using systemic administration of LV formulations are also provided.

15 Claims, 21 Drawing Sheets
Specification includes a Sequence Listing.

(56) References Cited

U.S. PATENT DOCUMENTS

| | | |
|---|---|---|
| 4,800,159 A | 1/1989 | Mullis et al. |
| 4,868,112 A | 9/1989 | Toole, Jr. |
| 4,965,188 A | 10/1990 | Mullis et al. |
| 5,112,950 A | 5/1992 | Meulien et al. |
| 5,171,844 A | 12/1992 | Van Ooyen et al. |
| 5,304,489 A | 4/1994 | Rosen |
| 5,543,502 A | 8/1996 | Nordfang et al. |
| 5,595,886 A | 1/1997 | Chapman et al. |
| 5,610,278 A | 3/1997 | Nordfang et al. |
| 5,648,260 A | 7/1997 | Winter et al. |
| 5,658,570 A | 8/1997 | Newman et al. |
| 5,712,122 A | 1/1998 | Boime et al. |
| 5,736,137 A | 4/1998 | Anderson et al. |
| 5,739,277 A | 4/1998 | Presta et al. |
| 5,741,957 A | 4/1998 | Deboer et al. |
| 5,789,203 A | 8/1998 | Chapman et al. |
| 5,834,250 A | 11/1998 | Wells et al. |
| 5,849,992 A | 12/1998 | Meade et al. |
| 5,869,046 A | 2/1999 | Presta et al. |
| 5,972,885 A | 10/1999 | Spira et al. |
| 6,030,613 A | 2/2000 | Blumberg et al. |
| 6,048,720 A | 4/2000 | Dalborg et al. |
| 6,060,447 A | 5/2000 | Chapman et al. |
| 6,086,875 A | 7/2000 | Blumberg et al. |
| 6,096,871 A | 8/2000 | Presta et al. |
| 6,121,022 A | 9/2000 | Presta et al. |
| 6,159,730 A | 12/2000 | Reff |
| 6,193,980 B1 | 2/2001 | Efstathiou et al. |
| 6,194,551 B1 | 2/2001 | Idusogie et al. |
| 6,207,455 B1 | 3/2001 | Chang |
| 6,228,620 B1 | 5/2001 | Chapman et al. |
| 6,242,195 B1 | 6/2001 | Idusogie et al. |
| 6,251,632 B1 | 6/2001 | Lillicrap et al. |
| 6,277,375 B1 | 8/2001 | Ward |
| 6,316,226 B1 | 11/2001 | Van Ooyen et al. |
| 6,346,513 B1 | 2/2002 | Van Ooyen et al. |
| 6,413,777 B1 | 7/2002 | Reff et al. |
| 6,458,563 B1 | 10/2002 | Lollar |
| 6,485,726 B1 | 11/2002 | Blumberg et al. |
| 6,528,624 B1 | 3/2003 | Idusogie et al. |
| 6,531,298 B2 | 3/2003 | Stafford et al. |
| 6,538,124 B1 | 3/2003 | Idusogie et al. |
| 6,615,782 B1 | 9/2003 | Hendriksma et al. |
| 6,696,245 B2 | 2/2004 | Winter et al. |
| 6,737,056 B1 | 5/2004 | Presta et al. |
| 6,808,905 B2 | 10/2004 | Mcarthur et al. |
| 6,818,439 B1 | 11/2004 | Jolly et al. |
| 6,821,505 B2 | 11/2004 | Ward |
| 6,924,365 B1 | 8/2005 | Miller et al. |
| 6,998,253 B1 | 2/2006 | Presta et al. |
| 7,041,635 B2 | 5/2006 | Kim et al. |
| 7,083,784 B2 | 8/2006 | Dall'Acqua et al. |
| 7,179,903 B2 | 2/2007 | Mcarthur et al. |
| 7,317,091 B2 | 1/2008 | Lazar et al. |
| 7,404,956 B2 | 7/2008 | Peters et al. |
| 7,745,179 B2 | 6/2010 | Mcarthur et al. |
| 8,326,547 B2 | 12/2012 | Liu et al. |
| 8,734,809 B2 | 5/2014 | Gao et al. |
| 9,050,269 B2 | 6/2015 | Discher et al. |
| 9,050,318 B2 | 6/2015 | Dumont et al. |
| 9,061,059 B2 | 6/2015 | Chakraborty et al. |
| 9,169,491 B2 | 10/2015 | Truran et al. |
| 10,000,748 B2 | 6/2018 | Schüttrumpf et al. |
| 10,058,624 B2 | 8/2018 | Doering et al. |
| 10,125,357 B2 | 11/2018 | Seifried et al. |
| 10,370,431 B2 | 8/2019 | Tan et al. |
| 11,008,561 B2 | 5/2021 | Tan et al. |
| 11,753,461 B2 | 9/2023 | Tan et al. |
| 11,787,951 B2 | 10/2023 | Tan et al. |
| 12,275,970 B2 | 4/2025 | Tan et al. |
| 2003/0069395 A1 | 4/2003 | Sato et al. |
| 2003/0077812 A1 | 4/2003 | Mcarthur et al. |
| 2003/0109478 A1 | 6/2003 | Fewel et al. |
| 2003/0235536 A1 | 12/2003 | Blumberg et al. |
| 2004/0147436 A1 | 7/2004 | Kim et al. |
| 2006/0003452 A1 | 1/2006 | Humeau et al. |
| 2007/0231329 A1 | 10/2007 | Lazar et al. |
| 2007/0237765 A1 | 10/2007 | Lazar et al. |
| 2007/0237766 A1 | 10/2007 | Lazar et al. |
| 2007/0237767 A1 | 10/2007 | Lazar et al. |
| 2007/0243188 A1 | 10/2007 | Lazar et al. |
| 2007/0248603 A1 | 10/2007 | Lazar et al. |
| 2007/0286859 A1 | 12/2007 | Lazar et al. |
| 2008/0004206 A1 | 1/2008 | Rosen et al. |
| 2008/0057056 A1 | 3/2008 | Lazar et al. |
| 2008/0076174 A1 | 3/2008 | Selden et al. |
| 2008/0153156 A1 | 6/2008 | Gray |
| 2008/0153751 A1 | 6/2008 | Rosen et al. |
| 2008/0161243 A1 | 7/2008 | Rosen et al. |
| 2008/0194481 A1 | 8/2008 | Rosen et al. |
| 2008/0260738 A1 | 10/2008 | Moore et al. |
| 2008/0261877 A1 | 10/2008 | Ballance et al. |
| 2009/0017533 A1 | 1/2009 | Selden et al. |
| 2009/0042283 A1 | 2/2009 | Selden et al. |
| 2009/0087411 A1 | 4/2009 | Fares et al. |
| 2010/0239554 A1 | 9/2010 | Schellenberger et al. |
| 2010/0284971 A1 | 11/2010 | Samulski |
| 2010/0292130 A1 | 11/2010 | Skerra et al. |
| 2010/0323956 A1 | 12/2010 | Schellenberger et al. |
| 2011/0046060 A1 | 2/2011 | Schellenberger et al. |
| 2011/0046061 A1 | 2/2011 | Schellenberger et al. |
| 2011/0077199 A1 | 3/2011 | Schellenberger et al. |
| 2011/0172146 A1 | 7/2011 | Schellenberger et al. |
| 2011/0244550 A1 | 10/2011 | Simioni |
| 2012/0178691 A1 | 7/2012 | Schellenberger et al. |
| 2013/0024960 A1 | 1/2013 | Nathwani et al. |
| 2013/0052191 A1 | 2/2013 | Blein et al. |
| 2013/0195801 A1 | 8/2013 | Gao et al. |
| 2014/0010861 A1 | 1/2014 | Bancel et al. |
| 2015/0023959 A1 | 1/2015 | Chhabra et al. |
| 2015/0056696 A1* | 2/2015 | Fan .............. A61P 9/10 435/320.1 |
| 2015/0158929 A1 | 6/2015 | Schellenberger et al. |
| 2015/0361158 A1 | 12/2015 | Tan et al. |
| 2016/0185817 A1 | 6/2016 | Zhu et al. |
| 2016/0304851 A1 | 10/2016 | Schüttrumpf et al. |
| 2017/0073702 A1 | 3/2017 | Truran et al. |
| 2017/0260516 A1 | 9/2017 | Tan et al. |
| 2017/0326256 A1 | 11/2017 | Doering et al. |
| 2019/0048362 A1 | 2/2019 | Kyostio-Moore et al. |
| 2019/0185543 A1 | 6/2019 | Tan et al. |
| 2019/0314291 A1* | 10/2019 | Besin .............. C07K 14/525 |
| 2020/0024327 A1 | 1/2020 | Tan et al. |
| 2020/0199626 A1 | 6/2020 | Liu et al. |
| 2021/0038744 A1 | 2/2021 | Annoni et al. |
| 2021/0115425 A1 | 4/2021 | Tan et al. |
| 2022/0033849 A1 | 2/2022 | Mayani et al. |
| 2022/0090130 A1 | 3/2022 | Maghodia et al. |
| 2024/0124555 A1 | 4/2024 | Tan et al. |
| 2024/0141019 A1 | 5/2024 | Tan et al. |

FOREIGN PATENT DOCUMENTS

| | | |
|---|---|---|
| EA | 028309 B1 | 11/2017 |
| EP | 0295597 A2 | 12/1988 |
| EP | 1395293 A1 | 3/2004 |
| EP | 2173890 B1 | 3/2011 |
| EP | 2829285 A1 | 1/2015 |
| EP | 2881463 A1 | 6/2015 |
| EP | 3160478 A1 | 5/2017 |
| EP | 3377618 A1 | 9/2018 |
| EP | 3411478 A1 | 12/2018 |
| EP | 2956477 B1 | 11/2020 |
| EP | 3746136 A1 | 12/2020 |
| EP | 3891289 A2 | 10/2021 |
| JP | 2015-509365 A | 3/2015 |
| JP | 2017-525344 A | 9/2017 |
| RU | 2500816 C1 | 12/2013 |
| RU | 2577979 C2 | 3/2016 |
| TW | 201406956 A | 2/2014 |
| WO | WO 1987/004187 A1 | 7/1987 |
| WO | WO 1988/000831 A1 | 2/1988 |
| WO | WO 1988/007089 A1 | 9/1988 |
| WO | WO 1991/009122 A1 | 6/1991 |

(56) References Cited

FOREIGN PATENT DOCUMENTS

| | | |
|---|---|---|
| WO | WO 1996/014339 A1 | 5/1996 |
| WO | WO 1997/012622 A1 | 4/1997 |
| WO | WO 1998/005787 A1 | 2/1998 |
| WO | WO 1998/009657 A2 | 3/1998 |
| WO | WO 1998/017815 A1 | 4/1998 |
| WO | WO 1998/017816 A1 | 4/1998 |
| WO | WO 1998/018934 A1 | 5/1998 |
| WO | WO 1998/023289 A1 | 6/1998 |
| WO | WO 1999/031251 A1 | 6/1999 |
| WO | WO 1999/051642 A1 | 10/1999 |
| WO | WO 1999/058572 A1 | 11/1999 |
| WO | WO 2000/009560 A2 | 2/2000 |
| WO | WO 2000/020561 A1 | 4/2000 |
| WO | WO 2000/032767 A1 | 6/2000 |
| WO | WO 2000/042072 A2 | 7/2000 |
| WO | WO 2000/066759 A1 | 11/2000 |
| WO | WO 2002/044215 A2 | 6/2002 |
| WO | WO 2002/060919 A2 | 8/2002 |
| WO | WO 2002/063025 A2 | 8/2002 |
| WO | WO 2002/040544 A3 | 10/2002 |
| WO | WO 2002/092134 A1 | 11/2002 |
| WO | WO 2003/020764 A2 | 3/2003 |
| WO | WO 2003/042361 A2 | 5/2003 |
| WO | WO 2003/042397 A2 | 5/2003 |
| WO | WO 2003/052051 A2 | 6/2003 |
| WO | WO 2003/057780 A1 | 7/2003 |
| WO | WO 2003/074569 A2 | 9/2003 |
| WO | WO 2003/077834 A2 | 9/2003 |
| WO | WO 2003/100053 A1 | 12/2003 |
| WO | WO 2004/016750 A2 | 2/2004 |
| WO | WO 2004/029207 A2 | 4/2004 |
| WO | WO 2004/035752 A2 | 4/2004 |
| WO | WO 2004/044859 A1 | 5/2004 |
| WO | WO 2004/063351 A2 | 7/2004 |
| WO | WO 2004/074455 A2 | 9/2004 |
| WO | WO 2004/094642 A2 | 11/2004 |
| WO | WO 2004/099249 A2 | 11/2004 |
| WO | WO-2005013901 A2 * | 2/2005 ........... C12N 15/111 |
| WO | WO 2005/040217 A2 | 5/2005 |
| WO | WO 2005/052171 A2 | 6/2005 |
| WO | WO 2005/070963 A1 | 8/2005 |
| WO | WO 2005/077981 A2 | 8/2005 |
| WO | WO 2005/092925 A2 | 10/2005 |
| WO | WO 2005/123780 A2 | 12/2005 |
| WO | WO 2006/019447 A1 | 2/2006 |
| WO | WO 2006/047350 A2 | 5/2006 |
| WO | WO 2006/085967 A2 | 8/2006 |
| WO | WO 2007/000668 A2 | 1/2007 |
| WO | WO 2007/004670 A1 | 1/2007 |
| WO | WO 2007/021494 A2 | 2/2007 |
| WO | WO 2007/046703 A2 | 4/2007 |
| WO | WO 2007/148971 A2 | 12/2007 |
| WO | WO 2007/149406 A2 | 12/2007 |
| WO | WO 2007/149852 A2 | 12/2007 |
| WO | WO 2008/012543 A1 | 1/2008 |
| WO | WO 2008/033413 A2 | 3/2008 |
| WO | WO 2008/118507 A2 | 10/2008 |
| WO | WO 2008/143954 A2 | 11/2008 |
| WO | WO 2008/155134 A1 | 12/2008 |
| WO | WO 2009/051717 A2 | 4/2009 |
| WO | WO 2009/058322 A1 | 5/2009 |
| WO | WO 2009/075772 A1 | 6/2009 |
| WO | WO 2009/130198 A2 | 10/2009 |
| WO | WO 2009/137254 A2 | 11/2009 |
| WO | WO 2009/140015 A2 | 11/2009 |
| WO | WO 2010/029178 A1 | 3/2010 |
| WO | WO 2010/055413 A1 | 5/2010 |
| WO | WO 2010/091122 A1 | 8/2010 |
| WO | WO 2010/115866 A1 | 10/2010 |
| WO | WO 2010/125471 A2 | 11/2010 |
| WO | WO 2010/140148 A1 | 12/2010 |
| WO | WO 2010/144502 A2 | 12/2010 |
| WO | WO 2010/144508 A1 | 12/2010 |
| WO | WO 2011/004361 A2 | 1/2011 |
| WO | WO 2011/005968 A1 | 1/2011 |
| WO | WO 2011/028228 A1 | 3/2011 |
| WO | WO 2011/028229 A1 | 3/2011 |
| WO | WO 2011/028344 A2 | 3/2011 |
| WO | WO 2011/033105 A1 | 3/2011 |
| WO | WO 2011/069164 A2 | 6/2011 |
| WO | WO 2012/006623 A1 | 1/2012 |
| WO | WO 2012/006624 A2 | 1/2012 |
| WO | WO 2012/006633 A1 | 1/2012 |
| WO | WO 2012/006635 A1 | 1/2012 |
| WO | WO 2012/028681 A1 | 3/2012 |
| WO | WO 2012/170289 A1 | 12/2012 |
| WO | WO 2013/009627 A2 | 1/2013 |
| WO | WO 2013/093760 A2 | 6/2013 |
| WO | WO 2013/122617 A1 | 8/2013 |
| WO | WO 2013/123457 A1 | 8/2013 |
| WO | WO 2013/192604 A1 | 12/2013 |
| WO | WO 2014/011819 A2 | 1/2014 |
| WO | WO 2014/127215 A1 | 8/2014 |
| WO | WO 2015/023891 A2 | 2/2015 |
| WO | WO 2015/038625 A1 | 3/2015 |
| WO | WO 2015/086406 A2 | 6/2015 |
| WO | WO 2015/106052 A1 | 7/2015 |
| WO | WO 2016/004113 A1 | 1/2016 |
| WO | WO 2016/009326 A1 | 1/2016 |
| WO | WO 2016/044334 A1 | 3/2016 |
| WO | WO 2016/168728 A2 | 10/2016 |
| WO | WO 2019/006390 A1 | 1/2017 |
| WO | WO 2017/024060 A1 | 2/2017 |
| WO | WO 2017/087861 A1 | 5/2017 |
| WO | WO 2017/139576 A1 | 8/2017 |
| WO | WO-2017136358 A1 * | 8/2017 ......... A61K 48/0016 |
| WO | WO 2018/183692 A1 | 10/2018 |
| WO | WO 2018/222792 A1 | 12/2018 |
| WO | WO 2019/152557 A1 | 8/2019 |
| WO | WO 2019/152692 A1 | 8/2019 |
| WO | WO 2020/113197 A1 | 6/2020 |
| WO | WO 2020/118069 A2 | 6/2020 |
| WO | WO 2021/067389 A1 | 4/2021 |

OTHER PUBLICATIONS

Armour, et al., Recombinant Human IgG Molecules Lacking Fc gamma Receptor I Binding And Monocyte Triggering Activities, European Journal of Immunology, vol. 29, No. 8, pp. 2613-2624, Aug. 1, 1999.

Benhar, et al., Cloning, Expression and Characterization of The Fv Fragments of The Anti-Carbohydrate mAbs B1 and B5 As Single-Chain Immunotoxins, Protein Engineering, Design and Selection, vol. 7, No. 12, pp. 1509-1515, Dec. 1, 1994.

Brown, et al., A microRNA-Regulated Lentiviral Vector Mediates Stable Correction of Hemophilia B Mice, Blood, vol. 110, No. 13, pp. 4144-4152, Dec. 15, 2007.

Brown, et al., Endogenous microRNA Regulation Suppresses Transgene Expression in Hematopoietic Lineages and Enables Stable Gene Transfer, Nature Medicine, vol. 12, No. 5, pp. 585-591, May 1, 2006.

Burmeister, et al., Crystal Structure of the Complex of Rat Neonatal Fc Receptor with Fc, Nature, vol. 372, No. 6504, pp. 379-383, Nov. 24, 1994.

Cantore, et al., Liver-Directed Lentiviral Gene Therapy in a Dog Model of Hemophilia B, Science Translational Medicine, vol. 7, Issue 277, 277ra28, pp. 1-27., Mar. 4, 2015.

Chen, et al., MicroRNAs As Regulators of Mammalian Hematopoiesis, Seminars in Immunology, vol. 17, No. 2, pp. 155-165, Apr. 1, 2005.

Coffin, et al., "The Interaction of Retroviruses and Their Hosts", Retroviruses, Cold Spring Harbor Laboratory Press, pp. 758-763, 1997.

Costa, et al., Transcriptional Control of The Mouse Prealbumin (Transthyretin) Gene: Both Promoter Sequences And A Distinct Enhancer Are Cell Specific, Molecular and Cellular Biology, vol. 6, No. 12, pp. 4697-4708, Jan. 1, 1986.

Dennis, et al., Albumin Binding as a General Strategy for Improving the Pharmacokinetics of Proteins, Journal of Biological Chemistry, vol. 277, No. 38, pp. 35035-35043, Sep. 20, 2009.

(56) References Cited

OTHER PUBLICATIONS

Dull, et al., A Third-Generation Lentivirus Vector with a Conditional Packaging System, Journal of Virology, vol. 72, No. 11, pp. 8463-8471, Nov. 1, 1998.
Fathallah, et al., Effects of Hypertonic Buffer Composition on Lymph Node Uptake and Bioavailability of Rituximab, After Subcutaneous Administration, Biopharmaceutics & Drug Disposition, vol. 36, No. 2, pp. 115-125, Mar. 2015.
Figueiredo, et al., Cis-Acting Elements and Transcription Factors Involved in the Promoter Activity of The Human Factor VIII Gene, Journal of Biological Chemistry, vol. 270, No. 20, pp. 11828-11838, May 19, 1995.
Friend, et al., Phase I Study of an Engineered Aglycosylated Humanized Cd3 Antibody in Renal Transplant Rejection1, Transplantation, vol. 68, Issue 11, pp. 1632-1637, Dec. 15, 1999.
Genbank, *Homo Sapiens* Transferrin (TF), mRNA, "Accession No. XM039847, Retrieved From <<https://www.ncbi.nlm.nih.gov/nuccore/XM_039847.1?report=genbank>>, Retrieved on Sep. 24, 2014", 2 Pages, Jul. 16, 2001.
Genbank, *Homo sapiens* transferrin (TF), mRNA, Accession No. XM039845, accessed at <<https://www.ncbi.nlm.nih.gov/nuccore/XM_039845.1?report=genbank>>, Accessed on Jan. 1, 2018, 2 pages, Jan. 1, 2018.
Genbank, *Homo Sapiens* Transferrin (TF), mRNA, Accession No. XM002793, Retrieved from: <<https://www.ncbi.nlm.nih.gov/nuccore/XM_002793.7?report=genbank>>, Retrieved on Sep. 24, 2014, 2 Pages, May 13, 2002.
Genbank, *Homo Sapiens* Transferrin (TF), Transcript Variant 1, mRNA, "Accession No. NM001063, Retrieved from: <<http://www.ncbi.nlm.nih.gov/nuccore/NM_001063>>", 5 Pages, Sep. 3, 2009.
Genbank, *Homo sapiens* Von Willebrand Factor (VWF), mRNA, NCBI Reference Sequence: NM_000552.3, Retrieved from :<<https://www.ncbi.nlm.nih.gov/nuccore/NM_000552.3>>, 10 Pages, Mar. 29, 2016.
Genbank, Human Transferrin mRNA, Complete cds, Accession No. M12530, Retrieved From: <<http://www.ncbi.nlm.nih.gov/nuccore/M12530>> Retrieved on Jan. 15, 2015, 2 Pages, Jan. 14, 1995.
Genbank, Synthetic Construct Hepatocyte-Restricted Expression Cassette, "Accession No. AY661265, Retrieved From: <<https://www.ncbi.nlm.nih.gov/nuccore/AY661265>>", 2 Pages, Sep. 29, 2009.
Genbank, Transferrin [Human, Liver, mRNA, 2347 nt], Accession No. S95936, Retrieved From:<<http://www.ncbi.nlm.nih.gov/nuccore/S95936>>, 2 pages, May 7, 1993.
Genbank, Transferrin Precursor [*Homo sapiens*], Accession No. AAA61140.1, Retrieved from :<<http://www.ncbi.nlm.nih.gov/protein/AAA61140>>, Retrieved on Mar. 29, 2016, 3 Pages, Jan. 14, 1995.
Genbank, Von Willebrand Factor Preproprotein [*Homo sapiens*], NCBI Reference Sequence: NP_000543.2, Retrieved from: <<http://www.ncbi.nlm.nih.gov/protein/NP_000543.2>>, 8 Pages, Mar. 29, 2016.
Higashikawa, et al., Kinetic Analyses of Stability of Simple and Complex Retroviral Vectors, Virology, vol. 280, No. 1, pp. 124-131, 2001.
Ho, et al., Site-Directed Mutagenesis by Overlap Extension Using The Polymerase Chain Reaction, Gene, vol. 77, No. 1, pp. 51-59, Apr. 15, 1989.
Holt, et al., Anti-Serum Albumin Domain Antibodies for Extending The Half-Lives Of Short Lived Drugs, Protein Engineering, Design and Selection, vol. 21, No. 5, pp. 283-288, May 1, 2008.
Horton, et al., Gene Splicing by Overlap Extension, Methods in Enzymology, vol. 217, pp. 270-279, Apr. 1, 1994.
Ill, et al., Optimization of The Human Factor VIII Complementary DNA Expression Plasmid For Gene Therapy of Hemophilia A, Blood Coagulation & Fibrinolysis: An International Journal In Haemostasis And Thrombosis, vol. 8, pp. S23-S30, Jan. 1, 1997.
International Search Report & Written Opinion Received for PCT Application No. PCT/US2020/053463, mailed on Feb. 4, 2021.
Israel, et al., Expression of The Neonatal Fc Receptor, FcRn, On Human Intestinal Epithelial Cells, Immunology, vol. 92, No. 1, pp. 69-74, Sep. 1997.
Klimatcheva, et al., Lentiviral Vectors and Gene Therapy, Frontiers in Bioscience, vol. 4, pp. 481-496, Jun. 1, 1999.
Kobayashi, et al., FcRn-Mediated Transcytosis of Immunoglobulin G In Human Renal Proximal Tubular Epithelial Cells, American Journal of Physiology—Renal Physiology, vol. 282, No. 2, pp. F358-F365, Feb. 2002.
Konig, et al., Use of an Albumin-Binding Domain for the Selective Immobilisation of Recombinant Capture Antibody Fragments on ELISA Plates, Journal of Immunological Methods, vol. 218, No. 1-2, pp. 73-83, Sep. 1, 1998.
Kraulis, et al., The Serum Albumin-Binding Domain of Streptococcal Protein G Is A Three-Helical Bundle: A Heteronuclear NMR Study, FEBS Letters, vol. 378, Issue 2, pp. 190-194, Jan. 8, 1996.
Larrick, et al., Rapid Cloning of Rearranged Immunoglobulin Genes from Human Hybridoma Cells using Mixed Primers and the Polymerase Chain Reaction, Biochemical and Biophysical Research Communications, vol. 160, No. 3, pp. 1250-1256, May 15, 1989.
Lenting, et al., Clearance Mechanisms of von Willebrand Factor and Factor VIII, Journal of Thrombosis and Haemostasis, vol. 5, No. 7, pp. 1353-1360, Jul. 1, 2007.
Lenting, et al., The Life Cycle of Coagulation Factor VIII in View of its Structure and Function, Blood, vol. 92, No. 11, pp. 3983-3996, Dec. 1, 1998.
Linhult, et al., Mutational Analysis of The Interaction Between Albumin-Binding Domain From Streptococcal Protein G And Human Serum Albumin, Protein Science, vol. 11, No. 2, pp. 206-213, Feb. 1, 2002.
Mount, et al., Sustained Phenotypic Correction of Hemophilia B Dogs With A Factor IX Null Mutation By Liver-Directed Gene Therapy, Blood, vol. 99, No. 8, pp. 2670-2676, Apr. 15, 2002.
Muller, et al., Recombinant Bispecific Antibodies for Cellular Cancer Immunotherapy, Current opinion in molecular therapeutics, vol. 9, No. 4, pp. 319-326, Aug. 1, 2007.
Narita, et al., The Low-Density Lipoprotein Receptor-Related Protein (LRP) Mediates Clearance Of Coagulation Factor Xa In Vivo, Blood, vol. 91, No. 2, pp. 555-560, Jan. 15, 1998.
Roovers, et al., Efficient Inhibition of EGFR Signaling and of Tumour Growth By Antagonistic anti-EFGR Nanobodies, Cancer Immunology, Immunotherapy, vol. 56, No. 3, pp. 303-317, Mar. 1, 2007.
Rouet, et al., A Potent Enhancer Made of Clustered Liver-Specific Elements In The Transcription Control Sequences Of Human Alpha 1-Microglobulin/Bikunin Gene, Journal of Biological Chemistry, vol. 267, No. 29, pp. 20765-20773, Jan. 1, 1992.
Rouet, et al., An Array of Binding Sites for Hepatocyte Nuclear Factor 4 Of High And Low Affinities Modulates The Liver-Specific Enhancer For The Human α1-Microglobulin/Bikunin Precursor, Biochemical Journal, vol. 334, No. 3, pp. 577-584, Jan. 1, 1998.
Rouet, et al., Hierarchy and Positive/Negative Interplays of The Hepatocyte Nuclear Factors HNF-1, -3 And -4 In the Liver-Specific Enhancer For The Human α-1-Microglobulin/Bikunin Precursor, Nucleic Acids Research, vol. 23, No. 3, pp. 395-404, Jan. 1, 1995.
Routledge, et al., The Effect of Aglycosylation On the Immunogenicity Of A Humanized Therapeutic CD3 Monoclonal Antibody, Transplantation, vol. 60, No. 8, pp. 847-853, Oct. 1, 1995.
Ruberti, et al., The Use of The RACE Method To Clone Hybridoma cDNA When V Region Primers Fail, Journal of Immunological Methods, vol. 173, No. 1, pp. 33-39, Jul. 12, 1994.
Shields, et al., High Resolution Mapping of the Binding Site on Human IgG1 for Fc Gamma RI, Fc Gamma RII, Fc Gamma RIII, and FcRn and Design of IgG1 Variants with Improved Binding to the Fc Gamma R, Journal of Biological Chemistry, vol. 276, No. 9, pp. 6591-6604, Mar. 2, 2001.
Sosale, et al., "Marker of Self" CD47 on Lentiviral Vectors Decreases Macrophage-Mediated Clearance and Increases Delivery to SIRPA-Expressing Lung Carcinoma Tumors, Molecular Therapy—Methods & Clinical Development, vol. 3, No. 16080, pp. 1-13, Dec. 7, 2016.
Story, et al., A Major Histocompatibility Complex Class I-like Fc Receptor Cloned from Human Placenta: Possible Role in Transfer

(56) References Cited

OTHER PUBLICATIONS of Immunoglobulin G from Mother to Fetus, Journal of Experimental Medicine, vol. 180, No. 6, pp. 2377-2381, Dec. 1, 1994.
Trussel, et al., New Strategy For The Extension Of The Serum Half-Life Of Antibody Fragments, Bioconjugate Chemistry, vol. 20, No. 12, pp. 2286-2292, Dec. 1, 2009.
Vigna, et al., Efficient Tet-Dependent Expression Of Human Factor IX In Vivo By A New Self-Regulating Lentiviral Vector, Molecular Therapy, vol. 11, No. 5, pp. 763-775, Jan. 1, 2005.
Ward, et al., The Effector Functions Of Immunoglobulins: Implications For Therapy, Therapeutic Immunology, vol. 2, No. 2, pp. 77-94, Apr. 1, 1995.
Zufferey, et al., Multiply Attenuated Lentiviral Vector Achieves Efficient Gene Delivery In Vivo, Nature Biotechnology, vol. 15, No. 9, pp. 871-875, Sep. 1, 1997.
Amendola et al. (2005) "Coordinate dual-gene transgenesis by lentiviral vector carrying synthetic bidriectional promoters," Nature Biotechnology, 23(1):108-116.
Andersson, et al., "Purification and Characterization of Human Factor IX", Thrombosis Research, vol. 7, Issue 3, pp. 451-459. (Sep. 1975).
Baekelandt et al., "Optimized lentiviral vector production and purification procedure prevents immune response after transduction of mouse brain Laboratory for Experimental", Jun. 2003, 10: 1933-1940.
Baldassarre, et al., "Production of Transgenic Goats By Pronuclear Microinjection Of In Vitro Produced Zygotes Derived From Oocytes Recovered By Laparoscopy", Theriogenology, vol. 59, Issues 3-4, pp. 831-839, Feb. 2003.
Benhar, et al., "Cloning, Expression and Characterization Of The Fv Fragments Of The Anti-Carbohydrate mAbs BI and B5 As Single-Chain Immunotoxins", Protein Engineering, Design and Selection, vol. 7, No. 12, pp. 1509-1515, Dec. 1994.
Biochemistry, 1990, Section 6-3 Chemical Evolution, pp. 126-129, John Wiley and Sons.
Bril et al. (2006) "Tolerance to factor VIII in a transgenic mouse expressing human factor VIII cDNA carrying an Arg$^{593}$ to Cys substitution", Thromb. Haemost. 95(2): 341-347.
Brinster, et al., "Expression of A Microinjected Immunoglobulin Gene In The Spleen Of Transgenic Mice", Nature, vol. 306, No. 5941, pp. 332-336, 1983.
Brinster, et al., "Factors Affecting the Efficiency Of Introducing Foreign DNA Into Mice By Microinjecting Eggs", Proceedings of the National Academy of Sciences of the United States of America, vol. 82, No. 13, pp. 4438-4442, Jul. 1, 1985.
Brown et al., "Endogenous microRNA can be broadly exploited to regulate transgene expression according to tissue, lineage and differentiation state", Nat. Biotechnol., Dec. 2007, 25(12): 1457-1467.
Brown, et al., "Production of Recombinant H1 Parvovirus Stocks Devoid of Replication-Competent Viruses", Human Gene Therapy, vol. 13, No. 18, pp. 2135-2145, Dec. 10, 2002.
Burgess-Brown et al., "Codon Optimization Can Improve Expression Of Human Genes In *Escherichia coli*: A Multi-Gene Study", Protein Expression and Purification, 2008, vol. 59, No. 1, pp. 94-102.
Cameron, C., et al., "The Canine Factor VIII cDNA and 5' Flanking Sequence," Thrombosis and Haemostasis 79(2):317-322, Schattauer, Germany (1998).
Cantore et al., "Liver-Directed Gene Therapy for Hemophilia B with Immune Stealth Lentiviral Vectors", Gene Therapy and Transfer: Gene Therapy for Hemophilia and Improving Lentiviral Vectors, Dec. 7, 2017 Blood, 130(Suppl. 1): 605.
Cantore et al., "Liver-directed lentiviral gene therapy in a dog model of hemophilia B", Science Translational Medicine, Mar. 4, 2015, 7(277): 277.
Cao et al., "Factor VIII Accelerates Proteolytic Cleavage of Von Willebrand Factor by ADAMTS13", PNAS May 27, 2008, 105(21): 7416-7421.

Capon et al. (1989) "Designing CD4 immunoadhesins for AIDS therapy," Nature, 337, 525-531.
Chiorini et al. (1997) "Cloning of Adeno-Associated Virus Type 4 (AAV4) and Generation of Recombinant AAV4 Particles," Journal of Virology, 71(9):6823-6833.
Chiorini et al. (1999) "Cloning and Characterization of Adeno-Associated Virus Type5," Journal of Virology, 73(2):1309-1319.
Cleland et al., "A novel long-acting human growth hormone fusion protein (vrs-317): enhanced in vivo potency and half-life", Journal of Pharmaceutical Sciences, 2012, 101(8): 2744-2754.
Codon Optimization for Increased Protein Expression, downloaded Mar. 26, 2018 from GenScript, OptimumGene—Codon Optimization.
Codon Usage Database, Retrieved from http://www.kazusa.or.jp/codon/, 2013, 1 page.
Comparison of codon usage frequency in SEQ ID No. 1 and SEQ ID: 3 of the Patent and SEQ ID: 5 of D2 (WO 2011/005968 A1, submitted with IDS dated Sep. 7, 2021)., Defensive Opposition regarding European Patent No. EP2956477 filed by Bioverative Therapeutics Inc., dated Mar. 11, 2022.
Comparison of in vivo FVIII activity after expression with codon optimised FVIII (SEQ ID: 1) and non-optimised FVIII (SEQ ID: 3), Defensive Opposition regarding European Patent No. EP2956477 filed by Bioverative Therapeutics Inc., dated Mar. 11, 2022.
Cutler et al., "The Identification and Classification Of 41 Novel Mutations In The Factor VIII Gene (F8c)", Human Mutation, Mar. 2002, vol. 19, No. 3, pp. 274-278.
Dalkara et al. (2013) "In vivo-directed evolution of a new adeno-associated virus for therapeutic outer retinal gene delivery from the vitreous," Sci. Transl. Med., 5(189):189ra76, 12 pages.
Database GENESEQ, "Human Codon-Optimized Clotting Factor IX (hFIX) Gene, SEQ ID No. 2", XP002776590, retrieved from EBI accession No. GSN: BBB41169 Database accession No. BBB41169, Feb. 27, 2014.
Defensive Opposition regarding European Patent No. EP2956477 filed by Bioverative Therapeutics Inc., dated Mar. 11, 2022, including Main Request and Auxiliary Requests 1, 1a, 2a, 3a, 3, 4, 5, 5a, 6a, 6, 7, 7a, 8, 9a, 9, 10a, 10, 11a, 11, 12, 13a, 13, 14, 14a, 15a, and 15.
Dellgren, et al., "Cell Surface Expression Level Variation between Two Common Human Leukocyte Antigen Alleles, HLA-A2 and HLA-B8, Is Dependent on the Structure of the C Terminal Part of the Alpha 2 and the Alpha 3 Domains", PLoS One, vol. 10, No. 8, e0135385, pp. 1-15, Aug. 25, 2010.
Ding et al., "Multivalent Antiviral XTEN-Peptide Conjugates with Long in Vivo Half-Life and Enhanced Solubility", Bioconjugate Chemistry, 2014, 25(7): 1351-1359.
Eaton, D.L., et al., "Construction and Characterization of an Active Factor VIII Variant Lacking the Central One-Third of the Molecule," Biochemistry 25(26):8343-8347, American Chemical Society, United States (1986).
Ellman et al. (1991) "Biosynthetic Method for Introducing Unnatural Amino Acids Site-Specifically into Proteins," Methods In Enzymology, 202 (15): 301-336.
ENSEMBL, Gene: B2M ENSG00000166710, Beta-2-Microglobulin, obtained from url: http://uswest.ensembl.org/Homo_sapiens/Gene/Summary?g=ENSG00000166710;r=15:44711477-44718877;mobileredirect=no.
Europapress (www.europapress.es), "European Commission Approves ReFacto AF(TM) as a Variation to the Refacto(R) Marketing Authorisation", Mar. 11, 2009, 2 pages.
Extended European Search Report for European Patent Application No. 20204866.6, mailed Aug. 9, 2021.
Extended European Search Report for European Patent Application No. 22176817.9, mailed Jan. 20, 2023.
Fallaux, F.J., et al., "The Human Clotting Factor VIII cDNA Contains an Autonomously Replicating Sequence Consensus- and Matrix Attachment Region-like Sequence That Binds a Nuclear Factor, Represses Heterologous Gene Expression, and Mediates the Transcriptional Effects of Sodium Butyrate," Molecular and Cellular Biology 16(8):4264-4272, American Society for Microbiology, United States (1996).

(56) References Cited

OTHER PUBLICATIONS

FDA Orphan Drug Designation and Approval for ReFacto, Feb. 8, 1996, 2 pages, Retrieved from www.accessdata.fda.gov.
Gaspar et al. (2012) "EuGene: maximizing synthetic gene design for heterologous expression," Bioinformatics, 28(20):2683-2684.
Genbank Database, "Adeno-associated virus 2, complete genome", GenBank Accession No. AF043303.1, May 20, 2010, Retrieved from: <<https://www.ncbi.nlm.nih.gov/nuccore/AF043303.1>>.
Genbank Database, "Adeno-associated virus 2, complete genome", GenBank Accession No. J01901.1, Apr. 27, 1993, Retrieved from: <<https://www.ncbi.nlm.nih.gov/nuccore/J01901.1>>.
Genbank Database, "Adeno-associated virus 4, complete genome", GenBank Accession No. U89790.1, Aug. 21, 1997, Retrieved from: <<https://www.ncbi.nlm.nih.gov/nuccore/U89790.1>>.
Genbank Database, "Adeno-associated virus 5 DNA binding trs helicase (Rep22) and capsid protein (VP1) genes, complete cds", GenBank Accession No. AF085716.1, Feb. 9, 1999, Retrieved from: <<https://www.ncbi.nlm.nih.gov/nuccore/AF085716.1>>.
Genbank, *Homo sapiens* von Willebrand Factor (VWF), mRNA, NCBI Reference Sequence: NM_000552.4, Retrieved from: <<https://www.ncbi.nlm.nih.gov/nuccore/NM_000552.4>>, 15 Pages, Apr. 28, 2016.
Generation Bio, "Generation Bio Announces Two Non-Viral Gene Therapy Milestone Achievements: Target Levels of Factor VIII Expression in Hemophilia A Mice and Translation of Expression from Mice to Non-Human Primates", Jan. 4, 2021, obtained from url: <https://www.globenewswire.com/en/news-release/2021/01/04/2152472/0/en/Generation-Bio-Announces-Two-Non-Viral-Gene-Therapy-Milestone-Achievements-Target-Levels-of-Factor-VIII-Expression-in-Hemophilia-A-Mice-and-Translation-of-Expression-from-Mice-to-N.html>.
Giangrande, Paul, "Haemophilia B: Christmas Disease", Expert Opinion On Pharmacotherapy, vol. 6, No. 9, pp. 1517-1524. (2005).
Graf, M., et al., "Concerted Action of Multiple Cis-acting Sequences Is Required for Rev Dependence of Late Human Immunodeficiency Vims Type 1 Gene Expression," Journal of Virology 74(22):10822-10826, American Society for Microbiology, United States (2000).
Hoeben, R.C., et al., "Expression of Functional Factor VIII in Primary Human Skin Fibroblasts after Retrovirus-mediated Gene Transfer," The Journal of Biological Chemistry 265(13):7318-7323, The American Society for Biochemistry and Molecular Biology, United States (1990).
Hoeben, R.C., et al., "Expression of the Blood-clotting Factor-VIII cDNA Is Repressed by a Transcriptional Silencer Located in Its Coding Region," Blood 85(9):2447-2454, American Society of Hematology, United States (1995).
Holt, et al., "Domain Antibodies: Proteins for therapy", Trends in Biotechnology, vol. 21, Issue 11, pp. 484-490, Nov. 2003.
International Preliminary Report on Patentability for PCT International Patent Application No. PCT/US2017/015879, mailed Aug. 7, 2018.
International Preliminary Report on Patentability for PCT International Patent Application No. PCT/US2019/016122, mailed Aug. 4, 2020.
International Search Report & Written Opinion for PCT International Patent Application No. PCT/US2019/016122, mailed Mar. 21, 2019.
International Search Report & Written Opinion for PCT International Patent Application No. PCT/US2021/038871, mailed Nov. 24, 2021.
International Search Report and Written Opinion for PCT International Application No. PCT/US2015/038678, mailed Dec. 8, 2015.
International Search Report and Written Opinion for PCT International Patent Application No. PCT/US2014/016441, mailed May 23, 2014.
International Search Report and Written Opinion for PCT International Patent Application No. PCT/US2017/015879, mailed Apr. 5, 2017.
International Search Report and Written Opinion for PCT International Patent Application No. PCT/US2019/064711, mailed Jun. 23, 2020.
Johnston et al., "Generation of an optimized lentiviral vector encoding a high-expression factor VIII transgene for gene therapy of hemophilia A", Gene Therapy, Jun. 2013, 20(6):607-615.
Kasuda et al., "Establishment Of Embryonic Stem Cells Secreting Human Factor VIII For Cell-Based Treatment Of Hemophilia A", Journal of Thrombosis and Haemostasis, Aug. 2008, vol. 6, No. 8, pp. 1352-1359.
Kimchi-Sarfaty et al., "A "Silent" Polymorphism In The Mdr1 Gene Changes Substrate Specificity", Science, 2007, vol. 315, No. 5811, pp. 525-528.
Koeberl, D.D., et al., "Sequences within the Coding Regions of Clotting Factor VIII and CFTR Block Transcriptional Elongation," Human Gene Therapy 6(4):469-479, M.A. Liebert, United States (1995).
Kotterman et al. (2014) "Engineering adeno-associated viruses for clinical gene therapy," Nat. Rev. Genet., 15(7):445-451.
Kudla et al. (2006) "High Guanine and Cytosine Content Increases mRNA Levels in Mammalian Cells," PloS Biol, e180.
Lange, et al., "Overexpression of Factor VIII After AAV Delivery Is Transiently Associated With Cellular Stress in Hemophilia A Mice", Molecular Therapy—Methods & Clinical Development, vol. 3, No. 16064, pp. 1-8, 2016.
Langner, K-D., et al., "Synthesis of Biologically Active Deletion Mutants of Human Factor VIII:C," Behring Institute Mitteilungen 82:16-25, Behringwerke AG, Germany (1988).
Le Bras et al., "Shielded vectors improve liver gene therapy", Lab Animal, 2019, 48: 238.
Lind et al., "Novel Forms of B-domain-deleted Recombinant Factor VIII molecules Construction and Biochemical Characterization", Eur Journ Biochem., Aug. 15, 1995, 232: 19-27.
Liu et al., "Codon Optimization Improves Factor IX Expression In Hemophilia B Mice By More Than 15-Fold", Human Gene Therapy, Oct. 2015, vol. 26, No. 10, p. A2.
Lynch, C.M., et al., "Sequences in the Coding Region of Clotting Factor VIII Act as Dominant Inhibitors of RNA Accumulation and Protein Production," Human Gene Therapy 4(3): 259-272, M.A. Liebert, United States (1993).
Malassagne, et al. (Apr. 14, 2003) "Hypodermin A, A New Inhibitor of Human Complement for the Prevention of Xenogeneic Hyperacute Rejection", Xenotransplantation, vol. 10, Issue 3, pp. 267-277.
Manco-Johnson, M.J., et al., "Prophylaxis Versus Episodic Treatment to Prevent Joint Disease in Boys with Severe Hemophilia," The New England Journal of Medicine 357(6):535-544, Massachusetts Medical Society, United States (2007).
Mannucci, P.M. and Tuddenham, E.G.D., "The Hemophilias—fromRoyal Genes to Gene Therapy," New England Journal of Medicine 344(23):1773-1779, Massachusetts Medical Society, United States (2001).
Maunder et al., "Enhancing titres of therapeutic viral vectors using the transgene repression in vector production (TRiP) system", Nature Communications, Mar. 2017, 8(1).
Mccue et al., "Application of a novel affinity adsorbent for the capture and purification of recombinant Factor VIII compounds", J. Chroma., Nov. 6, 2009, 1216(45): 7824-7830.
Mcknight, et al. (Sep. 1983) "Expression of The Chicken Transferrin Gene in Transgenic Mice", Cell, vol. 34, Issue 2, pp. 335-341.
Meulien, P., et al., "A New Recombinant Procoagulant Protein Derived from the cDNA Encoding Human Factor VIII," Protein Engineering 2(4):301-306, IRL Press Ltd., England (1988).
Miao et al., "Bioengineering of Coagulation Factor VIII for Improved Secretion", Blood, May 1, 2004, vol. 103, No. 9, pp. 3412-3419.
Milani et al., "Phagocytosis-shielded lentiviral vectors improve liver gene therapy in nonhuman primates", Sci Transl Med., May 22, 2019, 11(493): eaav7325.
Milani, et al., "Genome Editing For Scalable Production of Alloantigen-Free Lentiviral Vectors for In Vivo Gene Therapy", EMBO Molecular Medicine, Aug. 23, 2017, 9(11): 1558-1573.

(56) References Cited

OTHER PUBLICATIONS

Morfini, M., "Pharmacokinetics of Factor VIII and Factor IX," Haemophilia 9(Suppl. 1):94-100, Blackwell Publishing Ltd., England (2003).
Nair et al., "Computationally Designed Liver-Specific Transcriptional Modules And Hyperactive Factor IX Improve Hepatic Gene Therapy", Blood, 2014, vol. 123, No. 20, pp. 3195-3199.
Nair et al., "Computationally Designed Liver-Specific Transcriptional Modules and Hyperactive Factor IX Improve Hepatic Gene Therapy ERRATA 2007", Blood, Mar. 19, 2015, vol. 125, No. 12.
Nakamura et al. (2000) "Codon usage tabulated from international DNA sequence databases: status for the year 2000," Nucleic Acids Research, 28 (1): 292.
Nayak, et al., "Progress and Prospects: Immune Responses to Viral Vectors", Gene Therapy, Nov. 12, 2009, 17: 295-304.
Ncbi, "Beta-2-Microglobin [*Homo sapiens*]", GenBank Accession No. ABB01003.1, 2 Pages, 2005.
NCBI, "Codon Usage Database", Retrieved from <<http://www.kazusa.or.jp/codon/>>, 2013, pp. 1-2.
Neumann, et al., "Gene Transfer Into Mouse Lyoma Cells By Electroporation In High Electric Fields", The EMBO Journal, vol. 1, No. 7, pp. 841-845. (Jul. 1, 1982).
Noren et al. (1989) "A General Method for Site-Specific Incorporation of Unnatural Amino Acids into Proteins," Science, 244: 182-188.
Notice of Opposition for European Patent Application No. 14751254.5, mailed Aug. 23, 2021, 40 pages.
Otto-Wilhelm Merten et al., "Production of lentiviral vectors", Molecular Therapy—Methods & Clinical Development, Jan. 2016, 3: 1-14.
Partial European Search Report for European Patent Application No. 15814881.7, mailed on Jan. 12, 2018, 6 pages.
Peyvandi, F., et al., "Genetic Diagnosis of Gaemophilia and Other Inherited Bleeding Disorders," Haemophilia 12(Suppl 3):82-89, Blackwell Publishing Ltd., England (2006).
Pipe et al., "Functional Factor VIII Made With Von Willebrand Factor At High Levels In Transgenic Milk", Journal of Thrombosis and Haemostasis, Nov. 2011, vol. 9, No. 11, pp. 2235-2242.
Podust, "Extension of In Vivo Half-Life of Biologically Active Molecules by XTEN Protein Polymers", Journal of Controlled Release, Oct. 28, 2016, 240(6): 52-66.
Ritchie, et al. (Dec. 6, 1984) "Allelic Exclusion and Control of Endogenous Immunoglobulin Gene Rearrangement in K Transgenic Mice", Nature, vol. 312, No. 5994, pp. 517-520.
Robl, et al. (Jan. 1, 2003) "Artificial Chromosome Vectors and Expression of Complex Proteins in Transgenic Animals", Theriogenology, vol. 59, Issue 1, pp. 107-113.
Rodriguez-Merchan, E.C. "Management of Musculoskeletal Complications of Hemophilia," Seminars in Thrombosis and Hemostasis 29(1):87-96, Thieme, United States (2003).
Ruther et al., "Easy Identification of cDNA Clones," The EMBO Journal 2(10):1791-1794, IRL Press Ltd, England (1983).
Rutledge et al. (1998) "Infectious Clones and Vectors Derived from Adeno-Associated Virus (AAV) Serotypes Other Than AAV Type 2," Journal of Virology, 72(1):309-319.
Sandberg et al., "Structural and Functional Characterization of B-Domain Deleted Recombinant Factor VIII", Seminars in Hematology, Apr. 2001, 38(2), Suppl 4: 4-12.
Sarver, N., et al., "Stable Expression of Recombinant Factor VIII Molecules Using a Bovine Papillomavirus Vector," DNA 6(6):553-564, Mary Ann Liebert, Inc., United States (1987).
Schlapschy, et al., "Fusion of A Recombinant Antibody Fragment with A Homo-Amino-Acid Polymer: Effects On Biophysical Properties And Prolonged Plasma Half-Life", Protein Engineering, Design and Selection, vol. 20, No. 6, pp. 273-284, Jun. 1, 2007.
Sebastian et al., "Treatment of malignant pleural effusion with the trifunctional antibody catumaxomab (Removab) (anti-EpCAM x Anti-CD3): results of a phase 1/2 study", Journal of Immunotherapy, 2009, 32(2): 195-202.

Sequence alignment of SEQ ID No. 1 of the opposed patent and SEQ ID Nos. 5, 6, and 4 of D2, Retrieved Aug. 2, 2021.
Sequence alignment of SEQ ID Nos. 3 and 1 of the opposed patent original file name, Retrieved Aug. 2, 2021.
Sharp et al. (1987) "The codon adaptation index—a measure of directional synonymous codon usage bias, and its potential applications," Nucleic Acids Research, 15 (3): 1281-1295.
Simioni, et al. (Oct. 22, 2009) "X-Linked Thrombophilia with a Mutant Factor IX (Factor IX Padua)", The New England Journal of Medicine, vol. 361, No. 17, pp. 1671-1675.
Srivastava et al. (1983) "Nucleotide Sequence and Organization of the Adeno-Associated Virus 2 Genome," Journal of Virology, 45(2):555-564.
Strohl, "Fusion Proteins for Half-Life Extension of Biologics as a Strategy to Make Biobetters", BioDrugs, 2015, 29: 215-239.
Summons to Attend Oral Proceedings for European Patent Application No. 14751254.5, mailed Nov. 9, 2022.
Supplementary European Search Report for European Patent Application No. 15814881.7, mailed on Apr. 13, 2015, 7 pages.
Suwanmanee et al., "Integration-Deficient Lentiviral Vectors Expressing Codon-Optimized R338L Human FIX Restore Normal Hemostasis In Hemophilia B Mice", Molecular Therapy, 2014, vol. 22, No. 3, pp. 567-574.
Swystun, et al., "Gene Therapy for Coagulation Disorders", Circulation Research, vol. 118, No. 9, pp. 1443-1452, Apr. 29, 2016.
Third party observations against European Application No. 15814881.7, dated Oct. 2, 2020, 107 pages.
Toole, et al., "A Large Region (Approximately Equal To 95 kDa) Of Human Factor VIII Is Dispensable For In Vitro Procoagulant Activity", Proceedings of the National Academy of Sciences, vol. 83, No. 16, pp. 5939-5942, Aug. 1, 1986.
Torres-Torronteras et al. (2014) "Gene Therapy Using a Liver-targeted AAV Vector Restores Nucleoside and Nucleotide Homeostasis in a Murine Model of MNGIE," Molecular Therapy, 22(5):901-907.
Vehar et al., "Structure of Human Factor VIII", Nature, Nov. 22, 1984; 312(5992): 337-342.
Wagner, et al. (Oct. 1, 1981) "Microinjection of a Rabbit Beta-Globin Gene into Zygotes and Its Subsequent Expression in Adult Mice and Their Offspring", Proceedings of the National Academy of Sciences of the United States of America, vol. 78, No. 10, pp. 6376-6380.
Ward et al., "Codon Optimization of Human Factor VIII cDNAs Leads to High-Level Expression", Blood, Jan. 20, 2011, 117(3): 798-807.
White, G.C. II, et al., "A Multicenter Study of Recombinant Factor VIII (Recombinate(TM)) in Previously Treated Patients with Hemophilia A," Thrombosis and Haemostasis 77(4):660-667, F.K. Schattauer Verlagsgesellschaft mbH, Germany (1997).
Wigler, et al., "Biochemical Transfer of Single-Copy Eucaryotic Genes using Total Cellular DNA as Donor", Cell, vol. 14, No. 3, pp. 725-731. (Jul. 1978).
Wu et al. (2000) "Mutational Analysis of the Adeno-Associated Virus Type 2 (AAV2) Capsid Gene and Construction of AAV2 Vectors with Altered Tropism," Journal of Virology, 74(18):8635-8647.
Zhang et al., "An EpCAM/CD3 bispecific antibody efficiently eliminates hepatocellular carcinoma cells with limited galectin-1 expression", Cancer Immunology, Immunotherapy, 2014, 63(2): 121-132.
Extended European Search Report for European Patent Application No. 23165147.2, mailed Sep. 15, 2023.
GE Healthcare Life Sciences Size Exclusion Chromatography Principles and Methods, 2014.
Gelderblom et al., Medical Microbiology 4: Chapter 41 Structure and Classification of Viruses, 1996.
Human Proteome Project, (Human Proteome Organization), retrieved from url: <https://hupo.org/hpp-progress-to-date>, Accessed Oct. 25, 2023.
Koza et al., "Exclusion Chromatography for the Impurity Analysis of Adeno-Associated Virus Serotypes," The Application Notebook, Jun. 1, 2020, 38: 367-368.

(56) References Cited

OTHER PUBLICATIONS

Mazurkiewicz-Pisarek et al., "The factor VIII protein and its function," Acta Biochemica Polonica, 2016, 63: 11-16.

Shestapol et al., "Expression and characterization of a codon-optimized blood coagulation factor VIII," Journal of Thrombosis and Haemostasis, 2017, 15: 709-720.

Yamada et al., "Lentivirus Vector Purification Using Anion Exchange HPLC Leads to Improved Gene Transfer," BioTechniques, 2003, 34: 1074-1080.

U.S. Appl. No. 18/461,697, filed Sep. 6, 2023, Siyuan Tan, Optimized Factor VIII Gene.

U.S. Appl. No. 18/364,103, filed Aug. 2, 2023, Siyuan Tan, Optimized Factor VIII Genes.

U.S. Appl. No. 17/038,031 2021/0113634, filed Sep. 30, 2020 Apr. 22, 2021, Andrew Kroetsch, Lentiviral Vector Formulations.

U.S. Appl. No. 17/356,980 2020/0033849, filed Jun. 24, 2021 Feb. 3, 2022, Mukesh Mayani, Methods For The Purification Of Viral Vectors.

U.S. Appl. No. 14/767,425 2015/0361158 U.S. Pat. No. 10,370,431, filed Aug. 12, 2015 Dec. 17, 2015 Aug. 6, 2019, Siyuan Tan, Optimized Factor VIII Gene.

U.S. Appl. No. 16/452,010 2020/0024327 U.S. Pat. No. 11,787,951, filed Jun. 25, 2019 Jan. 23, 2020 Oct. 17, 2023, Siyuan Tan, Optimized Factor VIII Gene.

U.S. Appl. No. 18/461,697 2024/0141019, filed Sep. 6, 2023 May 2, 2024, Siyuan Tan, Optimized Factor VIII Gene.

U.S. Appl. No. 15/323,302 2017/0260516 U.S. Pat. No. 11,008,561, filed Dec. 30, 2016 Sep. 14, 2017 May 18, 2021, Siyuan Tan, Optimized Factor IX Gene.

U.S. Appl. No. 17/060,759 2021/0115425, filed Oct. 1, 2020 Apr. 22, 2021, Siyuan Tan, Optimized Factor IX Gene.

U.S. Appl. No. 16/074,729 2019/0185543 U.S. Pat. No. 11,753,461, filed Aug. 1, 2018 Jun. 20, 2019 Sep. 12, 2023, Siyuan Tan, Optimized Factor VIII Genes.

U.S. Appl. No. 18/364,103 2024/0124555, filed Aug. 2, 2023 Apr. 18, 2024, Siyuan Tan, Optimized Factor VIII Genes.

U.S. Appl. No. 16/965,895 2021/0038744, filed Jul. 29, 2020 Feb. 11, 2021, Andrea Annoni, Use Of Lentiviral Vectors Expressing Factor VIII.

U.S. Appl. No. 16/704,400 2020/0199626, filed Dec. 5, 2019 Jun. 25, 2020, Tongyao Liu, Use of Lentiviral Vectors Expressing Factor IX.

U.S. Appl. No. 17/038,031 2021/0113634, filed Sep. 30, 2020 Apr. 22, 2021, Andrew Kroetsch, Lentivieral Vector Formulations.

U.S. Appl. No. 17/356,980 2022/0033849, filed Jun. 24, 2021 Feb. 3, 2022, Mukesh Mayani, Methods For The Purification Of Viral Vectors.

CYTIVA, "HisTrap excel", Apr. 1, 2024, Retrieved from: <https://www.cytivalifesciences.com/en/us/shop/chromatography/prepacked-columns/affinity-tagged-protein/ histrap-excel-p-00310>.

CYTIVA, "VIIISelect Affinity Chromatography", 2020.

KIM et al., "Removal and Inactivation of Viruses during Manufacture of a High Purity Antihemophilic Factor VIII Concentrate from Human Plasma", J Microbiol Biotechnol., Jun. 28, 2001, 11(3): 497-503.

Kutner et al., "Simplified production and concentration of HIV-1-based lentiviral vectors using HYPERFlask vessels and anion exchange membrane chromatography", BMC Biotechnology Feb. 16, 2009, 9(10): 1-7.

Omar et al., "Mice Lacking γδ T Cells Exhibit Impaired Clearance ofPseudomonas aeruginosa Lung Infection and ExcessiveProduction of Inflammatory Cytokines", Infection and Immunity, Jun. 2020, 88(6): e00171-20.

Weigel et al., "A flow-through chromatography process for influenza A and B virus purification", Journal of Virological Methods, Jul. 1, 2014, 207: 45-53.

Höfig et al., "Abstract 4144: Improvement of tumor cell transduction with lentiviral vectors using chemical and cell targeting approaches", Cancer Res, Apr. 15, 2013, 73(8_Supplement): 4144.

Masiuk et al., "PGE2 and Poloxamer Synperonic F108 Enhance Transduction of Human HSPCs with a β-Globin Lentiviral Vector", Mol Ther Methods Clin Dev., Apr. 4, 2019, 4(13): 390-398, Epublished Jun. 14, 2019.

\* cited by examiner

SEQUENCE LISTING

<160> NUMBER OF SEQ ID NOS: 63

<210> SEQ ID NO 1

<211> LENGTH: 4371
<212> TYPE: DNA
<213> ORGANISM: Artificial Sequence
<220> FEATURE:
<223> OTHER INFORMATION: Synthetic polynucleotide sequence

<400> SEQUENCE: 1

| | | | | | |
|---|---|---|---|---|---|
| atgcagattg | agctgtccac | ttgtttcttc | ctgtgcctcc | tgcgcttctg | tttctccgcc | 60 |
| actcgccggt | actaccttgg | agccgtggag | ctttcatggg | actacatgca | gagcgacctg | 120 |
| ggcgaactcc | ccgtggatgc | cagattcccc | ccccgcgtgc | caaagtcctt | cccctttaac | 180 |
| acctccgtgg | tgtacaagaa | aaccctcttt | gtcgagttca | ctgaccacct | gttcaacatc | 240 |
| gccaagccgc | gcccaccttg | gatgggcctc | ctgggaccga | ccattcaagc | tgaagtgtac | 300 |
| gacaccgtgg | tgatcaccct | gaagaacatg | gcgtcccacc | ccgtgtccct | gcatgcggtc | 360 |
| ggagtgtcct | actggaaggc | ctccgaagga | gctgagtacg | acgaccagac | tagccagcgg | 420 |
| gaaaaggagg | acgataaagt | gttcccgggc | ggctcgcata | cttacgtgtg | gcaagtcctg | 480 |
| aaggaaaacg | gacctatggc | atccgatcct | ctgtgcctga | cttactccta | cctttcccat | 540 |
| gtggacctcg | tgaaggacct | gaacagcggg | ctgattggtg | cacttctcgt | gtgccgcgaa | 600 |
| ggttcgctcg | ctaaggaaaa | gacccagacc | ctccataagt | tcatccttt | gttcgctgtg | 660 |
| ttcgatgaag | gaaagtcatg | gcattccgaa | actaagaact | cgctgatgca | ggaccgggat | 720 |
| gccgcctcag | cccgcgcctg | gcctaaaatg | catacagtca | acggatacgt | gaatcggtca | 780 |
| ctgcccgggc | tcatcggttg | tcacagaaag | tccgtgtact | ggcacgtcat | cggcatgggc | 840 |
| actacgcctg | aagtgcactc | catcttcctg | gaagggcaca | ccttcctcgt | gcgcaaccac | 900 |
| cgccaggcct | ctctggaaat | ctccccgatt | acctttctga | ccgcccagac | tctgctcatg | 960 |
| gacctggggc | agttccttct | cttctgccac | atctccagcc | atcagcacga | cggaatggag | 1020 |
| gcctacgtga | aggtggactc | atgcccggaa | gaacctcagt | tgcggatgaa | gaacaacgag | 1080 |
| gaggccgagg | actatgacga | cgatttgact | gactccgaga | tggacgtcgt | gcggttcgat | 1140 |
| gacgacaaca | gccccagctt | catccagatt | cgcagcgtgg | ccaagaagca | ccccaaaacc | 1200 |
| tgggtgcact | acatcgcggc | cgaggaagaa | gattgggact | acgccccgtt | ggtgctggca | 1260 |
| cccgatgacc | ggtcgtacaa | gtcccagtat | ctgaacaatg | gtccgcagcg | gattggcaga | 1320 |
| aagtacaaga | aagtgcggtt | catggcgtac | actgacgaaa | cgtttaagac | ccgggaggcc | 1380 |
| attcaacatg | agagcggcat | tctgggacca | ctgctgtacg | agaggtcgg | cgataccctg | 1440 |
| ctcatcatct | tcaaaaacca | ggcctcccgg | ccttacaaca | tctaccctca | cggaatcacc | 1500 |
| gacgtgcggc | cactctactc | gcggcgcctg | ccgaagggcg | tcaagcacct | gaaagacttc | 1560 |
| cctatcctgc | cgggcgaaat | cttcaagtat | aagtggaccg | tcaccgtgga | ggacgggccc | 1620 |
| accaagagcg | atcctaggtg | tctgactcgg | tactactcca | gcttcgtgaa | catggaacgg | 1680 |
| gacctggcat | cgggactcat | tggaccgctg | ctgatctgct | acaaagagtc | ggtggatcaa | 1740 |
| cgcggcaacc | agatcatgtc | cgacaagcgc | aacgtgatcc | tgttctccgt | gtttgatgaa | 1800 |
| aacagatcct | ggtacctcac | tgaaaacatc | cagaggttcc | tcccaaaccc | cgcaggagtg | 1860 |
| caactggagg | accctgagtt | tcaggcctcg | aatatcatgc | actcgattaa | cggttacgtg | 1920 |
| ttcgactcgc | tgcagctgag | cgtgtgcctc | catgaagtcg | cttactggta | cattctgtcc | 1980 |
| atcggcgccc | agactgactt | cctgagcgtg | ttcttttccg | gttacacctt | taagcacaag | 2040 |
| atggtgtacg | aagatacct | gaccctgttc | cctttctccg | gcgaaacggt | gttcatgtcg | 2100 |
| atggagaacc | cgggtctgtg | gattctggga | tgccacaaca | gcgactttcg | gaaccgcgga | 2160 |

```
atgactgccc tgctgaaggt gtcctcatgc gacaagaaca ccggagacta ctacgaggac    2220
tcctacgagg atatctcagc ctacctcctg tccaagaaca acgcgatcga gccgcgcagc    2280
ttcagccaga acccgcctgt gctgaagagg caccagcgag aaattacccg gaccaccctc    2340
caatcggatc aggaggaaat cgactacgac gacaccatct cggtggaaat gaagaaggaa    2400
gatttcgata tctacgacga ggacgaaaat cagtcccctc gctcattcca aaagaaaact    2460
agacactact ttatcgccgc ggtggaaaga ctgtgggact atggaatgtc atccagccct    2520
cacgtccttc ggaaccgggc ccagagcgga tcggtgcctc agttcaagaa agtggtgttc    2580
caggagttca ccgacggcag cttcacccag ccgctgtacc gggagaact gaacgaacac    2640 ctgggcctgc tcggtcccta catccgcgcg gaagtggagg ataacatcat ggtgaccttc    2700
cgtaaccaag catccagacc ttactccttc tattcctccc tgatctcata cgaggaggac    2760
cagcgccaag gcgccgagcc ccgcaagaac ttcgtcaagc ccaacgagac taagacctac    2820
ttctggaagg tccaacacca tatggccccg accaaggatg agtttgactg caaggcctgg    2880
gcctacttct ccgacgtgga ccttgagaag gatgtccatt ccggcctgat cgggccgctg    2940
ctcgtgtgtc acaccaacac cctgaaccca gcgcatggac gccaggtcac cgtccaggag    3000
tttgctctgt tcttcaccat ttttgacgaa actaagtcct ggtacttcac cgagaatatg    3060
gagcgaaact gtagagcgcc ctgcaatatc cagatggaag atccgacttt caaggagaac    3120
tatagattcc acgccatcaa cgggtacatc atggatactc tgccggggct ggtcatggcc    3180
caggatcaga ggattcggtg gtacttgctg tcaatgggat cgaacgaaaa cattcactcc    3240
attcacttct ccggtcacgt gttcactgtg cgcaagaagg aggagtacaa gatggcgctg    3300
tacaatctgt accccggggt gttcgaaact gtggagatgc tgccgtccaa ggccggcatc    3360
tggagagtgg agtgcctgat cggagagcac ctccacgcgg ggatgtccac cctcttcctg    3420
gtgtactcga ataagtgcca gaccccgctg ggcatggcct cgggccacat cagagacttc    3480
cagatcacag caagcggaca atacggccaa tgggcgccga agctggcccg cttgcactac    3540
tccggatcga tcaacgcatg gtccaccaag gaaccgttct cgtggattaa ggtgacctc    3600 ctggccccta tgattatcca cggaattaag acccagggcg ccaggcagaa gttctcctcc    3660
ctgtacatct cgcaattcat catcatgtac agcctggacg ggaagaagtg gcagacttac    3720
aggggaaact ccaccggcac cctgatggtc ttttcggca acgtggattc ctccggcatt    3780
aagcacaaca tcttcaaccc accgatcata gccagatata ttaggctcca ccccactcac    3840
tactcaatcc gctcaactct tcggatggaa ctcatggggt gcgacctgaa ctcctgctcc    3900
atgccgttgg ggatggaatc aaaggctatt agcgacgccc agatcaccgc gagctcctac    3960
ttcactaaca tgttcgccac ctggagcccc tccaaggcca ggctgcactt gcagggacgg    4020
tcaaatgcct ggcggccgca agtgaacaat ccgaaggaat ggcttcaagt ggatttccaa    4080
aagaccatga agtgaccgg agtcaccacc caggagtga agtcccttct gacctcgatg    4140
tatgtgaagg agttcctgat tagcagcagc caggacgggc accagtggac cctgttcttc    4200
caaaacggaa aggtcaaggt gttccagggg aaccaggact cgttcacacc cgtggtgaac    4260
tccctggacc ccccactgct gacgcggtac ttgaggattc atcctcagtc ctgggtccat    4320
cagattgcat tgcgaatgga agtcctgggc tgcgaggccc aggacctgta c           4371
```

<210> SEQ ID NO 2
<211> LENGTH: 4812
<212> TYPE: DNA

<213> ORGANISM: Artificial Sequence
<220> FEATURE:
<223> OTHER INFORMATION: Synthetic polynucleotide sequence

<400> SEQUENCE: 2

| | |
|---|---:|
| atgcagattg agctgtccac ttgtttcttc ctgtgcctcc tgcgcttctg tttctccgcc | 60 |
| actcgccggt actaccttgg agccgtggag ctttcatggg actacatgca gagcgacctg | 120 |
| ggcgaactcc ccgtggatgc cagattcccc cccgcgtgc caaagtcctt cccctttaac | 180 |
| acctccgtgg tgtacaagaa aaccctcttt gtcgagttca ctgaccacct gttcaacatc | 240 |
| gccaagccgc gcccaccttg gatgggcctc ctgggaccga ccattcaagc tgaagtgtac | 300 |
| gacaccgtgg tgatcaccct gaagaacatg gcgtcccacc ccgtgtccct gcatgcggtc | 360 |
| ggagtgtcct actggaaggc ctccgaagga gctgagtacg acgaccagac tagccagcgg | 420 |
| gaaaaggagg acgataaagt gttcccgggc ggctcgcata cttacgtgtg caagtcctg | 480 |
| aaggaaaacg gacctatggc atccgatcct ctgtgcctga cttactccta cctttcccat | 540 |
| gtggacctcg tgaaggacct gaacagcggg ctgattggtg cacttctcgt gtgccgcgaa | 600 |
| ggttcgctcg ctaaggaaaa gacccagacc ctccataagt tcatccttt gttcgctgtg | 660 |
| ttcgatgaag aaagtcatg gcattccgaa actaagaact cgctgatgca ggaccgggat | 720 |
| gccgcctcag cccgcgcctg gcctaaaatg catacagtca acggatacgt gaatcggtca | 780 |
| ctgcccgggc tcatcggttg tcacagaaag tccgtgtact ggcacgtcat cggcatgggc | 840 |
| actacgcctg aagtgcactc catcttcctg gaagggcaca ccttcctcgt gcgcaaccac | 900 |
| cgccaggcct ctctggaaat ctccccgatt accttctga ccgcccagac tctgctcatg | 960 |
| gacctggggc agttccttct cttctgccac atctccagcc atcagcacga cggaatggag | 1020 |
| gcctacgtga aggtggactc atgcccggaa gaacctcagt gcggatgaa gaacaacgag | 1080 |
| gaggccgagg actatgacga cgatttgact gactccgaga tggacgtcgt gcggttcgat | 1140 |
| gacgacaaca gccccagctt catccagatt cgcagcgtgg ccaagaagca ccccaaaacc | 1200 |
| tgggtgcact acatcgcggc cgaggaagaa gattgggact acgcccgtt ggtgctggca | 1260 |
| cccgatgacc ggtcgtacaa gtcccagtat ctgaacaatg tccgcagcg gattggcaga | 1320 |
| aagtacaaga aagtgcggtt catggcgtac actgacgaaa cgtttaagac ccgggaggcc | 1380 |
| attcaacatg agagcggcat tctgggacca ctgctgtacg agaggtcgg cgataccctg | 1440 |
| ctcatcatct tcaaaaacca ggcctcccgg ccttacaaca tctaccctca cggaatcacc | 1500 |
| gacgtgcggc cactctactc gcggcgcctg ccgaagggcg tcaagcacct gaaagacttc | 1560 |
| cctatcctgc cgggcgaaat cttcaagtat aagtggaccg tcaccgtgga ggacgggccc | 1620 |
| accaagagcg atcctaggtg tctgactcgg tactactcca gcttcgtgaa catgaacgg | 1680 |
| gacctggcat cgggactcat tggaccgctg ctgatctgct acaaagagtc ggtggatcaa | 1740 |
| cgcggcaacc agatcatgtc cgacaagcgc aacgtgatcc tgttctccgt gtttgatgaa | 1800 |
| aacagatcct ggtacctcac tgaaaacatc cagaggttcc tcccaaaccc cgcaggagtg | 1860 |
| caactggagg accctgagtt tcaggcctcg aatatcatgc actcgattaa cggttacgtg | 1920 |
| ttcgactcgc tgcagctgag cgtgtgcctc catgaagtcg cttactggta cattctgtcc | 1980 |
| atcggcgccc agactgactt cctgagcgtg ttcttttccg gttacacctt taagcacaag | 2040 |
| atggtgtacg aagatccct gaccctgttc cctttctccg gcgaaacggt gttcatgtcg | 2100 |
| atggagaacc cgggtctgtg gattctggga tgccacaaca gcgactttcg gaaccgcgga | 2160 |
| atgactgccc tgctgaaggt gtcctcatgc gacaagaaca ccggagacta ctacgaggac | 2220 |

```
tcctacgagg atatctcagc ctacctcctg tccaagaaca acgcgatcga gccgcgcagc   2280
ttcagccaga acacatcaga gagcgccacc cctgaaagtg gtcccgggag cgagccagcc   2340
acatctgggt cggaaacgcc aggcacaagt gagtctgcaa ctcccgagtc cggacctggc   2400
tccgagcctg ccactagcgg ctccgagact ccgggaactt ccgagagcgc tacaccagaa   2460
agcggacccg gaaccagtac cgaacctagc gagggctctg ctccgggcag cccagccggc   2520
tctcctacat ccacggagga gggcacttcc gaatccgcca ccccgagtc agggccagga   2580 tctgaacccg ctacctcagg cagtgagacg ccaggaacga gcgagtccgc tacaccggag   2640
agtgggccag ggagccctgc tggatctcct acgtccactg aggaagggtc accagcgggc   2700
tcgcccacca gcactgaaga aggtgcctcg agcccgcctg tgctgaagag gcaccagcga   2760
gaaattaccc ggaccaccct ccaatcggat caggaggaaa tcgactacga cgacaccatc   2820
tcggtggaaa tgaagaagga agatttcgat atctacgacg aggacgaaaa tcagtcccct   2880
cgctcattcc aaaagaaaac tagacactac tttatcgccg cggtggaaag actgtgggac   2940
tatggaatgt catccagccc tcacgtcctt cggaaccggg cccagagcgg atcggtgcct   3000
cagttcaaga aagtggtgtt ccaggagttc accgacggca gcttcaccca gccgctgtac   3060
cggggagaac tgaacgaaca cctgggcctg ctcggtccct acatccgcgc ggaagtggag   3120
gataacatca tggtgacctt ccgtaaccaa gcatccagac cttactcctt ctattcctcc   3180
ctgatctcat acgaggagga ccagcgccaa ggcgccgagc cccgcaagaa cttcgtcaag   3240
cccaacgaga ctaagaccta cttctggaag gtccaacacc atatggcccc gaccaaggat   3300
gagtttgact gcaaggcctg ggcctacttc tccgacgtgg accttgagaa ggatgtccat   3360
tccggcctga tcgggccgct gctcgtgtgt cacaccaaca ccctgaaccc agcgcatgga   3420
cgccaggtca ccgtccagga gtttgctctg ttcttcacca tttttgacga aactaagtcc   3480
tggtacttca ccgagaatat ggagcgaaac tgtagagcgc cctgcaatat ccagatggaa   3540
gatccgactt tcaaggagaa ctatagattc cacgccatca acgggtacat catggatact   3600
ctgccggggc tggtcatggc ccaggatcag aggattcggt ggtacttgct gtcaatggga   3660
tcgaacgaaa acattcactc cattcacttc tccggtcacg tgttcactgt gcgcaagaag   3720
gaggagtaca agatggcgct gtacaatctg taccccgggg tgttcgaaac tgtggagatg   3780
ctgccgtcca aggccggcat ctggagagtg gagtgcctga tcgagagca cctccacgcg   3840 gggatgtcca ccctcttcct ggtgtactcg aataagtgcc agacccccgct gggcatggcc   3900 tcgggccaca tcagagactt ccagatcaca gcaagcggaa aatacggcca atgggcgccg   3960
aagctggccc gcttgcacta ctccggatcg atcaacgcat ggtccaccaa ggaaccgttc   4020
tcgtggatta aggtggacct cctggcccct atgattatcc acggaattaa gacccagggc   4080
gccaggcaga agttctcctc cctgtacatc tcgcaattca tcatcatgta cagcctggac   4140
gggaagaagt ggcagactta caggggaaac tccaccggca ccctgatggt cttttttcggc   4200 aacgtggatt cctccggcat taagcacaac atcttcaacc caccgatcat agccagatat   4260
attaggctcc accccactca ctactcaatc cgctcaactc ttcggatgga actcatgggg   4320
tgcgacctga actcctgctc catgccgttg gggatggaat caaaggctat tagcgacgcc   4380
cagatcaccg cgagctccta cttcactaac atgttcgcca cctggagccc ctccaaggcc   4440
aggctgcact gcagggacg gtcaaatgcc tggcggccgc aagtgaacaa tccgaaggaa   4500
tggcttcaag tggatttcca aaagaccatg aaagtgaccg gagtcaccac ccagggagtg   4560
```

```
aagtcccttc tgacctcgat gtatgtgaag gagttcctga ttagcagcag ccaggacggg    4620
caccagtgga ccctgttctt ccaaaacgga aaggtcaagg tgttccaggg gaaccaggac    4680
tcgttcacac ccgtggtgaa ctccctggac cccccactgc tgacgcggta cttgaggatt    4740
catcctcagt cctgggtcca tcagattgca ttgcgaatgg aagtcctggg ctgcgaggcc    4800
caggacctgt ac                                                        4812

<210> SEQ ID NO 3
<211> LENGTH: 1383
<212> TYPE: DNA
<213> ORGANISM: Artificial Sequence
<220> FEATURE:
<223> OTHER INFORMATION: Synthetic polynucleotide sequence

<400> SEQUENCE: 3
atgcagagag tcaacatgat tatggctgag tcacctgggc tgattactat ttgcctgctg      60
ggctacctgc tgtccgccga gtgtaccgtg ttcctggacc atgagaacgc aaataagatc     120
ctgaacaggc ccaaaagata caatagtggg aagctggagg aatttgtgca gggcaacctg     180
gagagagaat gcatggagga aaagtgtagc ttcgaggaag cccgcgaggt gtttgaaaat     240
acagagcgaa ccacagagtt ctggaagcag tatgtggacg gcgatcagtg cgagagcaac     300
ccctgtctga atggcggaag ttgcaaagac gatatcaact catacgaatg ctggtgtcct     360
ttcgggtttg aaggcaaaaa ttgcgagctg gacgtgacat gtaacattaa gaatggacgg     420
tgcgagcagt tttgtaaaaa ctctgccgat aataaggtgg tgtgcagctg tactgaagga     480
tatcgcctgg ctgagaacca gaagtcctgc gaaccagcag tgccctttcc ttgtgggagg     540
gtgagcgtct cccagacttc aaaactgacc agagcagaga cagtgtttcc cgacgtggat     600
tacgtcaaca gcactgaggc cgaaaccatc ctggacaaca ttactcagtc tacccagagt     660
ttcaatgact ttactcgggt ggtcggggc gaggatgcta aaccaggcca gttcccctgg     720
caggtggtcc tgaacggaaa ggtggatgca ttttgcggag ggtctatcgt gaatgagaaa     780
tggattgtca ccgccgctca ctgcgtggaa accggagtca agatcacagt ggtcgctggg     840
gagcacaaca ttgaggaaac agaacatact gagcagaagc ggaatgtgat ccgcatcatt     900
cctcaccata actacaatgc agccatcaac aaatacaatc atgacattgc cctgctggaa     960
ctggatgagc tctggtgct gaacagctac gtcactccaa tctgcattgc tgacaaagag    1020
tataccaata tcttcctgaa gtttggatca gggtacgtga gcggctgggg aagagtcttc    1080
cacaagggca ggagcgccct ggtgctccag tatctgcgag tgcctctggt cgatcgagct    1140
acctgtctgc tctctaccaa gtttacaatc tacaacaaca tgttctgcgc tgggtttcac    1200
gagggaggac gagactcctg tcaggcgat tctgggggcc acatgtgac agaggtcgaa    1260 ggcaccagct tcctgactgg catcattcc tggggagagg aatgtgcaat gaagggaaaa    1320
tacgggatct acaccaaagt gagccgctat gtgaactgga tcaaggaaaa aaccaaactg    1380
acc                                                                  1383

<210> SEQ ID NO 4
<211> LENGTH: 2332
<212> TYPE: PRT
<213> ORGANISM: Artificial Sequence
<220> FEATURE:
<223> OTHER INFORMATION: Synthetic amino acid sequence

<400> SEQUENCE: 4

Ala Thr Arg Arg Tyr Tyr Leu Gly Ala Val Glu Leu Ser Trp Asp Tyr
```

-continued

```
1               5                   10                  15
Met Gln Ser Asp Leu Gly Glu Leu Pro Val Asp Ala Arg Phe Pro Pro
            20                  25                  30
Arg Val Pro Lys Ser Phe Pro Phe Asn Thr Ser Val Val Tyr Lys Lys
            35                  40                  45
Thr Leu Phe Val Glu Phe Thr Asp His Leu Phe Asn Ile Ala Lys Pro
            50                  55                  60
Arg Pro Pro Trp Met Gly Leu Leu Gly Pro Thr Ile Gln Ala Glu Val
65                  70                  75                  80
Tyr Asp Thr Val Val Ile Thr Leu Lys Asn Met Ala Ser His Pro Val
                    85                  90                  95
Ser Leu His Ala Val Gly Val Ser Tyr Trp Lys Ala Ser Glu Gly Ala
                100                 105                 110
Glu Tyr Asp Asp Gln Thr Ser Gln Arg Glu Lys Glu Asp Asp Lys Val
                115                 120                 125
Phe Pro Gly Gly Ser His Thr Tyr Val Trp Gln Val Leu Lys Glu Asn
            130                 135                 140
Gly Pro Met Ala Ser Asp Pro Leu Cys Leu Thr Tyr Ser Tyr Leu Ser
145                 150                 155                 160
His Val Asp Leu Val Lys Asp Leu Asn Ser Gly Leu Ile Gly Ala Leu
                165                 170                 175
Leu Val Cys Arg Glu Gly Ser Leu Ala Lys Glu Lys Thr Gln Thr Leu
            180                 185                 190
His Lys Phe Ile Leu Leu Phe Ala Val Phe Asp Glu Gly Lys Ser Trp
            195                 200                 205
His Ser Glu Thr Lys Asn Ser Leu Met Gln Asp Arg Asp Ala Ala Ser
            210                 215                 220
Ala Arg Ala Trp Pro Lys Met His Thr Val Asn Gly Tyr Val Asn Arg
225                 230                 235                 240
Ser Leu Pro Gly Leu Ile Gly Cys His Arg Lys Ser Val Tyr Trp His
                    245                 250                 255
Val Ile Gly Met Gly Thr Thr Pro Glu Val His Ser Ile Phe Leu Glu
                260                 265                 270
Gly His Thr Phe Leu Val Arg Asn His Arg Gln Ala Ser Leu Glu Ile
            275                 280                 285
Ser Pro Ile Thr Phe Leu Thr Ala Gln Thr Leu Leu Met Asp Leu Gly
            290                 295                 300
Gln Phe Leu Leu Phe Cys His Ile Ser Ser His Gln His Asp Gly Met
305                 310                 315                 320
Glu Ala Tyr Val Lys Val Asp Ser Cys Pro Glu Glu Pro Gln Leu Arg
                    325                 330                 335
Met Lys Asn Asn Glu Glu Ala Glu Asp Tyr Asp Asp Asp Leu Thr Asp
                340                 345                 350
Ser Glu Met Asp Val Val Arg Phe Asp Asp Asn Ser Pro Ser Phe
            355                 360                 365
Ile Gln Ile Arg Ser Val Ala Lys Lys His Pro Lys Thr Trp Val His
            370                 375                 380
Tyr Ile Ala Ala Glu Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
                    405                 410                 415
Gln Arg Ile Gly Arg Lys Tyr Lys Lys Val Arg Phe Met Ala Tyr Thr
                420                 425                 430
```

```
Asp Glu Thr Phe Lys Thr Arg Glu Ala Ile Gln His Glu Ser Gly Ile
    435                 440                 445
Leu Gly Pro Leu Leu Tyr Gly Val Gly Asp Thr Leu Leu Ile Ile
450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
                485                 490                 495
His Leu Lys Asp Phe Pro Ile Leu Pro Gly Glu Ile Phe Lys Tyr Lys
                500                 505                 510
Trp Thr Val Thr Val Glu Asp Gly Pro Thr Lys Ser Asp Pro Arg Cys
    515                 520                 525
Leu Thr Arg Tyr Tyr Ser Ser Phe Val Asn Met Glu Arg Asp Leu Ala
530                 535                 540
Ser Gly Leu Ile Gly Pro Leu Leu Ile Cys Tyr Lys Glu Ser Val Asp
545                 550                 555                 560
Gln Arg Gly Asn Gln Ile Met Ser Asp Lys Arg Asn Val Ile Leu Phe
                565                 570                 575
Ser Val Phe Asp Glu Asn Arg Ser Trp Tyr Leu Thr Glu Asn Ile Gln
                580                 585                 590
Arg Phe Leu Pro Asn Pro Ala Gly Val Gln Leu Glu Asp Pro Glu Phe
            595                 600                 605
Gln Ala Ser Asn Ile Met His Ser Ile Asn Gly Tyr Val Phe Asp Ser
    610                 615                 620
Leu Gln Leu Ser Val Cys Leu His Glu Val Ala Tyr Trp Tyr Ile Leu
625                 630                 635                 640
Ser Ile Gly Ala Gln Thr Asp Phe Leu Ser Val Phe Phe Ser Gly Tyr
                645                 650                 655
Thr Phe Lys His Lys Met Val Tyr Glu Asp Thr Leu Thr Leu Phe Pro
            660                 665                 670
Phe Ser Gly Glu Thr Val Phe Met Ser Met Glu Asn Pro Gly Leu Trp
    675                 680                 685
Ile Leu Gly Cys His Asn Ser Asp Phe Arg Asn Arg Gly Met Thr Ala
            690                 695                 700
Leu Leu Lys Val Ser Ser Cys Asp Lys Asn Thr Gly Asp Tyr Tyr Glu
705                 710                 715                 720
Asp Ser Tyr Glu Asp Ile Ser Ala Tyr Leu Leu Ser Lys Asn Asn Ala
                725                 730                 735
Ile Glu Pro Arg Ser Phe Ser Gln Asn Ser Arg His Pro Ser Thr Arg
            740                 745                 750
Gln Lys Gln Phe Asn Ala Thr Thr Ile Pro Glu Asn Asp Ile Glu Lys
    755                 760                 765
Thr Asp Pro Trp Phe Ala His Arg Thr Pro Met Pro Lys Ile Gln Asn
770                 775                 780
Val Ser Ser Ser Asp Leu Leu Met Leu Leu Arg Gln Ser Pro Thr Pro
785                 790                 795                 800
His Gly Leu Ser Leu Ser Asp Leu Gln Glu Ala Lys Tyr Glu Thr Phe
                805                 810                 815
Ser Asp Asp Pro Ser Pro Gly Ala Ile Asp Ser Asn Asn Ser Leu Ser
            820                 825                 830
Glu Met Thr His Phe Arg Pro Gln Leu His His Ser Gly Asp Met Val
    835                 840                 845
```

-continued

Phe Thr Pro Glu Ser Gly Leu Gln Leu Arg Leu Asn Glu Lys Leu Gly
850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
            885                 890                 895

Gly Thr Asp Asn Thr Ser Ser Leu Gly Pro Pro Ser Met Pro Val His
                900                 905                 910

Tyr Asp Ser Gln Leu Asp Thr Thr Leu Phe Gly Lys Lys Ser Ser Pro
            915                 920                 925

Leu Thr Glu Ser Gly Gly Pro Leu Ser Leu Ser Glu Glu Asn Asn Asp
    930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
                965                 970                 975

Arg Ala His Gly Pro Ala Leu Leu Thr Lys Asp Asn Ala Leu Phe Lys
            980                 985                 990

Val Ser Ile Ser Leu Leu Lys Thr Asn Lys Thr Ser Asn Asn Ser Ala
            995                 1000                1005

Thr Asn Arg Lys Thr His Ile Asp Gly Pro Ser Leu Leu Ile Glu
    1010                1015                1020

Asn Ser Pro Ser Val Trp Gln Asn Ile Leu Glu Ser Asp Thr Glu
    1025                1030                1035

Phe Lys Lys Val Thr Pro Leu Ile His Asp Arg Met Leu Met Asp
    1040                1045                1050

Lys Asn Ala Thr Ala Leu Arg Leu Asn His Met Ser Asn Lys Thr
    1055                1060                1065

Thr Ser Ser Lys Asn Met Glu Met Val Gln Gln Lys Lys Glu Gly
    1070                1075                1080

Pro Ile Pro Pro Asp Ala Gln Asn Pro Asp Met Ser Phe Phe Lys
    1085                1090                1095

Met Leu Phe Leu Pro Glu Ser Ala Arg Trp Ile Gln Arg Thr His
    1100                1105                1110

Gly Lys Asn Ser Leu Asn Ser Gly Gln Gly Pro Ser Pro Lys Gln
    1115                1120                1125

Leu Val Ser Leu Gly Pro Glu Lys Ser Val Glu Gly Gln Asn Phe
    1130                1135                1140

Leu Ser Glu Lys Asn Lys Val Val Val Gly Lys Gly Glu Phe Thr
    1145                1150                1155

Lys Asp Val Gly Leu Lys Glu Met Val Phe Pro Ser Ser Arg Asn
    1160                1165                1170

Leu Phe Leu Thr Asn Leu Asp Asn Leu His Glu Asn Asn Thr His
    1175                1180                1185

Asn Gln Glu Lys Lys Ile Gln Glu Glu Ile Glu Lys Lys Glu Thr
    1190                1195                1200

Leu Ile Gln Glu Asn Val Val Leu Pro Gln Ile His Thr Val Thr
    1205                1210                1215

Gly Thr Lys Asn Phe Met Lys Asn Leu Phe Leu Leu Ser Thr Arg
    1220                1225                1230

Gln Asn Val Glu Gly Ser Tyr Asp Gly Ala Tyr Ala Pro Val Leu
    1235                1240                1245

Gln Asp Phe Arg Ser Leu Asn Asp Ser Thr Asn Arg Thr Lys Lys

-continued

```
            1250                1255                1260

His Thr Ala His Phe Ser Lys Lys Gly Glu Glu Asn Leu Glu
    1265                1270                1275

Gly Leu Gly Asn Gln Thr Lys Gln Ile Val Glu Lys Tyr Ala Cys
    1280                1285                1290

Thr Thr Arg Ile Ser Pro Asn Thr Ser Gln Gln Asn Phe Val Thr
    1295                1300                1305

Gln Arg Ser Lys Arg Ala Leu Lys Gln Phe Arg Leu Pro Leu Glu
    1310                1315                1320

Glu Thr Glu Leu Glu Lys Arg Ile Ile Val Asp Asp Thr Ser Thr
    1325                1330                1335

Gln Trp Ser Lys Asn Met Lys His Leu Thr Pro Ser Thr Leu Thr
    1340                1345                1350

Gln Ile Asp Tyr Asn Glu Lys Glu Lys Gly Ala Ile Thr Gln Ser
    1355                1360                1365

Pro Leu Ser Asp Cys Leu Thr Arg Ser His Ser Ile Pro Gln Ala
    1370                1375                1380

Asn Arg Ser Pro Leu Pro Ile Ala Lys Val Ser Ser Phe Pro Ser
    1385                1390                1395

Ile Arg Pro Ile Tyr Leu Thr Arg Val Leu Phe Gln Asp Asn Ser
    1400                1405                1410

Ser His Leu Pro Ala Ala Ser Tyr Arg Lys Lys Asp Ser Gly Val
    1415                1420                1425

Gln Glu Ser Ser His Phe Leu Gln Gly Ala Lys Lys Asn Asn Leu
    1430                1435                1440

Ser Leu Ala Ile Leu Thr Leu Glu Met Thr Gly Asp Gln Arg Glu
    1445                1450                1455

Val Gly Ser Leu Gly Thr Ser Ala Thr Asn Ser Val Thr Tyr Lys
    1460                1465                1470

Lys Val Glu Asn Thr Val Leu Pro Lys Pro Asp Leu Pro Lys Thr
    1475                1480                1485

Ser Gly Lys Val Glu Leu Leu Pro Lys Val His Ile Tyr Gln Lys
    1490                1495                1500

Asp Leu Phe Pro Thr Glu Thr Ser Asn Gly Ser Pro Gly His Leu
    1505                1510                1515

Asp Leu Val Glu Gly Ser Leu Leu Gln Gly Thr Glu Gly Ala Ile
    1520                1525                1530

Lys Trp Asn Glu Ala Asn Arg Pro Gly Lys Val Pro Phe Leu Arg
    1535                1540                1545

Val Ala Thr Glu Ser Ser Ala Lys Thr Pro Ser Lys Leu Leu Asp
    1550                1555                1560

Pro Leu Ala Trp Asp Asn His Tyr Gly Thr Gln Ile Pro Lys Glu
    1565                1570                1575

Glu Trp Lys Ser Gln Glu Lys Ser Pro Glu Lys Thr Ala Phe Lys
    1580                1585                1590

Lys Lys Asp Thr Ile Leu Ser Leu Asn Ala Cys Glu Ser Asn His
    1595                1600                1605

Ala Ile Ala Ala Ile Asn Glu Gly Gln Asn Lys Pro Glu Ile Glu
    1610                1615                1620

Val Thr Trp Ala Lys Gln Gly Arg Thr Glu Arg Leu Cys Ser Gln
    1625                1630                1635

Asn Pro Pro Val Leu Lys Arg His Gln Arg Glu Ile Thr Arg Thr
    1640                1645                1650
```

```
Thr Leu Gln Ser Asp Gln Glu Ile Asp Tyr Asp Asp Thr Ile
1655                1660                1665

Ser Val Glu Met Lys Lys Glu Asp Phe Asp Ile Tyr Asp Glu Asp
    1670                1675                1680

Glu Asn Gln Ser Pro Arg Ser Phe Gln Lys Lys Thr Arg His Tyr
1685                1690                1695

Phe Ile Ala Ala Val Glu Arg Leu Trp Asp Tyr Gly Met Ser Ser
1700                1705                1710

Ser Pro His Val Leu Arg Asn Arg Ala Gln Ser Gly Ser Val Pro
    1715                1720                1725

Gln Phe Lys Lys Val Val Phe Gln Glu Phe Thr Asp Gly Ser Phe
1730                1735                1740

Thr Gln Pro Leu Tyr Arg Gly Glu Leu Asn Glu His Leu Gly Leu
    1745                1750                1755

Leu Gly Pro Tyr Ile Arg Ala Glu Val Glu Asp Asn Ile Met Val
1760                1765                1770

Thr Phe Arg Asn Gln Ala Ser Arg Pro Tyr Ser Phe Tyr Ser Ser
    1775                1780                1785

Leu Ile Ser Tyr Glu Glu Asp Gln Arg Gln Gly Ala Glu Pro Arg
1790                1795                1800

Lys Asn Phe Val Lys Pro Asn Glu Thr Lys Thr Tyr Phe Trp Lys
    1805                1810                1815

Val Gln His His Met Ala Pro Thr Lys Asp Glu Phe Asp Cys Lys
1820                1825                1830

Ala Trp Ala Tyr Phe Ser Asp Val Asp Leu Glu Lys Asp Val His
    1835                1840                1845

Ser Gly Leu Ile Gly Pro Leu Leu Val Cys His Thr Asn Thr Leu
1850                1855                1860

Asn Pro Ala His Gly Arg Gln Val Thr Val Gln Glu Phe Ala Leu
    1865                1870                1875

Phe Phe Thr Ile Phe Asp Glu Thr Lys Ser Trp Tyr Phe Thr Glu
1880                1885                1890

Asn Met Glu Arg Asn Cys Arg Ala Pro Cys Asn Ile Gln Met Glu
    1895                1900                1905

Asp Pro Thr Phe Lys Glu Asn Tyr Arg Phe His Ala Ile Asn Gly
1910                1915                1920

Tyr Ile Met Asp Thr Leu Pro Gly Leu Val Met Ala Gln Asp Gln
    1925                1930                1935

Arg Ile Arg Trp Tyr Leu Leu Ser Met Gly Ser Asn Glu Asn Ile
1940                1945                1950

His Ser Ile His Phe Ser Gly His Val Phe Thr Val Arg Lys Lys
    1955                1960                1965

Glu Glu Tyr Lys Met Ala Leu Tyr Asn Leu Tyr Pro Gly Val Phe
1970                1975                1980

Glu Thr Val Glu Met Leu Pro Ser Lys Ala Gly Ile Trp Arg Val
    1985                1990                1995

Glu Cys Leu Ile Gly Glu His Leu His Ala Gly Met Ser Thr Leu
2000                2005                2010

Phe Leu Val Tyr Ser Asn Lys Cys Gln Thr Pro Leu Gly Met Ala
    2015                2020                2025

Ser Gly His Ile Arg Asp Phe Gln Ile Thr Ala Ser Gly Gln Tyr
2030                2035                2040
```

-continued

```
Gly Gln Trp Ala Pro Lys Leu Ala Arg Leu His Tyr Ser Gly Ser
    2045                2050                2055

Ile Asn Ala Trp Ser Thr Lys Glu Pro Phe Ser Trp Ile Lys Val
    2060                2065                2070

Asp Leu Leu Ala Pro Met Ile Ile His Gly Ile Lys Thr Gln Gly
    2075                2080                2085

Ala Arg Gln Lys Phe Ser Ser Leu Tyr Ile Ser Gln Phe Ile Ile
    2090                2095                2100

Met Tyr Ser Leu Asp Gly Lys Lys Trp Gln Thr Tyr Arg Gly Asn
    2105                2110                2115

Ser Thr Gly Thr Leu Met Val Phe Phe Gly Asn Val Asp Ser Ser
    2120                2125                2130

Gly Ile Lys His Asn Ile Phe Asn Pro Pro Ile Ile Ala Arg Tyr
    2135                2140                2145

Ile Arg Leu His Pro Thr His Tyr Ser Ile Arg Ser Thr Leu Arg
    2150                2155                2160

Met Glu Leu Met Gly Cys Asp Leu Asn Ser Cys Ser Met Pro Leu
    2165                2170                2175

Gly Met Glu Ser Lys Ala Ile Ser Asp Ala Gln Ile Thr Ala Ser
    2180                2185                2190

Ser Tyr Phe Thr Asn Met Phe Ala Thr Trp Ser Pro Ser Lys Ala
    2195                2200                2205

Arg Leu His Leu Gln Gly Arg Ser Asn Ala Trp Arg Pro Gln Val
    2210                2215                2220

Asn Asn Pro Lys Glu Trp Leu Gln Val Asp Phe Gln Lys Thr Met
    2225                2230                2235

Lys Val Thr Gly Val Thr Thr Gln Gly Val Lys Ser Leu Leu Thr
    2240                2245                2250

Ser Met Tyr Val Lys Glu Phe Leu Ile Ser Ser Ser Gln Asp Gly
    2255                2260                2265

His Gln Trp Thr Leu Phe Phe Gln Asn Gly Lys Val Lys Val Phe
    2270                2275                2280

Gln Gly Asn Gln Asp Ser Phe Thr Pro Val Val Asn Ser Leu Asp
    2285                2290                2295

Pro Pro Leu Leu Thr Arg Tyr Leu Arg Ile His Pro Gln Ser Trp
    2300                2305                2310

Val His Gln Ile Ala Leu Arg Met Glu Val Leu Gly Cys Glu Ala
    2315                2320                2325

Gln Asp Leu Tyr
    2330
```

<210> SEQ ID NO 5
<211> LENGTH: 1604
<212> TYPE: PRT
<213> ORGANISM: Artificial Sequence
<220> FEATURE:
<223> OTHER INFORMATION: Synthetic amino acid sequence

<400> SEQUENCE: 5

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45
```

```
Phe Pro Pro Arg Val Pro Lys Ser Phe Pro Phe Asn Thr Ser Val Val
 50                  55                  60
Tyr Lys Lys Thr Leu Phe Val Glu Phe Thr Asp His Leu Phe Asn Ile
 65                  70                  75                  80
Ala Lys Pro Arg Pro Pro Trp Met Gly Leu Leu Gly Pro Thr Ile Gln
                 85                  90                  95
Ala Glu Val Tyr Asp Thr Val Val Ile Thr Leu Lys Asn Met Ala Ser
                100                 105                 110
His Pro Val Ser Leu His Ala Val Gly Val Ser Tyr Trp Lys Ala Ser
                115                 120                 125
Glu Gly Ala Glu Tyr Asp Asp Gln Thr Ser Gln Arg Glu Lys Glu Asp
130                 135                 140
Asp Lys Val Phe Pro Gly Gly Ser His Thr Tyr Val Trp Gln Val Leu
145                 150                 155                 160
Lys Glu Asn Gly Pro Met Ala Ser Asp Pro Leu Cys Leu Thr Tyr Ser
                165                 170                 175
Tyr Leu Ser His Val Asp Leu Val Lys Asp Leu Asn Ser Gly Leu Ile
                180                 185                 190
Gly Ala Leu Leu Val Cys Arg Glu Gly Ser Leu Ala Lys Glu Lys Thr
                195                 200                 205
Gln Thr Leu His Lys Phe Ile Leu Leu Phe Ala Val Phe Asp Glu Gly
                210                 215                 220
Lys Ser Trp His Ser Glu Thr Lys Asn Ser Leu Met Gln Asp Arg Asp
225                 230                 235                 240
Ala Ala Ser Ala Arg Ala Trp Pro Lys Met His Thr Val Asn Gly Tyr
                245                 250                 255
Val Asn Arg Ser Leu Pro Gly Leu Ile Gly Cys His Arg Lys Ser Val
                260                 265                 270
Tyr Trp His Val Ile Gly Met Gly Thr Thr Pro Glu Val His Ser Ile
                275                 280                 285
Phe Leu Glu Gly His Thr Phe Leu Val Arg Asn His Arg Gln Ala Ser
                290                 295                 300
Leu Glu Ile Ser Pro Ile Thr Phe Leu Thr Ala Gln Thr Leu Leu Met
305                 310                 315                 320
Asp Leu Gly Gln Phe Leu Leu Phe Cys His Ile Ser Ser His Gln His
                325                 330                 335
Asp Gly Met Glu Ala Tyr Val Lys Val Asp Ser Cys Pro Glu Glu Pro
                340                 345                 350
Gln Leu Arg Met Lys Asn Asn Glu Glu Ala Glu Asp Tyr Asp Asp Asp
                355                 360                 365
Leu Thr Asp Ser Glu Met Asp Val Val Arg Phe Asp Asp Asp Asn Ser
370                 375                 380
Pro Ser Phe Ile Gln Ile Arg Ser Val Ala Lys Lys His Pro Lys Thr
385                 390                 395                 400
Trp Val His Tyr Ile Ala Ala Glu Glu Asp Trp Asp Tyr Ala Pro
                405                 410                 415
Leu Val Leu Ala Pro Asp Asp Arg Ser Tyr Lys Ser Gln Tyr Leu Asn
                420                 425                 430
Asn Gly Pro Gln Arg Ile Gly Arg Lys Tyr Lys Lys Val Arg Phe Met
                435                 440                 445
Ala Tyr Thr Asp Glu Thr Phe Lys Thr Arg Glu Ala Ile Gln His Glu
                450                 455                 460
Ser Gly Ile Leu Gly Pro Leu Leu Tyr Gly Glu Val Gly Asp Thr Leu
```

```
             465                 470                 475                 480
Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
                500                 505                 510

Gly Val Lys His Leu Lys Asp Phe Pro Ile Leu Pro Gly Glu Ile Phe
                515                 520                 525

Lys Tyr Lys Trp Thr Val Thr Val Glu Asp Gly Pro Thr Lys Ser Asp
530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
                580                 585                 590

Ile Leu Phe Ser Val Phe Asp Glu Asn Arg Ser Trp Tyr Leu Thr Glu
                595                 600                 605

Asn Ile Gln Arg Phe Leu Pro Asn Pro Ala Gly Val Gln Leu Glu Asp
                610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
                660                 665                 670

Ser Gly Tyr Thr Phe Lys His Lys Met Val Tyr Glu Asp Thr Leu Thr
                675                 680                 685

Leu Phe Pro Phe Ser Gly Glu Thr Val Phe Met Ser Met Glu Asn Pro
                690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
                740                 745                 750

Asn Asn Ala Ile Glu Pro Arg Ser Phe Ser Gln Asn Thr Ser Glu Ser
                755                 760                 765

Ala Thr Pro Glu Ser Gly Pro Gly Ser Glu Pro Ala Thr Ser Gly Ser
                770                 775                 780

Glu Thr Pro Gly Thr Ser Glu Ser Ala Thr Pro Glu Ser Gly Pro Gly
785                 790                 795                 800

Ser Glu Pro Ala Thr Ser Gly Ser Glu Thr Pro Gly Thr Ser Glu Ser
                805                 810                 815

Ala Thr Pro Glu Ser Gly Pro Gly Thr Ser Thr Glu Pro Ser Glu Gly
                820                 825                 830

Ser Ala Pro Gly Ser Pro Ala Gly Ser Pro Thr Ser Thr Glu Glu Gly
                835                 840                 845

Thr Ser Glu Ser Ala Thr Pro Glu Ser Gly Pro Gly Ser Glu Pro Ala
                850                 855                 860

Thr Ser Gly Ser Glu Thr Pro Gly Thr Ser Glu Ser Ala Thr Pro Glu
865                 870                 875                 880

Ser Gly Pro Gly Ser Pro Ala Gly Ser Pro Thr Ser Thr Glu Glu Gly
                885                 890                 895
```

-continued

Ser Pro Ala Gly Ser Pro Thr Ser Thr Glu Glu Gly Ala Ser Ser Pro
              900                 905                 910
Pro Val Leu Lys Arg His Gln Arg Glu Ile Thr Arg Thr Thr Leu Gln
         915                 920                 925
Ser Asp Gln Glu Glu Ile Asp Tyr Asp Asp Thr Ile Ser Val Glu Met
930                 935                 940
Lys Lys Glu Asp Phe Asp Ile Tyr Asp Glu Asp Glu Asn Gln Ser Pro
945                 950                 955                 960
Arg Ser Phe Gln Lys Lys Thr Arg His Tyr Phe Ile Ala Ala Val Glu
                 965                 970                 975
Arg Leu Trp Asp Tyr Gly Met Ser Ser Ser Pro His Val Leu Arg Asn
             980                 985                 990
Arg Ala Gln Ser Gly Ser Val Pro Gln Phe Lys Lys Val Val Phe Gln
         995                 1000                1005
Glu Phe Thr Asp Gly Ser Phe Thr Gln Pro Leu Tyr Arg Gly Glu
    1010                1015                1020
Leu Asn Glu His Leu Gly Leu Leu Gly Pro Tyr Ile Arg Ala Glu
    1025                1030                1035
Val Glu Asp Asn Ile Met Val Thr Phe Arg Asn Gln Ala Ser Arg
    1040                1045                1050
Pro Tyr Ser Phe Tyr Ser Ser Leu Ile Ser Tyr Glu Glu Asp Gln
    1055                1060                1065
Arg Gln Gly Ala Glu Pro Arg Lys Asn Phe Val Lys Pro Asn Glu
    1070                1075                1080
Thr Lys Thr Tyr Phe Trp Lys Val Gln His His Met Ala Pro Thr
    1085                1090                1095
Lys Asp Glu Phe Asp Cys Lys Ala Trp Ala Tyr Phe Ser Asp Val
    1100                1105                1110
Asp Leu Glu Lys Asp Val His Ser Gly Leu Ile Gly Pro Leu Leu
    1115                1120                1125
Val Cys His Thr Asn Thr Leu Asn Pro Ala His Gly Arg Gln Val
    1130                1135                1140
Thr Val Gln Glu Phe Ala Leu Phe Phe Thr Ile Phe Asp Glu Thr
    1145                1150                1155
Lys Ser Trp Tyr Phe Thr Glu Asn Met Glu Arg Asn Cys Arg Ala
    1160                1165                1170
Pro Cys Asn Ile Gln Met Glu Asp Pro Thr Phe Lys Glu Asn Tyr
    1175                1180                1185
Arg Phe His Ala Ile Asn Gly Tyr Ile Met Asp Thr Leu Pro Gly
    1190                1195                1200
Leu Val Met Ala Gln Asp Gln Arg Ile Arg Trp Tyr Leu Leu Ser
    1205                1210                1215
Met Gly Ser Asn Glu Asn Ile His Ser Ile His Phe Ser Gly His
    1220                1225                1230
Val Phe Thr Val Arg Lys Lys Glu Glu Tyr Lys Met Ala Leu Tyr
    1235                1240                1245
Asn Leu Tyr Pro Gly Val Phe Glu Thr Val Glu Met Leu Pro Ser
    1250                1255                1260
Lys Ala Gly Ile Trp Arg Val Glu Cys Leu Ile Gly Glu His Leu
    1265                1270                1275
His Ala Gly Met Ser Thr Leu Phe Leu Val Tyr Ser Asn Lys Cys
    1280                1285                1290

Gln Thr Pro Leu Gly Met Ala Ser Gly His Ile Arg Asp Phe Gln
    1295                1300                1305

Ile Thr Ala Ser Gly Gln Tyr Gly Gln Trp Ala Pro Lys Leu Ala
    1310                1315                1320

Arg Leu His Tyr Ser Gly Ser Ile Asn Ala Trp Ser Thr Lys Glu
    1325                1330                1335

Pro Phe Ser Trp Ile Lys Val Asp Leu Leu Ala Pro Met Ile Ile
    1340                1345                1350

His Gly Ile Lys Thr Gln Gly Ala Arg Gln Lys Phe Ser Ser Leu
    1355                1360                1365

Tyr Ile Ser Gln Phe Ile Ile Met Tyr Ser Leu Asp Gly Lys Lys
    1370                1375                1380

Trp Gln Thr Tyr Arg Gly Asn Ser Thr Gly Thr Leu Met Val Phe
    1385                1390                1395

Phe Gly Asn Val Asp Ser Ser Gly Ile Lys His Asn Ile Phe Asn
    1400                1405                1410

Pro Pro Ile Ile Ala Arg Tyr Ile Arg Leu His Pro Thr His Tyr
    1415                1420                1425

Ser Ile Arg Ser Thr Leu Arg Met Glu Leu Met Gly Cys Asp Leu
    1430                1435                1440

Asn Ser Cys Ser Met Pro Leu Gly Met Glu Ser Lys Ala Ile Ser
    1445                1450                1455

Asp Ala Gln Ile Thr Ala Ser Ser Tyr Phe Thr Asn Met Phe Ala
    1460                1465                1470

Thr Trp Ser Pro Ser Lys Ala Arg Leu His Leu Gln Gly Arg Ser
    1475                1480                1485

Asn Ala Trp Arg Pro Gln Val Asn Asn Pro Lys Glu Trp Leu Gln
    1490                1495                1500

Val Asp Phe Gln Lys Thr Met Lys Val Thr Gly Val Thr Thr Gln
    1505                1510                1515

Gly Val Lys Ser Leu Leu Thr Ser Met Tyr Val Lys Glu Phe Leu
    1520                1525                1530

Ile Ser Ser Ser Gln Asp Gly His Gln Trp Thr Leu Phe Phe Gln
    1535                1540                1545

Asn Gly Lys Val Lys Val Phe Gln Gly Asn Gln Asp Ser Phe Thr
    1550                1555                1560

Pro Val Val Asn Ser Leu Asp Pro Pro Leu Leu Thr Arg Tyr Leu
    1565                1570                1575

Arg Ile His Pro Gln Ser Trp Val His Gln Ile Ala Leu Arg Met
    1580                1585                1590

Glu Val Leu Gly Cys Glu Ala Gln Asp Leu Tyr
    1595                1600

<210> SEQ ID NO 6
<211> LENGTH: 461
<212> TYPE: PRT
<213> ORGANISM: Artificial Sequence
<220> FEATURE:
<223> OTHER INFORMATION: Synthetic amino acid sequence

<400> SEQUENCE: 6

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

```
Asp His Glu Asn Ala Asn Lys Ile Leu Asn Arg Pro Lys Arg Tyr Asn
         35                  40                  45

Ser Gly Lys Leu Glu Glu Phe Val Gln Gly Asn Leu Glu Arg Glu Cys
 50                  55                  60

Met Glu Glu Lys Cys Ser Phe Glu Glu Ala Arg Glu Val Phe Glu Asn
 65                  70                  75                  80

Thr Glu Arg Thr Thr Glu Phe Trp Lys Gln Tyr Val Asp Gly Asp Gln
                 85                  90                  95

Cys Glu Ser Asn Pro Cys Leu Asn Gly Gly Ser Cys Lys Asp Asp Ile
                100                 105                 110

Asn Ser Tyr Glu Cys Trp Cys Pro Phe Gly Phe Glu Gly Lys Asn Cys
            115                 120                 125

Glu Leu Asp Val Thr Cys Asn Ile Lys Asn Gly Arg Cys Glu Gln Phe
        130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
                180                 185                 190

Glu Thr Val Phe Pro Asp Val Asp Tyr Val Asn Ser Thr Glu Ala Glu
            195                 200                 205

Thr Ile Leu Asp Asn Ile Thr Gln Ser Thr Gln Ser Phe Asn Asp Phe
        210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
                260                 265                 270

Val Lys Ile Thr Val Val Ala Gly Glu His Asn Ile Glu Glu Thr Glu
            275                 280                 285

His Thr Glu Gln Lys Arg Asn Val Ile Arg Ile Ile Pro His His Asn
        290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
                340                 345                 350

Val Ser Gly Trp Gly Arg Val Phe His Lys Gly Arg Ser Ala Leu Val
            355                 360                 365

Leu Gln Tyr Leu Arg Val Pro Leu Val Asp Arg Ala Thr Cys Leu Leu
        370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
        435                 440                 445

Arg Tyr Val Asn Trp Ile Lys Glu Lys Thr Lys Leu Thr
```

<210> SEQ ID NO 7
<211> LENGTH: 23
<212> TYPE: DNA
<213> ORGANISM: Artificial Sequence
<220> FEATURE:
<223> OTHER INFORMATION: Synthetic polynucleotide sequence

<400> SEQUENCE: 7
tccataaagt aggaaacact aca                                            23

<210> SEQ ID NO 8
<211> LENGTH: 4
<212> TYPE: PRT
<213> ORGANISM: Artificial Sequence
<220> FEATURE:
<223> OTHER INFORMATION: Synthetic amino acid sequence

<400> SEQUENCE: 8

Glu Leu Leu Gly
1

<210> SEQ ID NO 9
<211> LENGTH: 32
<212> TYPE: PRT
<213> ORGANISM: Artificial Sequence
<220> FEATURE:
<223> OTHER INFORMATION: Synthetic amino acid sequence

<400> SEQUENCE: 9

Asp Pro Arg Phe Gln Asp Ser Ser Ser Ser Lys Ala Pro Pro Pro Ser
1               5                   10                  15

Leu Pro Ser Pro Ser Arg Leu Pro Gly Pro Ser Asp Thr Pro Ile Leu
            20                  25                  30

<210> SEQ ID NO 10
<211> LENGTH: 28
<212> TYPE: PRT
<213> ORGANISM: Artificial Sequence
<220> FEATURE:
<223> OTHER INFORMATION: Synthetic amino acid sequence

<400> SEQUENCE: 10

Ser Ser Ser Ser Lys Ala Pro Pro Pro Ser Leu Pro Ser Pro Ser Arg
1               5                   10                  15

Leu Pro Gly Pro Ser Asp Thr Pro Ile Leu Pro Gln
            20                  25

<210> SEQ ID NO 11
<211> LENGTH: 12
<212> TYPE: PRT
<213> ORGANISM: Artificial Sequence
<220> FEATURE:
<223> OTHER INFORMATION: Synthetic amino acid sequence

<400> SEQUENCE: 11

Gly Glu Ser Pro Gly Gly Ser Ser Gly Ser Glu Ser
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic amino acid sequence

```
<400> SEQUENCE: 12

Gly Ser Glu Gly Ser Ser Gly Pro Gly Glu Ser Ser
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Synthetic amino acid sequence

<400> SEQUENCE: 13

Gly Ser Ser Glu Ser Gly Ser Ser Glu Gly Gly Pro
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Synthetic amino acid sequence

<400> SEQUENCE: 14

Gly Ser Gly Gly Glu Pro Ser Glu Ser Gly Ser Ser
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Synthetic amino acid sequence

<400> SEQUENCE: 15

Gly Ser Pro Ala Gly Ser Pro Thr Ser Thr Glu Glu
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Synthetic amino acid sequence

<400> SEQUENCE: 16

Gly Ser Glu Pro Ala Thr Ser Gly Ser Glu Thr Pro
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Synthetic amino acid sequence

<400> SEQUENCE: 17

Gly Thr Ser Glu Ser Ala Thr Pro Glu Ser Gly Pro
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Synthetic amino acid sequence
```

```
<400> SEQUENCE: 18

Gly Thr Ser Thr Glu Pro Ser Glu Gly Ser Ala Pro
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Synthetic amino acid sequence

<400> SEQUENCE: 19

Gly Ser Thr Ser Glu Ser Pro Ser Gly Thr Ala Pro
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Synthetic amino acid sequence

<400> SEQUENCE: 20

Gly Thr Ser Thr Pro Glu Ser Gly Ser Ala Ser Pro
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Synthetic amino acid sequence

<400> SEQUENCE: 21

Gly Thr Ser Pro Ser Gly Glu Ser Ser Thr Ala Pro
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Synthetic amino acid sequence

<400> SEQUENCE: 22

Gly Ser Thr Ser Ser Thr Ala Glu Ser Pro Gly Pro
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Synthetic amino acid sequence

<400> SEQUENCE: 23

Gly Thr Pro Gly Ser Gly Thr Ala Ser Ser Ser Pro
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Synthetic amino acid sequence

<400> SEQUENCE: 24
```

```
Gly Ser Ser Thr Pro Ser Gly Ala Thr Gly Ser Pro
1               5                   10
```

<210> SEQ ID NO 25
<211> LENGTH: 12
<212> TYPE: PRT
<213> ORGANISM: Artificial Sequence
<220> FEATURE:
<223> OTHER INFORMATION: Synthetic amino acid sequence

<400> SEQUENCE: 25

```
Gly Ser Ser Pro Ser Ala Ser Thr Gly Thr Gly Pro
1               5                   10
```

<210> SEQ ID NO 26
<211> LENGTH: 12
<212> TYPE: PRT
<213> ORGANISM: Artificial Sequence
<220> FEATURE:
<223> OTHER INFORMATION: Synthetic amino acid sequence

<400> SEQUENCE: 26

```
Gly Ala Ser Pro Gly Thr Ser Ser Thr Gly Ser Pro
1               5                   10
```

<210> SEQ ID NO 27
<211> LENGTH: 12
<212> TYPE: PRT
<213> ORGANISM: Artificial Sequence
<220> FEATURE:
<223> OTHER INFORMATION: Synthetic amino acid sequence

<400> SEQUENCE: 27

```
Gly Glu Pro Ala Gly Ser Pro Thr Ser Thr Ser Glu
1               5                   10
```

<210> SEQ ID NO 28
<211> LENGTH: 12
<212> TYPE: PRT
<213> ORGANISM: Artificial Sequence
<220> FEATURE:
<223> OTHER INFORMATION: Synthetic amino acid sequence

<400> SEQUENCE: 28

```
Gly Thr Gly Glu Pro Ser Ser Thr Pro Ala Ser Glu
1               5                   10
```

<210> SEQ ID NO 29
<211> LENGTH: 12
<212> TYPE: PRT
<213> ORGANISM: Artificial Sequence
<220> FEATURE:
<223> OTHER INFORMATION: Synthetic amino acid sequence

<400> SEQUENCE: 29

```
Gly Ser Gly Pro Ser Thr Glu Ser Ala Pro Thr Glu
1               5                   10
```

<210> SEQ ID NO 30
<211> LENGTH: 12
<212> TYPE: PRT
<213> ORGANISM: Artificial Sequence
<220> FEATURE:
<223> OTHER INFORMATION: Synthetic amino acid sequence

<400> SEQUENCE: 30

Gly Ser Glu Thr Pro Ser Gly Pro Ser Glu Thr Ala
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Synthetic amino acid sequence

<400> SEQUENCE: 31

Gly Pro Ser Glu Thr Ser Thr Ser Glu Pro Gly Ala
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Synthetic amino acid sequence

<400> SEQUENCE: 32

Gly Ser Pro Ser Glu Pro Thr Glu Gly Thr Ser Ala
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Synthetic amino acid sequence

<400> SEQUENCE: 33

Gly Ser Gly Ala Ser Glu Pro Thr Ser Thr Glu Pro
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Synthetic amino acid sequence

<400> SEQUENCE: 34

Gly Ser Glu Pro Ala Thr Ser Gly Thr Glu Pro Ser
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Synthetic amino acid sequence

<400> SEQUENCE: 35

Gly Thr Ser Glu Pro Ser Thr Ser Glu Pro Gly Ala
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Synthetic amino acid sequence

<400> SEQUENCE: 36

Gly Thr Ser Thr Glu Pro Ser Glu Pro Gly Ser Ala

```
<210> SEQ ID NO 37
<211> LENGTH: 12
<212> TYPE: PRT
<213> ORGANISM: Artificial Sequence
<220> FEATURE:
<223> OTHER INFORMATION: Synthetic amino acid sequence

<400> SEQUENCE: 37

Gly Ser Thr Ala Gly Ser Glu Thr Ser Thr Glu Ala
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Synthetic amino acid sequence

<400> SEQUENCE: 38

Gly Ser Glu Thr Ala Thr Ser Gly Ser Glu Thr Ala
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Synthetic amino acid sequence

<400> SEQUENCE: 39

Gly Thr Ser Glu Ser Ala Thr Ser Glu Ser Gly Ala
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Synthetic amino acid sequence

<400> SEQUENCE: 40

Gly Thr Ser Thr Glu Ala Ser Glu Gly Ser Ala Ser
1               5                   10

<210> SEQ ID NO 41
<211> LENGTH: 42
<212> TYPE: PRT
<213> ORGANISM: Artificial Sequence
<220> FEATURE:
<223> OTHER INFORMATION: Synthetic amino acid sequence

<400> SEQUENCE: 41

Gly Ala Pro Gly Ser Pro Ala Gly Ser Pro Thr Ser Thr Glu Glu Gly
1               5                   10                  15

Thr Ser Glu Ser Ala Thr Pro Glu Ser Gly Pro Gly Ser Glu Pro Ala
            20                  25                  30

Thr Ser Gly Ser Glu Thr Pro Ala Ser Ser
        35                  40

<210> SEQ ID NO 42
<211> LENGTH: 144
<212> TYPE: PRT
<213> ORGANISM: Artificial Sequence
<220> FEATURE:
```

<223> OTHER INFORMATION: Synthetic amino acid sequence

<400> SEQUENCE: 42

```
Thr Ser Thr Glu Pro Ser Glu Gly Ser Ala Pro Gly Ser Pro Ala Gly
1               5                   10                  15
Ser Pro Thr Ser Thr Glu Glu Gly Thr Ser Thr Glu Pro Ser Glu Gly
            20                  25                  30
Ser Ala Pro Gly Thr Ser Thr Glu Pro Ser Glu Gly Ser Ala Pro Gly
        35                  40                  45
Thr Ser Glu Ser Ala Thr Pro Glu Ser Gly Pro Gly Thr Ser Thr Glu
    50                  55                  60
Pro Ser Glu Gly Ser Ala Pro Gly Thr Ser Glu Ser Ala Thr Pro Glu
65                  70                  75                  80
Ser Gly Pro Gly Ser Glu Pro Ala Thr Ser Gly Ser Glu Thr Pro Gly
                85                  90                  95
Thr Ser Thr Glu Pro Ser Glu Gly Ser Ala Pro Gly Thr Ser Thr Glu
            100                 105                 110
Pro Ser Glu Gly Ser Ala Pro Gly Thr Ser Glu Ser Ala Thr Pro Glu
        115                 120                 125
Ser Gly Pro Gly Thr Ser Glu Ser Ala Thr Pro Glu Ser Gly Pro Gly
    130                 135                 140
```

<210> SEQ ID NO 43
<211> LENGTH: 144
<212> TYPE: PRT
<213> ORGANISM: Artificial Sequence
<220> FEATURE:
<223> OTHER INFORMATION: Synthetic amino acid sequence

<400> SEQUENCE: 43

```
Ser Pro Ala Gly Ser Pro Thr Ser Thr Glu Glu Gly Thr Ser Glu Ser
1               5                   10                  15
Ala Thr Pro Glu Ser Gly Pro Gly Ser Glu Pro Ala Thr Ser Gly Ser
            20                  25                  30
Glu Thr Pro Gly Thr Ser Glu Ser Ala Thr Pro Glu Ser Gly Pro Gly
        35                  40                  45
Thr Ser Thr Glu Pro Ser Glu Gly Ser Ala Pro Gly Thr Ser Thr Glu
    50                  55                  60
Pro Ser Glu Gly Ser Ala Pro Gly Thr Ser Thr Glu Pro Ser Glu Gly
65                  70                  75                  80
Ser Ala Pro Gly Thr Ser Thr Glu Pro Ser Glu Gly Ser Ala Pro Gly
                85                  90                  95
Thr Ser Thr Glu Pro Ser Glu Gly Ser Ala Pro Gly Thr Ser Thr Glu
            100                 105                 110
Pro Ser Glu Gly Ser Ala Pro Gly Ser Pro Ala Gly Ser Pro Thr Ser
        115                 120                 125
Thr Glu Glu Gly Thr Ser Thr Glu Pro Ser Glu Gly Ser Ala Pro Gly
    130                 135                 140
```

<210> SEQ ID NO 44
<211> LENGTH: 144
<212> TYPE: PRT
<213> ORGANISM: Artificial Sequence
<220> FEATURE:
<223> OTHER INFORMATION: Synthetic amino acid sequence

<400> SEQUENCE: 44

Thr Ser Glu Ser Ala Thr Pro Glu Ser Gly Pro Gly Ser Glu Pro Ala

```
                    1               5                  10                 15
Thr Ser Gly Ser Glu Thr Pro Gly Thr Ser Glu Ser Ala Thr Pro Glu
            20                  25                 30

Ser Gly Pro Gly Ser Glu Pro Ala Thr Ser Gly Ser Glu Thr Pro Gly
            35                  40                 45

Thr Ser Glu Ser Ala Thr Pro Glu Ser Gly Pro Gly Thr Ser Thr Glu
            50                  55                 60

Pro Ser Glu Gly Ser Ala Pro Gly Thr Ser Glu Ser Ala Thr Pro Glu
65                  70                  75                 80

Ser Gly Pro Gly Ser Pro Ala Gly Ser Pro Thr Ser Thr Glu Glu Gly
            85                  90                 95

Ser Pro Ala Gly Ser Pro Thr Ser Thr Glu Glu Gly Ser Pro Ala Gly
           100                 105                110

Ser Pro Thr Ser Thr Glu Glu Gly Thr Ser Glu Ser Ala Thr Pro Glu
           115                 120                125

Ser Gly Pro Gly Thr Ser Thr Glu Pro Ser Glu Gly Ser Ala Pro Gly
           130                 135                140
```

<210> SEQ ID NO 45
<211> LENGTH: 144
<212> TYPE: PRT
<213> ORGANISM: Artificial Sequence
<220> FEATURE:
<223> OTHER INFORMATION: Synthetic amino acid sequence

<400> SEQUENCE: 45

```
Thr Ser Glu Ser Ala Thr Pro Glu Ser Gly Pro Gly Ser Glu Pro Ala
1               5                  10                 15

Thr Ser Gly Ser Glu Thr Pro Gly Thr Ser Glu Ser Ala Thr Pro Glu
            20                  25                 30

Ser Gly Pro Gly Ser Glu Pro Ala Thr Ser Gly Ser Glu Thr Pro Gly
            35                  40                 45

Thr Ser Glu Ser Ala Thr Pro Glu Ser Gly Pro Gly Thr Ser Thr Glu
            50                  55                 60

Pro Ser Glu Gly Ser Ala Pro Gly Ser Pro Ala Gly Ser Pro Thr Ser
65                  70                  75                 80

Thr Glu Glu Gly Thr Ser Glu Ser Ala Thr Pro Glu Ser Gly Pro Gly
            85                  90                 95

Ser Glu Pro Ala Thr Ser Gly Ser Glu Thr Pro Gly Thr Ser Glu Ser
           100                 105                110

Ala Thr Pro Glu Ser Gly Pro Gly Ser Pro Ala Gly Ser Pro Thr Ser
           115                 120                125

Thr Glu Glu Gly Ser Pro Ala Gly Ser Pro Thr Ser Thr Glu Glu Gly
           130                 135                140
```

<210> SEQ ID NO 46
<211> LENGTH: 144
<212> TYPE: PRT
<213> ORGANISM: Artificial Sequence
<220> FEATURE:
<223> OTHER INFORMATION: Synthetic amino acid sequence

<400> SEQUENCE: 46

```
Thr Ser Thr Glu Pro Ser Glu Gly Ser Ala Pro Gly Thr Ser Glu Ser
1               5                  10                 15

Ala Thr Pro Glu Ser Gly Pro Gly Thr Ser Glu Ser Ala Thr Pro Glu
            20                  25                 30
```

```
Ser Gly Pro Gly Thr Ser Glu Ser Ala Thr Pro Glu Ser Gly Pro Gly
            35                  40                  45

Ser Glu Pro Ala Thr Ser Gly Ser Glu Thr Pro Gly Ser Glu Pro Ala
    50                  55                  60

Thr Ser Gly Ser Glu Thr Pro Gly Ser Pro Ala Gly Ser Pro Thr Ser
65                  70                  75                  80

Thr Glu Glu Gly Thr Ser Thr Glu Pro Ser Glu Gly Ser Ala Pro Gly
                85                  90                  95

Thr Ser Thr Glu Pro Ser Glu Gly Ser Ala Pro Gly Ser Glu Pro Ala
                100                 105                 110

Thr Ser Gly Ser Glu Thr Pro Gly Thr Ser Glu Ser Ala Thr Pro Glu
                115                 120                 125

Ser Gly Pro Gly Thr Ser Thr Glu Pro Ser Glu Gly Ser Ala Pro Gly
            130                 135                 140

<210> SEQ ID NO 47
<211> LENGTH: 144
<212> TYPE: PRT
<213> ORGANISM: Artificial Sequence
<220> FEATURE:
<223> OTHER INFORMATION: Synthetic amino acid sequence

<400> SEQUENCE: 47

Pro Gly Ser Ser Pro Ser Ala Ser Thr Gly Thr Gly Pro Gly Ser Ser
1               5                   10                  15

Pro Ser Ala Ser Thr Gly Thr Gly Pro Gly Thr Pro Gly Ser Gly Thr
                20                  25                  30

Ala Ser Ser Ser Pro Gly Ser Ser Thr Pro Ser Gly Ala Thr Gly Ser
            35                  40                  45

Pro Gly Ser Ser Pro Ser Ala Ser Thr Gly Thr Gly Pro Gly Ala Ser
    50                  55                  60

Pro Gly Thr Ser Ser Thr Gly Ser Pro Gly Thr Pro Gly Ser Gly Thr
65                  70                  75                  80

Ala Ser Ser Ser Pro Gly Ser Ser Thr Pro Ser Gly Ala Thr Gly Ser
                85                  90                  95

Pro Gly Thr Pro Gly Ser Gly Thr Ala Ser Ser Ser Pro Gly Ala Ser
                100                 105                 110

Pro Gly Thr Ser Ser Thr Gly Ser Pro Gly Ala Ser Pro Gly Thr Ser
                115                 120                 125

Ser Thr Gly Ser Pro Gly Thr Pro Gly Ser Gly Thr Ala Ser Ser Ser
            130                 135                 140

<210> SEQ ID NO 48
<211> LENGTH: 144
<212> TYPE: PRT
<213> ORGANISM: Artificial Sequence
<220> FEATURE:
<223> OTHER INFORMATION: Synthetic amino acid sequence

<400> SEQUENCE: 48

Gly Ala Ser Pro Gly Thr Ser Ser Thr Gly Ser Pro Gly Ser Ser Pro
1               5                   10                  15

Ser Ala Ser Thr Gly Thr Gly Pro Gly Ser Ser Pro Ser Ala Ser Thr
                20                  25                  30

Gly Thr Gly Pro Gly Thr Pro Gly Ser Gly Thr Ala Ser Ser Ser Pro
            35                  40                  45

Gly Ser Ser Thr Pro Ser Gly Ala Thr Gly Ser Pro Gly Ser Ser Pro
    50                  55                  60
```

Ser Ala Ser Thr Gly Thr Gly Pro Gly Ala Ser Pro Gly Thr Ser Ser
65                  70                  75                  80

Thr Gly Ser Pro Gly Thr Pro Gly Ser Gly Thr Ala Ser Ser Ser Pro
                85                  90                  95

Gly Ser Ser Thr Pro Ser Gly Ala Thr Gly Ser Pro Gly Thr Pro Gly
            100                 105                 110

Ser Gly Thr Ala Ser Ser Ser Pro Gly Ala Ser Pro Gly Thr Ser Ser
        115                 120                 125

Thr Gly Ser Pro Gly Ala Ser Pro Gly Thr Ser Ser Thr Gly Ser Pro
    130                 135                 140

<210> SEQ ID NO 49
<211> LENGTH: 144
<212> TYPE: PRT
<213> ORGANISM: Artificial Sequence
<220> FEATURE:
<223> OTHER INFORMATION: Synthetic amino acid sequence

<400> SEQUENCE: 49

Gly Thr Pro Gly Ser Gly Thr Ala Ser Ser Pro Gly Ser Ser Thr
1               5                   10                  15

Pro Ser Gly Ala Thr Gly Ser Pro Gly Ala Ser Pro Gly Thr Ser Ser
                20                  25                  30

Thr Gly Ser Pro Gly Thr Pro Gly Ser Gly Thr Ala Ser Ser Ser Pro
            35                  40                  45

Gly Ser Ser Thr Pro Ser Gly Ala Thr Gly Ser Pro Gly Ser Ser Pro
        50                  55                  60

Ser Ala Ser Thr Gly Thr Gly Pro Gly Ser Ser Pro Ser Ala Ser Thr
65                  70                  75                  80

Gly Thr Gly Pro Gly Ser Ser Thr Pro Ser Gly Ala Thr Gly Ser Pro
                85                  90                  95

Gly Ser Ser Thr Pro Ser Gly Ala Thr Gly Ser Pro Gly Ala Ser Pro
            100                 105                 110

Gly Thr Ser Ser Thr Gly Ser Pro Gly Ala Ser Pro Gly Thr Ser Ser
        115                 120                 125

Thr Gly Ser Pro Gly Ala Ser Pro Gly Thr Ser Ser Thr Gly Ser Pro
    130                 135                 140

<210> SEQ ID NO 50
<211> LENGTH: 144
<212> TYPE: PRT
<213> ORGANISM: Artificial Sequence
<220> FEATURE:
<223> OTHER INFORMATION: Synthetic amino acid sequence

<400> SEQUENCE: 50

Gly Thr Pro Gly Ser Gly Thr Ala Ser Ser Pro Gly Ala Ser Pro
1               5                   10                  15

Gly Thr Ser Ser Thr Gly Ser Pro Gly Ala Ser Pro Gly Thr Ser Ser
                20                  25                  30

Thr Gly Ser Pro Gly Ala Ser Pro Gly Thr Ser Ser Thr Gly Ser Pro
            35                  40                  45

Gly Ser Ser Pro Ser Ala Ser Thr Gly Thr Gly Pro Gly Thr Pro Gly
        50                  55                  60

Ser Gly Thr Ala Ser Ser Ser Pro Gly Ala Ser Pro Gly Thr Ser Ser
65                  70                  75                  80

Thr Gly Ser Pro Gly Ala Ser Pro Gly Thr Ser Ser Thr Gly Ser Pro 85                  90                  95

Gly Ala Ser Pro Gly Thr Ser Thr Gly Ser Pro Gly Ser Ser Thr
            100                 105                 110

Pro Ser Gly Ala Thr Gly Ser Pro Gly Ser Ser Thr Pro Ser Gly Ala
        115                 120                 125

Thr Gly Ser Pro Gly Ala Ser Pro Gly Thr Ser Ser Thr Gly Ser Pro
    130                 135                 140

<210> SEQ ID NO 51
<211> LENGTH: 144
<212> TYPE: PRT
<213> ORGANISM: Artificial Sequence
<220> FEATURE:
<223> OTHER INFORMATION: Synthetic amino acid sequence

<400> SEQUENCE: 51

Gly Ser Ser Pro Ser Ala Ser Thr Gly Thr Gly Pro Gly Ser Ser Pro
1               5                   10                  15

Ser Ala Ser Thr Gly Thr Gly Pro Gly Ala Ser Pro Gly Thr Ser Ser
            20                  25                  30

Thr Gly Ser Pro Gly Ala Ser Pro Gly Thr Ser Ser Thr Gly Ser Pro
        35                  40                  45

Gly Ser Ser Thr Pro Ser Gly Ala Thr Gly Ser Pro Gly Ser Ser Pro
    50                  55                  60

Ser Ala Ser Thr Gly Thr Gly Pro Gly Ala Ser Pro Gly Thr Ser Ser
65                  70                  75                  80

Thr Gly Ser Pro Gly Ser Ser Pro Ser Ala Ser Thr Gly Thr Gly Pro
                85                  90                  95

Gly Thr Pro Gly Ser Gly Thr Ala Ser Ser Pro Gly Ser Ser Thr
            100                 105                 110

Pro Ser Gly Ala Thr Gly Ser Pro Gly Ser Ser Thr Pro Ser Gly Ala
        115                 120                 125

Thr Gly Ser Pro Gly Ala Ser Pro Gly Thr Ser Ser Thr Gly Ser Pro
    130                 135                 140

<210> SEQ ID NO 52
<211> LENGTH: 450
<212> TYPE: DNA
<213> ORGANISM: Artificial Sequence
<220> FEATURE:
<223> OTHER INFORMATION: Synthetic polynucleotide sequence

<400> SEQUENCE: 52
ggcgcgccaa catcagagag cgccacccct gaaagtggtc ccgggagcga gccagccaca      60
tctgggtcgg aaacgccagg cacaagtgag tctgcaactc ccgagtccgg acctggctcc    120
gagcctgcca ctagcggctc cgagactccg ggaacttccg agagcgctac accagaaagc    180
ggacccggaa ccagtaccga acctagcgag ggctctgctc gggcagccca gccggctct     240 cctacatcca cggaggaggg cacttccgaa tccgccaccc cggagtcagg gccaggatct    300
gaacccgcta cctcaggcag tgagacgcca ggaacgagcg agtccgctac accggagagt    360
gggccaggga gccctgctgg atctcctacg tccactgagg aagggtcacc agcgggctcg    420
cccaccagca ctgaagaagg tgcctcgagc                                     450

<210> SEQ ID NO 53
<211> LENGTH: 6
<212> TYPE: PRT
<213> ORGANISM: Artificial Sequence

```
<220> FEATURE:
<223> OTHER INFORMATION: Synthetic amino acid sequence
<220> FEATURE:
<221> NAME/KEY: MISC_FEATURE
<222> LOCATION: (2)..(2)
<223> OTHER INFORMATION: Xaa is Asp, Asn, Ser, Thr, or Trp
<220> FEATURE:
<221> NAME/KEY: MISC_FEATURE
<222> LOCATION: (3)..(3)
<223> OTHER INFORMATION: Xaa is Asn, Gln, His, Ile, Leu, or Lys
<220> FEATURE:
<221> NAME/KEY: MISC_FEATURE
<222> LOCATION: (4)..(4)
<223> OTHER INFORMATION: Xaa is Ala, Asp, Phe, Trp, or Tyr
<220> FEATURE:
<221> NAME/KEY: MISC_FEATURE
<222> LOCATION: (5)..(5)
<223> OTHER INFORMATION: Xaa is Asp, Gly, Leu, Phe, Ser, or Thr

<400> SEQUENCE: 53

Cys Xaa Xaa Xaa Xaa Cys
1               5

<210> SEQ ID NO 54
<211> LENGTH: 11
<212> TYPE: PRT
<213> ORGANISM: Artificial Sequence
<220> FEATURE:
<223> OTHER INFORMATION: Synthetic amino acid sequence

<400> SEQUENCE: 54

Asp Ile Cys Leu Pro Arg Trp Gly Cys Leu Trp
1               5                   10

<210> SEQ ID NO 55
<211> LENGTH: 20
<212> TYPE: PRT
<213> ORGANISM: Artificial Sequence
<220> FEATURE:
<223> OTHER INFORMATION: Synthetic amino acid sequence

<400> SEQUENCE: 55

Ala Ser Pro Ala Ala Pro Ala Pro Ala Ser Pro Ala Ala Pro Ala Pro
1               5                   10                  15

Ser Ala Pro Ala
            20

<210> SEQ ID NO 56
<211> LENGTH: 20
<212> TYPE: PRT
<213> ORGANISM: Artificial Sequence
<220> FEATURE:
<223> OTHER INFORMATION: Synthetic amino acid sequence

<400> SEQUENCE: 56

Ala Ala Pro Ala Ser Pro Ala Pro Ala Ala Pro Ser Ala Pro Ala Pro
1               5                   10                  15

Ala Ala Pro Ser
            20

<210> SEQ ID NO 57
<211> LENGTH: 20
<212> TYPE: PRT
<213> ORGANISM: Artificial Sequence
<220> FEATURE:
<223> OTHER INFORMATION: Synthetic amino acid sequence

<400> SEQUENCE: 57
```

```
Ala Pro Ser Ser Pro Ser Pro Ser Ala Pro Ser Ser Pro Ser Pro Ala
1               5                   10                  15

Ser Pro Ser Ser
            20

<210> SEQ ID NO 58
<211> LENGTH: 19
<212> TYPE: PRT
<213> ORGANISM: Artificial Sequence
<220> FEATURE:
<223> OTHER INFORMATION: Synthetic amino acid sequence

<400> SEQUENCE: 58

Ala Pro Ser Ser Pro Ser Pro Ser Ala Pro Ser Ser Pro Ser Pro Ala
1               5                   10                  15

Ser Pro Ser

<210> SEQ ID NO 59
<211> LENGTH: 20
<212> TYPE: PRT
<213> ORGANISM: Artificial Sequence
<220> FEATURE:
<223> OTHER INFORMATION: Synthetic amino acid sequence

<400> SEQUENCE: 59

Ser Ser Pro Ser Ala Pro Ser Pro Ser Ser Pro Ala Ser Pro Ser Pro
1               5                   10                  15

Ser Ser Pro Ala
            20

<210> SEQ ID NO 60
<211> LENGTH: 24
<212> TYPE: PRT
<213> ORGANISM: Artificial Sequence
<220> FEATURE:
<223> OTHER INFORMATION: Synthetic amino acid sequence

<400> SEQUENCE: 60

Ala Ala Ser Pro Ala Ala Pro Ser Ala Pro Pro Ala Ala Ala Ser Pro
1               5                   10                  15

Ala Ala Pro Ser Ala Pro Pro Ala
            20

<210> SEQ ID NO 61
<211> LENGTH: 20
<212> TYPE: PRT
<213> ORGANISM: Artificial Sequence
<220> FEATURE:
<223> OTHER INFORMATION: Synthetic amino acid sequence

<400> SEQUENCE: 61

Ala Ser Ala Ala Ala Pro Ala Ala Ala Ser Ala Ala Ala Ser Ala Pro
1               5                   10                  15

Ser Ala Ala Ala
            20

<210> SEQ ID NO 62
<211> LENGTH: 2813
<212> TYPE: PRT
<213> ORGANISM: Artificial Sequence
<220> FEATURE:
<223> OTHER INFORMATION: Synthetic amino acid sequence

<400> SEQUENCE: 62
```

-continued

```
Met Ile Pro Ala Arg Phe Ala Gly Val Leu Ala Leu Ala Leu Ile
1               5                  10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
            35                  40                  45

Ser Met Tyr Ser Phe Ala Gly Tyr Cys Ser Tyr Leu Leu Ala Gly Gly
        50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
            115                 120                 125

Leu Ser Gly Glu Ala Tyr Gly Phe Val Ala Arg Ile Asp Gly Ser Gly
        130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
        195                 200                 205

Ser Cys Asn Ile Ser Ser Gly Glu Met Gln Lys Gly Leu Trp Glu Gln
210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
        275                 280                 285

Ser Ala Cys Ser Pro Val Cys Pro Ala Gly Met Glu Tyr Arg Gln Cys
        290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
        355                 360                 365

Thr Cys Ile Cys Arg Asn Ser Gln Trp Ile Cys Ser Asn Glu Glu Cys
    370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
```

```
              420             425             430
Ala Asp Asp Arg Asp Ala Val Cys Thr Arg Ser Val Thr Val Arg Leu
            435             440             445
Pro Gly Leu His Asn Ser Leu Val Lys Leu Lys His Gly Ala Gly Val
            450             455             460
Ala Met Asp Gly Gln Asp Val Gln Leu Pro Leu Leu Lys Gly Asp Leu
465             470             475             480
Arg Ile Gln His Thr Val Thr Ala Ser Val Arg Leu Ser Tyr Gly Glu
                485             490             495
Asp Leu Gln Met Asp Trp Asp Gly Arg Gly Arg Leu Leu Val Lys Leu
                500             505             510
Ser Pro Val Tyr Ala Gly Lys Thr Cys Gly Leu Cys Gly Asn Tyr Asn
            515             520             525
Gly Asn Gln Gly Asp Asp Phe Leu Thr Pro Ser Gly Leu Ala Glu Pro
            530             535             540
Arg Val Glu Asp Phe Gly Asn Ala Trp Lys Leu His Gly Asp Cys Gln
545             550             555             560
Asp Leu Gln Lys Gln His Ser Asp Pro Cys Ala Leu Asn Pro Arg Met
                565             570             575
Thr Arg Phe Ser Glu Glu Ala Cys Ala Val Leu Thr Ser Pro Thr Phe
                580             585             590
Glu Ala Cys His Arg Ala Val Ser Pro Leu Pro Tyr Leu Arg Asn Cys
            595             600             605
Arg Tyr Asp Val Cys Ser Cys Ser Asp Gly Arg Glu Cys Leu Cys Gly
            610             615             620
Ala Leu Ala Ser Tyr Ala Ala Ala Cys Ala Gly Arg Gly Val Arg Val
625             630             635             640
Ala Trp Arg Glu Pro Gly Arg Cys Glu Leu Asn Cys Pro Lys Gly Gln
                645             650             655
Val Tyr Leu Gln Cys Gly Thr Pro Cys Asn Leu Thr Cys Arg Ser Leu
                660             665             670
Ser Tyr Pro Asp Glu Glu Cys Asn Glu Ala Cys Leu Glu Gly Cys Phe
            675             680             685
Cys Pro Pro Gly Leu Tyr Met Asp Glu Arg Gly Asp Cys Val Pro Lys
            690             695             700
Ala Gln Cys Pro Cys Tyr Tyr Asp Gly Glu Ile Phe Gln Pro Glu Asp
705             710             715             720
Ile Phe Ser Asp His His Thr Met Cys Tyr Cys Glu Asp Gly Phe Met
                725             730             735
His Cys Thr Met Ser Gly Val Pro Gly Ser Leu Leu Pro Asp Ala Val
                740             745             750
Leu Ser Ser Pro Leu Ser His Arg Ser Lys Arg Ser Leu Ser Cys Arg
            755             760             765
Pro Pro Met Val Lys Leu Val Cys Pro Ala Asp Asn Leu Arg Ala Glu
            770             775             780
Gly Leu Glu Cys Thr Lys Thr Cys Gln Asn Tyr Asp Leu Glu Cys Met
785             790             795             800
Ser Met Gly Cys Val Ser Gly Cys Leu Cys Pro Pro Gly Met Val Arg
                805             810             815
His Glu Asn Arg Cys Val Ala Leu Glu Arg Cys Pro Cys Phe His Gln
                820             825             830
Gly Lys Glu Tyr Ala Pro Gly Glu Thr Val Lys Ile Gly Cys Asn Thr
            835             840             845
```

-continued

```
Cys Val Cys Arg Asp Arg Lys Trp Asn Cys Thr Asp His Val Cys Asp
850                 855                 860
Ala Thr Cys Ser Thr Ile Gly Met Ala His Tyr Leu Thr Phe Asp Gly
865                 870                 875                 880
Leu Lys Tyr Leu Phe Pro Gly Glu Cys Gln Tyr Val Leu Val Gln Asp
                885                 890                 895
Tyr Cys Gly Ser Asn Pro Gly Thr Phe Arg Ile Leu Val Gly Asn Lys
                900                 905                 910
Gly Cys Ser His Pro Ser Val Lys Cys Lys Arg Val Thr Ile Leu
                915                 920                 925
Val Glu Gly Gly Glu Ile Glu Leu Phe Asp Gly Glu Val Asn Val Lys
930                 935                 940
Arg Pro Met Lys Asp Glu Thr His Phe Glu Val Val Glu Ser Gly Arg
945                 950                 955                 960
Tyr Ile Ile Leu Leu Leu Gly Lys Ala Leu Ser Val Val Trp Asp Arg
                965                 970                 975
His Leu Ser Ile Ser Val Val Leu Lys Gln Thr Tyr Gln Glu Lys Val
                980                 985                 990
Cys Gly Leu Cys Gly Asn Phe Asp Gly Ile Gln Asn Asn Asp Leu Thr
                995                 1000                1005
Ser Ser Asn Leu Gln Val Glu Glu Asp Pro Val Asp Phe Gly Asn
        1010                1015                1020
Ser Trp Lys Val Ser Ser Gln Cys Ala Asp Thr Arg Lys Val Pro
        1025                1030                1035
Leu Asp Ser Ser Pro Ala Thr Cys His Asn Asn Ile Met Lys Gln
        1040                1045                1050
Thr Met Val Asp Ser Ser Cys Arg Ile Leu Thr Ser Asp Val Phe
        1055                1060                1065
Gln Asp Cys Asn Lys Leu Val Asp Pro Glu Pro Tyr Leu Asp Val
        1070                1075                1080
Cys Ile Tyr Asp Thr Cys Ser Cys Glu Ser Ile Gly Asp Cys Ala
        1085                1090                1095
Cys Phe Cys Asp Thr Ile Ala Ala Tyr Ala His Val Cys Ala Gln
        1100                1105                1110
His Gly Lys Val Val Thr Trp Arg Thr Ala Thr Leu Cys Pro Gln
        1115                1120                1125
Ser Cys Glu Glu Arg Asn Leu Arg Glu Asn Gly Tyr Glu Cys Glu
        1130                1135                1140
Trp Arg Tyr Asn Ser Cys Ala Pro Ala Cys Gln Val Thr Cys Gln
        1145                1150                1155
His Pro Glu Pro Leu Ala Cys Pro Val Gln Cys Val Glu Gly Cys
        1160                1165                1170
His Ala His Cys Pro Pro Gly Lys Ile Leu Asp Glu Leu Leu Gln
        1175                1180                1185
Thr Cys Val Asp Pro Glu Asp Cys Pro Val Cys Glu Val Ala Gly
        1190                1195                1200
Arg Arg Phe Ala Ser Gly Lys Lys Val Thr Leu Asn Pro Ser Asp
        1205                1210                1215
Pro Glu His Cys Gln Ile Cys His Cys Asp Val Val Asn Leu Thr
        1220                1225                1230
Cys Glu Ala Cys Gln Glu Pro Gly Gly Leu Val Val Pro Pro Thr
        1235                1240                1245
```

-continued

```
Asp Ala Pro Val Ser Pro Thr Thr Leu Tyr Val Glu Asp Ile Ser
1250             1255                 1260

Glu Pro Pro Leu His Asp Phe Tyr Cys Ser Arg Leu Leu Asp Leu
1265             1270                 1275

Val Phe Leu Leu Asp Gly Ser Ser Arg Leu Ser Glu Ala Glu Phe
1280             1285                 1290

Glu Val Leu Lys Ala Phe Val Asp Met Met Glu Arg Leu Arg
1295             1300                 1305

Ile Ser Gln Lys Trp Val Arg Val Ala Val Val Glu Tyr His Asp
1310             1315                 1320

Gly Ser His Ala Tyr Ile Gly Leu Lys Asp Arg Lys Arg Pro Ser
1325             1330                 1335

Glu Leu Arg Arg Ile Ala Ser Gln Val Lys Tyr Ala Gly Ser Gln
1340             1345                 1350

Val Ala Ser Thr Ser Glu Val Leu Lys Tyr Thr Leu Phe Gln Ile
1355             1360                 1365

Phe Ser Lys Ile Asp Arg Pro Glu Ala Ser Arg Ile Thr Leu Leu
1370             1375                 1380

Leu Met Ala Ser Gln Glu Pro Gln Arg Met Ser Arg Asn Phe Val
1385             1390                 1395

Arg Tyr Val Gln Gly Leu Lys Lys Lys Lys Val Ile Val Ile Pro
1400             1405                 1410

Val Gly Ile Gly Pro His Ala Asn Leu Lys Gln Ile Arg Leu Ile
1415             1420                 1425

Glu Lys Gln Ala Pro Glu Asn Lys Ala Phe Val Leu Ser Ser Val
1430             1435                 1440

Asp Glu Leu Glu Gln Gln Arg Asp Glu Ile Val Ser Tyr Leu Cys
1445             1450                 1455

Asp Leu Ala Pro Glu Ala Pro Pro Pro Thr Leu Pro Pro Asp Met
1460             1465                 1470

Ala Gln Val Thr Val Gly Pro Gly Leu Leu Gly Val Ser Thr Leu
1475             1480                 1485

Gly Pro Lys Arg Asn Ser Met Val Leu Asp Val Ala Phe Val Leu
1490             1495                 1500

Glu Gly Ser Asp Lys Ile Gly Glu Ala Asp Phe Asn Arg Ser Lys
1505             1510                 1515

Glu Phe Met Glu Glu Val Ile Gln Arg Met Asp Val Gly Gln Asp
1520             1525                 1530

Ser Ile His Val Thr Val Leu Gln Tyr Ser Tyr Met Val Thr Val
1535             1540                 1545

Glu Tyr Pro Phe Ser Glu Ala Gln Ser Lys Gly Asp Ile Leu Gln
1550             1555                 1560

Arg Val Arg Glu Ile Arg Tyr Gln Gly Gly Asn Arg Thr Asn Thr
1565             1570                 1575

Gly Leu Ala Leu Arg Tyr Leu Ser Asp His Ser Phe Leu Val Ser
1580             1585                 1590

Gln Gly Asp Arg Glu Gln Ala Pro Asn Leu Val Tyr Met Val Thr
1595             1600                 1605

Gly Asn Pro Ala Ser Asp Glu Ile Lys Arg Leu Pro Gly Asp Ile
1610             1615                 1620

Gln Val Val Pro Ile Gly Val Gly Pro Asn Ala Asn Val Gln Glu
1625             1630                 1635

Leu Glu Arg Ile Gly Trp Pro Asn Ala Pro Ile Leu Ile Gln Asp
```

```
              1640                1645                1650

Phe Glu Thr Leu Pro Arg Glu Ala Pro Asp Leu Val Leu Gln Arg
    1655                1660                1665

Cys Cys Ser Gly Glu Gly Leu Gln Ile Pro Thr Leu Ser Pro Ala
    1670                1675                1680

Pro Asp Cys Ser Gln Pro Leu Asp Val Ile Leu Leu Leu Asp Gly
    1685                1690                1695

Ser Ser Ser Phe Pro Ala Ser Tyr Phe Asp Glu Met Lys Ser Phe
    1700                1705                1710

Ala Lys Ala Phe Ile Ser Lys Ala Asn Ile Gly Pro Arg Leu Thr
    1715                1720                1725

Gln Val Ser Val Leu Gln Tyr Gly Ser Ile Thr Thr Ile Asp Val
    1730                1735                1740

Pro Trp Asn Val Val Pro Glu Lys Ala His Leu Leu Ser Leu Val
    1745                1750                1755

Asp Val Met Gln Arg Glu Gly Gly Pro Ser Gln Ile Gly Asp Ala
    1760                1765                1770

Leu Gly Phe Ala Val Arg Tyr Leu Thr Ser Glu Met His Gly Ala
    1775                1780                1785

Arg Pro Gly Ala Ser Lys Ala Val Val Ile Leu Val Thr Asp Val
    1790                1795                1800

Ser Val Asp Ser Val Asp Ala Ala Ala Asp Ala Ala Arg Ser Asn
    1805                1810                1815

Arg Val Thr Val Phe Pro Ile Gly Ile Gly Asp Arg Tyr Asp Ala
    1820                1825                1830

Ala Gln Leu Arg Ile Leu Ala Gly Pro Ala Gly Asp Ser Asn Val
    1835                1840                1845

Val Lys Leu Gln Arg Ile Glu Asp Leu Pro Thr Met Val Thr Leu
    1850                1855                1860

Gly Asn Ser Phe Leu His Lys Leu Cys Ser Gly Phe Val Arg Ile
    1865                1870                1875

Cys Met Asp Glu Asp Gly Asn Glu Lys Arg Pro Gly Asp Val Trp
    1880                1885                1890

Thr Leu Pro Asp Gln Cys His Thr Val Thr Cys Gln Pro Asp Gly
    1895                1900                1905

Gln Thr Leu Leu Lys Ser His Arg Val Asn Cys Asp Arg Gly Leu
    1910                1915                1920

Arg Pro Ser Cys Pro Asn Ser Gln Ser Pro Val Lys Val Glu Glu
    1925                1930                1935

Thr Cys Gly Cys Arg Trp Thr Cys Pro Cys Val Cys Thr Gly Ser
    1940                1945                1950

Ser Thr Arg His Ile Val Thr Phe Asp Gly Gln Asn Phe Lys Leu
    1955                1960                1965

Thr Gly Ser Cys Ser Tyr Val Leu Phe Gln Asn Lys Glu Gln Asp
    1970                1975                1980

Leu Glu Val Ile Leu His Asn Gly Ala Cys Ser Pro Gly Ala Arg
    1985                1990                1995

Gln Gly Cys Met Lys Ser Ile Glu Val Lys His Ser Ala Leu Ser
    2000                2005                2010

Val Glu Leu His Ser Asp Met Glu Val Thr Val Asn Gly Arg Leu
    2015                2020                2025

Val Ser Val Pro Tyr Val Gly Gly Asn Met Glu Val Asn Val Tyr
    2030                2035                2040
```

-continued

Gly Ala Ile Met His Glu Val Arg Phe Asn His Leu Gly His Ile
2045                2050                2055

Phe Thr Phe Thr Pro Gln Asn Asn Glu Phe Gln Leu Gln Leu Ser
2060                2065                2070

Pro Lys Thr Phe Ala Ser Lys Thr Tyr Gly Leu Cys Gly Ile Cys
2075                2080                2085

Asp Glu Asn Gly Ala Asn Asp Phe Met Leu Arg Asp Gly Thr Val
2090                2095                2100

Thr Thr Asp Trp Lys Thr Leu Val Gln Glu Trp Thr Val Gln Arg
2105                2110                2115

Pro Gly Gln Thr Cys Gln Pro Ile Leu Glu Glu Gln Cys Leu Val
2120                2125                2130

Pro Asp Ser Ser His Cys Gln Val Leu Leu Leu Pro Leu Phe Ala
2135                2140                2145

Glu Cys His Lys Val Leu Ala Pro Ala Thr Phe Tyr Ala Ile Cys
2150                2155                2160

Gln Gln Asp Ser Cys His Gln Glu Gln Val Cys Glu Val Ile Ala
2165                2170                2175

Ser Tyr Ala His Leu Cys Arg Thr Asn Gly Val Cys Val Asp Trp
2180                2185                2190

Arg Thr Pro Asp Phe Cys Ala Met Ser Cys Pro Pro Ser Leu Val
2195                2200                2205

Tyr Asn His Cys Glu His Gly Cys Pro Arg His Cys Asp Gly Asn
2210                2215                2220

Val Ser Ser Cys Gly Asp His Pro Ser Glu Gly Cys Phe Cys Pro
2225                2230                2235

Pro Asp Lys Val Met Leu Glu Gly Ser Cys Val Pro Glu Glu Ala
2240                2245                2250

Cys Thr Gln Cys Ile Gly Glu Asp Gly Val Gln His Gln Phe Leu
2255                2260                2265

Glu Ala Trp Val Pro Asp His Gln Pro Cys Gln Ile Cys Thr Cys
2270                2275                2280

Leu Ser Gly Arg Lys Val Asn Cys Thr Thr Gln Pro Cys Pro Thr
2285                2290                2295

Ala Lys Ala Pro Thr Cys Gly Leu Cys Glu Val Ala Arg Leu Arg
2300                2305                2310

Gln Asn Ala Asp Gln Cys Cys Pro Glu Tyr Glu Cys Val Cys Asp
2315                2320                2325

Pro Val Ser Cys Asp Leu Pro Pro Val Pro His Cys Glu Arg Gly
2330                2335                2340

Leu Gln Pro Thr Leu Thr Asn Pro Gly Glu Cys Arg Pro Asn Phe
2345                2350                2355

Thr Cys Ala Cys Arg Lys Glu Glu Cys Lys Arg Val Ser Pro Pro
2360                2365                2370

Ser Cys Pro Pro His Arg Leu Pro Thr Leu Arg Lys Thr Gln Cys
2375                2380                2385

Cys Asp Glu Tyr Glu Cys Ala Cys Asn Cys Val Asn Ser Thr Val
2390                2395                2400

Ser Cys Pro Leu Gly Tyr Leu Ala Ser Thr Ala Thr Asn Asp Cys
2405                2410                2415

Gly Cys Thr Thr Thr Thr Cys Leu Pro Asp Lys Val Cys Val His
2420                2425                2430

```
Arg Ser Thr Ile Tyr Pro Val Gly Gln Phe Trp Glu Gly Cys
    2435            2440            2445

Asp Val Cys Thr Cys Thr Asp Met Glu Asp Ala Val Met Gly Leu
    2450            2455            2460

Arg Val Ala Gln Cys Ser Gln Lys Pro Cys Glu Asp Ser Cys Arg
    2465            2470            2475

Ser Gly Phe Thr Tyr Val Leu His Glu Gly Glu Cys Cys Gly Arg
    2480            2485            2490

Cys Leu Pro Ser Ala Cys Glu Val Val Thr Gly Ser Pro Arg Gly
    2495            2500            2505

Asp Ser Gln Ser Ser Trp Lys Ser Val Gly Ser Gln Trp Ala Ser
    2510            2515            2520

Pro Glu Asn Pro Cys Leu Ile Asn Glu Cys Val Arg Val Lys Glu
    2525            2530            2535

Glu Val Phe Ile Gln Gln Arg Asn Val Ser Cys Pro Gln Leu Glu
    2540            2545            2550

Val Pro Val Cys Pro Ser Gly Phe Gln Leu Ser Cys Lys Thr Ser
    2555            2560            2565

Ala Cys Cys Pro Ser Cys Arg Cys Glu Arg Met Glu Ala Cys Met
    2570            2575            2580

Leu Asn Gly Thr Val Ile Gly Pro Gly Lys Thr Val Met Ile Asp
    2585            2590            2595

Val Cys Thr Thr Cys Arg Cys Met Val Gln Val Gly Val Ile Ser
    2600            2605            2610

Gly Phe Lys Leu Glu Cys Arg Lys Thr Thr Cys Asn Pro Cys Pro
    2615            2620            2625

Leu Gly Tyr Lys Glu Glu Asn Asn Thr Gly Glu Cys Cys Gly Arg
    2630            2635            2640

Cys Leu Pro Thr Ala Cys Thr Ile Gln Leu Arg Gly Gly Gln Ile
    2645            2650            2655

Met Thr Leu Lys Arg Asp Glu Thr Leu Gln Asp Gly Cys Asp Thr
    2660            2665            2670

His Phe Cys Lys Val Asn Glu Arg Gly Glu Tyr Phe Trp Glu Lys
    2675            2680            2685

Arg Val Thr Gly Cys Pro Pro Phe Asp Glu His Lys Cys Leu Ala
    2690            2695            2700

Glu Gly Gly Lys Ile Met Lys Ile Pro Gly Thr Cys Cys Asp Thr
    2705            2710            2715

Cys Glu Glu Pro Glu Cys Asn Asp Ile Thr Ala Arg Leu Gln Tyr
    2720            2725            2730

Val Lys Val Gly Ser Cys Lys Ser Glu Val Glu Val Asp Ile His
    2735            2740            2745

Tyr Cys Gln Gly Lys Cys Ala Ser Lys Ala Met Tyr Ser Ile Asp
    2750            2755            2760

Ile Asn Asp Val Gln Asp Gln Cys Ser Cys Cys Ser Pro Thr Arg
    2765            2770            2775

Thr Glu Pro Met Gln Val Ala Leu His Cys Thr Asn Gly Ser Val
    2780            2785            2790

Val Tyr His Glu Val Leu Asn Ala Met Glu Cys Lys Cys Ser Pro
    2795            2800            2805

Arg Lys Cys Ser Lys
    2810
```

```
<210> SEQ ID NO 63
<211> LENGTH: 577
<212> TYPE: DNA
<213> ORGANISM: Artificial Sequence
<220> FEATURE:
<223> OTHER INFORMATION: Synthetic polynucleotide sequence

<400> SEQUENCE: 63
ctcgaggtca attcacgcga gttaataatt accagcgcgg gccaaataaa taatccgcga      60
ggggcaggtg acgtttgccc agcgcgcgct ggtaattatt aacctcgcga atattgattc     120
gaggccgcga ttgccgcaat cgcgaggggc aggtgacctt tgcccagcgc gcgttcgccc     180
cgccccggac ggtatcgata agcttaggag cttgggctgc aggtcgaggg cactgggagg     240
atgttgagta agatggaaaa ctactgatga cccttgcaga gacagagtat taggacatgt     300
ttgaacaggg gccgggcgat cagcaggtag ctctagagga tccccgtctg tctgcacatt     360
tcgtagagcg agtgttccga tactctaatc tccctaggca aggttcatat ttgtgtaggt     420
tacttattct cctttgttg actaagtcaa taatcagaat cagcaggttt ggagtcagct      480
tggcagggat cagcagcctg ggttggaagg aggggtata aaagcccctt caccaggaga     540
agccgtcaca cagatccaca agctcctgcc accatgg                              577
```

LENTIVIRAL VECTOR FORMULATIONS

RELATED APPLICATIONS

This application claims priority to U.S. Provisional Patent Application Ser. No. 62/908,390, filed Sep. 30, 2019, the disclosure of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Sep. 28, 2020, is named "710005_SA9-472_ST25.txt" and is 104,424 bytes in size.

FIELD OF THE INVENTION

The present disclosure concerns formulations of recombinant lentiviral vectors (LVs) and related pharmaceutical products for use in the treatment of disease. In particular, it relates to formulations that improve LV stability and quality, while also being compatible for use in systemic and other types of administration to subjects for treating diseases, including bleeding disorders, such as hemophilia A and hemophilia B.

BACKGROUND

Lentiviral vectors (LVs) and other viral vectors are an attractive tool for gene therapy (Thomas et al., 2003). LVs can transduce a broad range of tissues, including non-dividing cells such as hepatocytes, neurons and hematopoietic stem cells. Moreover, LVs can integrate into target cell genomes and provide long-term transgene expression.

An ongoing challenge in the field of gene therapy and vaccine development is to generate non-toxic liquid formulations that enable LVs to remain structurally stable and biologically active for longer periods of time and withstand conditions such as agitation, freeze/thawing, and storage at a range of temperatures. LV titer has been observed to decrease in a biphasic manner with increased freeze/thaw cycles and storage at higher temperatures (Kigashikawa and Chang 2001, Virology 280, 124-131). In order for gene therapy to be most effective, it is desirable to have lentiviral vectors that maintain their biological activity or potency.

The biological activity of an LV depends on the conformational integrity of an enclosed structure that consists of at least: (a) a core polynucleotide, (b) a shell of inter-linked capsid proteins surrounding the core polynucleotide, and (c) a glycoprotein-embedded lipid membrane surrounding the shell of inter-linked capsid proteins. Unlike organic and inorganic drugs, LVs are highly complex biological structures and minor chemical or physical stressors can contribute to the degradation of the structural integrity of the enclosed structure. Such stressors include osmolarity, buffer, pH, viscosity, electrolytes, agitation, and temperature fluctuations. The structural or conformational integrity of LVs is directly linked to their biological activity or potency. Thus, LVs may lose potency as a result of physical instabilities, including denaturation, soluble and insoluble aggregation, precipitation and adsorption, as well as chemical instabilities, including hydrolysis, deamidation, and oxidation. Any of these types of degradation can result in lowered biological activity, and can also potentially result in the formation of by-products or derivatives having increased toxicity and/or altered immunogenicity. A good formulation of LVs is thus crucially important to ensure not only a reasonable shelf-life, but also lowered toxicity upon administration to a subject, such as via systemic administration. Finding vehicles that stabilize LVs to result in robust formulations, in which the LVs are stable over a wide range of conditions, requires meticulous optimization of buffer type, pH, and excipients. For each set of conditions tested, the stability of the LVs needs to be measured via different experimental methods. Thus, in view of all of the factors that can be varied, finding optimal conditions for formulating LVs is challenging, and the composition of a good formulation is a priori unpredictable.

Accordingly, there is a need in the art to prepare formulations that are suitable for administration to a subject and that improve LV stability by preserving the quantity, structural integrity, and potency of the LVs under a range of conditions. Herein, we disclose formulations that demonstrate improved stability of LVs under a variety of conditions and that are suitable for systemic administration to subjects.

SUMMARY

The present disclosure is based on the unexpected finding that lentiviral vector (LV) formulations with improved stability can be achieved when the LVs are suspended in a vehicle comprising a TRIS-free buffer system (e.g., a phosphate or histidine buffer) in combination with a carbohydrate (e.g., sucrose), a surfactant (e.g., poloxamer or polysorbate), and a salt (e.g., NaCl or other chloride salt). The contribution of a surfactant, e.g., poloxamer, to LV stability was surprising because surfactants are known in the art to destabilize particles bound by lipid membranes. Also surprising was the observation that an LV formulation at a pH range of from about 6.0 to about 7.5 (e.g., a pH of 6.5), improved LV stability, instead of destabilizing LV surface proteins (e.g., capsid proteins and VSV-G proteins) and promoting LV disassembly or breakdown. Moreover, the instant disclosure demonstrates that the LV formulations of the disclosure are particularly suitable for systemic administration (e.g., intravenous administration) to a subject.

In one aspect, the present disclosure provides a recombinant lentiviral vector preparation comprising: (a) a therapeutically effective dose of a recombinant lentiviral vector; (b) a TRIS-free buffer system; (c) a salt; (d) a surfactant; and (e) a carbohydrate, wherein the pharmaceutical composition is suitable for systemic administration to a human patient.

In certain embodiments, the lentiviral vector comprises a nucleotide sequence encoding VSV-G or a fragment thereof.

In certain embodiments, the buffer system comprises a phosphate buffer.

In certain embodiments, the concentration of the phosphate buffer is between 5 mM and 30 mM.

In certain embodiments, the concentration of the phosphate buffer is about 10 to about 20 mM, about 10 to about 15 mM, about 20 to about 30 mM, about 20 to about 25 mM, or about 15 to about 20 mM.

In certain embodiments, the concentration of the salt is between 80 mM and 150 mM.

In certain embodiments, the concentration of the salt is about 100 mM, about 110 mM, about 130 mM, or about 150 mM.

In certain embodiments, the salt is a chloride salt.

In certain embodiments, the chloride salt is NaCl

In certain embodiments, the surfactant is a poloxamer.

In certain embodiments, the poloxamer is selected from the group consisting of poloxamer 101 (P101), poloxamer 105 (P105), poloxamer 108 (P108), poloxamer 122 (P122), poloxamer 123 (P123), poloxamer 124 (P124), poloxamer 181 (P181), poloxamer 182 (P182), poloxamer 183 (P183), poloxamer 184 (P184), poloxamer 185 (P185), poloxamer 188 (P188), poloxamer 212 (P212), poloxamer 215 (P215), poloxamer 217 (P217), poloxamer 231 (P231), poloxamer 234 (P234), poloxamer 235 (P235), poloxamer 237 (P237), poloxamer 238 (P238), poloxamer 282 (P282), poloxamer 284 (P284), poloxamer 288 (P288), poloxamer 331 (P331), poloxamer 333 (P333), poloxamer 334 (P334), poloxamer 335 (P335), poloxamer 338 (P338), poloxamer 401 (P401), poloxamer 402 (P402), poloxamer 403 (P403), poloxamer 407 (P407), and a combination thereof.

In certain embodiments, the poloxamer is poloxamer 188 (P188).

In certain embodiments, the poloxamer is poloxamer 407 (P407).

In certain embodiments, surfactant is a polysorbate.

In certain embodiments, the polysorbate is selected from the group consisting of polysorbate 20, polysorbate 40, polysorbate 60, polysorbate 80, and a combination thereof.

In certain embodiments, the concentration of the surfactant is between 0.01% (w/v) and 0.1% (w/v).

In certain embodiments, the concentration of surfactant is about 0.03% (w/v), about 0.05% (w/v), about 0.07% (w/v), or about 0.09% (w/v).

In certain embodiments, the concentration of the carbohydrate is between 0.5% (w/v) and 5% (w/v).

In certain embodiments, the concentration of the carbohydrate is about 1% (w/v), about 2% (w/v), about 3% (w/v), or about 4% (w/v).

In certain embodiments, the carbohydrate is sucrose.

In certain embodiments, the pH of the buffer system or of the preparation is between 6.0 and 8.0.

In certain embodiments, the pH is between 6.0 and 7.0.

In certain embodiments, the pH is about 6.5.

In certain embodiments, the pH is about 7.0 to about 8.0.

In certain embodiments, the pH is about 7.3.

In one aspect, the present invention is directed to a recombinant lentiviral vector preparation comprising: (a) a therapeutically effective dose of a recombinant lentiviral vector; (b) a histidine buffer system; (c) a salt; (d) a surfactant; and (e) a carbohydrate, wherein the pharmaceutical composition is suitable for systemic administration to a human patient.

In certain embodiments, the lentiviral vector comprises a nucleotide sequence encoding VSV-G or a fragment thereof.

In certain embodiments, the concentration of the histidine buffer is between 5 mM and 30 mM.

In certain embodiments, the concentration of the histidine buffer is about 10 to about 20 mM, about 10 to about 15 mM, about 20 to about 30 mM, about 20 to about 25 mM, or about 15 to about 20 mM.

In certain embodiments, the concentration of salt is between 80 mM and 150 mM.

In certain embodiments, the concentration of the salt is about 100 mM, about 110 mM, about 130 mM, or about 150 mM.

In certain embodiments, the salt is a chloride salt.

In certain embodiments, the chloride salt is NaCl

In certain embodiments, the surfactant is a poloxamer.

In certain embodiments, the poloxamer is selected from the group consisting of poloxamer 101 (P101), poloxamer 105 (P105), poloxamer 108 (P108), poloxamer 122 (P122), poloxamer 123 (P123), poloxamer 124 (P124), poloxamer 181 (P181), poloxamer 182 (P182), poloxamer 183 (P183), poloxamer 184 (P184), poloxamer 185 (P185), poloxamer 188 (P188), poloxamer 212 (P212), poloxamer 215 (P215), poloxamer 217 (P217), poloxamer 231 (P231), poloxamer 234 (P234), poloxamer 235 (P235), poloxamer 237 (P237), poloxamer 238 (P238), poloxamer 282 (P282), poloxamer 284 (P284), poloxamer 288 (P288), poloxamer 331 (P331), poloxamer 333 (P333), poloxamer 334 (P334), poloxamer 335 (P335), poloxamer 338 (P338), poloxamer 401 (P401), poloxamer 402 (P402), poloxamer 403 (P403), poloxamer 407 (P407), and a combination thereof.

In certain embodiments, the poloxamer is poloxamer 188 (P188).

In certain embodiments, the poloxamer is poloxamer 407 (P407).

In certain embodiments, surfactant is a polysorbate.

In certain embodiments, the polysorbate is selected from the group consisting of polysorbate 20, polysorbate 40, polysorbate 60, polysorbate 80, and a combination thereof.

In certain embodiments, the concentration of the surfactant is between 0.01% (w/v) and 0.1% (w/v).

In certain embodiments, the concentration of surfactant is about 0.03% (w/v), about 0.05% (w/v), about 0.07% (w/v), or about 0.09% (w/v).

In certain embodiments, the concentration of the carbohydrate is between 0.5% (w/v) and 5% (w/v).

In certain embodiments, the concentration of the carbohydrate is about 1% (w/v), about 2% (w/v), about 3% (w/v), or about 4% (w/v).

In certain embodiments, the carbohydrate is sucrose.

In certain embodiments, the pH of the buffer system or of the preparation is between 6.0 and 8.0.

In certain embodiments, the pH is between 6.0 and 7.0.

In certain embodiments, the pH is about 6.5.

In certain embodiments, the pH is about 7.0 to about 8.0.

In certain embodiments, the pH is about 7.3.

In one aspect, the present invention is directed to a recombinant lentiviral vector preparation comprising: (a) a therapeutically effective dose of a recombinant lentiviral vector; (b) a phosphate buffer system; (c) a salt; (d) a surfactant; and (e) a carbohydrate, wherein the pharmaceutical composition is suitable for systemic administration to a human patient.

In certain embodiments, the lentiviral vector comprises a nucleotide sequence encoding VSV-G or a fragment thereof.

In certain embodiments, the concentration of the phosphate buffer is between 5 mM and 30 mM.

In certain embodiments, the concentration of the phosphate buffer is about 10 to about 20 mM, about 10 to about 15 mM, about 20 to about 30 mM, about 20 to about 25 mM, or about 15 to about 20 mM.

In certain embodiments, the concentration of the salt is between 80 mM and 150 mM.

In certain embodiments, the concentration of the salt is about 100 mM, about 110 mM, about 130 mM, or about 150 mM.

In certain embodiments, the salt is a chloride salt.

In certain embodiments, the chloride salt is NaCl

In certain embodiments, the surfactant is a poloxamer.

In certain embodiments, the poloxamer is selected from the group consisting of poloxamer 101 (P101), poloxamer 105 (P105), poloxamer 108 (P108), poloxamer 122 (P122), poloxamer 123 (P123), poloxamer 124 (P124), poloxamer 181 (P181), poloxamer 182 (P182), poloxamer 183 (P183), poloxamer 184 (P184), poloxamer 185 (P185), poloxamer 188 (P188), poloxamer 212 (P212), poloxamer 215 (P215), poloxamer 217 (P217), poloxamer 231 (P231), poloxamer 234 (P234), poloxamer 235 (P235), poloxamer 237 (P237), poloxamer 238 (P238), poloxamer 282 (P282), poloxamer 284 (P284), poloxamer 288 (P288), poloxamer 331 (P331), poloxamer 333 (P333), poloxamer 334 (P334), poloxamer 335 (P335), poloxamer 338 (P338), poloxamer 401 (P401), poloxamer 402 (P402), poloxamer 403 (P403), poloxamer 407 (P407), and a combination thereof.

In certain embodiments, the poloxamer is poloxamer 188 (P188).

In certain embodiments, the poloxamer is poloxamer 407 (P407).

In certain embodiments, surfactant is a polysorbate.

In certain embodiments, the polysorbate is selected from the group consisting of polysorbate 20, polysorbate 40, polysorbate 60, polysorbate 80, and a combination thereof.

In certain embodiments, the concentration of the surfactant is between 0.01% (w/v) and 0.1% (w/v).

In certain embodiments, the concentration of surfactant is about 0.03% (w/v), about 0.05% (w/v), about 0.07% (w/v), or about 0.09% (w/v).

In certain embodiments, the concentration of the carbohydrate is between 0.5% (w/v) and 5% (w/v).

In certain embodiments, the concentration of the carbohydrate is about 1% (w/v), about 2% (w/v), about 3% (w/v), or about 4% (w/v).

In certain embodiments, the carbohydrate is sucrose.

In certain embodiments, the pH of the buffer system or of the preparation is between 6.0 and 8.0.

In certain embodiments, the pH is between 6.0 and 7.0.

In certain embodiments, the pH is about 6.5.

In certain embodiments, the pH is about 7.0 to about 8.0.

In certain embodiments, the pH is about 7.3.

In certain embodiments, the recombinant lentiviral vector further comprises a nucleotide sequence at least 80% identical to the Factor VIII (FVIII) coding sequence set forth in SEQ ID NO: 1 or SEQ ID NO: 2.

In certain embodiments, the recombinant lentiviral vector further comprises the Factor VIII (FVIII) coding sequence set forth in SEQ ID NO: 1 or SEQ ID NO: 2.

In certain embodiments, the recombinant lentiviral vector further comprises a nucleotide sequence at least 80% identical to the Factor IX (FIX) coding sequence set forth in SEQ ID NO: 3.

In certain embodiments, the recombinant lentiviral vector further comprises the Factor IX (FIX) coding sequence set forth in SEQ ID NO: 3.

In certain embodiments, the recombinant lentiviral vector further comprises an enhanced transthyretin (ET) promoter.

In certain embodiments, the recombinant lentiviral vector further comprises a nucleotide sequence at least 90% identical to the target sequence for miR-142 set forth in SEQ ID NO: 7.

In certain embodiments, the recombinant lentiviral vector is isolated from transfected host cells selected from the group of: a CHO cell, a HEK293 cell, a BHK21 cell, a PER.C6 cell, an NSO cell, and a CAP cell.

In certain embodiments, the host cells are CD47-positive host cells.

In one aspect, the present invention is directed to a method of treating a human patient with a disorder, wherein the human patient is administered a recombinant lentiviral vector preparation comprising: (a) a therapeutically effective dose of a recombinant lentiviral vector; (b) a TRIS-free buffer system; (c) a salt; (d) a surfactant; and (e) a carbohydrate, wherein the pharmaceutical composition is suitable for systemic administration to a human patient.

In certain embodiments, the preparation is administered systemically to the human patient.

In certain embodiments, the preparation is administered intravenously.

In certain embodiments, the disorder is a bleeding disorder.

In certain embodiments, the bleeding disorder is hemophilia A or hemophilia B.

In another aspect, a recombinant lentiviral vector preparation comprising: (a) a therapeutically effective dose of a recombinant lentiviral vector; (b) a TRIS-free buffer system; (c) a salt; (d) a surfactant; and (e) a carbohydrate, wherein the pH of the buffer system or of the preparation is from about 6.0 to about 7.5, and wherein the pharmaceutical composition is suitable for systemic administration to a human patient, is provided.

In certain exemplary embodiments, the lentiviral vector comprises a nucleotide sequence encoding VSV-G or a fragment thereof.

In certain exemplary embodiments, the buffer system comprises a phosphate buffer or a histidine buffer. In certain exemplary embodiments, the concentration of the phosphate buffer is from about 5 mM to about 30 mM. In certain exemplary embodiments, the concentration of the phosphate buffer is from about 10 mM to about 20 mM, from about 10 mM to about 15 mM, from about 20 mM to about 30 mM, from about 20 mM to about 25 mM, or from about 15 mM to about 20 mM. In certain exemplary embodiments, the concentration of the histidine buffer is from about 5 mM to about 30 mM. In certain exemplary embodiments, the concentration of the histidine buffer is from about 10 mM to about 20 mM, from about 10 mM to about 15 mM, from about 20 mM to about 30 mM, from about 20 mM to about 25 mM, or from about 15 mM to about 20 mM.

In certain exemplary embodiments, the concentration of the salt is from about 80 mM to about 150 mM. In certain exemplary embodiments, the concentration of the salt is about 100 mM, about 110 mM, about 130 mM, or about 150 mM. In certain exemplary embodiments, the salt is a chloride salt. In certain exemplary embodiments, the chloride salt is NaCl.

In certain exemplary embodiments, the surfactant is a poloxamer. In certain exemplary embodiments, the poloxamer is selected from the group consisting of poloxamer 101 (P101), poloxamer 105 (P105), poloxamer 108 (P108), poloxamer 122 (P122), poloxamer 123 (P123), poloxamer 124 (P124), poloxamer 181 (P181), poloxamer 182 (P182), poloxamer 183 (P183), poloxamer 184 (P184), poloxamer 185 (P185), poloxamer 188 (P188), poloxamer 212 (P212), poloxamer 215 (P215), poloxamer 217 (P217), poloxamer 231 (P231), poloxamer 234 (P234), poloxamer 235 (P235), poloxamer 237 (P237), poloxamer 238 (P238), poloxamer 282 (P282), poloxamer 284 (P284), poloxamer 288 (P288), poloxamer 331 (P331), poloxamer 333 (P333), poloxamer 334 (P334), poloxamer 335 (P335), poloxamer 338 (P338), poloxamer 401 (P401), poloxamer 402 (P402), poloxamer 403 (P403), poloxamer 407 (P407), and a combination thereof. In certain exemplary embodiments, the poloxamer is poloxamer 188 (P188). In certain exemplary embodiments, the poloxamer is poloxamer 407 (P407).

In certain exemplary embodiments, the surfactant is a polysorbate. In certain exemplary embodiments, the polysorbate is selected from the group consisting of polysorbate 20, polysorbate 40, polysorbate 60, polysorbate 80, and a combination thereof. In certain exemplary embodiments, the concentration of the surfactant is from about 0.01% (w/v) to about 0.1% (w/v). In certain exemplary embodiments, the concentration of surfactant is about 0.03% (w/v), about 0.05% (w/v), about 0.07% (w/v), or about 0.09% (w/v).

In certain exemplary embodiments, the concentration of the carbohydrate is from about 0.5% (w/v) to about 5% (w/v). In certain exemplary embodiments, the concentration of the carbohydrate is about 1% (w/v), about 2% (w/v), about 3% (w/v), or about 4% (w/v). In certain exemplary embodiments, the carbohydrate is sucrose.

In certain exemplary embodiments, the preparation comprises: (a) a therapeutically effective dose of a recombinant lentiviral vector; (b) about 10 mM phosphate; (c) about 100 mM sodium chloride; (d) about 0.05% (w/v) poloxamer 188; and (e) about 3% (w/v) sucrose, wherein the pH of the preparation is about 7.3, and wherein the pharmaceutical composition is suitable for systemic administration to a human patient.

In certain exemplary embodiments, the preparation comprises: (a) a therapeutically effective dose of a recombinant lentiviral vector; (b) about 10 mM phosphate; (c) about 130 mM sodium chloride; (d) about 0.05% (w/v) poloxamer 188; and (e) about 1% (w/v) sucrose, wherein the pH of the preparation is about 7.3, and wherein the pharmaceutical composition is suitable for systemic administration to a human patient.

In certain exemplary embodiments, the preparation comprises: (a) a therapeutically effective dose of a recombinant lentiviral vector; (b) about 20 mM histidine; (c) about 100 mM sodium chloride; (d) about 0.05% (w/v) poloxamer 188; and (e) about 3% (w/v) sucrose, wherein the pH of the preparation is about 6.5, and wherein the pharmaceutical composition is suitable for systemic administration to a human patient.

In certain exemplary embodiments, the preparation comprises: (a) a therapeutically effective dose of a recombinant lentiviral vector; (b) about 10 mM phosphate; (c) about 100 mM sodium chloride; (d) about 0.05% (w/v) poloxamer 188; and (e) about 3% (w/v) sucrose, wherein the pH of the preparation is about 7.0, and wherein the pharmaceutical composition is suitable for systemic administration to a human patient.

In certain exemplary embodiments, the preparation comprises: (a) a therapeutically effective dose of a recombinant lentiviral vector; (b) about 20 mM histidine; (c) about 100 mM sodium chloride; (d) about 0.05% (w/v) poloxamer 188; and (e) about 3% (w/v) sucrose, wherein the pH of the preparation is about 7.0, and wherein the pharmaceutical composition is suitable for systemic administration to a human patient.

In certain exemplary embodiments, the recombinant lentiviral vector comprises a nucleic acid comprising a nucleotide sequence at least 80%, at least 85%, at least 90%, at least 95%, or at least 99% identical to a Factor VIII (FVIII) coding sequence set forth in SEQ ID NO: 1 or SEQ ID NO: 2. In certain exemplary embodiments, the recombinant lentiviral vector comprises a nucleic acid comprising a Factor VIII (FVIII) coding sequence set forth in SEQ ID NO: 1 or SEQ ID NO: 2. In certain exemplary embodiments, the recombinant lentiviral vector comprises a nucleic acid consisting of a Factor VIII (FVIII) coding sequence set forth in SEQ ID NO: 1 or SEQ ID NO: 2.

In certain exemplary embodiments, the recombinant lentiviral vector comprises a nucleic acid comprising a nucleotide sequence at least 80%, at least 85%, at least 90%, at least 95%, or at least 99% identical to a Factor IX (FIX) coding sequence set forth in SEQ ID NO: 3. In certain exemplary embodiments, the recombinant lentiviral vector comprises a nucleic acid comprising the Factor IX (FIX) coding sequence set forth in SEQ ID NO: 3. In certain exemplary embodiments, the recombinant lentiviral vector comprises a nucleic acid consisting of the Factor IX (FIX) coding sequence set forth in SEQ ID NO: 3.

In certain exemplary embodiments, the recombinant lentiviral vector comprises an enhanced transthyretin (ET) promoter.

In certain exemplary embodiments, the recombinant lentiviral vector further comprises a nucleotide sequence at least 90% identical to the target sequence for miR-142 set forth in SEQ ID NO: 7.

In certain exemplary embodiments, the recombinant lentiviral vector is isolated from a transfected host cell selected from the group of: a CHO cell, a HEK293 cell, a BHK21 cell, a PER.C6 cell, an NSO cell, and a CAP cell. In certain exemplary embodiments, the host cell is a CD47-positive host cell.

In another aspect, a method of treating a human patient with a disorder, comprising administering to the human patient a recombinant lentiviral vector preparation described herein, is provided.

In certain exemplary embodiments, the preparation is administered systemically to the human patient. In certain exemplary embodiments, the preparation is administered intravenously.

In certain exemplary embodiments, the disorder is a bleeding disorder. In certain exemplary embodiments, the bleeding disorder is hemophilia A or hemophilia B.

BRIEF DESCRIPTION OF THE DRAWINGS

FIG. 5A shows that upon agitation stress the lentiviral particles only seem to grow slightly in size. The main peak is assumed to be monomeric lentiviral vector (~130 nm) and the smaller larger peaks may be degradation of the monomeric particle. FIG. 5B shows that the addition of 1% (w/v) poloxamer 188 (P188) did not interfere with the lentiviral particle.

FIG. 6B is normalized to time 0. Each group of bars represent a dilution series of: undiluted (no dilution), 20 fold dilution (20×), 100 fold dilution (100×).

FIG. 8A depict stability of lentiviral vectors (LVs) in the vehicle TSSM (20 mM TRIS, 100 mM NaCl, 1% (w/v) Sucrose, 1% (w/v) Mannitol, pH 7.3) at 37° C. as a function of incubation time in day and weeks, as measured by particle concentration and size using Nanosight. FIG. 8B is reporting the results of the 37° C. stability experiment on a log scale in order to more clearly see differences in particle size over time.

FIG. 10A is reporting the NanoSight data that is normalized to 1 in order to make differences in degradation peaks more visible. FIG. 10B presents the raw data showing a decrease in the monomeric peak over time at 37° C. incubation.

FIG. 12A shows data 3 days at room temperature (RT) and RT with agitation (orbital shaker, 350 rpm), while FIG. 12B shows data for 5 and 10 cycles of Freezing and Thawing (F/T).

DETAILED DESCRIPTION

Figure 1:
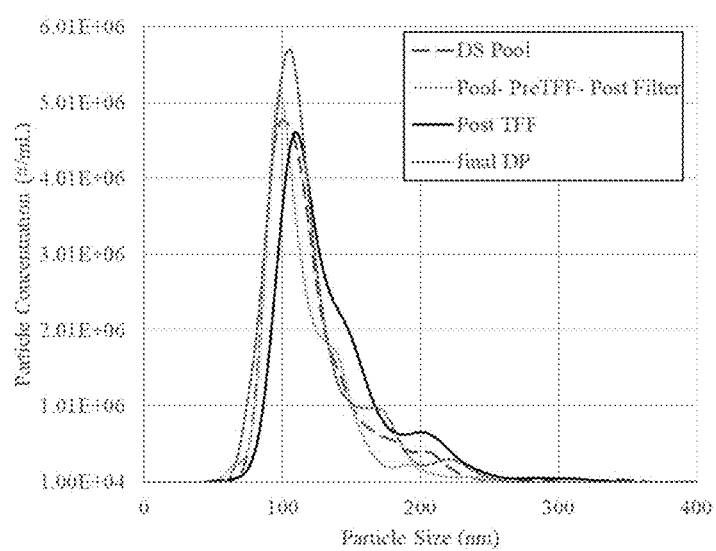
FIG. 1 depicts characterization of lentiviral vector (LV) formulation upon processing into the vehicle Phosphate (10 mM Phosphate, 100 mM NaCl, 3% (w/v) sucrose, 0.05% (w/v) P188, pH 7.3). The drug substance (DS) pool shows a clean monomeric peak, which after ultrafiltration/diafiltration into the final vehicle buffer (post tangential flow filtration—TFF) shifts slightly to a larger size and there is presence of some larger particles. Without being bound to theory this may be due to physical degradation of the particle during the stress of processing the material. The final DP has been filtered through a 0.22 μm sized filter membrane and the profile comes back in line with the DS pool at the start of processing. The effects of the TFF stress can be visually seen in the pictures shown in FIGS. 2A-2B.

This disclosure provides, among other things, preparations (formulations) and pharmaceutical compositions of lentiviral vectors (LVs), including recombinant LVs. The disclosure also provides methods of treating a subject with a disorder, including a bleeding disorder, such as hemophilia A or hemophilia B, using LV preparations. The disclosure further provides processes for producing LV preparations.

Generally, nomenclature used in connection with cell and tissue culture, molecular biology, biophysics, immunology, microbiology, genetics, and protein and nucleic acid chemistry described herein is well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein is well-known and commonly used in the art. Standard techniques are used for chemical syntheses, chemical analyses, pharmaceutical preparation, formulation, and delivery, and treatment of patients.

Unless otherwise defined herein, scientific and technical terms used herein have the meanings that are commonly understood by those of ordinary skill in the art. In the event of any latent ambiguity, definitions provided herein take precedence over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

So that the invention may be more readily understood, certain terms are first defined.

As used herein, the term "vector" refers to any vehicle for the cloning of and/or transfer of a nucleic acid into a host cell. A vector can be a replicon to which another nucleic acid segment can be attached so as to bring about the replication of the attached segment. A "replicon" refers to any genetic element (e.g., plasmid, phage, cosmid, chromosome, virus) that functions as an autonomous unit of replication in vivo, i.e., capable of replication under its own control. The term "vector" includes both viral and nonviral vehicles for introducing the nucleic acid into a cell in vitro, ex vivo or in vivo. A large number of vectors are known and used in the art including, for example, plasmids, modified eukaryotic viruses, or modified bacterial viruses. Insertion of a polynucleotide into a suitable vector can be accomplished by ligating the appropriate polynucleotide fragments into a chosen vector that has complementary cohesive termini.

As used herein, the phrase "recombinant lentiviral vector" refers to a vector with sufficient lentiviral genetic information to allow packaging of an RNA genome, in the presence of packaging components, into a viral particle capable of infecting a target cell. Infection of the target cell may include reverse transcription and integration into the target cell genome. The recombinant lentiviral vector carries non-viral coding sequences which are to be delivered by the vector to the target cell. A recombinant lentiviral vector is incapable of independent replication to produce infectious lentiviral particles within the final target cell. Usually the recombinant lentiviral vector lacks a functional gag-pol and/or env gene and/or other genes essential for replication. The vector of the present invention may be configured as a split-intron vector.

As used herein, the term "treat" refers to an amelioration or reduction of one or more symptoms of a disorder. Treating need not be a cure.

As used herein, the term "human patient" refers to a human being having a disease or disorder and in need of treatment for this disease or disorder.

As used herein, the phrase "systemically administer" refers to prescribing or giving a pharmaceutical composition comprising an LV to a subject, such that the LV is introduced directly into the bloodstream of the subject. Examples of routes of systemic administration include, but are not limited to, intravenous, e.g., intravenous injection and intravenous infusion, e.g., via central venous access.

As used herein, the term "about," when used in reference to a particular recited numerical value, means that the value may vary from the recited value by no more than 10%. For example, as used herein, the expression "about 100" includes 90 and 110 and all values in between (e.g., 90, 91, 92, 93, 94, 95, etc.).

A. Formulations of Lentiviral Vectors (LVs) Comprising TRIS-Free Buffering Systems In one aspect, the present invention is directed to a recombinant lentiviral vector preparation comprising: (a) an effective dose of a recombinant lentiviral vector; (b) a TRIS-free buffer system; (c) a salt; (d) a surfactant; and (e) a carbohydrate, wherein the pharmaceutical composition is suitable for systemic administration to a human patient. In certain embodiments, the vector comprises a nucleotide sequence encoding VSV-G or a fragment thereof. In certain embodiments, the pH of the buffer system is from about 6.0 to about 8.0. In certain embodiments, the pH of the buffer system is from about 6.0 to about 7.5. In certain embodiments, the pH of the buffer system is from about 6.0 to about 7.0. In certain embodiments, the pH of the buffer system is from about 6.0 to about 8.0. In certain embodiments, the pH of the buffer system is about 6.5. In certain embodiments, the pH of the buffer system is about 7.3. In certain embodiments, the buffer system is a phosphate buffer or a histidine buffer. In certain embodiments, the concentration of the phosphate or histidine buffer is from about 5 mM to about 30 mM. In certain embodiments, the concentration of the phosphate buffer is from about 10 mM to about 20 mM, from about 10 mM to about 15 mM, from about 20 mM to about 30 mM, from about 20 mM to about 25 mM, or from about 15 mM to about 20 mM. In certain embodiments, the salt is a chloride salt. In certain embodiments, the concentration of the chloride salt is from about 80 mM to about 150 mM. In certain embodiments, the concentration of the salt is about 100 mM, about 110 mM, about 130 mM, or about 150 mM. In certain embodiments, the surfactant is a poloxamer or a polysorbate. In certain embodiments, the concentration of the poloxamer or polysorbate is from about 0.01% (w/v) to about 0.1% (w/v). In certain embodiments, the carbohydrate is sucrose. In certain embodiments, the concentration of the carbohydrate is from about 0.5% (w/v) to about 5% (w/v). In certain embodiments, the chloride salt is sodium chloride (NaCl). In certain embodiments, the poloxamer is selected from the group consisting of poloxamer 101 (P101), poloxamer 105 (P105), poloxamer 108 (P108), poloxamer 122 (P122), poloxamer 123 (P123), poloxamer 124 (P124), poloxamer 181 (P181), poloxamer 182 (P182), poloxamer 183 (P183), poloxamer 184 (P184), poloxamer 185 (P185), poloxamer 188 (P188), poloxamer 212 (P212), poloxamer 215 (P215), poloxamer 217 (P217), poloxamer 231 (P231), poloxamer 234 (P234), poloxamer 235 (P235), poloxamer 237 (P237), poloxamer 238 (P238), poloxamer 282 (P282), poloxamer 284 (P284), poloxamer 288 (P288), poloxamer 331 (P331), poloxamer 333 (P333), poloxamer 334 (P334), poloxamer 335 (P335), poloxamer 338 (P338), poloxamer 401 (P401), poloxamer 402 (P402), poloxamer 403 (P403), poloxamer 407 (P407), and a combination thereof. In certain embodiments, the polysorbate is selected from the group consisting of polysorbate 20, polysorbate 40, polysorbate 60, polysorbate 80, and a combination thereof. In certain embodiments, the pH of the phosphate or histidine buffer is about 6.1, about 6.3, about 6.5, about 6.7, about 6.9, about 7.1, about 7.3, about 7.5, about 7.7, or about 7.9. In certain embodiments, the concentration of the phosphate or histidine buffer is about 10 mM, about 15 mM, about 20 mM, or about 25 mM. In certain embodiments, the chloride salt is about 100 mM, about 110 mM, about 130 mM, or about 150 mM. In certain embodiments, the concentration of the poloxamer or polysorbate is about 0.03% (w/v), about 0.05% (w/v), about 0.07% (w/v), or about 0.09% (w/v). In certain embodiments, the concentration of the carbohydrate is about 1% (w/v), about 2% (w/v), about 3% (w/v), or about 4% (w/v). In certain embodiments, the poloxamer is poloxamer 188 (P188). In certain embodiments, the poloxamer is poloxamer 407 (P407).

In certain embodiments, the present disclosure provides a recombinant lentiviral vector preparation comprising: (a) a therapeutically effective dose of a recombinant lentiviral vector; (b) about 10 mM phosphate; (c) about 100 mM sodium chloride; (d) about 0.05% (w/v) poloxamer 188; and (e) about 3% (w/v) sucrose, wherein the pH of the preparation is about 7.3, and wherein the pharmaceutical composition is suitable for systemic administration to a human patient.

In certain embodiments, the present disclosure provides a recombinant lentiviral vector preparation comprising: (a) a therapeutically effective dose of a recombinant lentiviral vector; (b) about 10 mM phosphate; (c) about 130 mM sodium chloride; (d) about 0.05% (w/v) poloxamer 188; and (e) about 1% (w/v) sucrose, wherein the pH of the preparation is about 7.3, and wherein the pharmaceutical composition is suitable for systemic administration to a human patient.

In certain embodiments, the present disclosure provides a recombinant lentiviral vector preparation comprising: (a) a therapeutically effective dose of a recombinant lentiviral vector; (b) about 20 mM histidine; (c) about 100 mM sodium chloride; (d) about 0.05% (w/v) poloxamer 188; and (e) about 3% (w/v) sucrose, wherein the pH of the preparation is about 6.5, and wherein the pharmaceutical composition is suitable for systemic administration to a human patient.

In certain embodiments, the present disclosure provides a recombinant lentiviral vector preparation comprising: (a) a therapeutically effective dose of a recombinant lentiviral vector; (b) about 10 mM phosphate; (c) about 100 mM sodium chloride; (d) about 0.05% (w/v) poloxamer 188; and (e) about 3% (w/v) sucrose, wherein the pH of the preparation is about 7.0, and wherein the pharmaceutical composition is suitable for systemic administration to a human patient.

In certain embodiments, the present disclosure provides a recombinant lentiviral vector preparation comprising: (a) a therapeutically effective dose of a recombinant lentiviral vector; (b) about 20 mM histidine; (c) about 100 mM sodium chloride; (d) about 0.05% (w/v) poloxamer 188; and (e) about 3% (w/v) sucrose, wherein the pH of the preparation is about 7.0, and wherein the pharmaceutical composition is suitable for systemic administration to a human patient.

A.1. Lentiviral Vectors

Lentiviral vectors are part of a larger group of retroviral vectors (Coffin et al. (1997) "Retroviruses" Cold Spring Harbor Laboratory Press Eds: J M Coffin, S M Hughes, H E Varmus pp 758-763). Examples of primate lentiviruses include: the human immunodeficiency virus (HIV) and the simian immunodeficiency virus (SIV). The lentivirus family differs from retroviruses in that lentiviruses have the capability to infect both dividing and non-dividing cells (Lewis et al. (1992); Lewis and Emerman (1994)).

A lentiviral vector, as used herein, is a vector which comprises at least one component part derivable from a lentivirus. Preferably, that component part is involved in the biological mechanisms by which the vector infects cells, expresses genes or is replicated. In a recombinant lentiviral vector at least part of one or more protein coding regions essential for replication may be removed from the virus. This makes the viral vector replication-defective. Portions of the viral genome may also be replaced by a transgene, thus rendering the vector capable of transducing a target non-dividing host cell and/or integrating its genome into a host genome.

A recombinant lentiviral is usually pseudotyped. Pseudotyping can confer one or more advantages. For example, the env gene product of the HIV based vectors would restrict these vectors to infecting only cells that express a protein called CD4. But if the env gene in these vectors has been substituted with env sequences from other RNA viruses, then they may have a broader infectious spectrum (Verma and Somia (1997)). The envelope glycoprotein (G) of Vesicular stomatitis virus (VSV), a rhabdovirus, is an envelope protein that has been shown to be capable of pseudotyping certain retroviruses. Pseudotyped VSV-G vectors may be used to transduce a wide range of mammalian cells. The incorporation of a non-lentiviral pseudotyping envelope, such as VSV-G protein gives the advantage that vector particles can be concentrated to a high titre without loss of infectivity (Akkina et al. (1996) J. Virol. 70:2581-5). Lentivirus and retrovirus envelope proteins are apparently unable to withstand the shearing forces during ultracentrifugation, probably because they consist of two non-covalently linked subunits. The interaction between the subunits may be disrupted by the centrifugation. In comparison the VSV glycoprotein is composed of a single unit. VSV-G protein pseudotyping can therefore offer potential advantages.

Lentiviruses include members of the bovine lentivirus group, equine lentivirus group, feline lentivirus group, ovinecaprine lentivirus group, and primate lentivirus group. The development of lentivirus vectors for gene therapy has been reviewed in Klimatcheva et al. (1999) Frontiers in Bioscience 4:481-496. The design and use of lentiviral vectors suitable for gene therapy is described for example in U.S. Pat. Nos. 6,207,455 and 6,615,782. Examples of lentivirus include, but are not limited to, HIV-1, HIV-2, HIV-1/HIV-2 pseudotype, HIV-1/SIV, FIV, caprine arthritis encephalitis virus (CAEV), equine infectious anemia virus, and bovine immunodeficiency virus.

In some embodiments, the lentiviral vector of the present disclosure is a "third-generation" lentiviral vector. As used herein, the term "third-generation" lentiviral vector refers to a lentiviral packaging system that has the characteristics of a second-generation vector system, and that further lacks a functional tat gene, such as one from which the tat gene has been deleted or inactivated. Typically, the gene encoding rev is provided on a separate expression construct. See, e.g., Dull et al. (1998) J. Virol. 72: 8463-8471. As used herein, a "second-generation" lentiviral vector system refers to a lentiviral packaging system that lacks functional accessory genes, such as one from which the accessory genes vif, vpr, vpu, and nef have been deleted or inactivated. See, e.g., Zufferey et al. (1997) Nat. Biotechnol. 15:871-875. As used herein, "packaging system" refers to a set of viral constructs comprising genes that encode viral proteins involved in packaging a recombinant virus. Typically, the constructs of the packaging system will ultimately be incorporated into a packaging cell.

In some embodiments, the third-generation lentiviral vector of the present disclosure is a self-inactivating lentiviral vector. In some embodiments, the lentiviral vector is a VSV.G pseudo type lentiviral vector. In some embodiments, the lentiviral vector comprises a hepatocyte-specific promoter for transgene expression. In some embodiments, the hepatocyte-specific promoter is an enhanced transthyretin promoter. In some embodiments, the lentiviral vector comprises one or more target sequences for miR-142 to reduce immune response to the transgene product. In some embodiments, incorporating one or more target sequences for miR-142 into a lentiviral vector of the present disclosure allows for a desired transgene expression profile. For example, incorporating one or more target sequences for miR-142 may suppress transgene expression in intravascular and extravascular hematopoietic lineages, whereas transgene expression is maintained in nonhematopoietic cells. No oncogenesis has been detected in tumor prone mice treated with the lentivirus vector system of the present disclosure. See Brown et al. (2007) Blood 110:4144-52, Brown at al. (2006) Nat. Ned. 12:585-91, and Cantore et al. (2015) Sci. Transl. Med. 7(277):277ra28.

Lentiviral vectors of the disclosure include codon optimized polynucleotides of transgenes encoding specific proteins, such as the FVIII or FIX protein described herein. In one embodiment, the optimized coding sequences for the FVIII or FIX protein is operably linked to an expression control sequence. As used herein, two nucleic acid sequences are operably linked when they are covalently linked in such a way as to permit each component nucleic acid sequence to retain its functionality. A coding sequence and a gene expression control sequence are said to be operably linked when they are covalently linked in such a way as to place the expression or transcription and/or translation of the coding sequence under the influence or control of the gene expression control sequence. Two DNA sequences are said to be operably linked if induction of a promoter in the 5' gene expression sequence results in the transcription of the coding sequence and if the nature of the linkage between the two DNA sequences does not (1) result in the introduction of a frame-shift mutation, (2) interfere with the ability of the promoter region to direct the transcription of the coding sequence, or (3) interfere with the ability of the corresponding RNA transcript to be translated into a protein. Thus, a gene expression sequence would be operably linked to a coding nucleic acid sequence if the gene expression sequence were capable of effecting transcription of that coding nucleic acid sequence such that the resulting transcript is translated into the desired protein or polypeptide.

In certain embodiments, the lentiviral vector is a vector of a recombinant lentivirus capable of infecting non-dividing cells. In certain embodiments, the lentiviral vector is a vector of a recombinant lentivirus capable of infecting liver cells (e.g., hepatocytes). The lentiviral genome and the proviral DNA typically have the three genes found in retroviruses: gag, pol and env, which are flanked by two long terminal repeat (LTR) sequences. The gag gene encodes the internal structural (matrix, capsid and nucleocapsid) proteins; the pol gene encodes the RNA-directed DNA polymerase (reverse transcriptase), a protease and an integrase; and the env gene encodes viral envelope glycoproteins. The 5' and 3' LTR's serve to promote transcription and polyadenylation of the virion RNA's. The LTR contains all other cis-acting sequences necessary for viral replication. Lentiviruses have additional genes including vif, vpr, tat, rev, vpu, nef and vpx (in HIV-1, HIV-2 and/or SIV).

Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virions) are missing from the viral genome, the cis defect prevents encapsidation of genomic RNA.

However, the resulting mutant remains capable of directing the synthesis of all virion proteins. The disclosure provides a method of producing a recombinant lentivirus capable of infecting a non-dividing cell comprising transfecting a suitable host cell with two or more vectors carrying the packaging functions, namely gag, pol and env, as well as rev and tat. As will be disclosed herein below, vectors lacking a functional tat gene are desirable for certain applications. Thus, for example, a first vector can provide a nucleic acid encoding a viral gag and a viral pol and another vector can provide a nucleic acid encoding a viral env to produce a packaging cell. Introducing a vector providing a heterologous gene, herein identified as a transfer vector, into that packaging cell yields a producer cell which releases infectious viral particles carrying the foreign gene of interest.

According to the above-indicated configuration of vectors and foreign genes, the second vector can provide a nucleic acid encoding a viral envelope (env) gene. The env gene can be derived from nearly any suitable virus, including retroviruses. In some embodiments, the env protein is an amphotropic envelope protein which allows transduction of cells of human and other species.

Examples of retroviral-derived env genes include, but are not limited to: Moloney murine leukemia virus (MoMuLV or MMLV), Harvey murine sarcoma virus (HaMuSV or HSV), murine mammary tumor virus (MuMTV or MMTV), gibbon ape leukemia virus (GaLV or GALV), human immunodeficiency virus (HIV) and Rous sarcoma virus (RSV). Other env genes such as Vesicular stomatitis virus (VSV) protein G (VSV-G), that of hepatitis viruses and of influenza also can be used. In some embodiments, the viral env nucleic acid sequence is associated operably with regulatory sequences described elsewhere herein. In certain embodiments, a formulation buffer of the present disclosure confers lentivirus stability and affords long term frozen storage, in particular, for lentivirus comprising VSV-G. A formulation buffer of the present invention offers enhanced lentivirus stability upon freezing and thawing as well as exposure to elevated temperatures, in particular, for lentivirus comprising VSV-G.

In certain embodiments, the lentiviral vector has the HIV virulence genes env, vif, vpr, vpu and nef deleted without compromising the ability of the vector to transduce non-dividing cells. In some embodiments, the lentiviral vector comprises a deletion of the U3 region of the 3' LTR. The deletion of the U3 region can be the complete deletion or a partial deletion.

In some embodiments, the lentiviral vector of the disclosure comprising the FVIII nucleotide sequence described herein can be transfected in a cell with (a) a first nucleotide sequence comprising a gag, a pol, or gag and pol genes and (b) a second nucleotide sequence comprising a heterologous env gene; wherein the lentiviral vector lacks a functional tat gene. In other embodiments, the cell is further transfected with a fourth nucleotide sequence comprising a rev gene. In certain embodiments, the lentiviral vector lacks functional genes selected from vif, vpr, vpu, vpx and nef, or a combination thereof.

In certain embodiments, a lentiviral vector of the instant disclosure comprises one or more nucleotide sequences encoding a gag protein, a Rev-response element, a central polypurine track (cPPT), or any combination thereof.

In some embodiments, the lentiviral vector expresses on its surface one or more polypeptides that improve the targeting and/or activity of the lentiviral vector or the encoded FVIII polypeptide. The one or more polypeptides can be encoded by the lentiviral vector or can be incorporated during budding of the lentiviral vector from a host cell. During lentiviral production, viral particles bud off from a producing host cell. During the budding process, the viral particle takes on a lipid coat, which is derived from the lipid membrane of the host cell. As a result, the lipid coat of the viral particle can include membrane bound polypeptides that were previously present on the surface of the host cell.

In some embodiments, the lentiviral vector expresses one or more polypeptides on its surface that inhibit an immune response to the lentiviral vector following administration to a human subject. In some embodiments, the surface of the lentiviral vector comprises one or more CD47 molecules. CD47 is a "marker of self" protein, which is ubiquitously expressed on human cells. Surface expression of CD47 inhibits macrophage-induced phagocytosis of endogenous cells through the interaction of CD47 and macrophage expressed-SIRPα. Cells expressing high levels of CD47 are less likely to be targeted and destroyed by human macrophages in vivo.

In some embodiments, the lentiviral vector comprises a high concentration of CD47 polypeptide molecules on its surface. In some embodiments, the lentiviral vector is produced in a cell line that has a high expression level of CD47. In certain embodiments, the lentiviral vector is produced in a $CD47^{high}$ cell, wherein the cell has high expression of CD47 on the cell membrane. In particular embodiments, the lentiviral vector is produced in a $CD47^{high}$ HEK 293T cell, wherein the HEK 293T is has high expression of CD47 on the cell membrane. In some embodiments, the HEK 293T cell is modified to have increased expression of CD47 relative to unmodified HEK 293T cells. In certain embodiments, the CD47 is human CD47.

In some embodiments, the lentiviral vector has little or no surface expression of major histocompatibility complex class I (MHC-I). Surface expressed MHC-I displays peptide fragments of "non-self" proteins from within a cell, such as protein fragments indicative of an infection, facilitating an immune response against the cell. In some embodiments, the lentiviral vector is produced in a $MHC-I^{low}$ cell, wherein the cell has reduced expression of MHC-I on the cell membrane. In some embodiments, the lentiviral vector is produced in an $MHC-I^-$ (or "$MHC-I^{free}$", "$MH-1^{neg}$" or "MHC-negative") cell, wherein the cell lacks expression of MHC-I.

In particular embodiments, the lentiviral vector comprises a lipid coat comprising a high concentration of CD47 polypeptides and lacking C-polypeptides. In certain embodiments, the lentiviral vector is produced in a $CD47^{high}$/$MHC-I^{low}$ cell line, e.g., a $CD47^{high}$/$MHC-I^{low}$ HEK 293T cell line. In some embodiments, the lentiviral vector is produced in a $CD47^{high}$/$MHC-I^{free}$ cell line, e.g., a $CD47^{high}$/$MHC-I^{free}$ HEK 293T cell line.

Examples of lentiviral vectors are disclosed in U.S. Pat. No. 9,050,269 and International Publication Nos. WO9931251, WO9712622, WO9817815, WO9817816, and WO9818934, which are incorporated herein by reference in their entireties.

In some embodiments, the present disclosure provides a lentiviral vector comprising an isolated nucleic acid molecule comprising a nucleotide sequence which comprises a nucleotide sequence as shown in Table 1.

TABLE 1

Sequences

| SEQ ID NO | Description | Sequence |
|---|---|---|
| 1 | FVIII coding sequence | ATGCAGATTGAGCTGTCCACTTGTTTCTTCCTGTGCCTCCTGC GCTTCTGTTTCTCCGCCACTCGCCGGTACTACCTTGGAGCCGT GGAGCTTTCATGGGACTACATGCAGAGCGACCTGGGCGAAC TCCCCGTGGATGCCAGATTCCCCCCCCGCGTGCCAAAGTCCT TCCCCTTTAACACCTCCGTGGTGTACAAGAAAACCCTCTTTG TCGAGTTCACTGACCACCTGTTCAACATCGCCAAGCCGCGCC CACCTTGGATGGGCCTCCTGGGACCGACCATTCAAGCTGAAG TGTACGACACCGTGGTGATCACCCTGAAGAACATGGCGTCCC ACCCCGTGTCCCTGCATGCGGTCGGAGTGTCCTACTGGAAGG CCTCCGAAGGAGCTGAGTACGACGACCAGACTAGCCAGCGG GAAAAGGAGGACGATAAAGTGTTCCCGGGCGGCTCGCATAC TTACGTGTGGCAAGTCCTGAAGGAAAACGGACCTATGGCAT CCGATCCTCTGTGCCTGACTTACTCCTACCTTTCCCATGTGGA CCTCGTGAAGGACCTGAACAGCGGGCTGATTGGTGCACTTCT CGTGTGCCGCGAAGGTTCGCTCGCTAAGGAAAAGACCCAGA CCCTCCATAAGTTCATCCTTTTGTTCGCTGTGTTCGATGAAGG AAAGTCATGGCATTCCGAAACTAAGAACTCGCTGATGCAGG ACCGGGATGCCGCCTCAGCCCGCGCCTGGCCTAAAATGCAT ACAGTCAACGGATACGTGAATCGGTCACTGCCCGGGCTCATC GGTTGTCACAGAAAGTCCGTGTACTGGCACGTCATCGGCATG GGCACTACGCCTGAAGTGCACTCCATCTTCCTGGAAGGGCAC ACCTTCCTCGTGCGCAACCACCGCCAGGCCTCTCTGGAAATC TCCCCGATTACCTTTCTGACCGCCCAGACTCTGCTCATGGAC CTGGGGCAGTTCCTTCTCTTCTGCCACATCTCCAGCCATCAG CACGACGGAATGGAGGCCTACGTGAAGGTGGACTCATGCCC GGAAGAACCTCAGTTGCGGATGAAGAACAACGAGGAGGCCG AGGACTATGACGACGATTTGACTGACTCCGAGATGGACGTC GTGCGGTTCGATGACGACAACAGCCCCAGCTTCATCCAGATT |

TABLE 1-continued

Sequences

| SEQ ID NO | Description | Sequence |
|---|---|---|
| | | CGCAGCGTGGCCAAGAAGCACCCCAAAACCTGGGTGCACTA
CATCGCGGCCGAGGAAGAAGATTGGGACTACGCCCCGTTGG
TGCTGGCACCCGATGACCGGTCGTACAAGTCCCAGTATCTGA
ACAATGGTCCGCAGCGGATTGGCAGAAAGTACAAGAAAGTG
CGGTTCATGGCGTACACTGACGAAACGTTTAAGACCCGGGA
GGCCATTCAACATGAGAGCGGCATTCTGGGACCACTGCTGTA
CGGAGAGGTCGGCGATACCCTGCTCATCATCTTCAAAAACCA
GGCCTCCCGGCCTTACAACATCTACCCTCACGGAATCACCGA
CGTGCGGCCACTCTACTCGCGGCGCCTGCCGAAGGGCGTCA
AGCACCTGAAAGACTTCCCTATCCTGCCGGGCGAAATCTTCA
AGTATAAGTGGACCGTCACCGTGGAGGACGGGCCCACCAAG
AGCGATCCTAGGTGTCTGACTCGGTACTACTCCAGCTTCGTG
AACATGGAACGGGACCTGGCATCGGGACTCATTGGACCGCT
GCTGATCTGCTACAAAGAGTCGGTGGATCAACGCGGCAACC
AGATCATGTCCGACAAGCGCAACGTGATCCTGTTCTCCGTGT
TTGATGAAAACAGATCCTGGTACCTCACTGAAAACATCCAG
AGGTTCCTCCCAAACCCCGCAGGAGTGCAACTGGAGGACCC
TGAGTTTCAGGCCTCGAATATCATGCACTCGATTAACGGTTA
CGTGTTCGACTCGCTGCAGCTGAGCGTGTGCCTCCATGAAGT
CGCTTACTGGTACATTCTGTCCATCGGCGCCCAGACTGACTT
CCTGAGCGTGTTCTTTTCCGGTTACACCTTTAAGCACAAGAT
GGTGTACGAAGATACCCTGACCCTGTTCCCTTTCTCCGGCGA
AACGGTGTTCATGTCGATGGAGAACCCGGGTCTGTGGATTCT
GGGATGCCACAACAGCGACTTTCGGAACCGCGGAATGACTG
CCCTGCTGAAGGTGTCCTCATGCGACAAGAACACCGGAGAC
TACTACGAGGACTCCTACGAGGATATCTCAGCCTACCTCCTG
TCCAAGAACAACGCGATCGAGCCGCGCAGCTTCAGCCAGAA
CCCGCCTGTGCTGAAGAGGCACCAGCGAGAAATTACCCGGA
CCACCCTCCAATCGGATCAGGAGGAAATCGACTACGACGAC
ACCATCTCGGTGGAAATGAAGAAGGAAGATTTCGATATCTA
CGACGAGGACGAAAATCAGTCCCCTCGCTCATTCCAAAAGA
AAACTAGACACTACTTTATCGCCGCGGTGGAAAGACTGTGG
GACTATGGAATGTCATCCAGCCCTCACGTCCTTCGGAACCGG
GCCCAGAGCGGATCGGTGCCTCAGTTCAAGAAAGTGGTGTT
CCAGGAGTTCACCGACGGCAGCTTCACCCAGCCGCTGTACC
GGGGAGAACTGAACGAACACCTGGGCCTGCTCGGTCCCTAC
ATCCGCGCGGAAGTGGAGGATAACATCATGGTGACCTTCCG
TAACCAAGCATCCAGACCTTACTCCTTCTATTCCTCCCTGATC
TCATACGAGGAGGACCAGCGCCAAGGCGCCGAGCCCCGCAA
GAACTTCGTCAAGCCCAACGAGACTAAGACCTACTTCTGGA
AGGTCCAACACCATATGGCCCCGACCAAGGATGAGTTTGAC
TGCAAGGCCTGGGCCTACTTCTCCGACGTGGACCTTGAGAAG
GATGTCCATTCCGGCCTGATCGGGCCGCTGCTCGTGTGTCAC
ACCAACACCCTGAACCCAGCGCATGGACGCCAGGTCACCGT
CCAGGAGTTTGCTCTGTTCTTCACCATTTTTGACGAAACTAA
GTCCTGGTACTTCACCGAGAATATGGAGCGAAACTGTAGAG
CGCCCTGCAATATCCAGATGGAAGATCCGACTTTCAAGGAG
AACTATAGATTCCACGCCATCAACGGGTACATCATGGATACT
CTGCCGGGGCTGGTCATGGCCCAGGATCAGAGGATTCGGTG
GTACTTGCTGTCAATGGGATCGAACGAAAACATTCACTCCAT
TCACTTCTCCGGTCACGTGTTCACTGTGCGCAAGAAGGAGGA
GTACAAGATGGCGCTGTACAATCTGTACCCCGGGGTGTTCGA
AACTGTGGAGATGCTGCCGTCCAAGGCCGGCATCTGGAGAG
TGGAGTGCCTGATCGGAGAGCACCTCCACGCGGGGATGTCC
ACCCTCTTCCTGGTGTACTCGAATAAGTGCCAGACCCCGCTG
GGCATGGCCTCGGGCCACATCAGAGACTTCCAGATCACAGC
AAGCGGACAATACGGCCAATGGGCGCCGAAGCTGGCCCGCT
TGCACTACTCCGGATCGATCAACGCATGGTCCACCAAGGAA
CCGTTCTCGTGGATTAAGGTGGACCTCCTGGCCCCTATGATT
ATCCACGGAATTAAGACCCAGGGCGCCAGGCAGAAGTTCTC
CTCCCTGTACATCTCGCAATTCATCATCATGTACAGCCTGGA
CGGGAAGAAGTGGCAGACTTACAGGGGAAACTCCACCGGCA
CCCTGATGGTCTTTTTCGGCAACGTGGATTCCTCCGGCATTA
AGCACAACATCTTCAACCCACCGATCATAGCCAGATATATTA
GGCTCCACCCCACTCACTACTCAATCCGCTCAACTCTTCGGA
TGGAACTCATGGGGTGCGACCTGAACTCCTGCTCCATGCCGT
TGGGGATGGAATCAAAGGCTATTAGCGACGCCCAGATCACC
GCGAGCTCCTACTTCACTAACATGTTCGCCACCTGGAGCCCC
TCCAAGGCCAGGCTGCACTTGCAGGGACGGTCAAATGCCTG
GCGGCCGCAAGTGAACAATCCGAAGGAATGGCTTCAAGTGG
ATTTCCAAAAGACCATGAAAGTGACCGGAGTCACCACCCAG
GGAGTGAAGTCCCTTCTGACCTCGATGTATGTGAAGGAGTTC
CTGATTAGCAGCAGCCAGGACGGGCACCAGTGGACCCTGTT
CTTCCAAAACGGAAAGGTCAAGGTGTTCCAGGGGAACCAGG |

TABLE 1-continued

Sequences

| SEQ ID NO | Description | Sequence |
|---|---|---|
|  |  | ACTCGTTCACACCCGTGGTGAACTCCCTGGACCCCCCACTGC TGACGCGGTACTTGAGGATTCATCCTCAGTCCTGGGTCCATC AGATTGCATTGCGAATGGAAGTCCTGGGCTGCGAGGCCCAG GACCTGTAC |
| 2 | FVIII coding sequence comprising XTEN (XTEN in bold and underline) | ATGCAGATTGAGCTGTCCACTTGTTTCTTCCTGTGCCTCCTGC GCTTCTGTTTCTCCGCCACTCGCCGGTACTACCTTGGAGCCGT GGAGCTTTCATGGGACTACATGCAGAGCGACCTGGGCGAAC TCCCCGTGGATGCCAGATTCCCCCCCCGCGTGCCAAAGTCCT TCCCCTTTAACACCTCCGTGGTGTACAAGAAAACCCTCTTTG TCGAGTTCACTGACCACCTGTTCAACATCGCCAAGCCGCGCC CACCTTGGATGGGCCTCCTGGGACCGACCATTCAAGCTGAAG TGTACGACACCGTGGTGATCACCCTGAAGAACATGGCGTCCC ACCCCGTGTCCCTGCATGCGGTCGGAGTGTCCTACTGGAAGG CCTCCGAAGGAGCTGAGTACGACGACCAGACTAGCCAGCGG GAAAAGGAGGACGATAAAGTGTTCCCGGGCGGCTCGCATAC TTACGTGTGGCAAGTCCTGAAGGAAAACGGACCTATGGCAT CCGATCCTCTGTGCCTGACTTACTCCTACCTTTCCCATGTGGA CCTCGTGAAGGACCTGAACAGCGGGCTGATTGGTGCACTTCT CGTGTGCCGCGAAGGTTCGCTCGCTAAGGAAAAGACCCAGA CCCTCCATAAGTTCATCCTTTTGTTCGCTGTGTTCGATGAAGG AAAGTCATGGCATTCCGAAACTAAGAACTCGCTGATGCAGG ACCGGGATGCCGCCTCAGCCCGCGCCTGGCCTAAAATGCAT ACAGTCAACGGATACGTGAATCGGTCACTGCCCGGGCTCATC GGTTGTCACAGAAAGTCCGTGTACTGGCACGTCATCGGCATG GGCACTACGCCTGAAGTGCACTCCATCTTCCTGGAAGGGCAC ACCTTCCTCGTGCGCAACCACCGCCAGGCCTCTCTGGAAATC TCCCCGATTACCTTTCTGACCGCCCAGACTCTGCTCATGGAC CTGGGGCAGTTCCTTCTCTTCTGCCACATCTCCAGCCATCAG CACGACGGAATGGAGGCCTACGTGAAGGTGGACTCATGCCC GGAAGAACCTCAGTTGCGGATGAAGAACAACGAGGAGGCCG AGGACTATGACGACGATTTGACTGACTCCGAGATGGACGTC GTGCGGTTCGATGACGACAACAGCCCCAGCTTCATCCAGATT CGCAGCGTGGCCAAGAAGCACCCCAAAACCTGGGTGCACTA CATCGCGGCCGAGGAAGAAGATTGGGACTACGCCCCGTTGG TGCTGGCACCCGATGACCGGTCGTACAAGTCCCAGTATCTGA ACAATGGTCCGCAGCGGATTGGCAGAAAGTACAAGAAAGTG CGGTTCATGGCGTACACTGACGAAACGTTTAAGACCCGGGA GGCCATTCAACATGAGAGCGGCATTCTGGGACCACTGCTGTA CGGAGAGGTCGGCGATACCCTGCTCATCATCTTCAAAAACCA GGCCTCCCGGCCTTACAACATCTACCCTCACGGAATCACCGA CGTGCGGCCACTCTACTCGCGGCGCCTGCCGAAGGGCGTCA AGCACCTGAAAGACTTCCCTATCCTGCCGGGCGAAATCTTCA AGTATAAGTGGACCGTCACCGTGGAGGACGGGCCCACCAAG AGCGATCCTAGGTGTCTGACTCGGTACTACTCCAGCTTCGTG AACATGGAACGGGACCTGGCATCGGGACTCATTGGACCGCT GCTGATCTGCTACAAAGAGTCGGTGGATCAACGCGGCAACC AGATCATGTCCGACAAGCGCAACGTGATCCTGTTCTCCGTGT TTGATGAAAACAGATCCTGGTACCTCACTGAAAACATCCAG AGGTTCCTCCCAAACCCCGCAGGAGTGCAACTGGAGGACCC TGAGTTTCAGGCCTCGAATATCATGCACTCGATTAACGGTTA CGTGTTCGACTCGCTGCAGCTGAGCGTGTGCCTCCATGAAGT CGCTTACTGGTACATTCTGTCCATCGGCGCCCAGACTGACTT CCTGAGCGTGTTCTTTTCCGGTTACACCTTTAAGCACAAGAT GGTGTACGAAGATACCCTGACCCTGTTCCCTTTCTCCGGCGA AACGGTGTTCATGTCGATGGAGAACCCGGGTCTGTGGATTCT GGGATGCCACAACAGCGACTTTCGGAACCGCGGAATGACTG CCCTGCTGAAGGTGTCCTCATGCGACAAGAACACCGGAGAC TACTACGAGGACTCCTACGAGGATATCTCAGCCTACCTCCTG TCCAAGAACAACGCGATCGAGCCGCGCAGCTTCAGCCAGAA CACATCAGAGAGCGCCACCCCTGAAAGTGGTCCCGGGAG CGAGCCAGCCACATCTGGGTCGGAAACGCCAGGCACAAG TGAGTCTGCAACTCCCGAGTCCGGACCTGGCTCCGAGCC TGCCACTAGCGGCTCCGAGACTCCGGGAACTTCCGAGAG CGCTACACCAGAAAGCGGACCCGAACCAGTACCGAACC TAGCGAGGGCTCTGCTCCGGGCAGCCCAGCCGGCTCTCC TACATCCACGGAGGAGGGCACTTCCGAATCCGCCACCCC GGAGTCAGGGCCAGGATCTGAACCCGCTACCTCAGGCAG TGAGACGCCAGGAACGAGCGAGTCCGCTACACCGGAGA GTGGGCCAGGGAGCCCTGCTGGATCTCCTACGTCCACTG AGGAAGGGTCACCAGCGGGCTCGCCCACCAGCACTGAAG AAGGTGCCTCGAGCCCGCCTGTGCTGAAGAGGCACCAGCG AGAAATTACCCGGACCACCCTCCAATCGGATCAGGAGGAAA TCGACTACGACGACACCATCTCGGTGGAAATGAAGAAGGAA |

TABLE 1-continued

Sequences

| SEQ ID NO | Description | Sequence |
|---|---|---|
| | | GATTTCGATATCTACGACGAGGACGAAAATCAGTCCCCTCGC
TCATTCCAAAAGAAAACTAGACACTACTTTATCGCCGCGGTG
GAAAGACTGTGGGACTATGGAATGTCATCCAGCCCTCACGTC
CTTCGGAACCGGGCCCAGAGCGGATCGGTGCCTCAGTTCAA
GAAAGTGGTGTTCCAGGAGTTCACCGACGGCAGCTTCACCC
AGCCGCTGTACCGGGGAGAACTGAACGAACACCTGGGCCTG
CTCGGTCCCTACATCCGCGCGGAAGTGGAGGATAACATCAT
GGTGACCTTCCGTAACCAAGCATCCAGACCTTACTCCTTCTA
TTCCTCCCTGATCTCATACGAGGAGGACCAGCGCCAAGGCGC
CGAGCCCCGCAAGAACTTCGTCAAGCCCAACGAGACTAAGA
CCTACTTCTGGAAGGTCCAACACCATATGGCCCCGACCAGG
ATGAGTTTGACTGCAAGGCCTGGGCCTACTTCTCCGACGTGG
ACCTTGAGAAGGATGTCCATTCCGGCCTGATCGGGCCGCTGC
TCGTGTGTCACACCAACACCCTGAACCCAGCGCATGGACGC
CAGGTCACCGTCCAGGAGTTTGCTCTGTTCTTCACCCATTTTG
ACGAAACTAAGTCCTGGTACTTCACCGAGAATATGGAGCGA
AACTGTAGAGCGCCCTGCAATATCCAGATGGAAGATCCGAC
TTTCAAGGAGAACTATAGATTCCACGCCATCAACGGGTACAT
CATGGATACTCTGCCGGGGCTGGTCATGGCCCAGGATCAGA
GGATTCGGTGGTACTTGCTGTCAATGGGATCGAACGAAAAC
ATTCACTCCATTCACTTCTCCGGTCACGTGTTCACTGTGCGCA
AGAAGGAGGAGTACAAGATGGCGCTGTACAATCTGTACCCC
GGGGTGTTCGAAACTGTGGAGATGCTGCCGTCCAAGGCCGG
CATCTGGAGAGTGGAGTGCCTGATCGGAGAGCACCTCCACG
CGGGGATGTCCACCCTCTTCCTGGTGTACTCGAATAAGTGCC
AGACCCCGCTGGGCATGGCCTCGGGCCACATCAGAGACTTC
CAGATCACAGCAAGCGGACAATACGGCCAATGGGCGCCGAA
GCTGGCCCGCTTGCACTACTCCGGATCGATCAACGCATGGTC
CACCAAGGAACCGTTCTCGTGGATTAAGGTGGACCTCCTGGC
CCCTATGATTATCCACGGAATTAAGACCCAGGGCGCCAGGC
AGAAGTTCTCCTCCCTGTACATCTCGCAATTCATCATCATGT
ACAGCCTGGACGGGAAGAAGTGGCAGACTTACAGGGGAAAC
TCCACCGGCACCCTGATGGTCTTTTTCGGCAACGTGGATTCC
TCCGGCATTAAGCACAACATCTTCAACCCACCGATCATAGCC
AGATATATTAGGCTCCACCCCACTCACTACTCAATCCGCTCA
ACTCTTCGGATGGAACTCATGGGGTGCGACCTGAACTCCTGC
TCCATGCCGTTGGGGATGGAATCAAAGGCTATTAGCGACGC
CCAGATCACCGCGAGCTCCTACTTCACTAACATGTTCGCCAC
CTGGAGCCCCTCCAAGGCCAGGCTGCACTTGCAGGGACGGT
CAAATGCCTGGCGGCCGCAAGTGAACAATCCGAAGGAATGG
CTTCAAGTGGATTTCCAAAAGACCATGAAAGTGACCGGAGT
CACCACCCAGGGAGTGAAGTCCCTTCTGACCTCGATGTATGT
GAAGGAGTTCCTGATTAGCAGCAGCCAGGACGGGCACCAGT
GGACCCTGTTCTTCCAAAACGGAAAGGTCAAGGTGTTCCAG
GGGAACCAGGACTCGTTCACACCCGTGGTGAACTCCCTGGA
CCCCCCACTGCTGACGCGGTACTTGAGGATTCATCCTCAGTC
CTGGGTCCATCAGATTGCATTGCGAATGGAAGTCCTGGGCTG
CGAGGCCCAGGACCTGTAC |
| 3 | FIX-R338L coding sequence (signal peptide in bold and underline) | **ATGCAGAGAGTCAACATGATTATGGCTGAGTCACCTGGG
CTGATTACTATTTGCCTGCTGGGCTACCTGCTGTCCGCC
GAGTGTACCGTGTTCCTGGACCATGAGAACGCAAATAAG
ATCCTGAACAGGCCCAAAAGA**TACAATAGTGGGAAGCTGG
AGGAATTTGTGCAGGGCAACCTGGAGAGAGAATGCATGGAG
GAAAAGTGTAGCTTCGAGGAAGCCCGCGAGGTGTTTGAAAA
TACAGAGCGAACCACAGAGTTCTGGAAGCAGTATGTGGACG
GCGATCAGTGCGAGAGCAACCCCTGTCTGAATGGCGGAAGT
TGCAAAGACGATATCAACTCATACGAATGCTGGTGTCCTTTC
GGGTTTGAAGGCAAAAATTGCGAGCTGGACGTGACATGTAA
CATTAAGAATGGACGGTGCGAGCAGTTTTGTAAAAACTCTGC
CGATAATAAGGTGGTGTGCAGCTGTACTGAAGGATATCGCCT
GGCTGAGAACCAGAAGTCCTGCGAACCAGCAGTGCCCTTCC
CTTGTGGGAGGGTGAGCGTCTCCCAGACTTCAAAACTGACCA
GAGCAGAGACAGTGTTTCCCGACGTGGATTACGTCAACAGC
ACTGAGGCCGAAACCATCCTGGACAACATTACTCAGTCTACC
CAGAGTTTCAATGACTTTACTCGGGTGGTCGGGGGCGAGGAT
GCTAAACCAGGCCAGTTCCCCTGGCAGGTGGTCCTGAACGG
AAAGGTGGATGCATTTTGCGGAGGGTCTATCGTGAATGAGA
AATGGATTGTCACCGCCGCTCACTGCGTGGAAACCGGAGTC
AAGATCACAGTGGTCGCTGGGGAGCACAACATTGAGGAAAC
AGAACATACTGAGCAGAAGCGGAATGTGATCCGCATCATTC
CTCACCATAACTACAATGCAGCCATCAACAAATACAATCATG
ACATTGCCCTGCTGGAACTGGATGAGCCTCTGGTGCTGAACA
GCTACGTCACTCCAATCTGCATTGCTGACAAAGAGTATACCA |

TABLE 1-continued

Sequences

| SEQ ID NO | Description | Sequence |
|---|---|---|
| | | ATATCTTCCTGAAGTTTGGATCAGGGTACGTGAGCGGCTGGG<br>GAAGAGTCTTCCACAAGGGCAGGAGCGCCCTGGTGCTCCAG<br>TATCTGCGAGTGCCTCTGGTCGATCGAGCTACCTGTCTGCTC<br>TCTACCAAGTTTACAATCTACAACAACATGTTCTGCGCTGGG<br>TTTCACGAGGGAGGACGAGACTCCTGTCAGGGCGATTCTGG<br>GGGCCCACATGTGACAGAGGTCGAAGGCACCAGCTTCCTGA<br>CTGGCATCATTTCCTGGGGAGAGGAATGTGCAATGAAGGGA<br>AAATACGGGATCTACACCAAAGTGAGCCGCTATGTGAACTG<br>GATCAAGGAAAAAACCAAACTGACC |
| 4 | Mature FVIII polypeptide | ATRRYYLGAVELSWDYMQSDLGELPVDARFPPRVPKSFPFNTS<br>VVYKKTLFVEFTDHLFNIAKPRPPWMGLLGPTIQAEVYDTVVIT<br>LKNMASHPVSLHAVGVSYWKASEGAEYDDQTSQREKEDDKVF<br>PGGSHTYVWQVLKENGPMASDPLCLTYSYLSHVDLVKDLNSG<br>LIGALLVCREGSLAKEKTQTLHKFILLFAVFDEGKSWHSETKNS<br>LMQDRDAASARAWPKMHTVNGYVNRSLPGLIGCHRKSVYWH<br>VIGMGTTPEVHSIFLEGHTFLVRNHRQASLEISPITFLTAQTLLM<br>DLGQFLLFCHISSHQHDGMEAYVKVDSCPEEPQLRMKNNEEAE<br>DYDDDLTDSEMDVVRFDDDNSPSFIQIRSVAKKHPKTWVHYIA<br>AEEEDWDYAPLVLAPDDRSYKSQYLNNGPQRIGRKYKKVRFM<br>AYTDETFKTREAIQHESGILGPLLYGEVGDTLLIIFKNQASRPYNI<br>YPHGITDVRPLYSRRLPKGVKHLKDFPILPGEIFKYKWTVTVED<br>GPTKSDPRCLTRYYSSFVNMERDLASGLIGPLLICYKESVDQRG<br>NQIMSDKRNVILFSVFDENRSWYLTENIQRFLPNPAGVQLEDPE<br>FQASNIMHSINGYVFDSLQLSVCLHEVAYWYILSIGAQTDFLSV<br>FFSGYTFKHKMVYEDTLTLFPFSGETVFMSMENPGLWILGCHN<br>SDFRNRGMTALLKVSSCDKNTGDYYEDSYEDISAYLLSKNNAI<br>EPRSFSQNSRHPSTRQKQFNATTIPENDIEKTDPWFAHRTPMPKI<br>QNVSSSDLLMLLRQSPTPHGLSLSDLQEAKYETFSDDPSPGAIDS<br>NNSLSEMTHFRPQLHHSGDMVFTPESGLQLRLNEKLGTTAATE<br>LKKLDFKVSSTSNNLISTIPSDNLAAGTDNTSSLGPPSMPVHYDS<br>QLDTTLFGKKSSPLTESGGPLSLSEENNDSKLLESGLMNSQESS<br>WGKNVSSTESGRLFKGKRAHGPALLTKDNALFKVSISLLKTNK<br>TSNNSATNRKTHIDGPSLLIENSPSVWQNILESDTEFKKVTPLIH<br>DRMLMDKNATALRLNHMSNKTTSSKNMEMVQQKKEGPIPPD<br>AQNPDMSFFKMLFLPESARWIQRTHGKNSLNSGQGPSPKQLVS<br>LGPEKSVEGQNFLSEKNKVVVGKGEFTKDVGLKEMVFPSSRNL<br>FLTNLDNLHENNTHNQEKKIQEEIEKKETLIQENVVLPQIHTVTG<br>TKNFMKNLFLLSTRQNVEGSYDGAYAPVLQDFRSLNDSTNRTK<br>KHTAHFSKKGEEENLEGLGNQTKQIVEKYACTTRISPNTSQQNF<br>VTQRSKRALKQFRLPLEETELEKRIIVDDTSTQWSKNMKHLTPS<br>TLTQIDYNEKEKGAITQSPLSDCLTRSHSIPQANRSPLPIAKVSSF<br>PSIRPIYLTRVLFQDNSSHLPAASYRKKDSGVQESSHFLQGAKK<br>NNLSLAILTLEMTGDQREVGSLGTSATNSVTYKKVENTVLPKP<br>DLPKTSGKVELLPKVHIYQKDLFPTETSNGSPGHLDLVEGSLLQ<br>GTEGAIKWNEANRPGKVPFLRVATESSAKTPSKLLDPLAWDNH<br>YGTQIPKEEWKSQEKSPEKTAFKKKDTILSLNACESNHAIAAINE<br>GQNKPEIEVTWAKQGRTERLCSQNPPVLKRHQREITRTTLQSDQ<br>EEIDYDDTISVEMKKEDFDIYDEDENQSPRSFQKKTRHYFIAAV<br>ERLWDYGMSSSPHVLRNRAQSGSVPQFKKVVFQEFTDGSFTQP<br>LYRGELNEHLGLLGPYIRAEVEDNIMVTFRNQASRPYSFYSSLIS<br>YEEDQRQGAEPRKNFVKPNETKTYFWKVQHHMAPTKDEFDCK<br>AWAYFSDVDLEKDVHSGLIGPLLVCHTNTLNPAHGRQVTVQEF<br>ALFFTIFDETKSWYFTENMERNCRAPCNIQMEDPTFKENYRFHA<br>INGYIMDTLPGLVMAQDQRIRWYLLSMGSNENIHSIHFSGHVFT<br>VRKKEEYKMALYNLYPGVFETVEMLPSKAGIWRVECLIGEHLH<br>AGMSTLFLVYSNKCQTPLGMASGHIRDFQITASGQYGQWAPKL<br>ARLHYSGSINAWSTKEPFSWIKVDLLAPMIIHGIKTQGARQKFSS<br>LYISQFIEVIYSLDGKKWQTYRGNSTGTLMVFFGNVDSSGIKHNI<br>FNPPIIARYIRLHPTHYSIRSTLRMELMGCDLNSCSMPLGMESKA<br>ISDAQITASSYFTNMFATWSPSKARLHLQGRSNAWRPQVNNPK<br>EWLQVDFQKTMKVTGVTTQGVKSLLTSMYVKEFLISSSQDGH<br>QWTLFFQNGKVKVFQGNQDSFTPVVNSLDPPLLTRYLRIHPQS<br>WVHQIALRMEVLGCEAQDLY |
| 5 | FVIII amino acid sequence comprising XTEN (XTEN in bold and underline) | MQIELSTCFFLCLLRFCFSATRRYYLGAVELSWDYMQSDLGELP<br>VDARFPPRVPKSFPFNTSVVYKKTLFVEFTDHLFNIAKPRPPWM<br>GLLGPTIQAEVYDTVVITLKNMASHPVSLHAVGVSYWKASEGA<br>EYDDQTSQREKEDDKVFPGGSHTYVWQVLKENGPMASDPLCL<br>TYSYLSHVDLVKDLNSGLIGALLVCREGSLAKEKTQTLHKFILL<br>FAVFDEGKSWHSETKNSLMQDRDAASARAWPKMHTVNGYVN<br>RSLPGLIGCHRKSVYWHVIGMGTTPEVHSIFLEGHTFLVRNHRQ<br>ASLEISPITFLTAQTLLMDLGQFLLFCHISSHQHDGMEAYVKVD<br>SCPEEPQLRMKNNEEAEDYDDDLTDSEMDVVRFDDDNSPSFIQI |

TABLE 1-continued

Sequences

| SEQ ID NO | Description | Sequence |
|---|---|---|
| | | RSVAKKHPKTWVHYIAAEEEDWDYAPLVLAPDDRSYKSQYLN NGPQRIGRKYKKVRFMAYTDETFKTREAIQHESGILGPLLYGEV GDTLLIIFKNQASRPYNIYPHGITDVRPLYSRRLPKGVKHLKDFP ILPGEIFKYKWTVTVEDGPTKSDPRCLTRYYSSFVNMERDLASG LIGPLLICYKESVDQRGNQIMSDKRNVILFSVFDENRSWYLTENI QRFLPNPAGVQLEDPEFQASNIMHSINGYVFDSLQLSVCLHEVA YWYILSIGAQTDFLSVFFSGYTFKHKMVYEDTLTLFPFSGETVF MSMENPGLWILGCHNSDFRNRGMTALLKVSSCDKNTGDYYED SYEDISAYLLSKNNAIEPRSFSQNTSESATPESGPGSEPATSGSE TPGTSESATPESGPGSEPATSGSETPGTSESATPESGPGTSTE PSEGSAPGSPAGSPTSTEEGTSESATPESGPGSEPATSGSETP GTSESATPESGPGSPAGSPTSTEEGSPAGSPTSTEEGASSPPVL KRHQREITRTTLQSDQEEIDYDDTISVEMKKEDFDIYDEDENQS PRSFQKKTRHYFIAAVERLWDYGMSSSPHVLRNRAQSGSVPQF KKVVFQEFTDGSFTQPLYRGELNEHLGLLGPYIRAEVEDNIMVT FRNQASRPYSFYSSLISYEEDQRQGAEPRKNFVKPNETKTYFWK VQHFIMAPTKDEFDCKAWAYFSDVDLEKDVHSGLIGPLLVCHT NTLNPAHGRQVTVQEFALFFTIFDETKSWYFTENMERNCRAPC NIQMEDPTFKENYRFHAINGYIMDTLPGLVMAQDQRIRWYLLS MGSNENIHSIHFSGHVFTVRKKEEYKMALYNLYPGVFETVEML PSKAGIWRVECLIGEHLHAGMSTLFLVYSNKCQTPLGMASGHI RDFQITASGQYGQWAPKLARLHYSGSINAWSTKEPFSWIKVDL LAPMIIHGIKTQGARQKFSSLYISQFIIMYSLDGKKWQTYRGNST GTLMVFFGNVDSSGIKHNIFNPPIIARYIRLHPTHYSIRSTLRMEL MGCDLNSCSMPLGMESKAISDAQITASSYFTNMFATWSPSKAR LHLQGRSNAWRPQVNNPKEWLQVDFQKTMKVTGVTTQGVKS LLTSMYVKEFLISSSQDGHQWTLFFQNGKVKVFQGNQDSFTPV VNSLDPPLLTRYLRIHPQSWVHQIALRMEVLGCEAQDLY |
| 6 | FIX-R338L amino acid sequence (signal peptide in bold and underline) | <u>MQRVNMIMAESPGLITICLLGYLLSAECTVFLDHENANKIL NRPKR</u>YNSGKLEEFVQGNLERECMEEKCSFEEAREVFENTERT TEFWKQYVDGDQCESNPCLNGGSCKDDINSYECWCPFGFEGK NCELDVTCNIKNGRCEQFCKNSADNKVVCSCTEGYRLAENQKS CEPAVPFPCGRVSVSQTSKLTRAETVFPDVDYVNSTEAETILDNI TQSTQSFNDFTRVVGGEDAKPGQFPWQVVLNGKVDAFCGGSIV NEKWIVTAAHCVETGVKITVVAGEHNIEETEHTEQKRNVIRIIPH HNYNAAINKYNHDIALLELDEPLVLNSYVTPICIADKEYTNIFLK FGSGYVSGWGRVFHKGRSALVLQYLRVPLVDRATCLLSTKFTI YNNMFCAGFHEGGRDSCQGDSGGPHVTEVEGTSFLTGIISWGE ECAMKGKYGIYTKVSRYVNWIKEKTKLT |
| 7 | Target sequence for miR-142 | tccataaagtaggaaacactaca |

The lentiviral vectors of the present disclosure are therapeutically effective when administered at doses of 5×10¹⁰ TU/kg or lower, 10⁹ TU/kg or lower, or 10⁸ TU/kg or lower. At such dosages, the administration of the lentiviral vectors of the disclosure can result in an increase in plasma FVIII activity in a subject in need thereof at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 20-fold, at least about 25-fold, at least about 30-fold, at least about 35-fold, at least about 40-fold, at least about 45-fold, at least about 50-fold, at least about 55-fold, at least about 60-fold, at least about 65-fold, at least about 70-fold, at least about 75-fold, at least about 80-fold, at least about 85-fold, at least about 90-fold, at least about 95-fold, at least about 100-fold, at least about 110-fold, at least about 120-fold, at least about 130-fold, at least about 140-fold, at least about 150-fold, at least about 160-fold, at least about 170-fold, at least about 180-fold, at least about 190-fold, or at least about 200-fold with respect to basal levels in the subject, relative to levels in a subject administered a control lentiviral vector, relative to levels in a subject administered a control nucleic acid molecule, or relative to levels in a subject after administration of a polypeptide encoded by the control nucleic acid molecule.

In certain embodiments, it will be useful to include within the lentiviral vector one or more miRNA target sequences which, for example, are operably linked to the transgene, such as the optimized FVIII transgene. Thus, the disclosure also provides at least one miRNA sequence target operably linked to the optimized FVIII or optimized FIX nucleotide sequence or otherwise inserted within a lentiviral vector. More than one copy of a miRNA target sequence included in the lentiviral vector can increase the effectiveness of the system.

Also included are different miRNA target sequences. For example, lentiviral vectors which express more than one transgene can have the transgene under control of more than one miRNA target sequence, which can be the same or different. The miRNA target sequences can be in tandem, but other arrangements are also included. The transgene expression cassette, containing miRNA target sequences, can also be inserted within the lentiviral vector in antisense orientation. Antisense orientation can be useful in the production of viral particles to avoid expression of gene products which can otherwise be toxic to the producer cells.

In other embodiments, the lentiviral vector comprises 1, 2, 3, 4, 5, 6, 7 or 8 copies of the same or different miRNA target sequence. In certain embodiments, the lentiviral vector does not include any miRNA target sequence. Choice of whether or not to include an miRNA target sequence (and how many) will be guided by known parameters such as the intended tissue target, the level of expression required, etc.

In one embodiment, the target sequence is an miR-223 target which has been reported to block expression most effectively in myeloid committed progenitors and at least partially in the more primitive HSPC. miR-223 target can block expression in differentiated myeloid cells including granulocytes, monocytes, macrophages, myeloid dendritic cells. miR-223 target can also be suitable for gene therapy applications relying on robust transgene expression in the lymphoid or erythroid lineage. miR-223 target can also block expression very effectively in human HSC.

In another embodiment, the target sequence is an miR142 target (tccataaagtaggaaacactaca (SEQ ID NO: 7)). In one embodiment, the lentiviral vector comprises 4 copies of miR-142 target sequences. In certain embodiments, the complementary sequence of hematopoietic-specific microRNAs, such as miR-142 (142T), is incorporated into the 3' untranslated region of a lentiviral vector, making the transgene-encoding transcript susceptible to miRNA-mediated down-regulation. By this method, transgene expression can be prevented in hematopoietic-lineage antigen presenting cells (APC), while being maintained in non-hematopoietic cells (Brown et al., Nat Med 2006). This strategy can impose a stringent post-transcriptional control on transgene expression and thus enables stable delivery and long-term expression of transgenes. In some embodiments, miR-142 regulation prevents immune-mediated clearance of transduced cells and/or induce antigen-specific Regulatory T cells (T regs) and mediate robust immunological tolerance to the transgene-encoded antigen.

In some embodiments, the target sequence is an miR181 target. Chen C-Z and Lodish H, Seminars in Immunology (2005) 17(2):155-165 discloses miR-181, a miRNA specifically expressed in B cells within mouse bone marrow (Chen and Lodish, 2005). It also discloses that some human miRNAs are linked to leukemias.

The target sequence can be fully or partially complementary to the miRNA. The term "fully complementary" means that the target sequence has a nucleic acid sequence which is 100% complementary to the sequence of the miRNA which recognizes it. The term "partially complementary" means that the target sequence is only in part complementary to the sequence of the miRNA which recognizes it, whereby the partially complementary sequence is still recognized by the miRNA. In other words, a partially complementary target sequence in the context of the present disclosure is effective in recognizing the corresponding miRNA and effecting prevention or reduction of transgene expression in cells expressing that miRNA. Examples of the miRNA target sequences are described at W2007/000668, WO2004/094642, WO2010/055413, or WO2010/125471, which are incorporated herein by reference in their entireties.

A.2. Excipients, Carriers, and Other Constituents of Formulations

For purposes of gene therapy, lentiviral vectors (LVs) are often administered systemically, i.e., directly into the bloodstream of patients. Thus, it is of wide interest to create formulations of LVs that are not toxic, yet still maintain stability and potency of the LVs. When testing vehicles to create LV formulations suitable for systemic administration, certain core principles must be kept in mind. To ensure minimal shock to the subject to which the formulation is being administered, pH, ionic concentration, and osmolarity must be optimized to match physiological conditions. The combination of which buffers, salts, and carbohydrates (to regulate pH, ionic concentration, and osmolarity, respectively) is not a priori determinable and must be tested experimentally.

For example, US20170073702A1 discloses the TSSM vehicle (20 mM TRIS, 100 mM NaCl, 1% (w/v) Sucrose, 1% (w/v) Mannitol, pH 7.3), which could have been predicted to be non-toxic in systemic administration to mammals. However, it was found (see Example 2) that a formulation using TSSM alone or in combination with LVs was toxic to mice. Surprisingly, however, when a Phosphate vehicle (10 mM phosphate, 100 mM NaCl, 3% (w/v) sucrose, 0.05% (w/v) P188, pH 7.3) or Histidine vehicle (20 mM histidine, 100 mM NaCl, 3% (w/v) sucrose, 0.05% (w/v) P188, pH 6.5) was used, the formulation was not toxic to mice.

As would not have been predicted a priori, the formulation with the Phosphate vehicle resulted in higher stability and integrity of LVs as compared to the TSSM formulation (Example 3 and Example 4). Unexpectedly, the Histidine vehicle conferred greater stability on LVs than the Phosphate vehicle (Example 4). This key feature of the Histidine formulation, namely the compatibility of the lentiviral vector with the lower pH of the vehicle (pH 6.5) as compared to the neutral pH (pH 7.3) of phosphate or TRIS buffers, was surprising at least for the following reason. The VSV-G envelope protein is an important component of the lentiviral vector, which facilitates its infectivity into the cell. The pI (isoelectric point) of VSV-G is approx. 5, which means that as the pH of the solution nears the pI, the charge on the protein becomes more neutral. As proteins become more neutral in charge, their ability to attract one another is greater and this may lead to aggregation (degradation mechanism) thereby losing the ability to infect.

Also surprising was that the inclusion of a surfactant, poloxamer 188 (P188), in the Phosphate and Histidine formulations conferred increased LV stability and integrity as compared to the TSSM formulation. This was unexpected because surfactants would have been predicted to destabilize the outer lipid membrane envelope of the LVs, thus decreasing LV stability and integrity. Similarly, the removal of mannitol from the formulation would not have been a priori obvious to result in formulations with higher LV stability and integrity (Example 3 and Example 4).

As such, based on the findings described herein, a lentiviral vector preparation comprising a TRIS-free buffer system was found to provide increased lentiviral vector stability and integrity. It will be appreciated by those of skill in the art that a TRIS-free buffer system refers to any buffer system that does not comprise TRIS (also known as tris(hydroxymethyl)aminomethane, tromethamine, or THAM). In certain embodiments, the TRIS-free buffer system comprises phosphate. In certain embodiments, the TRIS-free buffer system comprises histidine.

In certain embodiments, the pH of the TRIS-free buffer system or of the preparation is from about 6.0 to about 8.0. In certain embodiments, the pH of the TRIS-free buffer system or of the preparation is from about 6.0 to about 7.5. In certain embodiments, the pH of the TRIS-free buffer system or of the preparation is from about 6.0 to about 7.0.

In certain embodiments, the pH of the TRIS-free buffer system or of the preparation is from about 7.0 to about 8.0. In certain embodiments, the pH of the TRIS-free buffer system or of the preparation is about 6.5. In certain embodiments, the pH of the TRIS-free buffer system or of the preparation is about 7.3.

The skilled artisan will be able to determine a suitable buffer component to be employed in a TRIS-free buffer system of a preparation disclosed herein in order to maintain the target pH or target pH range. In certain embodiments, the TRIS-free buffer system comprises a buffer component having an effective pH buffering range of from about 6.0 to about 8.0. In certain embodiments, the TRIS-free buffer system comprises a buffer component having an effective pH buffering range of from about 6.0 to about 7.5. In certain embodiments, the TRIS-free buffer system comprises a buffer component having an effective pH buffering range of from about 6.0 to about 7.0. In certain embodiments, the TRIS-free buffer system comprises a buffer component having an effective pH buffering range of from about 7.0 to about 8.0. In certain embodiments, the TRIS-free buffer system comprises a buffer component having an effective pH buffering range that can maintain a pH of 6.5. In certain embodiments, the TRIS-free buffer system comprises a buffer component having an effective pH buffering range that can maintain a pH of 7.3.

Compositions containing a lentiviral gene therapy vector disclosed herein, or a host cell of the present disclosure (e.g., a hepatocyte targeted with a lentiviral gene therapy vector disclosed herein) can contain a suitable pharmaceutically acceptable carrier. For example, they can contain excipients and/or auxiliaries that facilitate processing of the active compounds into preparations designed for delivery to the site of action.

The pharmaceutical composition can be formulated for parenteral administration (i.e. intravenous, subcutaneous, or intramuscular) by bolus injection. Formulations for injection can be presented in unit dosage form, e.g., in ampoules or in multidose containers with an added preservative. The compositions can take such forms as suspensions, solutions, or emulsions in oily or aqueous vehicles, and contain formulatory agents such as suspending, stabilizing and/or dispersing agents. Alternatively, the active ingredient can be in powder form for constitution with a suitable vehicle, e.g., pyrogen free water.

Suitable formulations for parenteral administration also include aqueous solutions of the active compounds in water-soluble form, for example, water-soluble salts. In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides. Aqueous injection suspensions can contain substances, which increase the viscosity of the suspension, including, for example, sodium carboxymethyl cellulose, sorbitol and dextran. Optionally, the suspension can also contain stabilizers. Liposomes also can be used to encapsulate the molecules of the disclosure for delivery into cells or interstitial spaces. Exemplary pharmaceutically acceptable carriers are physiologically compatible solvents, dispersion media, coatings, antibacterial and antifungal agents, isotonic and absorption delaying agents, water, saline, phosphate buffered saline, dextrose, glycerol, ethanol and the like. In some embodiments, the composition comprises isotonic agents, for example, sugars, polyalcohols such as mannitol, sorbitol, or sodium chloride. In other embodiments, the compositions comprise pharmaceutically acceptable substances such as wetting agents or minor amounts of auxiliary substances such as wetting or emulsifying agents, preservatives or buffers, which enhance the shelf life or effectiveness of the active ingredients.

Compositions of the disclosure can be in a variety of forms, including, for example, liquid (e.g., injectable and infusible solutions), dispersions, suspensions, semi-solid and solid dosage forms. The preferred form depends on the mode of administration and therapeutic application.

The composition can be formulated as a solution, micro emulsion, dispersion, liposome, or other ordered structure suitable to high drug concentration. Sterile injectable solutions can be prepared by incorporating the active ingredient in the required amount in an appropriate solvent with one or a combination of ingredients enumerated above, as required, followed by filtered sterilization. Generally, dispersions are prepared by incorporating the active ingredient into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The active ingredient can be formulated with a controlled-release formulation or device. Examples of such formulations and devices include implants, transdermal patches, and microencapsulated delivery systems. Biodegradable, biocompatible polymers can be used, for example, ethylene vinyl acetate, polyanhydrides, polyglycolic acid, collagen, polyorthoesters, and polylactic acid. Methods for the preparation of such formulations and devices are known in the art. See, e.g., Sustained and Controlled Release Drug Delivery Systems, J. R. Robinson, ed., Marcel Dekker, Inc., New York, 1978.

Injectable depot formulations can be made by forming microencapsulated matrices of the drug in biodegradable polymers such as polylactide-polyglycolide. Depending on the ratio of drug to polymer, and the nature of the polymer employed, the rate of drug release can be controlled. Other exemplary biodegradable polymers are polyorthoesters and polyanhydrides. Depot injectable formulations also can be prepared by entrapping the drug in liposomes or microemulsions.

Supplementary active compounds can be incorporated into the compositions. In one embodiment, the chimeric protein of the disclosure is formulated with another clotting factor, or a variant, fragment, analogue, or derivative thereof. For example, the clotting factor includes, but is not limited to, factor V, factor VII, factor VIII, factor IX, factor X, factor XI, factor XII, factor XIII, prothrombin, fibrinogen, von Willebrand factor or recombinant soluble tissue factor (rsTF) or activated forms of any of the preceding. The clotting factor of hemostatic agent can also include anti-fibrinolytic drugs, e.g., epsilon-amino-caproic acid, tranexamic acid.

Dosage regimens can be adjusted to provide the optimum desired response. For example, a single bolus can be administered, several divided doses can be administered over time, or the dose can be proportionally reduced or increased as indicated by the exigencies of the therapeutic situation. It is advantageous to formulate parenteral compositions in dosage unit form for ease of administration and uniformity of dosage. See, e.g., Remington's Pharmaceutical Sciences (Mack Pub. Co., Easton, Pa. 1980).

In addition to the active compound, the liquid dosage form can contain inert ingredients such as water, ethyl alcohol, ethyl carbonate, ethyl acetate, benzyl alcohol, benzyl benzoate, propylene glycol, 1,3-butylene glycol, dimethylformamide, oils, glycerol, tetrahydrofurfuryl alcohol, polyethylene glycols, and fatty acid esters of sorbitan.

Non-limiting examples of suitable pharmaceutical carriers are also described in Remington's Pharmaceutical Sciences by E. W. Martin. Some examples of excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition can also contain pH buffering reagents, and wetting or emulsifying agents.

For oral administration, the pharmaceutical composition can take the form of tablets or capsules prepared by conventional means. The composition can also be prepared as a liquid for example a syrup or a suspension. The liquid can include suspending agents (e.g., sorbitol syrup, cellulose derivatives or hydrogenated edible fats), emulsifying agents (lecithin or acacia), non-aqueous vehicles (e.g., almond oil, oily esters, ethyl alcohol, or fractionated vegetable oils), and preservatives (e.g., methyl or propyl-p-hydroxybenzoates or sorbic acid). The preparations can also include flavoring, coloring and sweetening agents. Alternatively, the composition can be presented as a dry product for constitution with water or another suitable vehicle.

For buccal administration, the composition can take the form of tablets or lozenges according to conventional protocols.

For administration by inhalation, the compounds for use according to the present disclosure are conveniently delivered in the form of a nebulized aerosol with or without excipients or in the form of an aerosol spray from a pressurized pack or nebulizer, with optionally a propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The pharmaceutical composition can also be formulated for rectal administration as a suppository or retention enema, e.g., containing conventional suppository bases such as cocoa butter or other glycerides.

In one embodiment, the pharmaceutical composition comprises a lentiviral vector comprising an optimized nucleic acid molecule encoding a polypeptide having Factor VIII or Factor IX activity, and a pharmaceutically acceptable carrier. In another embodiment, the pharmaceutical composition comprises a host cell (e.g., a hepatocyte) comprising a lentiviral vector comprising an optimized nucleic acid molecule encoding a polypeptide having Factor VIII or Factor IX activity, and a pharmaceutically acceptable carrier.

In some embodiments, the composition is administered by a route selected from the group consisting of topical administration, intraocular administration, parenteral administration, intrathecal administration, subdural administration and oral administration. The parenteral administration can be intravenous or subcutaneous administration.

A fundamental aspect for ensuring the transition of therapeutic formulations from the lab into manufacturable and marketable products of high and consistent quality is their stability in the dosage form. Owing to their complex chemistry and structure, proteins, such as surface and capsid proteins of viruses, are susceptible to various forms of physical and chemical degradation that can compromise the biological efficacy and safety of the final drug product. Protein aggregation for example is a key quality attribute that is routinely monitored for protein-based products and is critical to the determination of product shelf life. At a fundamental level, protein aggregation is linked to the stability of the native form of the protein, with a growth in non-native cell (e.g., a non-native mammalian cell) generally linked to an increased rate and extent of aggregation. Thus, it is no surprise that attempts to control and minimize aggregation during product shelf life (kinetic stability) are often mediated through the use of excipients or formulation conditions intended to increase conformational stability of the protein. Essentially, the intent is to stabilize the protein in its native conformation in order to minimize the population of aggregation-competent "non-native" species. Sugars and polyols, such as sucrose, trehalose, mannitol, sorbitol etc. are often used to stabilize proteins in their native state and reduce rates of aggregation. However, an unwanted effect of using these stabilizers is the concentration-dependent increase in solution viscosity.

Solution viscosity is a key attribute of protein products especially those that are formulated at high protein concentrations and it can critically impact the utility and success of the product. The manufacturability of a product and the end use by the patient or healthcare practitioner is intimately linked to the ability of a solution to flow seamlessly. High viscosity, for example, can necessitate the use of specialized administration devices or protocols which may not always be suitable for the desired population thereby limiting the use of the product. In other instances, high solution viscosity may require the application of manufacturing technologies which may negatively impact the stability of the protein (for example high-temperature processing). It is thus not unusual to employ viscosity-reducing excipients, such as salts and amino acids, in high protein concentration solutions. However, these excipients can negatively impact the stability of the protein thereby resulting in solutions with an increased aggregation rate compared to high-viscosity control solutions lacking the viscosity-reducing agent. In essence, commonly employed stabilizers and the viscosity-reducing excipients can have an opposite effect on product performance thereby complicating its development.

Another critical attribute for injectable products (most protein-based products) that needs to be considered is its osmolality. While intravenous solutions generally need to be isotonic, it is not unusual for subcutaneous solutions to be hypertonic. In fact, there is evidence in literature of hypertonic formulations resulting in enhanced protein bioavailability following subcutaneous administration (Fathallah, A. M. et al, Biopharm Drug Dispos. 2015 March; 36(2):115-25). Thus, the impact of solution osmolality (and thus tonicity) on injection site discomfort and/or reaction as well as bioavailability in the patient population needs to be carefully monitored and characterized during clinical development phases.

Formulations may sometimes contain surfactants, such as poloxamers and polysorbates, which may confer certain benefits. Poloxamers are non-ionic poly (ethylene oxide)

(PEO)-poly (propylene oxide) (PPO) copolymers. They are used in pharmaceutical formulations as surfactants, emulsifying agents, solubilizing agents, dispersing agents, and in vivo absorbance enhances. Poloxamers are synthetic triblock copolymers with the following core formula: (PEO) a-(PPO)b-(PEO)a. All poloxamers have similar chemical structures but with different molecular weights and composition of the hydrophilic PEO block and hydrophobic PPO block. Two of the most commonly used poloxamers are poloxamer 188 (a=80, b=27) with molecular weight ranging from 7680 to 9510 Da, and poloxamer 407 (a=101, b=56) with molecular weight ranging from 9840 to 14600 Da. Other poloxamers include: poloxamer 101 (P101), poloxamer 105 (P105), poloxamer 108 (P108), poloxamer 122 (P122), poloxamer 123 (P123), poloxamer 124 (P124), poloxamer 181 (P181), poloxamer 182 (P182), poloxamer 183 (P183), poloxamer 184 (P184), poloxamer 185 (P185), poloxamer 212 (P212), poloxamer 215 (P215), poloxamer 217 (P217), poloxamer 231 (P231), poloxamer 234 (P234), poloxamer 235 (P235), poloxamer 237 (P237), poloxamer 238 (P238), poloxamer 282 (P282), poloxamer 284 (P284), poloxamer 288 (P288), poloxamer 331 (P331), poloxamer 333 (P333), poloxamer 334 (P334), poloxamer 335 (P335), poloxamer 338 (P338), poloxamer 401 (P401), poloxamer 402 (P402), and poloxamer 403 (P403).

Polysorbates are a class of emulsifiers used in some pharmaceutical and food preparation formulations. Polysorbates are oily liquids derived from ethoxylated sorbitan, a derivative of sorbitol, esterified with fatty acids. Common brand names for polysorbates include Scattics, Alkest, Canarcel, and Tween. The naming convention for polysorbates usually follows: polysorbate x (polyoxyethylene (y) sorbitan mono'z'), where x is related to the type of fatty acid (z) associated with the polyoxyethylene sorbitan and y refers to the total number of oxyethylene —$(CH_2CH_2O)$— groups found in the polysorbate molecule. Examples of polysorbates include: (a) polysorbate 20 (polyoxyethylene (20) sorbitan monolaurate), (b) polysorbate 40 (polyoxyethylene (20) sorbitan monopalmitate), (c) polysorbate 60 (polyoxyethylene (20) sorbitan monostearate), and (d) polysorbate 80 (polyoxyethylene (20) sorbitan monooleate).

B. Lentiviral vector (LV) Formulations for Use in Treating Blood Disorders

In one aspect, the present invention is directed to a recombinant lentiviral vector preparation comprising: (a) an effective dose of a recombinant lentiviral vector; (b) a TRIS-free buffer system; (c) a salt; (d) a surfactant; (e) a carbohydrate, and (f) a nucleotide sequence at least 80% identical to the Factor VIII (FVIII) coding sequence set forth in SEQ ID NO: 1 or SEQ ID NO: 2 or the Factor IX (FIX) coding sequence set forth in SEQ ID NO: 3, wherein the pharmaceutical composition is suitable for systemic administration to a human patient. In certain embodiments, the vector comprises the Factor VIII (FVIII) coding sequence set forth in SEQ ID NO: 1 or SEQ ID NO: 2. In certain embodiments, the vector comprises the Factor IX (FIX) coding sequence set forth in SEQ ID NO: 3.

In another aspect, the present invention provides a recombinant lentiviral vector preparation comprising: (a) a therapeutically effective dose of a recombinant lentiviral vector; (b) a TRIS-free buffer system; (c) a salt; (d) a surfactant; and (e) a carbohydrate, wherein the recombinant lentiviral vector comprises a nucleic acid comprising a nucleotide sequence at least 80%, at least 85%, at least 90%, at least 95%, or at least 99% identical to a Factor VIII (FVIII) coding sequence set forth in SEQ ID NO: 1 or SEQ ID NO: 2, or a nucleotide sequence at least 80%, at least 85%, at least 90%, at least 95%, or at least 99% identical to the Factor IX (FIX) coding sequence set forth in SEQ ID NO: 3, and wherein the pharmaceutical composition is suitable for systemic administration to a human patient. In certain embodiments, the recombinant lentiviral vector comprises a nucleic acid comprising a Factor VIII (FVIII) coding sequence set forth in SEQ ID NO: 1 or SEQ ID NO: 2. In certain embodiments, the recombinant lentiviral vector comprises a nucleic acid comprising the Factor IX (FIX) coding sequence set forth in SEQ ID NO: 3. In certain embodiments, the recombinant lentiviral vector comprises a nucleic acid consisting of a Factor VIII (FVIII) coding sequence set forth in SEQ ID NO: 1 or SEQ ID NO: 2. In certain embodiments, the recombinant lentiviral vector comprises a nucleic acid consisting of the Factor IX (FIX) coding sequence set forth in SEQ ID NO: 3.

In certain embodiments, the pH of the buffer system is from about 6.0 to about 8.0. In certain embodiments, the pH of the buffer system is from about 6.0 to about 7.5. In certain embodiments, the pH of the buffer system is from about 6.0 to about 7.0. In certain embodiments, the pH of the buffer system is from about 6.0 to about 8.0. In certain embodiments, the pH of the buffer system is about 6.5. In certain embodiments, the pH of the buffer system is about 7.3. In certain embodiments, the buffer system is a phosphate buffer or a histidine buffer. In certain embodiments, the concentration of the phosphate or histidine buffer is from about 5 mM to about 30 mM. In certain embodiments, the concentration of the phosphate buffer is from about 10 mM to about 20 mM, from about 10 mM to about 15 mM, from about 20 mM to about 30 mM, from about 20 mM to about 25 mM, or from about 15 mM to about 20 mM. In certain embodiments, the salt is a chloride salt. In certain embodiments, the concentration of the chloride salt is from about 80 mM to about 150 mM. In certain embodiments, the concentration of the salt is about 100 mM, about 110 mM, about 130 mM, or about 150 mM. In certain embodiments, the surfactant is a poloxamer or a polysorbate. In certain embodiments, the concentration of the poloxamer or polysorbate is from about 0.01% (w/v) to about 0.1% (w/v). In certain embodiments, the carbohydrate is sucrose. In certain embodiments, the concentration of the carbohydrate is from about 0.5% (w/v) to about 5% (w/v). In certain embodiments, the chloride salt is sodium chloride (NaCl). In certain embodiments, the poloxamer is selected from the group consisting of poloxamer 101 (P101), poloxamer 105 (P105), poloxamer 108 (P108), poloxamer 122 (P122), poloxamer 123 (P123), poloxamer 124 (P124), poloxamer 181 (P181), poloxamer 182 (P182), poloxamer 183 (P183), poloxamer 184 (P184), poloxamer 185 (P185), poloxamer 188 (P188), poloxamer 212 (P212), poloxamer 215 (P215), poloxamer 217 (P217), poloxamer 231 (P231), poloxamer 234 (P234), poloxamer 235 (P235), poloxamer 237 (P237), poloxamer 238 (P238), poloxamer 282 (P282), poloxamer 284 (P284), poloxamer 288 (P288), poloxamer 331 (P331), poloxamer 333 (P333), poloxamer 334 (P334), poloxamer 335 (P335), poloxamer 338 (P338), poloxamer 401 (P401), poloxamer 402 (P402), poloxamer 403 (P403), poloxamer 407 (P407), and a combination thereof. In certain embodiments, the polysorbate is selected from the group consisting of polysorbate 20, polysorbate 40, polysorbate 60, polysorbate 80, and a combination thereof. In certain embodiments, the pH of the phosphate or histidine buffer is about 6.1, about 6.3, about 6.5, about 6.7, about 6.9, about 7.1, about 7.3, about 7.5, about 7.7, or about 7.9. In certain embodiments, the concentration of the phosphate or histidine buffer is about 10 mM, about 15 mM, about 20 mM, or about 25 mM. In certain embodiments, the chloride salt is about 100 mM, about 110 mM, about 130 mM, or about 150 mM. In certain embodiments, the concentration of the poloxamer or polysorbate is about 0.03% (w/v), about 0.05% (w/v), about 0.07% (w/v), or about 0.09% (w/v). In certain embodiments, the concentration of the carbohydrate is about 1% (w/v), about 2% (w/v), about 3% (w/v), or about 4% (w/v). In certain embodiments, the poloxamer is poloxamer 188 (P188). In certain embodiments, the poloxamer is poloxamer 407 (P407).

In certain embodiments, the present disclosure provides a recombinant lentiviral vector preparation comprising: (a) a therapeutically effective dose of a recombinant lentiviral vector; (b) about 10 mM phosphate; (c) about 100 mM sodium chloride; (d) about 0.05% (w/v) poloxamer 188; and (e) about 3% (w/v) sucrose, wherein the pH of the preparation is about 7.3, wherein the pharmaceutical composition is suitable for systemic administration to a human patient, and wherein the recombinant lentiviral vector comprises a nucleic acid comprising a nucleotide sequence at least 80%, at least 85%, at least 90%, at least 95%, or at least 99% identical to a Factor VIII (FVIII) coding sequence set forth in SEQ ID NO: 1 or SEQ ID NO: 2, or a nucleotide sequence at least 80%, at least 85%, at least 90%, at least 95%, or at least 99% identical to the Factor IX (FIX) coding sequence set forth in SEQ ID NO: 3, and wherein the pharmaceutical composition is suitable for systemic administration to a human patient. In certain embodiments, the recombinant lentiviral vector comprises a nucleic acid comprising a Factor VIII (FVIII) coding sequence set forth in SEQ ID NO: 1 or SEQ ID NO: 2. In certain embodiments, the recombinant lentiviral vector comprises a nucleic acid comprising the Factor IX (FIX) coding sequence set forth in SEQ ID NO: 3. In certain embodiments, the recombinant lentiviral vector comprises a nucleic acid consisting of a Factor VIII (FVIII) coding sequence set forth in SEQ ID NO: 1 or SEQ ID NO: 2. In certain embodiments, the recombinant lentiviral vector comprises a nucleic acid consisting of the Factor IX (FIX) coding sequence set forth in SEQ ID NO: 3.

In certain embodiments, the present disclosure provides a recombinant lentiviral vector preparation comprising: (a) a therapeutically effective dose of a recombinant lentiviral vector; (b) about 10 mM phosphate; (c) about 130 mM sodium chloride; (d) about 0.05% (w/v) poloxamer 188; and (e) about 1% (w/v) sucrose, wherein the pH of the preparation is about 7.3, wherein the pharmaceutical composition is suitable for systemic administration to a human patient, and wherein the recombinant lentiviral vector comprises a nucleic acid comprising a nucleotide sequence at least 80%, at least 85%, at least 90%, at least 95%, or at least 99% identical to a Factor VIII (FVIII) coding sequence set forth in SEQ ID NO: 1 or SEQ ID NO: 2, or a nucleotide sequence at least 80%, at least 85%, at least 90%, at least 95%, or at least 99% identical to the Factor IX (FIX) coding sequence set forth in SEQ ID NO: 3, and wherein the pharmaceutical composition is suitable for systemic administration to a human patient. In certain embodiments, the recombinant lentiviral vector comprises a nucleic acid comprising a Factor VIII (FVIII) coding sequence set forth in SEQ ID NO: 1 or SEQ ID NO: 2. In certain embodiments, the recombinant lentiviral vector comprises a nucleic acid comprising the Factor IX (FIX) coding sequence set forth in SEQ ID NO: 3. In certain embodiments, the recombinant lentiviral vector comprises a nucleic acid consisting of a Factor VIII (FVIII) coding sequence set forth in SEQ ID NO: 1 or SEQ ID NO: 2. In certain embodiments, the recombinant lentiviral vector comprises a nucleic acid consisting of the Factor IX (FIX) coding sequence set forth in SEQ ID NO: 3.

In certain embodiments, the present disclosure provides a recombinant lentiviral vector preparation comprising: (a) a therapeutically effective dose of a recombinant lentiviral vector; (b) about 20 mM histidine; (c) about 100 mM sodium chloride; (d) about 0.05% (w/v) poloxamer 188; and (e) about 3% (w/v) sucrose, wherein the pH of the preparation is about 6.5, wherein the pharmaceutical composition is suitable for systemic administration to a human patient, and wherein the recombinant lentiviral vector comprises a nucleic acid comprising a nucleotide sequence at least 80%, at least 85%, at least 90%, at least 95%, or at least 99% identical to a Factor VIII (FVIII) coding sequence set forth in SEQ ID NO: 1 or SEQ ID NO: 2, or a nucleotide sequence at least 80%, at least 85%, at least 90%, at least 95%, or at least 99% identical to the Factor IX (FIX) coding sequence set forth in SEQ ID NO: 3, and wherein the pharmaceutical composition is suitable for systemic administration to a human patient. In certain embodiments, the recombinant lentiviral vector comprises a nucleic acid comprising a Factor VIII (FVIII) coding sequence set forth in SEQ ID NO: 1 or SEQ ID NO: 2. In certain embodiments, the recombinant lentiviral vector comprises a nucleic acid comprising the Factor IX (FIX) coding sequence set forth in SEQ ID NO: 3. In certain embodiments, the recombinant lentiviral vector comprises a nucleic acid consisting of a Factor VIII (FVIII) coding sequence set forth in SEQ ID NO: 1 or SEQ ID NO: 2. In certain embodiments, the recombinant lentiviral vector comprises a nucleic acid consisting of the Factor IX (FIX) coding sequence set forth in SEQ ID NO: 3.

In certain embodiments, the present disclosure provides a recombinant lentiviral vector preparation comprising: (a) a therapeutically effective dose of a recombinant lentiviral vector; (b) about 10 mM phosphate; (c) about 100 mM sodium chloride; (d) about 0.05% (w/v) poloxamer 188; and (e) about 3% (w/v) sucrose, wherein the pH of the preparation is about 7.0, wherein the pharmaceutical composition is suitable for systemic administration to a human patient, and wherein the recombinant lentiviral vector comprises a nucleic acid comprising a nucleotide sequence at least 80%, at least 85%, at least 90%, at least 95%, or at least 99% identical to a Factor VIII (FVIII) coding sequence set forth in SEQ ID NO: 1 or SEQ ID NO: 2, or a nucleotide sequence at least 80%, at least 85%, at least 90%, at least 95%, or at least 99% identical to the Factor IX (FIX) coding sequence set forth in SEQ ID NO: 3, and wherein the pharmaceutical composition is suitable for systemic administration to a human patient. In certain embodiments, the recombinant lentiviral vector comprises a nucleic acid comprising a Factor VIII (FVIII) coding sequence set forth in SEQ ID NO: 1 or SEQ ID NO: 2. In certain embodiments, the recombinant lentiviral vector comprises a nucleic acid comprising the Factor IX (FIX) coding sequence set forth in SEQ ID NO: 3. In certain embodiments, the recombinant lentiviral vector comprises a nucleic acid consisting of a Factor VIII (FVIII) coding sequence set forth in SEQ ID NO: 1 or SEQ ID NO: 2. In certain embodiments, the recombinant lentiviral vector comprises a nucleic acid consisting of the Factor IX (FIX) coding sequence set forth in SEQ ID NO: 3.

In certain embodiments, the present disclosure provides a recombinant lentiviral vector preparation comprising: (a) a therapeutically effective dose of a recombinant lentiviral vector; (b) about 20 mM histidine; (c) about 100 mM sodium chloride; (d) about 0.05% (w/v) poloxamer 188; and (e) about 3% (w/v) sucrose, wherein the pH of the preparation is about 7.0, wherein the pharmaceutical composition is suitable for systemic administration to a human patient, and wherein the recombinant lentiviral vector comprises a nucleic acid comprising a nucleotide sequence at least 80%, at least 85%, at least 90%, at least 95%, or at least 99% identical to a Factor VIII (FVIII) coding sequence set forth in SEQ ID NO: 1 or SEQ ID NO: 2, or a nucleotide sequence at least 80%, at least 85%, at least 90%, at least 95%, or at least 99% identical to the Factor IX (FIX) coding sequence set forth in SEQ ID NO: 3, and wherein the pharmaceutical composition is suitable for systemic administration to a human patient. In certain embodiments, the recombinant lentiviral vector comprises a nucleic acid comprising a Factor VIII (FVIII) coding sequence set forth in SEQ ID NO: 1 or SEQ ID NO: 2. In certain embodiments, the recombinant lentiviral vector comprises a nucleic acid comprising the Factor IX (FIX) coding sequence set forth in SEQ ID NO: 3. In certain embodiments, the recombinant lentiviral vector comprises a nucleic acid consisting of a Factor VIII (FVIII) coding sequence set forth in SEQ ID NO: 1 or SEQ ID NO: 2. In certain embodiments, the recombinant lentiviral vector comprises a nucleic acid consisting of the Factor IX (FIX) coding sequence set forth in SEQ ID NO: 3.

In certain embodiments, the recombinant lentiviral vector comprises a nucleotide sequence encoding VSV-G or a fragment thereof. In certain embodiments, the recombinant lentiviral vector comprises an enhanced transthyretin (ET) promoter. In certain embodiments, the recombinant lentiviral vector comprises a nucleotide sequence at least 90% identical to the target sequence for miR-142 set forth in SEQ ID NO: 7.

In certain embodiments, the recombinant lentiviral vector is isolated from a transfected host cell, including a CHO cell, a HEK293 cell, a BHK21 cell, a PER.C6 cell, an NSO cell, and a CAP cell. In certain embodiments, the host cell is a CD47-positive host cell.

In certain embodiments, the preparation is administered systemically to the human patient. In certain embodiments, the preparation is administered intravenously.

In certain embodiments, the pH of the buffer system is between 6.0 and 8.0. In certain embodiments, the buffer system is a phosphate buffer or a histidine buffer. In certain embodiments, the concentration of the phosphate or histidine buffer is between 5 mM and 30 mM. In certain embodiments, the concentration of the phosphate buffer is about 10 to about 20 mM, about 10 to about 15 mM, about 20 to about 30 mM, about 20 to about 25 mM, or about 15 to about 20 mM. In certain embodiments, the salt is a chloride salt. In certain embodiments, the concentration of the chloride salt is between 80 mM and 150 mM. In certain embodiments, the concentration of the salt is about 100 mM, about 110 mM, about 130 mM, or about 150 mM. In certain embodiments, the surfactant is a poloxamer or a polysorbate. In certain embodiments, the concentration of the poloxamer or polysorbate is between 0.01% (w/v) and 0.1% (w/v). In certain embodiments, the carbohydrate is sucrose. In certain embodiments, the concentration of the carbohydrate is between 0.5% (w/v) and 5% (w/v). In certain embodiments, the chloride salt is NaCl. In certain embodiments, the poloxamer is selected from the group consisting of poloxamer 101 (P101), poloxamer 105 (P105), poloxamer 108 (P108), poloxamer 122 (P122), poloxamer 123 (P123), poloxamer 124 (P124), poloxamer 181 (P181), poloxamer 182 (P182), poloxamer 183 (P183), poloxamer 184 (P184), poloxamer 185 (P185), poloxamer 188 (P188), poloxamer 212 (P212), poloxamer 215 (P215), poloxamer 217 (P217), poloxamer 231 (P231), poloxamer 234 (P234), poloxamer 235 (P235), poloxamer 237 (P237), poloxamer 238 (P238), poloxamer 282 (P282), poloxamer 284 (P284), poloxamer 288 (P288), poloxamer 331 (P331), poloxamer 333 (P333), poloxamer 334 (P334), poloxamer 335 (P335), poloxamer 338 (P338), poloxamer 401 (P401), poloxamer 402 (P402), poloxamer 403 (P403), poloxamer 407 (P407), and a combination thereof. In certain embodiments, the polysorbate is selected from the group consisting of polysorbate 20, polysorbate 40, polysorbate 60, polysorbate 80, and a combination thereof. In certain embodiments, the pH of the phosphate or histidine buffer is 6.1, 6.3, 6.5, 6.7, 6.9, 7.1, 7.3, 7.5, 7.7, or 7.9. In certain embodiments, the concentration of the phosphate or histidine buffer is 10 mM, 15 mM, 20 mM, or 25 mM. In certain embodiments, the chloride salt is 100 mM, 110 mM, 130 mM, or 150 mM. In certain embodiments, the concentration of the poloxamer or polysorbate is 0.03% (w/v), 0.05% (w/v), 0.07% (w/v), or 0.09% (w/v). In certain embodiments, the concentration of the carbohydrate is 1% (w/v), 2% (w/v), 3% (w/v), or 4% (w/v). In certain embodiments, the poloxamer is poloxamer 188 (P188). In certain embodiments, the poloxamer is poloxamer 407 (P407).

In one aspect, the present invention is directed to a recombinant lentiviral vector preparation comprising: (a) an effective dose of a recombinant lentiviral vector; (b) a TRIS-free buffer system; (c) a salt; (d) a surfactant; (e) a carbohydrate, and (f) an enhanced transthyretin (ET) promoter, wherein the pharmaceutical composition is suitable for systemic administration to a human patient. In certain embodiments, the vector further comprises a nucleotide sequence at least 80% identical to the Factor VIII (FVIII) coding sequence set forth in SEQ ID NO: 1 or SEQ ID NO: 2 or the Factor IX (FIX) coding sequence set forth in SEQ ID NO: 3, wherein the pharmaceutical composition is suitable for systemic administration to a human patient. In certain embodiments, the vector comprises the Factor VIII (FVIII) coding sequence set forth in SEQ ID NO: 1 or SEQ ID NO: 2. In certain embodiments, the vector comprises the Factor IX (FIX) coding sequence set forth in SEQ ID NO: 3.

In certain embodiments, the vector further comprises a nucleotide sequence encoding VSV-G or a fragment thereof. In certain embodiments, the pH of the buffer system is between 6.0 and 8.0. In certain embodiments, the buffer system is a phosphate buffer or a histidine buffer. In certain embodiments, the concentration of the phosphate or histidine buffer is between 5 mM and 30 mM. In certain embodiments, the concentration of the phosphate buffer is about 10 to about 20 mM, about 10 to about 15 mM, about 20 to about 30 mM, about 20 to about 25 mM, or about 15 to about 20 mM. In certain embodiments, the salt is a chloride salt. In certain embodiments, the concentration of the chloride salt is between 80 mM and 150 mM. In certain embodiments, the concentration of the salt is about 100 mM, about 110 mM, about 130 mM, or about 150 mM. In certain embodiments, the surfactant is a poloxamer or a polysorbate. In certain embodiments, the concentration of the poloxamer or polysorbate is between 0.01% (w/v) and 0.1% (w/v). In certain embodiments, the carbohydrate is sucrose. In certain embodiments, the concentration of the carbohydrate is between 0.5% (w/v) and 5% (w/v). In certain embodiments, the chloride salt is NaCl. In certain embodiments, the poloxamer is selected from the group consisting of poloxamer 101 (P101), poloxamer 105 (P105), poloxamer 108

(P108), poloxamer 122 (P122), poloxamer 123 (P123), poloxamer 124 (P124), poloxamer 181 (P181), poloxamer 182 (P182), poloxamer 183 (P183), poloxamer 184 (P184), poloxamer 185 (P185), poloxamer 188 (P188), poloxamer 212 (P212), poloxamer 215 (P215), poloxamer 217 (P217), poloxamer 231 (P231), poloxamer 234 (P234), poloxamer 235 (P235), poloxamer 237 (P237), poloxamer 238 (P238), poloxamer 282 (P282), poloxamer 284 (P284), poloxamer 288 (P288), poloxamer 331 (P331), poloxamer 333 (P333), poloxamer 334 (P334), poloxamer 335 (P335), poloxamer 338 (P338), poloxamer 401 (P401), poloxamer 402 (P402), poloxamer 403 (P403), poloxamer 407 (P407), and a combination thereof. In certain embodiments, the polysorbate is selected from the group consisting of polysorbate 20, polysorbate 40, polysorbate 60, polysorbate 80, and a combination thereof. In certain embodiments, the pH of the phosphate or histidine buffer is 6.1, 6.3, 6.5, 6.7, 6.9, 7.1, 7.3, 7.5, 7.7, or 7.9. In certain embodiments, the concentration of the phosphate or histidine buffer is 10 mM, 15 mM, 20 mM, or 25 mM. In certain embodiments, the chloride salt is 100 mM, 110 mM, 130 mM, or 150 mM. In certain embodiments, the concentration of the poloxamer or polysorbate is 0.03% (w/v), 0.05% (w/v), 0.07% (w/v), or 0.09% (w/v). In certain embodiments, the concentration of the carbohydrate is 1% (w/v), 2% (w/v), 3% (w/v), or 4% (w/v). In certain embodiments, the poloxamer is poloxamer 188 (P188). In certain embodiments, the poloxamer is poloxamer 407 (P407). In one aspect, the present invention is directed to a recombinant lentiviral vector preparation comprising: (a) an effective dose of a recombinant lentiviral vector; (b) a TRIS-free buffer system; (c) a salt; (d) a surfactant; (e) a carbohydrate, and (f) a nucleotide sequence at least 90% identical to the target sequence for miR-142 set forth in SEQ ID NO: 7, wherein the pharmaceutical composition is suitable for systemic administration to a human patient. In certain embodiments, the vector further comprises an enhanced transthyretin (ET) promoter. In certain embodiments, the vector further comprises a nucleotide sequence at least 80% identical to the Factor VIII (FVIII) coding sequence set forth in SEQ ID NO: 1 or SEQ ID NO: 2 or the Factor IX (FIX) coding sequence set forth in SEQ ID NO: 3. In certain embodiments, the vector comprises the Factor VIII (FVIII) coding sequence set forth in SEQ ID NO: 1 or SEQ ID NO: 2. In certain embodiments, the vector comprises the Factor IX (FIX) coding sequence set forth in SEQ ID NO: 3.

In certain embodiments, the vector further comprises a nucleotide sequence encoding VSV-G or a fragment thereof. In certain embodiments, the pH of the buffer system is between 6.0 and 8.0. In certain embodiments, the buffer system is a phosphate buffer or a histidine buffer. In certain embodiments, the concentration of the phosphate or histidine buffer is between 5 mM and 30 mM. In certain embodiments, the concentration of the phosphate buffer is about 10 to about 20 mM, about 10 to about 15 mM, about 20 to about 30 mM, about 20 to about 25 mM, or about 15 to about 20 mM. In certain embodiments, the salt is a chloride salt. In certain embodiments, the concentration of the chloride salt is between 80 mM and 150 mM. In certain embodiments, the concentration of the salt is about 100 mM, about 110 mM, about 130 mM, or about 150 mM. In certain embodiments, the surfactant is a poloxamer or a polysorbate. In certain embodiments, the concentration of the poloxamer or polysorbate is between 0.01% (w/v) and 0.1% (w/v). In certain embodiments, the carbohydrate is sucrose. In certain embodiments, the concentration of the carbohydrate is between 0.5% (w/v) and 5% (w/v). In certain embodiments, the chloride salt is NaCl. In certain embodiments, the poloxamer is selected from the group consisting of poloxamer 101 (P101), poloxamer 105 (P105), poloxamer 108 (P108), poloxamer 122 (P122), poloxamer 123 (P123), poloxamer 124 (P124), poloxamer 181 (P181), poloxamer 182 (P182), poloxamer 183 (P183), poloxamer 184 (P184), poloxamer 185 (P185), poloxamer 188 (P188), poloxamer 212 (P212), poloxamer 215 (P215), poloxamer 217 (P217), poloxamer 231 (P231), poloxamer 234 (P234), poloxamer 235 (P235), poloxamer 237 (P237), poloxamer 238 (P238), poloxamer 282 (P282), poloxamer 284 (P284), poloxamer 288 (P288), poloxamer 331 (P331), poloxamer 333 (P333), poloxamer 334 (P334), poloxamer 335 (P335), poloxamer 338 (P338), poloxamer 401 (P401), poloxamer 402 (P402), poloxamer 403 (P403), poloxamer 407 (P407), and a combination thereof. In certain embodiments, the polysorbate is selected from the group consisting of polysorbate 20, polysorbate 40, polysorbate 60, polysorbate 80, and a combination thereof. In certain embodiments, the pH of the phosphate or histidine buffer is 6.1, 6.3, 6.5, 6.7, 6.9, 7.1, 7.3, 7.5, 7.7, or 7.9. In certain embodiments, the concentration of the phosphate or histidine buffer is 10 mM, 15 mM, 20 mM, or 25 mM. In certain embodiments, the chloride salt is 100 mM, 110 mM, 130 mM, or 150 mM. In certain embodiments, the concentration of the poloxamer or polysorbate is 0.03% (w/v), 0.05% (w/v), 0.07% (w/v), or 0.09% (w/v). In certain embodiments, the concentration of the carbohydrate is 1% (w/v), 2% (w/v), 3% (w/v), or 4% (w/v). In certain embodiments, the poloxamer is poloxamer 188 (P188). In certain embodiments, the poloxamer is poloxamer 407 (P407).

In one aspect, the present invention is directed to a recombinant lentiviral vector preparation, wherein the recombinant lentiviral vector is isolated from transfected host cells, including CHO cells, HEK293 cells, BHK21 cells, PER.C6 cells, NSO cells, and CAP cells, and wherein the recombinant lentiviral vector preparation comprises: (a) an effective dose of a recombinant lentiviral vector; (b) a TRIS-free buffer system; (c) a salt; (d) a surfactant; and (e) a carbohydrate, wherein the pharmaceutical composition is suitable for systemic administration to a human patient. In certain embodiments, the host cells are CD47-positive host cells. In certain embodiments, the vector further comprises an enhanced transthyretin (ET) promoter. In certain embodiments, the vector further comprises a nucleotide sequence at least 90% identical to the target sequence for miR-142 set forth in SEQ ID NO: 7. In certain embodiments, the vector further comprises a nucleotide sequence at least 80% identical to the Factor VIII (FVIII) coding sequence set forth in SEQ ID NO: 1 or SEQ ID NO: 2 or the Factor IX (FIX) coding sequence set forth in SEQ ID NO: 3. In certain embodiments, the vector comprises the Factor VIII (FVIII) coding sequence set forth in SEQ ID NO: 1 or SEQ ID NO: 2. In certain embodiments, the vector comprises the Factor IX (FIX) coding sequence set forth in SEQ ID NO: 3.

In certain embodiments, the vector further comprises a nucleotide sequence encoding VSV-G or a fragment thereof. In certain embodiments, the pH of the buffer system is between 6.0 and 8.0. In certain embodiments, the buffer system is a phosphate buffer or a histidine buffer. In certain embodiments, the concentration of the phosphate or histidine buffer is between 5 mM and 30 mM. In certain embodiments, the concentration of the phosphate buffer is about 10 to about 20 mM, about 10 to about 15 mM, about 20 to about 30 mM, about 20 to about 25 mM, or about 15 to about 20 mM. In certain embodiments, the salt is a chloride salt. In certain embodiments, the concentration of the chloride salt is between 80 mM and 150 mM. In certain embodiments, the concentration of the salt is about 100 mM, about 110 mM, about 130 mM, or about 150 mM. In certain embodiments, the surfactant is a poloxamer or a polysorbate. In certain embodiments, the concentration of the poloxamer or polysorbate is between 0.01% (w/v) and 0.1% (w/v). In certain embodiments, the carbohydrate is sucrose. In certain embodiments, the concentration of the carbohydrate is between 0.5% (w/v) and 5% (w/v). In certain embodiments, the chloride salt is NaCl. In certain embodiments, the poloxamer is selected from the group consisting of poloxamer 101 (P101), poloxamer 105 (P105), poloxamer 108 (P108), poloxamer 122 (P122), poloxamer 123 (P123), poloxamer 124 (P124), poloxamer 181 (P181), poloxamer 182 (P182), poloxamer 183 (P183), poloxamer 184 (P184), poloxamer 185 (P185), poloxamer 188 (P188), poloxamer 212 (P212), poloxamer 215 (P215), poloxamer 217 (P217), poloxamer 231 (P231), poloxamer 234 (P234), poloxamer 235 (P235), poloxamer 237 (P237), poloxamer 238 (P238), poloxamer 282 (P282), poloxamer 284 (P284), poloxamer 288 (P288), poloxamer 331 (P331), poloxamer 333 (P333), poloxamer 334 (P334), poloxamer 335 (P335), poloxamer 338 (P338), poloxamer 401 (P401), poloxamer 402 (P402), poloxamer 403 (P403), poloxamer 407 (P407), and a combination thereof. In certain embodiments, the polysorbate is selected from the group consisting of polysorbate 20, polysorbate 40, polysorbate 60, polysorbate 80, and a combination thereof. In certain embodiments, the pH of the phosphate or histidine buffer is 6.1, 6.3, 6.5, 6.7, 6.9, 7.1, 7.3, 7.5, 7.7, or 7.9. In certain embodiments, the concentration of the phosphate or histidine buffer is 10 mM, 15 mM, 20 mM, or 25 mM. In certain embodiments, the chloride salt is 100 mM, 110 mM, 130 mM, or 150 mM. In certain embodiments, the concentration of the poloxamer or polysorbate is 0.03% (w/v), 0.05% (w/v), 0.07% (w/v), or 0.09% (w/v). In certain embodiments, the concentration of the carbohydrate is 1% (w/v), 2% (w/v), 3% (w/v), or 4% (w/v). In certain embodiments, the poloxamer is poloxamer 188 (P188). In certain embodiments, the poloxamer is poloxamer 407 (P407).

In one aspect, the present invention is directed to a method of treating a human patient with a disorder, wherein the human patient is systemically administered a recombinant lentiviral vector preparation comprising: (a) (a) an effective dose of a recombinant lentiviral vector; (b) a TRIS-free buffer system; (c) a salt; (d) a surfactant; and (e) a carbohydrate, wherein the pharmaceutical composition is suitable for systemic administration to a human patient. In certain embodiments, the preparation is administered systemically to the human patient. In certain embodiments, the preparation is administered intravenously.

In certain embodiments, the disorder is a bleeding disorder. In certain embodiments, the bleeding disorder is hemophilia A or hemophilia B.

In certain embodiments, the vector further comprises an enhanced transthyretin (ET) promoter. In certain embodiments, the vector further comprises a nucleotide sequence at least 90% identical to the target sequence for miR-142 set forth in SEQ ID NO: 7. In certain embodiments, the vector further comprises a nucleotide sequence at least 80% identical to the Factor VIII (FVIII) coding sequence set forth in SEQ ID NO: 1 or SEQ ID NO: 2 or the Factor IX (FIX) coding sequence set forth in SEQ ID NO: 3. In certain embodiments, the vector comprises the Factor VIII (FVIII) coding sequence set forth in SEQ ID NO: 1 or SEQ ID NO: 2. In certain embodiments, the vector comprises the Factor IX (FIX) coding sequence set forth in SEQ ID NO: 3.

In certain embodiments, the vector further comprises a nucleotide sequence encoding VSV-G or a fragment thereof. In certain embodiments, the pH of the buffer system is between 6.0 and 8.0. In certain embodiments, the buffer system is a phosphate buffer or a histidine buffer. In certain embodiments, the concentration of the phosphate or histidine buffer is between 5 mM and 30 mM. In certain embodiments, the concentration of the phosphate buffer is about 10 to about 20 mM, about 10 to about 15 mM, about 20 to about 30 mM, about 20 to about 25 mM, or about 15 to about 20 mM. In certain embodiments, the salt is a chloride salt. In certain embodiments, the concentration of the chloride salt is between 80 mM and 150 mM. In certain embodiments, the concentration of the salt is about 100 mM, about 110 mM, about 130 mM, or about 150 mM. In certain embodiments, the surfactant is a poloxamer or a polysorbate. In certain embodiments, the concentration of the poloxamer or polysorbate is between 0.01% (w/v) and 0.1% (w/v). In certain embodiments, the carbohydrate is sucrose. In certain embodiments, the concentration of the carbohydrate is between 0.5% (w/v) and 5% (w/v). In certain embodiments, the chloride salt is NaCl. In certain embodiments, the poloxamer is selected from the group consisting of poloxamer 101 (P101), poloxamer 105 (P105), poloxamer 108 (P108), poloxamer 122 (P122), poloxamer 123 (P123), poloxamer 124 (P124), poloxamer 181 (P181), poloxamer 182 (P182), poloxamer 183 (P183), poloxamer 184 (P184), poloxamer 185 (P185), poloxamer 188 (P188), poloxamer 212 (P212), poloxamer 215 (P215), poloxamer 217 (P217), poloxamer 231 (P231), poloxamer 234 (P234), poloxamer 235 (P235), poloxamer 237 (P237), poloxamer 238 (P238), poloxamer 282 (P282), poloxamer 284 (P284), poloxamer 288 (P288), poloxamer 331 (P331), poloxamer 333 (P333), poloxamer 334 (P334), poloxamer 335 (P335), poloxamer 338 (P338), poloxamer 401 (P401), poloxamer 402 (P402), poloxamer 403 (P403), poloxamer 407 (P407), and a combination thereof. In certain embodiments, the polysorbate is selected from the group consisting of polysorbate 20, polysorbate 40, polysorbate 60, polysorbate 80, and a combination thereof. In certain embodiments, the pH of the phosphate or histidine buffer is 6.1, 6.3, 6.5, 6.7, 6.9, 7.1, 7.3, 7.5, 7.7, or 7.9. In certain embodiments, the concentration of the phosphate or histidine buffer is 10 mM, 15 mM, 20 mM, or 25 mM. In certain embodiments, the chloride salt is 100 mM, 110 mM, 130 mM, or 150 mM. In certain embodiments, the concentration of the poloxamer or polysorbate is 0.03% (w/v), 0.05% (w/v), 0.07% (w/v), or 0.09% (w/v). In certain embodiments, the concentration of the carbohydrate is 1% (w/v), 2% (w/v), 3% (w/v), or 4% (w/v). In certain embodiments, the poloxamer is poloxamer 188 (P188). In certain embodiments, the poloxamer is poloxamer 407 (P407).

B.1. Bleeding Disorders

Bleeding disorders are a result of the impairment of the blood's ability to form a clot at the site of blood vessel injury. There are several types of bleeding disorders, including hemophilia A, hemophilia B, von Willebrand disease, and rare factor deficiencies. Hemophilia A results from a deficiency in Factor VIII (FVIII) caused by a mutated or under-expressed gene for Factor VIII, while hemophilia B results from a deficiency in Factor IX (FIX) caused by a mutated or under-expressed gene for Factor IX.

According to the US Centers for Disease Control and Prevention, hemophilia occurs in approximately 1 in 5,000 live births. There are about 20,000 people with hemophilia in the US. All races and ethnic groups are affected. Hemophilia A is four times as common as hemophilia B while more than half of patients with hemophilia A have the severe form of hemophilia. People suffering from hemophilia require extensive medical monitoring throughout their lives. In the absence of intervention, afflicted individuals suffer from spontaneous bleeding in the joints, which produces severe pain and debilitating immobility. Bleeding into muscles results in the accumulation of blood in those tissues, while spontaneous bleeding in the throat and neck can cause asphyxiation if not immediately treated. Renal bleeding and severe bleeding following surgery, minor accidental injuries, or dental extractions also are prevalent.

Disclosed herein are formulations used to treat a bleeding disease or condition in a subject in need thereof. The bleeding disease or condition is selected from the group consisting of a bleeding coagulation disorder, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, bleeding in the illiopsoas sheath and any combinations thereof. In still other embodiments, the subject is scheduled to undergo a surgery. In yet other embodiments, the treatment is prophylactic or on-demand.

Gene therapy using stable and potent formulations of lentiviral vectors (LVs) show great promise for treating individuals suffering from hemophilia A or B through the stable integration into cells of Factor VIII or Factor IX genes that result in the expression of adequate levels of functional Favor VIII or Factor IX.

Somatic gene therapy has been explored as a possible treatment for bleeding disorders. Gene therapy is a particularly appealing treatment for hemophilia because of its potential to cure the disease through continuous endogenous production of FVIII or FIX following a single administration of a vector encoding the respective clotting factor. Hemophilia A (deficiency in FVIII) and hemophilia B (deficiency in FIX) are well suited for a gene replacement approach because its clinical manifestations are entirely attributable to the lack of a single gene product (FVIII or FIX) that circulates in minute amounts (200 ng/ml) in the plasma.

Lentiviruses are gaining prominence as gene delivery vehicles due to their large capacity and ability to sustain transgene expression via integration. Lentiviruses have been evaluated in numerous ex-vivo cell therapy clinical programs with promising efficacy and safety profiles, gaining wide experience over the past ten years. As the use of lentiviral in vivo gene therapy is gaining popularity, there is a need in the art for providing improved formulations that enhance the stability of lentiviruses for long term storage.

The present disclosure meets an important need in the art by providing formulation buffers, or vehicles, that confer lentivirus stability, which affords long term frozen storage. In certain exemplary embodiments, the formulation buffers confer lentivirus stability and affords long term frozen storage where the route of administration is systemic. In some embodiments, the lentivirus is processed into a formulation buffer, or vehicle, of the present disclosure after purification. Upon formulating, the lentivirus is stored frozen. A formulation buffer, or vehicle, of the present invention offers enhanced stability upon freezing and thawing as well as exposure to elevated temperatures.

Provided herein are lentiviral vectors comprising a codon optimized FVIII sequence or codon optimized FIX sequence that demonstrates increased expression in a subject and potentially results in greater therapeutic efficacy when used in gene therapy methods. Embodiments of the present disclosure are directed to lentiviral vectors comprising one or more codon optimized nucleic acid molecules encoding a polypeptide with FVIII activity, or lentiviral vectors comprising one or more codon optimized nucleic acid molecules encoding a polypeptide with FIX activity as described herein, host cells (e.g., hepatocytes) comprising the lentiviral vectors, and methods of use of the disclosed lentiviral vectors (e.g., treatments for bleeding disorders using the lentiviral vectors disclosed herein). In certain embodiments, during scale-up processing, the lentiviral vector is packaged into lentivirus that is processed into a formulation buffer, or vehicle, of the present disclosure.

In general, the methods of treatment disclosed herein involve administration of a lentiviral vector comprising a nucleic acid molecule comprising at least one codon optimized nucleic acid sequence encoding a FVIII clotting factor, or a lentiviral vector comprising a nucleic acid molecule comprising at least one codon optimized nucleic acid sequence encoding a FIX clotting factor. In some embodiments, the nucleic acid sequence encoding a FVIII clotting factor is operably linked to suitable expression control sequences, which in some embodiments are incorporated into the lentiviral vector (e.g., a replication-defective lentiviral viral vector). In some embodiments, the nucleic acid sequence encoding a FIX clotting factor is operably linked to suitable expression control sequences, which in some embodiments are incorporated into the lentiviral vector (e.g., a replication-defective lentiviral viral vector).

The present disclosure provides methods of treating a bleeding disorder (e.g., hemophilia A or hemophilia B) in a subject in need thereof comprising administering to the subject at least one dose of a lentiviral vector comprising a nucleic acid molecule comprising a nucleotide sequence encoding a polypeptide with FVIII or FIX activity. In certain embodiments, the lentiviral vector is packaged into lentivirus that is processed into a formulation buffer of the present invention. In certain embodiments, the nucleotide sequence encoding a polypeptide with FVIII activity comprises a nucleotide sequence having at least 80%, at least 81%, at least 82%, at least 83%, at least 84%, at least 85%, at least 86%, at least 87%, at least 88%, or at least 89%, at least 90%, at least 91%, at least 92%, at least 93%, at least 94%, at least 95%, at least 96%, at least 97%, at least 98%, at least 99%, or at least 100% sequence identity to the nucleic acid sequence set forth in SEQ ID NO:1, as shown in Table 1. In certain embodiments the nucleotide sequence encoding a polypeptide with FVIII activity consists of the nucleotide sequence set forth in SEQ ID NO:1, as shown in Table 1. In certain embodiments, the nucleotide sequence encoding a polypeptide with FVIII activity comprises a nucleotide sequence having at least 80%, at least 81%, at least 82%, at least 83%, at least 84%, at least 85%, at least 86%, at least 87%, at least 88%, or at least 89%, at least 90%, at least 91%, at least 92%, at least 93%, at least 94%, at least 95%, at least 96%, at least 97%, at least 98%, at least 99%, or at least 100% sequence identity to the nucleic acid sequence set forth in SEQ ID NO:2, as shown in Table 1. In certain embodiments, the nucleotide sequence encoding a polypeptide with FVIII activity consists of the nucleotide sequence set forth in SEQ ID NO:2, as shown in Table 1. In certain embodiments, the nucleotide sequence encoding a polypeptide with FIX activity comprises a nucleotide sequence having at least 80%, at least 81%, at least 82%, at least 83%, at least 84%, at least 85%, at least 86%, at least 87%, at least 88%, or at least 89%, at least 90%, at least 91%, at least 92%, at least 93%, at least 94%, at least 95%, at least 96%, at least 97%, at least 98%, at least 99%, or at least 100% sequence identity to the nucleic acid sequence set forth in SEQ ID NO:3, as shown in Table 1. In certain embodiments, the nucleotide sequence encoding a polypeptide with FIX activity consists of the nucleotide sequence set forth in SEQ ID NO:3, as shown in Table 1.

The present disclosure provides methods of treating a bleeding disorder (e.g., hemophilia A or hemophilia B) in a subject in need thereof comprising administering to the subject at least one dose a lentiviral vector comprising nucleic acid molecule comprising a nucleotide sequence encoding a polypeptide with FVIII or FIX activity. In certain embodiments, the lentiviral vector is packaged into lentivirus that is processed into a formulation buffer, or vehicle, of the present invention. In certain embodiments, the subject is administered at least one dose of $5 \times 10^{10}$ or less transducing units/kg (TU/kg) (or $10^9$ TU/kg or less, or 10 TU/kg or less) of a lentiviral vector comprising nucleic acid molecule comprising a nucleotide sequence encoding a polypeptide with FVIII or FIX activity as described herein.

In some embodiments, the dose is about $5.0 \times 10^{10}$ TU/kg, about $4.9 \times 10^{10}$ TU/kg, about $4.8 \times 10^{10}$ TU/kg, about $4.7 \times 10^{10}$ TU/kg, about $4.6 \times 10^{10}$ TU/kg, about $4.5 \times 10^{10}$ TU/kg, about $4.4 \times 10^{10}$ TU/kg, about $4.3 \times 10^{10}$ TU/kg, about $4.2 \times 10^{10}$ TU/kg, about $4.1 \times 10^{10}$ TU/kg, about $4.0 \times 10^{10}$ TU/kg, about $3.9 \times 10^{10}$ TU/kg, about $3.8 \times 10^{10}$ TU/kg, about $3.7 \times 10^{10}$ TU/kg, about $3.6 \times 10^{10}$ TU/kg, about $3.5 \times 10^{10}$ TU/kg, about $3.4 \times 10^{10}$ TU/kg, about $3.3 \times 10^{10}$ TU/kg, about $3.2 \times 10^{10}$ TU/kg, about $3.1 \times 10^{10}$ TU/kg, about $3.0 \times 10^{10}$ TU/kg, about $2.9 \times 10^{10}$ TU/kg, about $2.8 \times 10^{10}$ TU/kg, about $2.7 \times 10^{10}$ TU/kg, about $2.6 \times 10^{10}$ TU/kg, about $2.5 \times 10^{10}$ TU/kg, about $2.4 \times 10^{10}$ TU/kg, about $2.3 \times 10^{10}$ TU/kg, about $2.2 \times 10^{10}$ TU/kg, about $2.1 \times 10^{10}$ TU/kg, about $2.0 \times 10^{10}$ TU/kg, about $1.9 \times 10^{10}$ TU/kg, about $1.8 \times 10^{10}$ TU/kg, about $1.7 \times 10^{10}$ TU/kg, about $1.6 \times 10^{10}$ TU/kg, about $1.5 \times 10^{10}$ TU/kg, about $1.4 \times 10^{10}$ TU/kg, about $1.3 \times 10^{10}$ TU/kg, about $1.2 \times 10^{10}$ TU/kg, about $1.1 \times 10^{10}$ TU/kg, or about $1.0 \times 10^{10}$ TU/kg.

In some embodiments, the dose is about $9.9 \times 10^9$ TU/kg, about $9.8 \times 10^9$ TU/kg, about $9.7 \times 10^9$ TU/kg, about $9.6 \times 10^9$ TU/kg, about $9.5 \times 10^9$ TU/kg, about $9.4 \times 10^9$ TU/kg, about $9.3 \times 10^9$ TU/kg, about $9.2 \times 10^9$ TU/kg, about $9.1 \times 10^9$ TU/kg, about $9.0 \times 10^9$ TU/kg, about $8.9 \times 10^9$ TU/kg, about $8.8 \times 10^9$ TU/kg, about $8.7 \times 10^9$ TU/kg, about $8.6 \times 10^9$ TU/kg, about $8.5 \times 10^9$ TU/kg, about $8.4 \times 10^9$ TU/kg, about $8.3 \times 10^9$ TU/kg, about $8.2 \times 10^9$ TU/kg, about $8.1 \times 10^9$ TU/kg, about $8.0 \times 10^9$ TU/kg, about $7.9 \times 10^9$ TU/kg, about $7.8 \times 10^9$ TU/kg, about $7.7 \times 10^9$ TU/kg, about $7.6 \times 10^9$ TU/kg, about $7.5 \times 10^9$ TU/kg, about $7.4 \times 10^9$ TU/kg, about $7.3 \times 10^9$ TU/kg, about $7.2 \times 10^9$ TU/kg, about $7.1 \times 10^9$ TU/kg, about $7.0 \times 10^9$ TU/kg, about $6.9 \times 10^9$ TU/kg, about $6.8 \times 10^9$ TU/kg, about $6.7 \times 10^9$ TU/kg, about $6.6 \times 10^9$ TU/kg, about $6.5 \times 10^9$ TU/kg, about $6.4 \times 10^9$ TU/kg, about $6.3 \times 10^9$ TU/kg, about $6.2 \times 10^9$ TU/kg, about $6.1 \times 10^9$ TU/kg, about $6.0 \times 10^9$ TU/kg, about $5.9 \times 10^9$ TU/kg, about $5.8 \times 10^9$ TU/kg, about $5.7 \times 10^9$ TU/kg, about $5.6 \times 10^9$ TU/kg, about $5.5 \times 10^9$ TU/kg, about $5.4 \times 10^9$ TU/kg, about $5.3 \times 10^9$ TU/kg, about $5.2 \times 10^9$ TU/kg, about $5.1 \times 10^9$ TU/kg, about $5.0 \times 10^9$ TU/kg, about $4.9 \times 10^9$ TU/kg, about $4.8 \times 10^9$ TU/kg, about $4.7 \times 10^9$ TU/kg, about $4.6 \times 10^9$ TU/kg, about $4.5 \times 10^9$ TU/kg, about $4.4 \times 10^9$ TU/kg, about $4.3 \times 10^9$ TU/kg, about $4.2 \times 10^9$ TU/kg, about $4.1 \times 10^9$ TU/kg, about $4.0 \times 10^9$ TU/kg, about $3.9 \times 10^9$ TU/kg, about $3.8 \times 10^9$ TU/kg, about $3.7 \times 10^9$ TU/kg, about $3.6 \times 10^9$ TU/kg, about $3.5 \times 10^9$ TU/kg, about $3.4 \times 10^9$ TU/kg, about $3.3 \times 10^9$ TU/kg, about $3.2 \times 10^9$ TU/kg, about $3.1 \times 10^9$ TU/kg, about $3.0 \times 10^9$ TU/kg, about $2.9 \times 10^9$ TU/kg, about $2.8 \times 10^9$ TU/kg, about $2.7 \times 10^9$ TU/kg, about $2.6 \times 10^9$ TU/kg, about $2.5 \times 10^9$ TU/kg, about $2.4 \times 10^9$ TU/kg, about $2.3 \times 10^9$ TU/kg, about $2.2 \times 10^9$ TU/kg, about $2.1 \times 10^9$ TU/kg, about $2.0 \times 10^9$ TU/kg, about $1.9 \times 10^9$ TU/kg, about $1.8 \times 10^9$ TU/kg, about $1.7 \times 10^9$ TU/kg, about $1.6 \times 10^9$ TU/kg, about $1.5 \times 10^9$ TU/kg, about $1.4 \times 10^9$ TU/kg, about $1.3 \times 10^9$ TU/kg, about $1.2 \times 10^9$ TU/kg, about $1.1 \times 10^9$ TU/kg, or about $1.0 \times 10^9$ TU/kg.

In some embodiments, the dose is about $9.9 \times 10^8$ TU/kg, about $9.8 \times 10^8$ TU/kg, about $9.7 \times 10^8$ TU/kg, about $9.6 \times 10^8$ TU/kg, about $9.5 \times 10^8$ TU/kg, about $9.4 \times 10^8$ TU/kg, about $9.3 \times 10^8$ TU/kg, about $9.2 \times 10^8$ TU/kg, about $9.1 \times 10^8$ TU/kg, about $9.0 \times 10^8$ TU/kg, about $8.9 \times 10^8$ TU/kg, about $8.8 \times 10^8$ TU/kg, about $8.7 \times 10^8$ TU/kg, about $8.6 \times 10^8$ TU/kg, about $8.5 \times 10^8$ TU/kg, about $8.4 \times 10^8$ TU/kg, about $8.3 \times 10^8$ TU/kg, about $8.2 \times 10^8$ TU/kg, about $8.1 \times 10^8$ TU/kg, about $8.0 \times 10^8$ TU/kg, about $7.9 \times 10^8$ TU/kg, about $7.8 \times 10^8$ TU/kg, about $7.7 \times 10^8$ TU/kg, about $7.6 \times 10^8$ TU/kg, about $7.5 \times 10^8$ TU/kg, about $7.4 \times 10^8$ TU/kg, about $7.3 \times 10^8$ TU/kg, about $7.2 \times 10^8$ TU/kg, about $7.1 \times 10^8$ TU/kg, about $7.0 \times 10^8$ TU/kg, about $6.9 \times 10^8$ TU/kg, about $6.8 \times 10^8$ TU/kg, about $6.7 \times 10^8$ TU/kg, about $6.6 \times 10^8$ TU/kg, about $6.5 \times 10^8$ TU/kg, about $6.4 \times 10^8$ TU/kg, about $6.3 \times 10^8$ TU/kg, about $6.2 \times 10^8$ TU/kg, about $6.1 \times 10^8$ TU/kg, about $6.0 \times 10^8$ TU/kg, about $5.9 \times 10^8$ TU/kg, about $5.8 \times 10^8$ TU/kg, about $5.7 \times 10^8$ TU/kg, about $5.6 \times 10^8$ TU/kg, about $5.5 \times 10^8$ TU/kg, about $5.4 \times 10^8$ TU/kg, about $5.3 \times 10^8$ TU/kg, about $5.2 \times 10^8$ TU/kg, about $5.1 \times 10^8$ TU/kg, about $5.0 \times 10^8$ TU/kg, about $4.9 \times 10^8$ TU/kg, about $4.8 \times 10^8$ TU/kg, about $4.7 \times 10^8$ TU/kg, about $4.6 \times 10^8$ TU/kg, about $4.5 \times 10^8$ TU/kg, about $4.4 \times 10^8$ TU/kg, about $4.3 \times 10^8$ TU/kg, about $4.2 \times 10^8$ TU/kg, about $4.1 \times 10^8$ TU/kg, about $4.0 \times 10^8$ TU/kg, about $3.9 \times 10^8$ TU/kg, about $3.8 \times 10^8$ TU/kg, about $3.7 \times 10^8$ TU/kg, about $3.6 \times 10^8$ TU/kg, about $3.5 \times 10^8$ TU/kg, about $3.4 \times 10^8$ TU/kg, about $3.3 \times 10^8$ TU/kg, about $3.2 \times 10^8$ TU/kg, about $3.1 \times 10^8$ TU/kg, about $3.0 \times 10^8$ TU/kg, about $2.9 \times 10^8$ TU/kg, about $2.8 \times 10^8$ TU/kg, about $2.7 \times 10^8$ TU/kg, about $2.6 \times 10^8$ TU/kg, about $2.5 \times 10^8$ TU/kg, about $2.4 \times 10^8$ TU/kg, about $2.3 \times 10^8$ TU/kg, about $2.2 \times 10^8$ TU/kg, about $2.1 \times 10^8$ TU/kg, about $2.0 \times 10^8$ TU/kg, about $1.9 \times 10^8$ TU/kg, about $1.8 \times 10^8$ TU/kg, about $1.7 \times 10^8$ TU/kg, about $1.6 \times 10^8$ TU/kg, about $1.5 \times 10^8$ TU/kg, about $1.4 \times 10^8$ TU/kg, about $1.3 \times 10^8$ TU/kg, about $1.2 \times 10^8$ TU/kg, about $1.1 \times 10^8$ TU/kg, or about $1.0 \times 10^8$ TU/kg.

In some embodiments, the dose is less than $5.0 \times 10^{10}$ TU/kg, less than $4.9 \times 10^{10}$ TU/kg, less than $4.8 \times 10^{10}$ TU/kg, less than $4.7 \times 10^{10}$ TU/kg, less than $4.6 \times 10^{10}$ TU/kg, less than $4.5 \times 10^{10}$ TU/kg, less than $4.4 \times 10^{10}$ TU/kg, less than $4.3 \times 10^{10}$ TU/kg, less than $4.2 \times 10^{10}$ TU/kg, less than $4.1 \times 10^{10}$ TU/kg, less than $4.0 \times 10^{10}$ TU/kg, less than $3.9 \times 10^{10}$ TU/kg, less than $3.8 \times 10^{10}$ TU/kg, less than $3.7 \times 10^{10}$ TU/kg, less than $3.6 \times 10^{10}$ TU/kg, less than $3.5 \times 10^{10}$ TU/kg, less than $3.4 \times 10^{10}$ TU/kg, less than $3.3 \times 10^{10}$ TU/kg, less than $3.2 \times 10^{10}$ TU/kg, less than $3.1 \times 10^{10}$ TU/kg, less than $3.0 \times 10^{10}$ TU/kg, less than $2.9 \times 10^{10}$ TU/kg, less than $2.8 \times 10^{10}$ TU/kg, less than $2.7 \times 10^{10}$ TU/kg, less than $2.6 \times 10^{10}$ TU/kg, less than $2.5 \times 10^{10}$ TU/kg, less than $2.4 \times 10^{10}$ TU/kg, less than $2.3 \times 10^{10}$ TU/kg, less than $2.2 \times 10^{10}$ TU/kg, less than $2.1 \times 10^{10}$ TU/kg, less than $2.0 \times 10^{10}$ TU/kg, less than $1.9 \times 10^{10}$ TU/kg, less than $1.8 \times 10^{10}$ TU/kg, less than $1.7 \times 10^{10}$ TU/kg, less than $1.6 \times 10^{10}$ TU/kg, less than $1.5 \times 10^{10}$ TU/kg, less than $1.4 \times 10^{10}$ TU/kg, less than $1.3 \times 10^{10}$ TU/kg, less than $1.2 \times 10^{10}$ TU/kg, less than $1.1 \times 10^{10}$ TU/kg, or less than $1.0 \times 10^{10}$ TU/kg.

In some embodiments, the dose is less than $9.9 \times 10^9$ TU/kg, less than $9.8 \times 10^9$ TU/kg, less than $9.7 \times 10^9$ TU/kg, less than $9.6 \times 10^9$ TU/kg, less than $9.5 \times 10^9$ TU/kg, less than $9.4 \times 10^9$ TU/kg, less than $9.3 \times 10^9$ TU/kg, less than $9.2 \times 10^9$ TU/kg, less than $9.1 \times 10^9$ TU/kg, less than $9.0 \times 10^9$ TU/kg, less than $8.9 \times 10^9$ TU/kg, less than $8.8 \times 10^9$ TU/kg, less than $8.7 \times 10^9$ TU/kg, less than $8.6 \times 10^9$ TU/kg, less than $8.5 \times 10^9$ TU/kg, less than $8.4 \times 10^9$ TU/kg, less than $8.3 \times 10^9$ TU/kg, less than $8.2 \times 10^9$ TU/kg, less than $8.1 \times 10^9$ TU/kg, less than $8.0 \times 10^9$ TU/kg, less than $7.9 \times 10^9$ TU/kg, less than $7.8 \times 10^9$ TU/kg, less than $7.7 \times 10^9$ TU/kg, less than $7.6 \times 10^9$ TU/kg, less than $7.5 \times 10^9$ TU/kg, less than $7.4 \times 10^9$ TU/kg, less than $7.3 \times 10^9$ TU/kg, less than $7.2 \times 10^9$ TU/kg, less than $7.1 \times 10^9$ TU/kg, less than $7.0 \times 10^9$ TU/kg, less than $6.9 \times 10^9$ TU/kg, less than $6.8 \times 10^9$ TU/kg, less than $6.7 \times 10^9$ TU/kg, less than $6.6 \times 10^9$ TU/kg, less than $6.5 \times 10^9$ TU/kg, less than $6.4 \times 10^9$ TU/kg, less than $6.3 \times 10^9$ TU/kg, less than $6.2 \times 10^9$ TU/kg, less than $6.1 \times 10^9$ TU/kg, less than $6.0 \times 10^9$ TU/kg, less than $5.9 \times 10^9$ TU/kg, less than $5.8 \times 10^9$ TU/kg, less than $5.7 \times 10^9$ TU/kg, less than $5.6 \times 10^9$ TU/kg, less than $5.5 \times 10^9$ TU/kg, less than $5.4 \times 10^9$ TU/kg, less than $5.3 \times 10^9$ TU/kg, less than $5.2 \times 10^9$ TU/kg, less than $5.1 \times 10^9$ TU/kg, less than $5.0 \times 10^9$ TU/kg, less than $4.9 \times 10^9$ TU/kg, less than $4.8 \times 10^9$ TU/kg, less than $4.7 \times 10^9$ TU/kg, less than $4.6 \times 10^9$ TU/kg, less than $4.5 \times 10^9$ TU/kg, less than $4.4 \times 10^9$ TU/kg, less than $4.3 \times 10^9$ TU/kg, less than $4.2 \times 10^9$ TU/kg, less than $4.1 \times 10^9$ TU/kg, less than $4.0 \times 10^9$ TU/kg, less than $3.9 \times 10^9$ TU/kg, less than $3.8 \times 10^9$ TU/kg, less than $3.7 \times 10^9$ TU/kg, less than $3.6 \times 10^9$ TU/kg, less than $3.5 \times 10^9$ TU/kg, less than $3.4 \times 10^9$ TU/kg, less than $3.3 \times 10^9$ TU/kg, less than $3.2 \times 10^9$ TU/kg, less than $3.1 \times 10^9$ TU/kg, less than $3.0 \times 10^9$ TU/kg, less than $2.9 \times 10^9$ TU/kg, less than $2.8 \times 10^9$ TU/kg, less than $2.7 \times 10^9$ TU/kg, less than $2.6 \times 10^9$ TU/kg, less than $2.5 \times 10^9$ TU/kg, less than $2.4 \times 10^9$ TU/kg, less than $2.3 \times 10^9$ TU/kg, less than $2.2 \times 10^9$ TU/kg, less than $2.1 \times 10^9$ TU/kg, less than $2.0 \times 10^9$ TU/kg, less than $1.9 \times 10^9$ TU/kg, less than $1.8 \times 10^9$ TU/kg, less than $1.7 \times 10^9$ TU/kg, less than $1.6 \times 10^9$ TU/kg, less than $1.5 \times 10^9$ TU/kg, less than $1.4 \times 10^9$ TU/kg, less than $1.3 \times 10^9$ TU/kg, less than $1.2 \times 10^9$ TU/kg, less than $1.1 \times 10^9$ TU/kg, or less than $1.0 \times 10^9$ TU/kg.

In some embodiments, the dose is less than $9.9 \times 10^8$ TU/kg, less than $9.8 \times 10^8$ TU/kg, less than $9.7 \times 10^8$ TU/kg, less than $9.6 \times 10^8$ TU/kg, less than $9.5 \times 10^8$ TU/kg, less than $9.4 \times 10^8$ TU/kg, less than $9.3 \times 10^8$ TU/kg, less than $9.2 \times 10^8$ TU/kg, less than $9.1 \times 10^8$ TU/kg, less than $9.0 \times 10^8$ TU/kg, less than $8.9 \times 10^8$ TU/kg, less than $8.8 \times 10^8$ TU/kg, less than $8.7 \times 10^8$ TU/kg, less than $8.6 \times 10^8$ TU/kg, less than $8.5 \times 10^8$ TU/kg, less than $8.4 \times 10^8$ TU/kg, less than $8.3 \times 10^8$ TU/kg, less than $8.2 \times 10^8$ TU/kg, less than $8.1 \times 10^8$ TU/kg, less than $8.0 \times 10^8$ TU/kg, less than $7.9 \times 10^8$ TU/kg, less than $7.8 \times 10^8$ TU/kg, less than $7.7 \times 10^8$ TU/kg, less than $7.6 \times 10^8$ TU/kg, less than $7.5 \times 10^8$ TU/kg, less than $7.4 \times 10^8$ TU/kg, less than $7.3 \times 10^8$ TU/kg, less than $7.2 \times 10^8$ TU/kg, less than $7.1 \times 10^8$ TU/kg, less than $7.0 \times 10^8$ TU/kg, less than $6.9 \times 10^8$ TU/kg, less than $6.8 \times 10$ TU/kg, less than $6.7 \times 10^8$ TU/kg, less than $6.6 \times 10^8$ TU/kg, less than $6.5 \times 10^8$ TU/kg, less than $6.4 \times 10^8$ TU/kg, less than $6.3 \times 10^8$ TU/kg, less than $6.2 \times 10^8$ TU/kg, less than $6.1 \times 10^8$ TU/kg, less than $6.0 \times 10^8$ TU/kg, less than $5.9 \times 10^8$ TU/kg, less than $5.8 \times 10^8$ TU/kg, less than $5.7 \times 10^8$ TU/kg, less than $5.6 \times 10^8$ TU/kg, less than $5.5 \times 10^8$ TU/kg, less than $5.4 \times 10^8$ TU/kg, less than $5.3 \times 10$ TU/kg, less than $5.2 \times 10^8$ TU/kg, less than $5.1 \times 10^8$ TU/kg, less than $5.0 \times 10^8$ TU/kg, less than $4.9 \times 10^8$ TU/kg, less than $4.8 \times 10^8$ TU/kg, less than $4.7 \times 10^8$ TU/kg, less than $4.6 \times 10^8$ TU/kg, less than $4.5 \times 10^8$ TU/kg, less than $4.4 \times 10^8$ TU/kg, less than $4.3 \times 10^8$ TU/kg, less than $4.2 \times 10^8$ TU/kg, less than $4.1 \times 10^8$ TU/kg, less than $4.0 \times 10^8$ TU/kg, less than $3.9 \times 10^8$ TU/kg, less than $3.8 \times 10$ TU/kg, less than $3.7 \times 10^8$ TU/kg, less than $3.6 \times 10^8$ TU/kg, less than $3.5 \times 10^8$ TU/kg, less than $3.4 \times 10^8$ TU/kg, less than $3.3 \times 10^8$ TU/kg, less than $3.2 \times 10^8$ TU/kg, less than $3.1 \times 10^8$ TU/kg, less than $3.0 \times 10^8$ TU/kg, less than $2.9 \times 10^8$ TU/kg, less than $2.8 \times 10^8$ TU/kg, less than $2.7 \times 10^8$ TU/kg, less than $2.6 \times 10^8$ TU/kg, less than $2.5 \times 10^8$ TU/kg, less than $2.4 \times 10^8$ TU/kg, less than $2.3 \times 10$ TU/kg, less than $2.2 \times 10^8$ TU/kg, less than $2.1 \times 10^8$ TU/kg, less than $2.0 \times 10^8$ TU/kg, less than $1.9 \times 10^8$ TU/kg, less than $1.8 \times 10^8$ TU/kg, less than $1.7 \times 10^8$ TU/kg, less than $1.6 \times 10^8$ TU/kg, less than $1.5 \times 10^8$ TU/kg, less than $1.4 \times 10^8$ TU/kg, less than $1.3 \times 10^8$ TU/kg, less than $1.2 \times 10^8$ TU/kg, less than $1.1 \times 10^8$ TU/kg, or less than $1.0 \times 10^8$ TU/kg.

In some embodiments, the dose is between $1 \times 10^8$ TU/kg and $5 \times 10^{10}$ TU/kg, between $1.5 \times 10^8$ TU/kg and $5 \times 10^{10}$ TU/kg, between $2 \times 10^8$ TU/kg and $5 \times 10^{10}$ TU/kg, between $2.5 \times 10^8$ TU/kg and $5 \times 10^{10}$ TU/kg, between $3 \times 10^8$ TU/kg and $5 \times 10^{10}$ TU/kg, between $3.5 \times 10$ TU/kg and $5 \times 10^{10}$ TU/kg, between $4 \times 10^8$ TU/kg and $5 \times 10^{10}$ TU/kg, between $4.5 \times 10^8$ TU/kg and $5 \times 10^{10}$ TU/kg, between $5 \times 10^8$ TU/kg and $5 \times 10^{10}$ TU/kg, between $5.5 \times 10^8$ TU/kg and $5 \times 10^{10}$ TU/kg, between $6 \times 10^8$ TU/kg and $5 \times 10^{10}$ TU/kg, between $6.5 \times 10^8$ TU/kg and $5 \times 10^{10}$ TU/kg, between $7 \times 10^8$ TU/kg and $5 \times 10^{10}$ TU/kg, between $7.5 \times 10^8$ TU/kg and $5 \times 10^{10}$ TU/kg, between $8 \times 10^8$ TU/kg and $5 \times 10^{10}$ TU/kg, between $8.5 \times 10^8$ TU/kg and $5 \times 10^{10}$ TU/kg, between $9 \times 10^8$ TU/kg and $5 \times 10^{10}$ TU/kg, between $9.5 \times 10^8$ TU/kg and $5 \times 10^{10}$ TU/kg, between $1 \times 10^9$ TU/kg and $5 \times 10^{10}$ TU/kg, between $1.5 \times 10^9$ TU/kg and $5 \times 10^{10}$ TU/kg, between $2 \times 10^9$ TU/kg and $5 \times 10^{10}$ TU/kg, between $2.5 \times 10^9$ TU/kg and $5 \times 10^{10}$ TU/kg, between $3 \times 10^9$ TU/kg and $5 \times 10^{10}$ TU/kg, between $3.5 \times 10^9$ TU/kg and $5 \times 10^{10}$ TU/kg, between $4 \times 10^9$ TU/kg and $5 \times 10^{10}$ TU/kg, between $4.5 \times 10^9$ TU/kg and $5 \times 10^{10}$ TU/kg, between $5 \times 10^9$ TU/kg and $5 \times 10^{10}$ TU/kg, between $5.5 \times 10^9$ TU/kg and $5 \times 10^{10}$ TU/kg, between $6 \times 10^9$ TU/kg and $5 \times 10^{10}$ TU/kg, between $6.5 \times 10^9$ TU/kg and $5 \times 10^{10}$ TU/kg, between $7 \times 10^9$ TU/kg and $5 \times 10^{10}$ TU/kg, between $7.5 \times 10^9$ TU/kg and $5 \times 10^{10}$ TU/kg, between $8 \times 10^9$ TU/kg and $5 \times 10^{10}$ TU/kg, between $8.5 \times 10^9$ TU/kg and $5 \times 10^{10}$ TU/kg, between $9 \times 10^9$ TU/kg and $5 \times 10^{10}$ TU/kg, between $9.5 \times 10^9$ TU/kg and $5 \times 10^{10}$ TU/kg, between $10^{10}$ TU/kg and $5 \times 10^{10}$ TU/kg, between $1.5 \times 10^{10}$ TU/kg and $5 \times 10^{10}$ TU/kg, between $2 \times 10^{10}$ TU/kg and $5 \times 10^{10}$ TU/kg, between $2.5 \times 10^{10}$ TU/kg and $5 \times 10^{10}$ TU/kg, between $3 \times 10^{10}$ TU/kg and $5 \times 10^{10}$ TU/kg, between $3.5 \times 10^{10}$ TU/kg and $5 \times 10^{10}$ TU/kg, between $4 \times 10^{10}$ TU/kg and $5 \times 10^{10}$ TU/kg, or between $4.5 \times 10^{10}$ TU/kg and $5 \times 10^{10}$ TU/kg.

In some embodiments, the dose is between $1 \times 10^8$ TU/kg and $5 \times 10^{10}$ TU/kg, between $1 \times 10^8$ TU/kg and $4.5 \times 10^{10}$ TU/kg, between $1 \times 10^8$ TU/kg and $4 \times 10^{10}$ TU/kg, between $1 \times 10^8$ TU/kg and $3.5 \times 10^{10}$ TU/kg, between $1 \times 10^8$ TU/kg and $3 \times 10^{10}$ TU/kg, between $1 \times 10^8$ TU/kg and $2.5 \times 10^{10}$ TU/kg, between $1 \times 10^8$ TU/kg and $2 \times 10^{10}$ TU/kg, between $1 \times 10^8$ TU/kg and $1.5 \times 10^{10}$ TU/kg, between $1 \times 10^8$ TU/kg and $10^{10}$ TU/kg, between $1 \times 10^8$ TU/kg and $9 \times 10^9$ TU/kg, between $1 \times 10^8$ TU/kg and $8.5 \times 10^9$ TU/kg, between $1 \times 10^8$ TU/kg and $8 \times 10^9$ TU/kg, between $1 \times 10^8$ TU/kg and $7.5 \times 10^9$ TU/kg, between $1 \times 10^8$ TU/kg and $7 \times 10^9$ TU/kg, between $1 \times 10^8$ TU/kg and $6.5 \times 10^9$ TU/kg, between $1 \times 10^8$ TU/kg and $6 \times 10^9$ TU/kg, between $1 \times 10^8$ TU/kg and $5.5 \times 10^9$ TU/kg, between $1 \times 10^8$ TU/kg and $5 \times 10^9$ TU/kg, between $1 \times 10^8$ TU/kg and $4.5 \times 10^9$ TU/kg, between $1 \times 10^8$ TU/kg and $4 \times 10^9$ TU/kg, between $1 \times 10^8$ TU/kg and $3.5 \times 10^9$ TU/kg, between $1 \times 10^8$ TU/kg and $3 \times 10^9$ TU/kg, between $1 \times 10^8$ TU/kg and $2.5 \times 10^9$ TU/kg, between $1 \times 10^8$ TU/kg and $2 \times 10^9$, between $1 \times 10^8$ TU/kg and $1.5 \times 10^9$ TU/kg, between $1 \times 10^8$ TU/kg and $1 \times 10^9$ TU/kg, between $1 \times 10^8$ TU/kg and $9.5 \times 10^8$ TU/kg, between $1 \times 10^8$ TU/kg and $9 \times 10^8$ TU/kg, between $1 \times 10^8$ TU/kg and $8.5 \times 10^8$ TU/kg, between $1 \times 10^8$ TU/kg and $8 \times 10^8$ TU/kg, between $1 \times 10^8$ TU/kg and $7.5 \times 10^8$ TU/kg, between $1 \times 10^8$ TU/kg and $7 \times 10^8$ TU/kg, between $1 \times 10^8$ TU/kg and $6.5 \times 10^8$ TU/kg, between $1 \times 10^8$ TU/kg and $6 \times 10^8$ TU/kg, between 1×10⁸ TU/kg and 5.5×10⁸ TU/kg, between 1×10⁸ TU/kg and 5×10⁸ TU/kg, between 1×10⁸ TU/kg and 4.5×10⁸ TU/kg, between 1×10⁸ TU/kg and 4×10⁸ TU/kg, between 1×10⁸ TU/kg and 3.5×10⁸ TU/kg, between 1×10⁸ TU/kg and 3×10⁸ TU/kg, between 1×10⁸ TU/kg and 2.5×10⁸ TU/kg, between 1×10⁸ TU/kg and 2×10⁸, or between 1×10⁸ TU/kg and 1.5×10⁸ TU/kg, In some embodiments, the dose is between $1 \times 10^{10}$ TU/kg and $2 \times 10^{10}$ TU/kg, between $1.1 \times 10^{10}$ TU/kg and $1.9 \times 10^{10}$ TU/kg, between $1.2 \times 10^{10}$ TU/kg and $1.8 \times 10^{10}$ TU/kg, between $1.3 \times 10^{10}$ TU/kg and $1.7 \times 10^{10}$ TU/kg, or between $1.4 \times 10^{10}$ TU/kg and $1.6 \times 10^{10}$ TU/kg. In some embodiments, the dose is about $1.5 \times 10^{10}$ TU/kg. In some embodiments, the dose is $1.5 \times 10^{10}$ TU/kg.

In some embodiments, the dose is between $1 \times 10^{9}$ TU/kg and $2 \times 10^{9}$ TU/kg, between $1.1 \times 10^{9}$ TU/kg and $1.9 \times 10^{9}$ TU/kg, between $1.2 \times 10^{9}$ TU/kg and $1.8 \times 10^{9}$ TU/kg, between $1.3 \times 10^{9}$ TU/kg and $1.7 \times 10^{9}$ TU/kg, or between $1.4 \times 10^{9}$ TU/kg and $1.6 \times 10^{9}$ TU/kg. In some embodiments, the dose is $1.5 \times 10^{9}$ TU/kg. In certain embodiments, the dose is about $3.0 \times 10^{9}$ TU/kg.

In some embodiments, plasma FVIII activity at 24 hours, 36 hours, or 48 hours post administration of a lentiviral vector of the present disclosure is increased relative to the plasma FVIII activity in a subject administered a control lentiviral vector. In some embodiments, plasma FVIII activity at 24 hours, 36 hours, or 48 hours post administration of a lentiviral vector of the present disclosure is increased relative to the plasma FVIII activity in a subject administered a control nucleic acid molecule.

In some embodiments, plasma FIX activity at 24 hours, 36 hours, or 48 hours post administration of a lentiviral vector of the present disclosure is increased relative to the plasma FIX activity in a subject administered a control lentiviral vector. In some embodiments, plasma FIX activity at 24 hours, 36 hours, or 48 hours post administration of a lentiviral vector of the present disclosure is increased relative to the plasma FIX activity in a subject administered a control nucleic acid molecule.

In some embodiments, plasma FVIII or plasma FIX activity is increased at about 6 hours, at about 12 hours, at about 18 hours, at about 24 hours, at about 36 hours, at about 48 hours, at about 3 days, at about 4 days, at about 5 days, at about 6 days, at about 7 days, at about 8 days, at about 9 days, at about 10 days, at about 11 days, at about 12 days, at about 13 days, at about 14 days, at about 15 days, at about 16 days, at about 17 days, at about 18 days, at about 19 days, at about 20 days, at about 21 days, at about 22 days, at about 23 days, at about 24 days, at about 25 days, at about 26 days, at about 27 days, or at about 28 days post administration of a lentiviral vector of the present disclosure relative to a subject administered a a control lentiviral vector or a control nucleic acid molecule.

In some embodiments, the plasma FVIII or plasma FIX activity in the subject is increased by at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 20-fold, at least about 25-fold, at least about 30-fold, at least about 35-fold, at least about 40-fold, at least about 45-fold, at least about 50-fold, at least about 55-fold, at least about 60-fold, at least about 65-fold, at least about 70-fold, at least about 75-fold, at least about 80-fold, at least about 85-fold, at least about 90-fold, at least about 95-fold, at least about 100-fold, at least about 110-fold, at least about 120-fold, at least about 130-fold, at least about 140-fold, at least about 150-fold, at least about 160-fold, at least about 170-fold, at least about 180-fold, at least about 190-fold, or at least about 200-fold with respect to basal levels in the subject, relative to levels in a subject administered a control lentiviral vector or a control nucleic acid molecule.

In some embodiments, the lentiviral vector is administered as a single dose or multiple doses. In some embodiments, the lentiviral vector dose is administered at once or divided into multiple sub-dose, e.g., two sub-doses, three sub-doses, four sub-doses, five sub-doses, six sub-doses, or more than six sub-doses. In some embodiments, more than one lentiviral vector is administered.

In some embodiments, the dose of lentiviral vector is administered repeated at least twice, at least three times, at least four times, at least five times, at least six times, at least seven times, at least eight times, at least nine times, or at least ten times. In some embodiments, the lentiviral vector is administered via intravenous injection.

In some embodiments, the subject is a pediatric subject. In some embodiments, the subject is an adult subject.

In some embodiments, the lentiviral vector comprises at least one tissue specific promoter, i.e., a promoter that would regulate the expression of the polypeptide with FVIII activity or the polypeptide with FIX activity in a particular tissue or cell type. In some embodiments, a tissue specific promoter in the lentiviral vector selectively enhances expression of the polypeptide with FVIII activity in a target liver cell. In some embodiments, the tissue specific promoter that selectively enhances expression of the polypeptide with FVIII activity in a target liver cell comprises an mTTR promoter. In some embodiments, the tissue specific promoter that selectively enhances expression of the polypeptide with FIX activity in a target liver cell comprises an APOA2 promoter, SERPINA1 (hAAT) promoter, mTTR promoter, MIR122 promoter, the ET promoter (GenBank No. AY661265; see also Vigna et al., *Molecular Therapy* 11(5):763 (2005)), or any combination thereof. In some embodiments, the target liver cell is a hepatocyte.

Since the lentiviral vector can transduce all liver cell types, the expression of the transgene (e.g., FVIII or FIX) in different cell types can be controlled by using different promoters in the lentiviral vector. Thus, the lentiviral vector can comprise specific promoters which would control expression of the FVIII transgene or the FIX transgene in different tissues or cells types, such as different hepatic tissues or cell types. Thus, in some embodiments, the lentiviral vector can comprise an endothelial specific promoter which would control expression of the FVIII transgene or the FIX transgene in hepatic endothelial tissue, or a hepatocyte specific promoter which would control expression of the FVIII transgene or the FIX transgene in hepatocytes, or both.

In some embodiments, the lentiviral vector comprises a tissue-specific promoter or tissue-specific promoters that control the expression of the FVIII transgene or the FIX transgene in tissues other than liver. In some embodiments, the isolated nucleic acid molecule is stably integrated into the genome of the target cell or target tissue, for example, in the genome of a hepatocyte or in the genome of a hepatic endothelial cell.

In some embodiments, the isolated nucleic acid molecule in a lentiviral vector of the present disclosure further comprises a heterologous nucleotide sequence encoding a heterologous amino acid sequence (e.g., a half-life extender). In some embodiments, the heterologous amino acid sequence is an immunoglobulin constant region or a portion thereof, XTEN, transferrin, albumin, or a PAS sequence. In some embodiments, the heterologous amino acid sequence is linked to the N-terminus or the C-terminus of the amino acid sequence encoded by the nucleotide sequence, or inserted between two amino acids in the amino acid sequence encoded by the nucleotide sequence at one or more insertion site selected from Table 2. Heterologous nucleotide sequences are further described herein.

In some embodiments, the polypeptide with FVIII activity is a human FVIII. In some embodiments, the polypeptide with FVIII activity is a full length FVIII. In some embodiments, the polypeptide with FVIII activity is a B domain deleted FVIII.

In some embodiments, the polypeptide with FIX activity is a human FIX. In some embodiments, the polypeptide with FIX activity is a full length FIX. In some embodiments, the polypeptide with FIX activity is a variant of human FIX. In certain embodiments, the polypeptide with FIX activity is a R338L variant of human FIX. In certain embodiments, the polypeptide with FIX activity is the Padua variant.

The lentiviral vectors disclosed herein can be used in vivo in a mammal, e.g., a human patient, using a gene therapy approach to treatment of a bleeding disease or disorder selected from the group consisting of a bleeding coagulation disorder, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, and bleeding in the illiopsoas sheath would be therapeutically beneficial. In one embodiment, the bleeding disease or disorder is hemophilia. In another embodiment, the bleeding disease or disorder is hemophilia A. In another embodiment, the blooding disease or disorder is hemophilia B.

In some embodiments, target cells (e.g., hepatocytes) are treated in vitro with the lentiviral vectors disclosed herein before being administered to the patient. In certain embodiments, target cells (e.g., hepatocytes) are treated in vitro with the lentiviral vectors disclosed herein before being administered to the patient. In yet another embodiment, cells from the patient (e.g., hepatocytes) are treated ex vivo with the lentiviral vectors disclosed herein before being administered to the patient.

In some embodiments, plasma FVIII activity post administration of a lentiviral vectors disclosed herein (administered, e.g., at $10^{10}$ TU/kg or lower, $10^9$ TU/kg or lower, or $10^8$ TU/kg or lower) is increased by at least about 100%, at least about 110%, at least about 120%, at least about 130%, at least about 140%, at least about 150%, at least about 160%, at least about 170%, at least about 180%, at least about 190%, at least about 200%, at least about 210%, at least about 220%, at least about 230%, at least about 240%, at least about 250%, at least about 260%, at least about 270%, at least about 280%, at least about 290%, or at least about 300%, relative to physiologically normal circulating FVIII levels.

In some embodiments, plasma FIX activity post administration of a lentiviral vectors disclosed herein (administered, e.g., at $10^{10}$ TU/kg or lower, $10^9$ TU/kg or lower, or $10^8$ TU/kg or lower) is increased by at least about 100%, at least about 110%, at least about 120%, at least about 130%, at least about 140%, at least about 150%, at least about 160%, at least about 170%, at least about 180%, at least about 190%, at least about 200%, at least about 210%, at least about 220%, at least about 230%, at least about 240%, at least about 250%, at least about 260%, at least about 270%, at least about 280%, at least about 290%, or at least about 300%, relative to physiologically normal circulating FIX levels.

In one embodiment, the plasma FVIII activity post administration of a lentiviral vector of the present disclosure is increased by at least about 3,000% to about 5,000% relative to physiologically normal circulating FVIII levels. In some embodiments, post administration of a lentiviral vector comprising a codon-optimized gene encoding polypeptides with Factor VIII (FVIII) activity described herein, plasma FVIII activity is increased by at least about 10-fold, at least about 20-fold, at least about 30-fold, at least about 40-fold, at least about 50-fold, at least about 60-fold, at least about 70-fold, at least about 80-fold, at least about 90-fold, at least about 100-fold, at least about 110-fold, at least about 120-fold, at least about 130-fold, at least about 140-fold, at least about 150-fold, at least about 160-fold, at least about 170-fold, at least about 180-fold, at least about 190-fold, or at least about 200-fold relative to a subject administered a control lentiviral vector or a control nucleic acid molecule.

In one embodiment, the plasma FIX activity post administration of a lentiviral vector of the present disclosure is increased by at least about 3,000% to about 5,000% relative to physiologically normal circulating FIX levels. In some embodiments, post administration of a lentiviral vector comprising a codon-optimized gene encoding polypeptides with Factor IX (FIX) activity described herein, plasma FIX activity is increased by at least about 10-fold, at least about 20-fold, at least about 30-fold, at least about 40-fold, at least about 50-fold, at least about 60-fold, at least about 70-fold, at least about 80-fold, at least about 90-fold, at least about 100-fold, at least about 110-fold, at least about 120-fold, at least about 130-fold, at least about 140-fold, at least about 150-fold, at least about 160-fold, at least about 170-fold, at least about 180-fold, at least about 190-fold, or at least about 200-fold relative to a subject administered a control lentiviral vector or a control nucleic acid molecule.

The present disclosure also provides methods of treating, preventing. Or ameliorating a hemostatic disorder (e.g., a bleeding disorder such as hemophilia A or hemophilia B) in a subject in need thereof comprising administering to the subject a therapeutically effective amount of a lentiviral vector comprising an isolated nucleic acid molecule comprising a nucleotide sequence encoding a polypeptide with FVIII activity or a polypeptide with FIX activity.

The treatment, amelioration, and prevention by the lentiviral vector of the present disclosure can be a bypass therapy. The subject receiving bypass therapy can have already developed an inhibitor to a clotting factor, e.g., FVIII or FIX, or is subject to developing a clotting factor inhibitor.

The lentiviral vectors of the present disclosure treat or prevent a hemostatic disorder by promoting the formation of a fibrin clot. The polypeptide having FVIII or FIX activity encoded by the nucleic acid molecule of the disclosure can activate a member of a coagulation cascade. The clotting factor can be a participant in the extrinsic pathway, the intrinsic pathway or both.

The lentiviral vectors of the present disclosure can be used to treat hemostatic disorders known to be treatable with FVIII or FIX. The hemostatic disorders that can be treated using methods of the disclosure include, but are not limited to, hemophilia A, hemophilia B, von Willebrand's disease, Factor XI deficiency (PTA deficiency), Factor XII deficiency, as well as deficiencies or structural abnormalities in fibrinogen, prothrombin, Factor V, Factor VII, Factor X, or Factor XIII, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, and bleeding in the illiopsoas sheath.

Compositions for administration to a subject include lentiviral vectors comprising nucleic acid molecules which comprise an optimized nucleotide sequence of the disclosure encoding a FVIII clotting factor or a FIX clotting factor (for gene therapy applications) as well as FVIII or FIX polypeptide molecules. In some embodiments, the composition for administration is a cell contacted with a lentiviral vector of the present disclosure, either in vivo, in vitro, or ex vivo.

In some embodiments, the hemostatic disorder is an inherited disorder. In one embodiment, the subject has hemophilia A. In other embodiments, the hemostatic disorder is the result of a deficiency in FVIII. In other embodiments, the hemostatic disorder can be the result of a defective FVIII clotting factor. In one embodiment, the subject has hemophilia B. In other embodiments, the hemostatic disorder is the result of a deficiency in FIX. In other embodiments, the hemostatic disorder can be the result of a defective FIX clotting factor.

In another embodiment, the hemostatic disorder can be an acquired disorder. The acquired disorder can result from an underlying secondary disease or condition. The unrelated condition can be, as an example, but not as a limitation, cancer, an autoimmune disease, or pregnancy. The acquired disorder can result from old age or from medication to treat an underlying secondary disorder (e.g., cancer chemotherapy).

The disclosure also relates to methods of treating a subject that does not have a hemostatic disorder or a secondary disease or condition resulting in acquisition of a hemostatic disorder. The disclosure thus relates to a method of treating a subject in need of a general hemostatic agent comprising administering a therapeutically effective amount of a lentiviral vector of the present disclosure. For example, in one embodiment, the subject in need of a general hemostatic agent is undergoing, or is about to undergo, surgery. The lentiviral vector of the disclosure can be administered prior to or after surgery as a prophylactic.

The lentiviral vector of the disclosure can be administered during or after surgery to control an acute bleeding episode. The surgery can include, but is not limited to, liver transplantation, liver resection, or stem cell transplantation.

In another embodiment, the lentiviral vector of the disclosure can be used to treat a subject having an acute bleeding episode who does not have a hemostatic disorder. The acute bleeding episode can result from severe trauma, e.g., surgery, an automobile accident, wound, laceration gun shot, or any other traumatic event resulting in uncontrolled bleeding.

The lentiviral vector can be used to prophylactically treat a subject with a hemostatic disorder. The lentiviral vector can also be used to treat an acute bleeding episode in a subject with a hemostatic disorder.

In another embodiment, the administration of a lentiviral vector disclosed herein and/or subsequent expression of FVIII protein or FIX protein does not induce an immune response in a subject. In some embodiments, the immune response comprises development of antibodies against FVIII or FIX. In some embodiments, the immune response comprises cytokine secretion. In some embodiments, the immune response comprises activation of B cells, T cells, or both B cells and T cells. In some embodiments, the immune response is an inhibitory immune response, wherein the immune response in the subject reduces the activity of the FVIII protein relative to the activity of the FVIII in a subject that has not developed an immune response. In certain embodiments, expression of FVIII protein by administering the lentiviral vector of the disclosure prevents an inhibitory immune response against the FVIII protein or the FVIII protein expressed from the isolated nucleic acid molecule or the lentiviral vector. In some embodiments, the immune response is an inhibitory immune response, wherein the immune response in the subject reduces the activity of the FIX protein relative to the activity of the FIX in a subject that has not developed an immune response. In certain embodiments, expression of FIX protein by administering the lentiviral vector of the disclosure prevents an inhibitory immune response against the FIX protein or the FIX protein expressed from the isolated nucleic acid molecule or the lentiviral vector.

In some embodiments, a lentiviral vector of the disclosure is administered in combination with at least one other agent that promotes hemostasis. Said other agent that promotes hemostasis in a therapeutic with demonstrated clotting activity. As an example, but not as a limitation, the hemostatic agent can include Factor V, Factor VII, Factor IX, Factor X, Factor XI, Factor XII, Factor XIII, prothrombin, or fibrinogen or activated forms of any of the preceding. The clotting factor or hemostatic agent can also include anti-fibrinolytic drugs, e.g., epsilon-amino-caproic acid, tranexamic acid.

In one embodiment of the disclosure, the composition (e.g., the lentiviral vector) is one in which the FVIII is present in activatable form when administered to a subject. In one embodiment of the disclosure, the composition (e.g., the lentiviral vector) is one in which the FIX is present in activatable form when administered to a subject. Such an activatable molecule can be activated in vivo at the site of clotting after administration to a subject.

The lentiviral vector of the disclosure can be administered intravenously, subcutaneously, intramuscularly, or via any mucosal surface, e.g., orally, sublingually, buccally, sublingually, nasally, rectally, vaginally or via pulmonary route. The lentiviral vector can be implanted within or linked to a biopolymer solid support that allows for the slow release of the vector to the desired site.

In one embodiment, the route of administration of the lentiviral vectors is parenteral. The term parenteral as used herein includes intravenous, intraarterial, intraperitoneal, intramuscular, subcutaneous, rectal or vaginal administration. The intravenous form of parenteral administration is preferred. While all these forms of administration are clearly contemplated as being within the scope of the disclosure, a form for administration would be a solution for injection, in particular for intravenous or intraarterial injection or drip. Usually, a suitable pharmaceutical composition for injection can comprise a buffer (e.g. acetate, phosphate or citrate buffer), a surfactant (e.g. polysorbate), optionally a stabilizer agent (e.g. human albumin), etc. However, in other methods compatible with the teachings herein, the lentiviral vector can be delivered directly to the site of the adverse cellular population thereby increasing the exposure of the diseased tissue to the therapeutic agent.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the subject disclosure, pharmaceutically acceptable carriers include, but are not limited to, 0.01-0.1M and preferably 0.05M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives can also be present such as for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., a polypeptide by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations can be packaged and sold in the form of a kit. Such articles of manufacture will preferably have labels or package inserts indicating that the associated compositions are useful for treating a subject suffering from, or predisposed to clotting disorders.

The pharmaceutical composition can also be formulated for rectal administration as a suppository or retention enema, e.g., containing conventional suppository bases such as cocoa butter or other glycerides.

Effective doses of the compositions of the present disclosure, for the treatment of conditions vary depending upon many different factors, including means of administration, target site, physiological state of the patient, whether the patient is human or an animal, other medications administered, and whether treatment is prophylactic or therapeutic. Usually, the patient is a human, but non-human mammals including transgenic mammals can also be treated. Treatment dosages can be titrated using routine methods known to those of skill in the art to optimize safety and efficacy.

The lentiviral vector can be administered as a single dose or as multiple doses, wherein the multiple doses can be administered continuously or at specific timed intervals. In vitro assays can be employed to determine optimal dose ranges and/or schedules for administration. In vitro assays that measure clotting factor activity are known in the art. Additionally, effective doses can be extrapolated from dose-response curves obtained from animal models, e.g., a hemophiliac dog (Mount et al. 2002, Blood 99 (8): 2670).

Doses intermediate in the above ranges are also intended to be within the scope of the disclosure. Subjects can be administered such doses daily, on alternative days, weekly or according to any other schedule determined by empirical analysis. An exemplary treatment entails administration in multiple dosages over a prolonged period, for example, of at least six months.

The lentiviral vector of the disclosure can be administered on multiple occasions. Intervals between single dosages can be daily, weekly, monthly or yearly. Intervals can also be irregular as indicated by measuring blood levels of modified polypeptide or antigen in the patient. Dosage and frequency of the lentiviral vectors of the disclosure vary depending on the half-life of the FVIII polypeptide or the FIX polypeptide encoded by the transgene in the patient.

The dosage and frequency of administration of the lentiviral vectors of the disclosure can vary depending on whether the treatment is prophylactic or therapeutic. In prophylactic applications, compositions containing the lentiviral vector of the disclosure are administered to a patient not already in the disease state to enhance the patient's resistance or minimize effects of disease. Such an amount is defined to be a "prophylactic effective dose." A relatively low dosage is administered at relatively infrequent intervals over a long period of time. Some patients continue to receive treatment for the rest of their lives.

The lentiviral vector of the disclosure can optionally be administered in combination with other agents that are effective in treating the disorder or condition in need of treatment (e.g., prophylactic or therapeutic).

As used herein, the administration of lentiviral vectors of the disclosure in conjunction or combination with an adjunct therapy means the sequential, simultaneous, coextensive, concurrent, concomitant or contemporaneous administration or application of the therapy and the disclosed polypeptides. Those skilled in the art will appreciate that the administration or application of the various components of the combined therapeutic regimen can be timed to enhance the overall effectiveness of the treatment. A skilled artisan (e.g., a physician) would be readily be able to discern effective combined therapeutic regimens without undue experimentation based on the selected adjunct therapy and the teachings of the instant specification.

It will further be appreciated that the lentiviral vectors of the disclosure can be used in conjunction or combination with an agent or agents (e.g., to provide a combined therapeutic regimen). Exemplary agents with which a lentiviral vector of the instant disclosure can be combined include agents that represent the current standard of care for a particular disorder being treated. Such agents can be chemical or biologic in nature. The term "biologic" or "biologic agent" refers to any pharmaceutically active agent made from living organisms and/or their products which is intended for use as a therapeutic.

The amount of agent to be used in combination with the lentiviral vectors of the instant disclosure can vary by subject or can be administered according to what is known in the art. See, e.g., Bruce A Chabner et al., *Antineoplastic Agents, in* GOODMAN & GILMAN'S THE PHARMACOLOGICAL BASIS OF THERAPEUTICS 1233-1287 ((Joel G. Hardman et al., eds., 9th ed. 1996). In another embodiment, an amount of such an agent consistent with the standard of care is administered.

In certain embodiments, the lentiviral vectors of the present disclosure are administered in conjunction with an immunosuppressive, anti-allergic, or anti-inflammatory agent. These agents generally refer to substances that act to suppress or mask the immune system of the subject being treated herein. These agents include substances that suppress cytokine production, downregulate or suppress self-antigen expression, or mask the MHC antigens. Examples of such agents include 2-amino-6-aryl-5-substituted pyrimidines; azathioprine; cyclophosphamide; bromocryptine; danazol; dapsone; glutaraldehyde; anti-idiotypic antibodies for MHC antigens and MHC fragments; cyclosporin A; steroids such as glucocorticosteroids, e.g., prednisone, methylprednisolone, and dexamethasone; cytokine or cytokine receptor antagonists including anti-interferon-$\gamma$, -$\beta$, or -$\alpha$ antibodies, anti-tumor necrosis factor-$\alpha$ antibodies, anti-tumor necrosis factor-$\beta$ antibodies, anti-interleukin-2 antibodies and anti-IL-2 receptor antibodies; anti-LFA-1 antibodies, including anti-CD11a and anti-CD18 antibodies; anti-L3T4 antibodies; heterologous anti-lymphocyte globulin; pan-T antibodies; soluble peptide containing a LFA-3 binding domain; streptokinase; TGF-0; streptodornase; FK506; RS-61443; deoxyspergualin; and rapamycin. In certain embodiments, the agent is an antihistamine. An "antihistamine" as used herein is an agent that antagonizes the physiological effect of histamine. Examples of antihistamines are chlorpheniramine, diphenhydramine, promethazine, cromolyn sodium, astemizole, azatadine maleate, bropheniramine maleate, carbinoxamine maleate, cetirizine hydrochloride, clemastine fumarate, cyproheptadine hydrochloride, dexbrompheniramine maleate, dexchlorpheniramine maleate, dimenhydrinate, diphenhydramine hydrochloride, doxylamine succinate, fexofendadine hydrochloride, terphenadine hydrochloride, hydroxyzine hydrochloride, loratidine, meclizine hydrochloride, tripelannamine citrate, tripelennamine hydrochloride, and triprolidine hydrochloride.

Immunosuppressive, anti-allergic, or anti-inflammatory agents may be incorporated into the lentiviral vector administration regimen. For example, administration of immunosuppressive or anti-inflammatory agents may commence prior to administration of the disclosed lentiviral vectors, and may continue with one or more doses thereafter. In certain embodiments, the immunosuppressive or anti-inflammatory agents are administered as premedication to the lentiviral vectors.

As previously discussed, the lentiviral vectors of the present disclosure, can be administered in a pharmaceutically effective amount for the in vivo treatment of clotting disorders. In this regard, it will be appreciated that the lentiviral vectors of the disclosure can be formulated to facilitate administration and promote stability of the active agent. Preferably, pharmaceutical compositions in accordance with the present disclosure comprise a pharmaceutically acceptable, non-toxic, sterile carrier such as physiological saline, non-toxic buffers, preservatives and the like. Of course, the pharmaceutical compositions of the present disclosure can be administered in single or multiple doses to provide for a pharmaceutically effective amount of the polypeptide.

A number of tests are available to assess the function of the coagulation system: activated partial thromboplastin time (aPTT) test, chromogenic assay, ROTEM® assay, prothrombin time (PT) test (also used to determine INR), fibrinogen testing (often by the Clauss method), platelet count, platelet function testing (often by PFA-100), TCT, bleeding time, mixing test (whether an abnormality corrects if the patient's plasma is mixed with normal plasma), coagulation factor assays, antiphosholipid antibodies, D-dimer, genetic tests (e.g., factor V Leiden, prothrombin mutation G20210A), dilute Russell's viper venom time (dRVVT), miscellaneous platelet function tests, thromboelastography (TEG or Sonoclot), thromboelastometry (TEM®, e.g, ROTEM®), or euglobulin lysis time (ELT).

The aPTT test is a performance indicator measuring the efficacy of both the "intrinsic" (also referred to the contact activation pathway) and the common coagulation pathways. This test is commonly used to measure clotting activity of commercially available recombinant clotting factors, e.g., FVIII or FIX. It is used in conjunction with prothrombin time (PT), which measures the extrinsic pathway.

ROTEM® analysis provides information on the whole kinetics of haemostasis: clotting time, clot formation, clot stability and lysis. The different parameters in thromboelastometry are dependent on the activity of the plasmatic coagulation system, platelet function, fibrinolysis, or many factors which influence these interactions. This assay can provide a complete view of secondary haemostasis.

B.2. Tissue Specific Expression

In certain embodiments, it will be useful to include within the lentiviral vector one or more miRNA target sequences which, for example, are operably linked to the optimized FVIII transgene. Thus, the disclosure also provides at least one miRNA sequence target operably linked to the optimized FVIII or optimized FIX nucleotide sequence or otherwise inserted within a lentiviral vector. More than one copy of a miRNA target sequence included in the lentiviral vector can increase the effectiveness of the system.

Also included are different miRNA target sequences. For example, lentiviral vectors which express more than one transgene can have the transgene under control of more than one miRNA target sequence, which can be the same or different. The miRNA target sequences can be in tandem, but other arrangements are also included. The transgene expression cassette, containing miRNA target sequences, can also be inserted within the lentiviral vector in antisense orientation. Antisense orientation can be useful in the production of viral particles to avoid expression of gene products which can otherwise be toxic to the producer cells.

In other embodiments, the lentiviral vector comprises 1, 2, 3, 4, 5, 6, 7 or 8 copies of the same or different miRNA target sequence. In certain embodiments, the lentiviral vector does not include any miRNA target sequence. Choice of whether or not to include an miRNA target sequence (and how many) will be guided by known parameters such as the intended tissue target, the level of expression required, etc.

In one embodiment, the target sequence is an miR-223 target which has been reported to block expression most effectively in myeloid committed progenitors and at least partially in the more primitive HSPC. miR-223 target can block expression in differentiated myeloid cells including granulocytes, monocytes, macrophages, myeloid dendritic cells. miR-223 target can also be suitable for gene therapy applications relying on robust transgene expression in the lymphoid or erythroid lineage. miR-223 target can also block expression very effectively in human HSC.

In another embodiment, the target sequence is an miR142 target (tccataaagtaggaaacactaca (SEQ ID NO: 7)). In one embodiment, the lentiviral vector comprises 4 copies of miR-142 target sequences. In certain embodiments, the complementary sequence of hematopoietic-specific microRNAs, such as miR-142 (142T), is incorporated into the 3' untranslated region of a lentiviral vector, making the transgene-encoding transcript susceptible to miRNA-mediated down-regulation. By this method, transgene expression can be prevented in hematopoietic-lineage antigen presenting cells (APC), while being maintained in non-hematopoietic cells (Brown et al., Nat Med 2006). This strategy can imposes a stringent post-transcriptional control on transgene expression and thus enables stable delivery and long-term expression of transgenes. In some embodiments, miR-142 regulation prevents immune-mediated clearance of transduced cells and/or induce antigen-specific Regulatory T cells (T regs) and mediate robust immunological tolerance to the transgene-encoded antigen.

In some embodiments, the target sequence is an miR181 target. Chen C-Z and Lodish H, Seminars in Immunology (2005) 17(2):155-165 discloses miR-181, a miRNA specifically expressed in B cells within mouse bone marrow (Chen and Lodish, 2005). It also discloses that some human miRNAs are linked to leukemias.

The target sequence can be fully or partially complementary to the miRNA. The term "fully complementary" means that the target sequence has a nucleic acid sequence which is 100% complementary to the sequence of the miRNA which recognizes it. The term "partially complementary" means that the target sequence is only in part complementary to the sequence of the miRNA which recognizes it, whereby the partially complementary sequence is still recognized by the miRNA. In other words, a partially complementary target sequence in the context of the present disclosure is effective in recognizing the corresponding miRNA and effecting prevention or reduction of transgene expression in cells expressing that miRNA. Examples of the miRNA target sequences are described at W2007/000668, WO2004/094642, WO2010/055413, or WO2010/125471, which are incorporated herein by reference in their entireties.

B.3. Heterologous Nucleotide Sequences

In some embodiments, the isolated nucleic acid molecule further comprises a heterologous nucleotide sequence. In some embodiments, the isolated nucleic acid molecule further comprises at least one heterologous nucleotide sequence. The heterologous nucleotide sequence can be linked with the FVIII or FIX coding sequences of the disclosure at the 5' end, at the 3' end, or inserted into the middle. Thus, in some embodiments, the heterologous amino acid sequence encoded by the heterologous nucleotide sequence is linked to the N-terminus or the C-terminus of the FVIII amino acid sequence or the FIX amino acid sequence encoded by the nucleotide sequence or inserted between two amino acids in the FVIII amino acid sequence or the FIX amino acid sequence. In some embodiments, the heterologous amino acid sequence can be inserted between two amino acids of an FVIII polypeptide at one or more insertion site selected from Table 2. In some embodiments, the heterologous amino acid sequence can be inserted within the FVIII polypeptide encoded by the nucleic acid molecule of the disclosure at any site disclosed in International Publication No. WO 2013/123457 A1 and WO 2015/106052 A1 or U.S. Publication No. 2015/0158929 A1, which are herein incorporated by reference in their entirety.

In some embodiments, the heterologous amino acid sequence encoded by the heterologous nucleotide sequence is inserted within the B domain or a fragment thereof. In some embodiments, the heterologous amino acid sequence is inserted within the FVIII immediately downstream of an amino acid corresponding to amino acid 745 of mature human FVIII (SEQ ID NO:4). In one particular embodiment, the FVIII comprises a deletion of amino acids 746-1646, corresponding to mature human FVIII (SEQ ID NO:4), and the heterologous amino acid sequence encoded by the heterologous nucleotide sequence is inserted immediately downstream of amino acid 745, corresponding to mature human FVIII (SEQ ID NO:4).

TABLE 2

Heterologous Moiety Insertion Sites

| Insertion Site | Domain |
|---|---|
| 3 | A1 |
| 18 | A1 |
| 22 | A1 |
| 26 | A1 |
| 40 | A1 |
| 60 | A1 |
| 65 | A1 |
| 81 | A1 |
| 116 | A1 |
| 119 | A1 |
| 130 | A1 |
| 188 | A1 |
| 211 | A1 |
| 216 | A1 |
| 220 | A1 |
| 224 | A1 |
| 230 | A1 |
| 333 | A1 |
| 336 | A1 |
| 339 | A1 |
| 375 | A2 |
| 378 | A2 |
| 399 | A2 |
| 403 | A2 |
| 409 | A2 |
| 416 | A2 |
| 442 | A2 |
| 487 | A2 |
| 490 | A2 |
| 494 | A2 |
| 500 | A2 |
| 518 | A2 |
| 599 | A2 |
| 603 | A2 |
| 713 | A2 |
| 745 | B |
| 1656 | a3 region |
| 1711 | A3 |
| 1720 | A3 |
| 1725 | A3 |
| 1749 | A3 |
| 1796 | A3 |
| 1802 | A3 |
| 1827 | A3 |
| 1861 | A3 |
| 1896 | A3 |
| 1900 | A3 |
| 1904 | A3 |
| 1905 | A3 |
| 1910 | A3 |
| 1937 | A3 |
| 2019 | A3 |
| 2068 | C1 |
| 2111 | C1 |
| 2120 | C1 |
| 2171 | C2 |

TABLE 2-continued

Heterologous Moiety Insertion Sites

| Insertion Site | Domain |
|---|---|
| 2188 | C2 |
| 2227 | C2 |
| 2332 | CT |

Note:
Insertion sites indicate the amino acid position corresponding to an amino acid position of mature human FVIII (SEQ ID NO: 4).

In other embodiments, the isolated nucleic acid molecule further comprise two, three, four, five, six, seven, or eight heterologous nucleotide sequences. In some embodiments, all the heterologous nucleotide sequences are identical. In some embodiments, at least one heterologous nucleotide sequence is different from the other heterologous nucleotide sequences. In some embodiments, the disclosure can comprise two, three, four, five, six, or more than seven heterologous nucleotide sequences in tandem.

In some embodiments, the heterologous nucleotide sequence encodes an amino acid sequence. In some embodiments, the amino acid sequence encoded by the heterologous nucleotide sequence is a heterologous moiety that can increase the half-life (a "half-life extender") of an FVIII molecule.

In some embodiments, the heterologous moiety is a peptide or a polypeptide with either unstructured or structured characteristics that are associated with the prolongation of in vivo half-life when incorporated in a protein of the disclosure. Non-limiting examples include albumin, albumin fragments, Fc fragments of immunoglobulins, the C-terminal peptide (CTP) of the β subunit of human chorionic gonadotropin, a HAP sequence, an XTEN sequence, a transferrin or a fragment thereof, a PAS polypeptide, polyglycine linkers, polyserine linkers, albumin-binding moieties, or any fragments, derivatives, variants, or combinations of these polypeptides. In one particular embodiment, the heterologous amino acid sequence is an immunoglobulin constant region or a portion thereof, transferrin, albumin, or a PAS sequence.

In some aspects, a heterologous moiety includes von Willebrand factor or a fragment thereof. In other related aspects a heterologous moiety can include an attachment site (e.g., a cysteine amino acid) for a non-polypeptide moiety such as polyethylene glycol (PEG), hydroxyethyl starch (HES), polysialic acid, or any derivatives, variants, or combinations of these elements. In some aspects, a heterologous moiety comprises a cysteine amino acid that functions as an attachment site for a non-polypeptide moiety such as polyethylene glycol (PEG), hydroxyethyl starch (HES), polysialic acid, or any derivatives, variants, or combinations of these elements.

In one specific embodiment, a first heterologous nucleotide sequence encodes a first heterologous moiety that is a half-life extending molecule which is known in the art, and a second heterologous nucleotide sequence encodes a second heterologous moiety that can also be a half-life extending molecule which is known in the art. In certain embodiments, the first heterologous moiety (e.g., a first Fc moiety) and the second heterologous moiety (e.g., a second Fc moiety) are associated with each other to form a dimer. In one embodiment, the second heterologous moiety is a second Fc moiety, wherein the second Fc moiety is linked to or associated with the first heterologous moiety, e.g., the first Fc moiety. For example, the second heterologous moiety (e.g., the second Fc moiety) can be linked to the first heterologous moiety (e.g., the first Fc moiety) by a linker or associated with the first heterologous moiety by a covalent or non-covalent bond.

In some embodiments, the heterologous moiety is a polypeptide comprising, consisting essentially of, or consisting of at least about 10, at least about 100, at least about 200, at least about 300, at least about 400, at least about 500, at least about 600, at least about 700, at least about 800, at least about 900, at least about 1000, at least about 1100, at least about 1200, at least about 1300, at least about 1400, at least about 1500, at least about 1600, at least about 1700, at least about 1800, at least about 1900, at least about 2000, at least about 2500, at least about 3000, or at least about 4000 amino acids.

In other embodiments, the heterologous moiety is a polypeptide comprising, consisting essentially of, or consisting of about 100 to about 200 amino acids, about 200 to about 300 amino acids, about 300 to about 400 amino acids, about 400 to about 500 amino acids, about 500 to about 600 amino acids, about 600 to about 700 amino acids, about 700 to about 800 amino acids, about 800 to about 900 amino acids, or about 900 to about 1000 amino acids.

In certain embodiments, a heterologous moiety improves one or more pharmacokinetic properties of the FVIII or FIX protein without significantly affecting its biological activity or function.

In certain embodiments, a heterologous moiety increases the in vivo and/or in vitro half-life of the FVIII or FIX protein of the disclosure. In other embodiments, a heterologous moiety facilitates visualization or localization of the FVIII or FIX protein of the disclosure or a fragment thereof (e.g., a fragment comprising a heterologous moiety after proteolytic cleavage of the FVIII or FIX protein). Visualization and/or location of the FVIII or FIX protein of the disclosure or a fragment thereof can be in vivo, in vitro, ex vivo, or combinations thereof.

In other embodiments, a heterologous moiety increases stability of the FVIII or FIX protein of the disclosure or a fragment thereof (e.g., a fragment comprising a heterologous moiety after proteolytic cleavage of the FVIII or FIX protein). As used herein, the term "stability" refers to an art-recognized measure of the maintenance of one or more physical properties of the FVIII or FIX protein in response to an environmental condition (e.g., an elevated or lowered temperature). In certain aspects, the physical property can be the maintenance of the covalent structure of the FVIII or FIX protein (e.g., the absence of proteolytic cleavage, unwanted oxidation or deamidation). In other aspects, the physical property can also be the presence of the FVIII or FIX protein in a properly folded state (e.g., the absence of soluble or insoluble aggregates or precipitates).

In one aspect, the stability of the FVIII or FIX protein is measured by assaying a biophysical property of the FVIII or FIX protein, for example thermal stability, pH unfolding profile, stable removal of glycosylation, solubility, biochemical function (e.g., ability to bind to a protein, receptor or ligand), etc., and/or combinations thereof. In another aspect, biochemical function is demonstrated by the binding affinity of the interaction. In one aspect, a measure of protein stability is thermal stability, i.e., resistance to thermal challenge. Stability can be measured using methods known in the art, such as, HPLC (high performance liquid chromatography), SEC (size exclusion chromatography), DLS (dynamic light scattering), etc. Methods to measure thermal stability include, but are not limited to differential scanning calorimetry (DSC), differential scanning fluorimetry (DSF), circular dichroism (CD), and thermal challenge assay.

In certain aspects, a FVIII or FIX protein encoded by the nucleic acid molecule of the disclosure comprises at least one half-life extender, i.e., a heterologous moiety which increases the in vivo half-life of the FVIII or FIX protein with respect to the in vivo half-life of the corresponding FVIII or FIX protein lacking such heterologous moiety. In vivo half-life of a FVIII or FIX protein can be determined by any methods known to those of skill in the art, e.g., activity assays (chromogenic assay or one stage clotting aPTT assay), ELISA, ROTEM™, etc.

In some embodiments, the presence of one or more half-life extenders results in the half-life of the FVIII or FIX protein to be increased compared to the half-life of the corresponding protein lacking such one or more half-life extenders. The half-life of the FVIII or FIX protein comprising a half-life extender is at least about 1.5 times, at least about 2 times, at least about 2.5 times, at least about 3 times, at least about 4 times, at least about 5 times, at least about 6 times, at least about 7 times, at least about 8 times, at least about 9 times, at least about 10 times, at least about 11 times, or at least about 12 times longer than the in vivo half-life of the corresponding FVIII or FIX protein lacking such half-life extender.

In one embodiment, the half-life of the FVIII or FIX protein comprising a half-life extender is about 1.5-fold to about 20-fold, about 1.5 fold to about 15 fold, or about 1.5 fold to about 10 fold longer than the in vivo half-life of the corresponding protein lacking such half-life extender. In another embodiment, the half-life of FVIII or FIX protein comprising a half-life extender is extended about 2-fold to about 10-fold, about 2-fold to about 9-fold, about 2-fold to about 8-fold, about 2-fold to about 7-fold, about 2-fold to about 6-fold, about 2-fold to about 5-fold, about 2-fold to about 4-fold, about 2-fold to about 3-fold, about 2.5-fold to about 10-fold, about 2.5-fold to about 9-fold, about 2.5-fold to about 8-fold, about 2.5-fold to about 7-fold, about 2.5-fold to about 6-fold, about 2.5-fold to about 5-fold, about 2.5-fold to about 4-fold, about 2.5-fold to about 3-fold, about 3-fold to about 10-fold, about 3-fold to about 9-fold, about 3-fold to about 8-fold, about 3-fold to about 7-fold, about 3-fold to about 6-fold, about 3-fold to about 5-fold, about 3-fold to about 4-fold, about 4-fold to about 6 fold, about 5-fold to about 7-fold, or about 6-fold to about 8 fold as compared to the in vivo half-life of the corresponding protein lacking such half-life extender.

In other embodiments, the half-life of the FVIII or FIX protein comprising a half-life extender is at least about 17 hours, at least about 18 hours, at least about 19 hours, at least about 20 hours, at least about 21 hours, at least about 22 hours, at least about 23 hours, at least about 24 hours, at least about 25 hours, at least about 26 hours, at least about 27 hours, at least about 28 hours, at least about 29 hours, at least about 30 hours, at least about 31 hours, at least about 32 hours, at least about 33 hours, at least about 34 hours, at least about 35 hours, at least about 36 hours, at least about 48 hours, at least about 60 hours, at least about 72 hours, at least about 84 hours, at least about 96 hours, or at least about 108 hours.

In still other embodiments, the half-life of the FVIII or FIX protein comprising a half-life extender is about 15 hours to about two weeks, about 16 hours to about one week, about 17 hours to about one week, about 18 hours to about one week, about 19 hours to about one week, about 20 hours to about one week, about 21 hours to about one week, about 22 hours to about one week, about 23 hours to about one week, about 24 hours to about one week, about 36 hours to about one week, about 48 hours to about one week, about 60 hours to about one week, about 24 hours to about six days, about 24 hours to about five days, about 24 hours to about four days, about 24 hours to about three days, or about 24 hours to about two days.

In some embodiments, the average half-life per subject of the FVIII or FIX protein comprising a half-life extender is about 15 hours, about 16 hours, about 17 hours, about 18 hours, about 19 hours, about 20 hours, about 21 hours, about 22 hours, about 23 hours, about 24 hours (1 day), about 25 hours, about 26 hours, about 27 hours, about 28 hours, about 29 hours, about 30 hours, about 31 hours, about 32 hours, about 33 hours, about 34 hours, about 35 hours, about 36 hours, about 40 hours, about 44 hours, about 48 hours (2 days), about 54 hours, about 60 hours, about 72 hours (3 days), about 84 hours, about 96 hours (4 days), about 108 hours, about 120 hours (5 days), about six days, about seven days (one week), about eight days, about nine days, about 10 days, about 11 days, about 12 days, about 13 days, or about 14 days.

One or more half-life extenders can be fused to C-terminus or N-terminus of FVIII or FIX or inserted within FVIII or FIX.

B.3.a. An Immunoglobulin Constant Region or a Portion Thereof

In another aspect, a heterologous moiety comprises one or more immunoglobulin constant regions or portions thereof (e.g., an Fc region). In one embodiment, an isolated nucleic acid molecule of the disclosure further comprises a heterologous nucleic acid sequence that encodes an immunoglobulin constant region or a portion thereof. In some embodiments, the immunoglobulin constant region or portion thereof is an Fc region.

An immunoglobulin constant region is comprised of domains denoted CH (constant heavy) domains (CH1, CH2, etc.). Depending on the isotype, (i.e. IgG, IgM, IgA IgD, or IgE), the constant region can be comprised of three or four CH domains. Some isotypes (e.g. IgG) constant regions also contain a hinge region. See Janeway et al. 2001, *Immunobiology*, Garland Publishing, N.Y., N.Y.

An immunoglobulin constant region or a portion thereof for producing the FVIII protein of the present disclosure can be obtained from a number of different sources. In one embodiment, an immunoglobulin constant region or a portion thereof is derived from a human immunoglobulin. It is understood, however, that the immunoglobulin constant region or a portion thereof can be derived from an immunoglobulin of another mammalian species, including for example, a rodent (e.g., a mouse, rat, rabbit, guinea pig) or non-human primate (e.g., chimpanzee, macaque) species. Moreover, the immunoglobulin constant region or a portion thereof can be derived from any immunoglobulin class, including IgM, IgG, IgD, IgA and IgE, and any immunoglobulin isotype, including IgG1, IgG2, IgG3 and IgG4. In one embodiment, the human isotype IgG1 is used.

A variety of the immunoglobulin constant region gene sequences (e.g., human constant region gene sequences) are available in the form of publicly accessible deposits. Constant region domains sequence can be selected having a particular effector function (or lacking a particular effector function) or with a particular modification to reduce immunogenicity. Many sequences of antibodies and antibody-encoding genes have been published and suitable Ig constant region sequences (e.g., hinge, CH2, and/or CH3 sequences, or portions thereof) can be derived from these sequences using art recognized techniques. The genetic material obtained using any of the foregoing methods can then be altered or synthesized to obtain polypeptides of the present disclosure. It will further be appreciated that the scope of this disclosure encompasses alleles, variants and mutations of constant region DNA sequences.

The sequences of the immunoglobulin constant region or a portion thereof can be cloned, e.g., using the polymerase chain reaction and primers which are selected to amplify the domain of interest. To clone a sequence of the immunoglobulin constant region or a portion thereof from an antibody, mRNA can be isolated from hybridoma, spleen, or lymph cells, reverse transcribed into DNA, and antibody genes amplified by PCR. PCR amplification methods are described in detail in U.S. Pat. Nos. 4,683,195; 4,683,202; 4,800,159; 4,965,188; and in, e.g., "PCR Protocols: A Guide to Methods and Applications" Innis et al. eds., Academic Press, San Diego, CA (1990); Ho et al. 1989. Gene 77:51; Horton et al. 1993. *Methods Enzymol.* 217:270). PCR can be initiated by consensus constant region primers or by more specific primers based on the published heavy and light chain DNA and amino acid sequences. PCR also can be used to isolate DNA clones encoding the antibody light and heavy chains. In this case the libraries can be screened by consensus primers or larger homologous probes, such as mouse constant region probes. Numerous primer sets suitable for amplification of antibody genes are known in the art (e.g., 5' primers based on the N-terminal sequence of purified antibodies (Benhar and Pastan. 1994. *Protein Engineering* 7:1509); rapid amplification of cDNA ends (Ruberti, F. et al. 1994. *J. Immunol. Methods* 173:33); antibody leader sequences (Larrick et al. 1989 *Biochem. Biophys. Res. Commun.* 160:1250). The cloning of antibody sequences is further described in Newman et al., U.S. Pat. No. 5,658,570, filed Jan. 25, 1995, which is incorporated by reference herein.

An immunoglobulin constant region used herein can include all domains and the hinge region or portions thereof. In one embodiment, the immunoglobulin constant region or a portion thereof comprises CH2 domain, CH3 domain, and a hinge region, i.e., an Fc region or an FcRn binding partner.

As used herein, the term "Fc region" is defined as the portion of a polypeptide which corresponds to the Fc region of native Ig, i.e., as formed by the dimeric association of the respective Fc domains of its two heavy chains. A native Fc region forms a homodimer with another Fc region. In contrast, the term "genetically-fused Fc region" or "single-chain Fc region" (scFc region), as used herein, refers to a synthetic dimeric Fc region comprised of Fc domains genetically linked within a single polypeptide chain (i.e., encoded in a single contiguous genetic sequence). See International Publication No. WO 2012/006635, incorporated herein by reference in its entirety.

In one embodiment, the "Fc region" refers to the portion of a single Ig heavy chain beginning in the hinge region just upstream of the papain cleavage site (i.e. residue 216 in IgG, taking the first residue of heavy chain constant region to be 114) and ending at the C-terminus of the antibody. Accordingly, a complete Fc region comprises at least a hinge domain, a CH2 domain, and a CH3 domain.

An immunoglobulin constant region or a portion thereof can be an FcRn binding partner. FcRn is active in adult epithelial tissues and expressed in the lumen of the intestines, pulmonary airways, nasal surfaces, vaginal surfaces, colon and rectal surfaces (U.S. Pat. No. 6,485,726). An FcRn binding partner is a portion of an immunoglobulin that binds to FcRn.

The FcRn receptor has been isolated from several mammalian species including humans. The sequences of the human FcRn, monkey FcRn, rat FcRn, and mouse FcRn are known (Story et al. 1994, J. Exp. Med. 180:2377). The FcRn receptor binds IgG (but not other immunoglobulin classes such as IgA, IgM, IgD, and IgE) at relatively low pH, actively transports the IgG transcellularly in a luminal to serosal direction, and then releases the IgG at relatively higher pH found in the interstitial fluids. It is expressed in adult epithelial tissue (U.S. Pat. Nos. 6,485,726, 6,030,613, 6,086,875; WO 03/077834; US2003-0235536A1) including lung and intestinal epithelium (Israel et al. 1997, *Immunology* 92:69) renal proximal tubular epithelium (Kobayashi et al. 2002, *Am. J. Physiol. Renal Physiol.* 282:F358) as well as nasal epithelium, vaginal surfaces, and biliary tree surfaces.

FcRn binding partners useful in the present disclosure encompass molecules that can be specifically bound by the FcRn receptor including whole IgG, the Fc fragment of IgG, and other fragments that include the complete binding region of the FcRn receptor. The region of the Fc portion of IgG that binds to the FcRn receptor has been described based on X-ray crystallography (Burmeister et al. 1994, *Nature* 372:379). The major contact area of the Fc with the FcRn is near the junction of the CH2 and CH3 domains. Fc-FcRn contacts are all within a single Ig heavy chain. The FcRn binding partners include whole IgG, the Fc fragment of IgG, and other fragments of IgG that include the complete binding region of FcRn. The major contact sites include amino acid residues 248, 250-257, 272, 285, 288, 290-291, 308-311, and 314 of the CH2 domain and amino acid residues 385-387, 428, and 433-436 of the CH3 domain. References made to amino acid numbering of immunoglobulins or immunoglobulin fragments, or regions, are all based on Kabat et al. 1991, Sequences of Proteins of Immunological Interest, U.S. Department of Public Health, Bethesda, Md.

Fc regions or FcRn binding partners bound to FcRn can be effectively shuttled across epithelial barriers by FcRn, thus providing a non-invasive means to systemically administer a desired therapeutic molecule. Additionally, fusion proteins comprising an Fc region or an FcRn binding partner are endocytosed by cells expressing the FcRn. But instead of being marked for degradation, these fusion proteins are recycled out into circulation again, thus increasing the in vivo half-life of these proteins. In certain embodiments, the portions of immunoglobulin constant regions are an Fc region or an FcRn binding partner that typically associates, via disulfide bonds and other non-specific interactions, with another Fc region or another FcRn binding partner to form dimers and higher order multimers.

Two FcRn receptors can bind a single Fc molecule. Crystallographic data suggest that each FcRn molecule binds a single polypeptide of the Fc homodimer. In one embodiment, linking the FcRn binding partner, e.g., an Fc fragment of an IgG, to a biologically active molecule provides a means of delivering the biologically active molecule orally, buccally, sublingually, rectally, vaginally, as an aerosol administered nasally or via a pulmonary route, or via an ocular route. In another embodiment, the FVIII protein can be administered invasively, e.g., subcutaneously, intravenously.

An FcRn binding partner region is a molecule or portion thereof that can be specifically bound by the FcRn receptor with consequent active transport by the FcRn receptor of the Fc region. Specifically bound refers to two molecules forming a complex that is relatively stable under physiologic conditions. Specific binding is characterized by a high affinity and a low to moderate capacity as distinguished from nonspecific binding which usually has a low affinity with a moderate to high capacity. Typically, binding is considered specific when the affinity constant KA is higher than $10^6$ $M^{-1}$, or higher than $10^8$ $M^{-1}$. If necessary, non-specific binding can be reduced without substantially affecting specific binding by varying the binding conditions. The appropriate binding conditions such as concentration of the molecules, ionic strength of the solution, temperature, time allowed for binding, concentration of a blocking agent (e.g., serum albumin, milk casein), etc., can be optimized by a skilled artisan using routine techniques.

In certain embodiments, a FVIII protein encoded by the nucleic acid molecule of the disclosure comprises one or more truncated Fc regions that are nonetheless sufficient to confer Fc receptor (FcR) binding properties to the Fc region. For example, the portion of an Fc region that binds to FcRn (i.e., the FcRn binding portion) comprises from about amino acids 282-438 of IgG1, EU numbering (with the primary contact sites being amino acids 248, 250-257, 272, 285, 288, 290-291, 308-311, and 314 of the CH2 domain and amino acid residues 385-387, 428, and 433-436 of the CH3 domain. Thus, an Fc region of the disclosure can comprise or consist of an FcRn binding portion. FcRn binding portions can be derived from heavy chains of any isotype, including IgG, IgG2, IgG3 and IgG4. In one embodiment, an FcRn binding portion from an antibody of the human isotype IgG1 is used. In another embodiment, an FcRn binding portion from an antibody of the human isotype IgG4 is used.

The Fc region can be obtained from a number of different sources. In one embodiment, an Fc region of the polypeptide is derived from a human immunoglobulin. It is understood, however, that an Fc moiety can be derived from an immunoglobulin of another mammalian species, including for example, a rodent (e.g., a mouse, rat, rabbit, guinea pig) or non-human primate (e.g., chimpanzee, macaque) species. Moreover, the polypeptide of the Fc domains or portions thereof can be derived from any immunoglobulin class, including IgM, IgG, IgD, IgA and IgE, and any immunoglobulin isotype, including IgG1, IgG2, IgG3 and IgG4. In another embodiment, the human isotype IgG1 is used.

In certain embodiments, the Fc variant confers a change in at least one effector function imparted by an Fc moiety comprising said wild-type Fc domain (e.g., an improvement or reduction in the ability of the Fc region to bind to Fc receptors (e.g. FcγRI, FcγRII, or FcγRIII) or complement proteins (e.g. C1q), or to trigger antibody-dependent cytotoxicity (ADCC), phagocytosis, or complement-dependent cytotoxicity (CDCC)). In other embodiments, the Fc variant provides an engineered cysteine residue.

The Fc region of the disclosure can employ art-recognized Fc variants which are known to impart a change (e.g., an enhancement or reduction) in effector function and/or FcR or FcRn binding. Specifically, an Fc region of the disclosure can include, for example, a change (e.g., a substitution) at one or more of the amino acid positions disclosed in International PCT Publications WO88/07089A1, WO96/14339A1, WO98/05787A1, WO98/23289A1, WO99/51642A1, WO99/58572A1, WO00/09560A2, WO00/32767A1, WO00/42072A2, WO02/44215A2, WO02/060919A2, WO03/074569A2, WO04/016750A2, WO04/029207A2, WO04/035752A2, WO04/063351A2, WO04/074455A2, WO04/099249A2, WO05/040217A2, WO04/044859, WO05/070963A1, WO05/077981A2, WO05/092925A2, WO05/123780A2, WO06/019447A1, WO06/047350A2, and WO06/085967A2; US Patent Publication Nos. US2007/0231329, US2007/0231329, US2007/0237765, US2007/0237766, US2007/0237767, US2007/0243188, US2007/0248603, US2007/0286859, US2008/0057056; or U.S. Pat. Nos. 5,648,260; 5,739,277; 5,834,250; 5,869,046; 6,096,871; 6,121,022; 6,194,551; 6,242,195; 6,277,375; 6,528,624; 6,538,124; 6,737,056; 6,821,505; 6,998,253; 7,083,784; 7,404,956, and 7,317,091, each of which is incorporated by reference herein. In one embodiment, the specific change (e.g., the specific substitution of one or more amino acids disclosed in the art) can be made at one or more of the disclosed amino acid positions. In another embodiment, a different change at one or more of the disclosed amino acid positions (e.g., the different substitution of one or more amino acid position disclosed in the art) can be made.

The Fc region or FcRn binding partner of IgG can be modified according to well recognized procedures such as site directed mutagenesis and the like to yield modified IgG or Fc fragments or portions thereof that will be bound by FcRn. Such modifications include modifications remote from the FcRn contact sites as well as modifications within the contact sites that preserve or even enhance binding to the FcRn. For example, the following single amino acid residues in human IgG1 Fc (Fc□1) can be substituted without significant loss of Fc binding affinity for FcRn: P238A, S239A, K246A, K248A, D249A, M252A, T256A, E258A, T260A, D265A, S267A, H268A, E269A, D270A, E272A, L274A, N276A, Y278A, D280A, V282A, E283A, H285A, N286A, T289A, K290A, R292A, E293A, E294A, Q295A, Y296 F, N297A, S298A, Y300F, R301A, V303A, V305A, T307A, L309A, Q311A, D312A, N315A, K317A, E318A, K320A, K322A, S324A, K326A, A327Q, P329A, A330Q, P331A, E333A, K334A, T335A, S337A, K338A, K340A, Q342A, R344A, E345A, Q347A, R355A, E356A, M358A, T359A, K360A, N361A, Q362A, Y373A, S375A, D376A, A378Q, E380A, E382A, S383A, N384A, Q386A, E388A, N389A, N390A, Y391F, K392A, L398A, S400A, D401A, D413A, K414A, R416A, Q418A, Q419A, N421A, V422A, S424A, E430A, N434A, T437A, Q438A, K439A, S440A, S444A, and K447A, where for example P238A represents wild type proline substituted by alanine at position number 238. As an example, a specific embodiment incorporates the N297A mutation, removing a highly conserved N-glycosylation site. In addition to alanine other amino acids can be substituted for the wild type amino acids at the positions specified above. Mutations can be introduced singly into Fc giving rise to more than one hundred Fc regions distinct from the native Fc. Additionally, combinations of two, three, or more of these individual mutations can be introduced together, giving rise to hundreds more Fc regions.

Certain of the above mutations can confer new functionality upon the Fc region or FcRn binding partner. For example, one embodiment incorporates N297A, removing a highly conserved N-glycosylation site. The effect of this mutation is to reduce immunogenicity, thereby enhancing circulating half-life of the Fc region, and to render the Fc region incapable of binding to FcγRI, FcγRIIA, FcγRIIB, and FcγRIIIA, without compromising affinity for FcRn (Routledge et al. 1995, *Transplantation* 60:847; Friend et al. 1999, *Transplantation* 68:1632; Shields et al. 1995, *J. Biol. Chem.* 276:6591). As a further example of new functionality arising from mutations described above affinity for FcRn can be increased beyond that of wild type in some instances. This increased affinity can reflect an increased "on" rate, a decreased "off" rate or both an increased "on" rate and a decreased "off" rate. Examples of mutations believed to impart an increased affinity for FcRn include, but not limited to, T256A, T307A, E380A, and N434A (Shields et al. 2001, *J. Biol. Chem.* 276:6591).

Additionally, at least three human Fc gamma receptors appear to recognize a binding site on IgG within the lower hinge region, generally amino acids 234-237. Therefore, another example of new functionality and potential decreased immunogenicity can arise from mutations of this region, as for example by replacing amino acids 233-236 of human IgG1 "ELLG" (SEQ ID NO:8) to the corresponding sequence from IgG2 "PVA" (with one amino acid deletion). It has been shown that FcγRI, FcγRII, and FcγRIII, which mediate various effector functions will not bind to IgG1 when such mutations have been introduced. Ward and Ghetie 1995, *Therapeutic Immunology* 2:77 and Armour et al. 1999, *Eur. J. Immunol.* 29:2613.

In another embodiment, the immunoglobulin constant region or a portion thereof comprises an amino acid sequence in the hinge region or a portion thereof that forms one or more disulfide bonds with a second immunoglobulin constant region or a portion thereof. The second immunoglobulin constant region or a portion thereof can be linked to a second polypeptide, bringing the FVIII protein and the second polypeptide together. In some embodiments, the second polypeptide is an enhancer moiety. As used herein, the term "enhancer moiety" refers to a molecule, fragment thereof or a component of a polypeptide which is capable of enhancing the procoagulant activity of FVIII. The enhancer moiety can be a cofactor, such as soluble tissue factor (sTF), or a procoagulant peptide. Thus, upon activation of FVIII, the enhancer moiety is available to enhance FVIII activity.

In certain embodiments, a FVIII protein encoded by a nucleic acid molecule of the disclosure comprises an amino acid substitution to an immunoglobulin constant region or a portion thereof (e.g., Fc variants), which alters the antigen-independent effector functions of the Ig constant region, in particular the circulating half-life of the protein.

B.3.b. scFc Regions

In another aspect, a heterologous moiety comprises a scFc (single chain Fc) region. In one embodiment, an isolated nucleic acid molecule of the disclosure further comprises a heterologous nucleic acid sequence that encodes a scFc region. The scFc region comprises at least two immunoglobulin constant regions or portions thereof (e.g., Fc moieties or domains (e.g., 2, 3, 4, 5, 6, or more Fc moieties or domains)) within the same linear polypeptide chain that are capable of folding (e.g., intramolecularly or intermolecularly folding) to form one functional scFc region which is linked by an Fc peptide linker. For example, in one embodiment, a polypeptide of the disclosure is capable of binding, via its scFc region, to at least one Fc receptor (e.g., an FcRn, an FcγR receptor (e.g., FcγRIII), or a complement protein (e.g., C1q)) in order to improve half-life or trigger an immune effector function (e.g., antibody-dependent cytotoxicity (ADCC), phagocytosis, or complement-dependent cytotoxicity (CDCC) and/or to improve manufacturability).

B.3.c. CTP

In another aspect, a heterologous moiety comprises one C-terminal peptide (CTP) of the Rsubunit of human chorionic gonadotropin or fragment, variant, or derivative thereof. One or more CTP peptides inserted into a recombinant protein is known to increase the in vivo half-life of that protein. See, e.g., U.S. Pat. No. 5,712,122, incorporated by reference herein in its entirety.

Exemplary CTP peptides include DPRFQDSSSSKAPPPSLPSPSRLPGPSDTPIL (SEQ ID NO:9) or SSSSKAPPPSLPSPSRLPGPSDTPILPQ (SEQ ID NO:10). See, e.g., U.S. Patent Application Publication No. US 2009/0087411 A1, incorporated by reference.

B.3.d. XTEN Sequence

In some embodiments, a heterologous moiety comprises one or more XTEN sequences, fragments, variants, or derivatives thereof. As used here "XTEN sequence" refers to extended length polypeptides with non-naturally occurring, substantially non-repetitive sequences that are composed mainly of small hydrophilic amino acids, with the sequence having a low degree or no secondary or tertiary structure under physiologic conditions. As a heterologous moiety, XTENs can serve as a half-life extension moiety. In addition, XTEN can provide desirable properties including but are not limited to enhanced pharmacokinetic parameters and solubility characteristics.

The incorporation of a heterologous moiety comprising an XTEN sequence into a protein of the disclosure can confer to the protein one or more of the following advantageous properties: conformational flexibility, enhanced aqueous solubility, high degree of protease resistance, low immunogenicity, low binding to mammalian receptors, or increased hydrodynamic (or Stokes) radii.

In certain aspects, an XTEN sequence can increase pharmacokinetic properties such as longer in vivo half-life or increased area under the curve (AUC), so that a protein of the disclosure stays in vivo and has procoagulant activity for an increased period of time compared to a protein with the same but without the XTEN heterologous moiety.

In some embodiments, the XTEN sequence useful for the disclosure is a peptide or a polypeptide having greater than about 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, or 2000 amino acid residues. In certain embodiments, XTEN is a peptide or a polypeptide having greater than about 20 to about 3000 amino acid residues, greater than 30 to about 2500 residues, greater than 40 to about 2000 residues, greater than 50 to about 1500 residues, greater than 60 to about 1000 residues, greater than 70 to about 900 residues, greater than 80 to about 800 residues, greater than 90 to about 700 residues, greater than 100 to about 600 residues, greater than 110 to about 500 residues, or greater than 120 to about 400 residues. In one particular embodiment, the XTEN comprises an amino acid sequence of longer than 42 amino acids and shorter than 144 amino acids in length.

The XTEN sequence of the disclosure can comprise one or more sequence motif of 5 to 14 (e.g., 9 to 14) amino acid residues or an amino acid sequence at least 80%, 90%, 91%, 92%, 93%, 94%, 95%, 96%, 97%, 98%, or 99% identical to the sequence motif, wherein the motif comprises, consists essentially of, or consists of 4 to 6 types of amino acids (e.g., 5 amino acids) selected from the group consisting of glycine (G), alanine (A), serine (S), threonine (T), glutamate (E) and proline (P). See US 2010-0239554 A1.

In some embodiments, the XTEN comprises non-overlapping sequence motifs in which about 80%, or at least about 85%, or at least about 90%, or about 91%, or about 92%, or about 93%, or about 94%, or about 95%, or about 96%, or about 97%, or about 98%, or about 99% or about 100% of the sequence consists of multiple units of non-overlapping sequences selected from a single motif family selected from Table 3, resulting in a family sequence.

As used herein, "family" means that the XTEN has motifs selected only from a single motif category from Table 3; i.e., AD, AE, AF, AG, AM, AQ, BC, or BD XTEN, and that any other amino acids in the XTEN not from a family motif are selected to achieve a needed property, such as to permit incorporation of a restriction site by the encoding nucleotides, incorporation of a cleavage sequence, or to achieve a better linkage to FVIII. In some embodiments of XTEN families, an XTEN sequence comprises multiple units of non-overlapping sequence motifs of the AD motif family, or of the AE motif family, or of the AF motif family, or of the AG motif family, or of the AM motif family, or of the AQ motif family, or of the BC family, or of the BD family, with the resulting XTEN exhibiting the range of homology described above. In other embodiments, the XTEN comprises multiple units of motif sequences from two or more of the motif families of Table 3.

These sequences can be selected to achieve desired physical/chemical characteristics, including such properties as net charge, hydrophilicity, lack of secondary structure, or lack of repetitiveness that are conferred by the amino acid composition of the motifs, described more fully below. In the embodiments hereinabove described in this paragraph, the motifs incorporated into the XTEN can be selected and assembled using the methods described herein to achieve an XTEN of about 36 to about 3000 amino acid residues.

TABLE 3

XTEN Sequence Motifs of 12 Amino Acids and Motif Families

| Motif Family* | MOTIF SEQUENCE | SEQ ID NO: |
|---|---|---|
| AD | GESPGGSSGSES | 11 |
| AD | GSEGSSGPGESS | 12 |
| AD | GSSESGSSEGGP | 13 |
| AD | GSGGEPSESGSS | 14 |
| AE, AM | GSPAGSPTSTEE | 15 |
| AE, AM, AQ | GSEPATSGSETP | 16 |
| AE, AM, AQ | GTSESATPESGP | 17 |
| AE, AM, AQ | GTSTEPSEGSAP | 18 |
| AF, AM | GSTSESPSGTAP | 19 |
| AF, AM | GTSTPESGSASP | 20 |
| AF, AM | GTSPSGESSTAP | 21 |
| AF, AM | GSTSSTAESPGP | 22 |
| AG, AM | GTPGSGTASSSP | 23 |
| AG, AM | GSSTPSGATGSP | 24 |
| AG, AM | GSSPSASTGTGP | 25 |
| AG, AM | GASPGTSSTGSP | 26 |
| AQ | GEPAGSPTSTSE | 27 |
| AQ | GTGEPSSTPASE | 28 |
| AQ | GSGPSTESAPTE | 29 |
| AQ | GSETPSGPSETA | 30 |
| AQ | GPSETSTSEPGA | 31 |
| AQ | GSPSEPTEGTSA | 32 |
| BC | GSGASEPTSTEP | 33 |

TABLE 3-continued

XTEN Sequence Motifs of 12 Amino Acids and Motif Families

| Motif Family* | MOTIF SEQUENCE | SEQ ID NO: |
|---|---|---|
| BC | GSEPATSGTEPS | 34 |
| BC | GTSEPSTSEPGA | 35 |
| BC | GTSTEPSEPGSA | 36 |
| BD | GSTAGSETSTEA | 37 |
| BD | GSETATSGSETA | 38 |
| BD | GTSESATSESGA | 39 |
| BD | GTSTEASEGSAS | 40 |

*Denotes individual motif sequences that, when used together in various permutations, results in a "family sequence"

Examples of XTEN sequences that can be used as heterologous moieties in chimeric proteins of the disclosure are disclosed, e.g., in U.S. Patent Publication Nos. 2010/0239554 A1, 2010/0323956 A1, 2011/0046060 A1, 2011/0046061 A1, 2011/0077199 A1, or 2011/0172146 A1, or International Patent Publication Nos. WO 2010/091122 A1, WO 2010/144502 A2, WO 2010/144508 A1, WO 2011/028228 A1, WO 2011/028229 A1, or WO 2011/028344 A2, each of which is incorporated by reference herein in its entirety.

XTEN can have varying lengths for insertion into or linkage to FVIII. In one embodiment, the length of the XTEN sequence(s) is chosen based on the property or function to be achieved in the fusion protein. Depending on the intended property or function, XTEN can be short or intermediate length sequence or longer sequence that can serve as carriers. In certain embodiments, the XTEN includes short segments of about 6 to about 99 amino acid residues, intermediate lengths of about 100 to about 399 amino acid residues, and longer lengths of about 400 to about 1000 and up to about 3000 amino acid residues. Thus, the XTEN inserted into or linked to FVIII can have lengths of about 6, about 12, about 36, about 40, about 42, about 72, about 96, about 144, about 288, about 400, about 500, about 576, about 600, about 700, about 800, about 864, about 900, about 1000, about 1500, about 2000, about 2500, or up to about 3000 amino acid residues in length. In other embodiments, the XTEN sequences is about 6 to about 50, about 50 to about 100, about 100 to 150, about 150 to 250, about 250 to 400, about 400 to about 500, about 500 to about 900, about 900 to 1500, about 1500 to 2000, or about 2000 to about 3000 amino acid residues in length.

The precise length of an XTEN inserted into or linked to FVIII can vary without adversely affecting the activity of the FVIII. In one embodiment, one or more of the XTENs used herein have 42 amino acids, 72 amino acids, 144 amino acids, 288 amino acids, 576 amino acids, or 864 amino acids in length and can be selected from one or more of the XTEN family sequences; i.e., AD, AE, AF, AG, AM, AQ, BC or BD.

In some embodiments, the XTEN sequence used in the disclosure is at least 60%, 70%, 80%, 85%, 90%, 91%, 92%, 93%, 94%, 95%, 96%, 97%, 98%, 99%, or 100% identical to a sequence selected from the group consisting of AE42, AG42, AE48, AM48, AE72, AG72, AE108, AG108, AE144, AF144, AG144, AE180, AG180, AE216, AG216, AE252, AG252, AE288, AG288, AE324, AG324, AE360, AG360, AE396, AG396, AE432, AG432, AE468, AG468, AE504, AG504, AF504, AE540, AG540, AF540, AD576, AE576, AF576, AG576, AE612, AG612, AE624, AE648, AG648, AG684, AE720, AG720, AE756, AG756, AE792, AG792, AE828, AG828, AD836, AE864, AF864, AG864, AM875, AE912, AM923, AM1318, BC864, BD864, AE948, AE1044, AE1140, AE1236, AE1332, AE1428, AE1524, AE1620, AE1716, AE1812, AE1908, AE2004A, AG948, AG1044, AG1140, AG1236, AG1332, AG1428, AG1524, AG1620, AG1716, AG1812, AG1908, AG2004, and any combination thereof. See US 2010-0239554 A1. In one particular embodiment, the XTEN comprises AE42, AE72, AE144, AE288, AE576, AE864, AG 42, AG72, AG144, AG288, AG576, AG864, or any combination thereof.

Exemplary XTEN sequences that can be used as heterologous moieties in chimeric protein of the disclosure include XTEN AE42-4 (SEQ ID NO:41), XTEN 144-2A (SEQ ID NO:42), XTEN A144-3B (SEQ ID NO:43), XTEN AE144-4A (SEQ ID NO:44), XTEN AE144-5A (SEQ ID NO:45), XTEN AE144-6B (SEQ ID NO:46), XTEN AG144-1 (SEQ ID NO:47), XTEN AG144-A (SEQ ID NO:48), XTEN AG144-B (SEQ ID NO:49), XTEN AG144-C(SEQ ID NO:50), and XTEN AG144-F (SEQ ID NO:51). In one particular embodiment, the XTEN is encoded by SEQ ID NO:52.

In some embodiments, less than 100% of amino acids of an XTEN are selected from glycine (G), alanine (A), serine (S), threonine (T), glutamate (E) and proline (P), or less than 100% of the sequence consists of the sequence motifs from Table 3 or an XTEN sequence provided herein. In such embodiments, the remaining amino acid residues of the XTEN are selected from any of the other 14 natural L-amino acids, but can be preferentially selected from hydrophilic amino acids such that the XTEN sequence contains at least about 90%, 91%, 92%, 93%, 94%, 95%, 96%, 97%, 98%, or at least about 99% hydrophilic amino acids.

The content of hydrophobic amino acids in the XTEN utilized in the conjugation constructs can be less than 5%, or less than 2%, or less than 1% hydrophobic amino acid content. Hydrophobic residues that are less favored in construction of XTEN include tryptophan, phenylalanine, tyrosine, leucine, isoleucine, valine, and methionine. Additionally, XTEN sequences can contain less than 5% or less than 4% or less than 3% or less than 2% or less than 1% or none of the following amino acids: methionine (for example, to avoid oxidation), or asparagine and glutamine (to avoid desamidation).

The one or more XTEN sequences can be inserted at the C-terminus or at the N-terminus of the amino acid sequence encoded by the nucleotide sequence or inserted between two amino acids in the amino acid sequence encoded by the nucleotide sequence. For example, the XTEN can be inserted between two amino acids at one or more insertion site selected from Table 2. Examples of sites within FVIII that are permissible for XTEN insertion can be found in, e.g., International Publication No. WO 2013/123457 A1 or U.S. Publication No. 2015/0158929 A1, which are herein incorporated by reference in their entirety.

B.3.e. Albumin or Fragment, Derivative, or Variant Thereof

In some embodiments, a heterologous moiety comprises albumin or a functional fragment thereof. Human serum albumin (HSA, or HA), a protein of 609 amino acids in its full-length form, is responsible for a significant proportion of the osmotic pressure of serum and also functions as a carrier of endogenous and exogenous ligands. The term "albumin" as used herein includes full-length albumin or a functional fragment, variant, derivative, or analog thereof.

Examples of albumin or the fragments or variants thereof are disclosed in US Pat. Publ. Nos. 2008/0194481A1, 2008/0004206 A1, 2008/0161243 A1, 2008/0261877 A1, or 2008/0153751 A1 or PCT Appl. Publ. Nos. WO 2008/033413 A2, WO 2009/058322 A1, or WO 2007/021494 A2, which are incorporated herein by reference in their entireties.

In one embodiment, the FVIII protein encoded by a nucleic acid molecule of the disclosure comprises albumin, a fragment, or a variant thereof which is further linked to a second heterologous moiety selected from the group consisting of an immunoglobulin constant region or portion thereof (e.g., an Fc region), a PAS sequence, HES, and PEG.

B.3.f. Albumin-Binding Moiety

In certain embodiments, the heterologous moiety is an albumin-binding moiety, which comprises an albumin-binding peptide, a bacterial albumin-binding domain, an albumin-binding antibody fragment, or any combinations thereof.

For example, the albumin-binding protein can be a bacterial albumin-binding protein, an antibody or an antibody fragment including domain antibodies (see U.S. Pat. No. 6,696,245). An albumin-binding protein, for example, can be a bacterial albumin-binding domain, such as the one of streptococcal protein G (Konig, T. and Skerra, A. (1998) *J. Immunol. Methods* 218, 73-83). Other examples of albumin-binding peptides that can be used as conjugation partner are, for instance, those having a Cys-$Xaa_1$-$Xaa_2$-$Xaa_3$-$Xaa_4$-Cys (SEQ ID NO:52) consensus sequence, wherein $Xaa_1$ is Asp, Asn, Ser, Thr, or Trp; $Xaa_2$ is Asn, Gln, His, Ile, Leu, or Lys; $Xaa_3$ is Ala, Asp, Phe, Trp, or Tyr; and $Xaa_4$ is Asp, Gly, Leu, Phe, Ser, or Thr as described in US Patent Application Publication No. 2003/0069395 or Dennis et al. (Dennis et al. (2002) *J. Biol. Chem.* 277, 35035-35043).

Domain 3 from streptococcal protein G, as disclosed by Kraulis et al., *FEBS Lett.* 378:190-194 (1996) and Linhult et al., *Protein Sci.* 11:206-213 (2002) is an example of a bacterial albumin-binding domain. Examples of albumin-binding peptides include a series of peptides having the core sequence DICLPRWGCLW (SEQ ID NO:54). See, e.g., Dennis et al., *J. Biol. Chem.* 2002, 277: 35035-35043 (2002). Examples of albumin-binding antibody fragments are disclosed in Muller and Kontermann, *Curr. Opin. Mol. Ther.* 9:319-326 (2007); Roovers et al., *Cancer Immunol. Immunother.* 56:303-317 (2007), and Holt et al., *Prot. Eng. Design Sci.*, 21:283-288 (2008), which are incorporated herein by reference in their entireties. An example of such albumin-binding moiety is 2-(3-maleimidopropanamido)-6-(4-(4-iodophenyl)butanamido) hexanoate ("Albu" tag) as disclosed by Trussel et al., *Bioconjugate Chem.* 20:2286-2292 (2009).

Fatty acids, in particular long chain fatty acids (LCFA) and long chain fatty acid-like albumin-binding compounds can be used to extend the in vivo half-life of FVIII proteins of the disclosure. An example of a LCFA-like albumin-binding compound is 16-(1-(3-(9-(((2,5-dioxopyrrolidin-1-yloxy) carbonyloxy)-methyl)-7-sulfo-9H-fluoren-2-ylamino)-3-oxopropyl)-2,5-dioxopyrrolidin-3-ylthio) hexadecanoic acid (see, e.g., WO 2010/140148).

B.3.g. PAS Sequence

In other embodiments, the heterologous moiety is a PAS sequence. A PAS sequence, as used herein, means an amino acid sequence comprising mainly alanine and serine residues or comprising mainly alanine, serine, and proline residues, the amino acid sequence forming random coil conformation under physiological conditions. Accordingly, the PAS sequence is a building block, an amino acid polymer, or a sequence cassette comprising, consisting essentially of, or consisting of alanine, serine, and proline which can be used as a part of the heterologous moiety in the chimeric protein. Yet, the skilled person is aware that an amino acid polymer also can form random coil conformation when residues other than alanine, serine, and proline are added as a minor constituent in the PAS sequence.

The term "minor constituent" as used herein means that amino acids other than alanine, serine, and proline can be added in the PAS sequence to a certain degree, e.g., up to about 12%, i.e., about 12 of 100 amino acids of the PAS sequence, up to about 10%, i.e. about 10 of 100 amino acids of the PAS sequence, up to about 9%, i.e., about 9 of 100 amino acids, up to about 8%, i.e., about 8 of 100 amino acids, about 6%, i.e., about 6 of 100 amino acids, about 5%, i.e., about 5 of 100 amino acids, about 4%, i.e., about 4 of 100 amino acids, about 3%, i.e., about 3 of 100 amino acids, about 2%, i.e., about 2 of 100 amino acids, about 1%, i.e., about 1 of 100 of the amino acids. The amino acids different from alanine, serine and proline can be selected from the group consisting of Arg, Asn, Asp, Cys, Gln, Glu, Gly, His, Ile, Leu, Lys, Met, Phe, Thr, Trp, Tyr, and Val.

Under physiological conditions, the PAS sequence stretch forms a random coil conformation and thereby can mediate an increased in vivo and/or in vitro stability to the FVIII protein. Since the random coil domain does not adopt a stable structure or function by itself, the biological activity mediated by the FVIII protein is essentially preserved. In other embodiments, the PAS sequences that form random coil domain are biologically inert, especially with respect to proteolysis in blood plasma, immunogenicity, isoelectric point/electrostatic behavior, binding to cell surface receptors or internalisation, but are still biodegradable, which provides clear advantages over synthetic polymers such as PEG.

Non-limiting examples of the PAS sequences forming random coil conformation comprise an amino acid sequence selected from the group consisting of ASPAAPA-PASPAAPAPSAPA (SEQ ID NO:55), AAPASPAPAAP-SAPAPAAPS (SEQ ID NO:56), APSSPSP-SAPSSPSPASPSS (SEQ ID NO:57), APSSPSPSAPSSPSPASPS (SEQ ID NO:58), SSP-SAPSPSSPASPSPSSPA (SEQ ID NO:59), AASPAAPSAP-PAAASPAAPSAPPA (SEQ ID NO:60) and ASAAAPAAASAAASAPSAAA (SEQ ID NO:61) or any combinations thereof. Additional examples of PAS sequences are known from, e.g., US Pat. Publ. No. 2010/0292130 A1 and PCT Appl. Publ. No. WO 2008/155134 A1.

B.3.h. HAP Sequence

In certain embodiments, the heterologous moiety is a glycine-rich homo-amino-acid polymer (HAP). The HAP sequence can comprise a repetitive sequence of glycine, which has at least 50 amino acids, at least 100 amino acids, 120 amino acids, 140 amino acids, 160 amino acids, 180 amino acids, 200 amino acids, 250 amino acids, 300 amino acids, 350 amino acids, 400 amino acids, 450 amino acids, or 500 amino acids in length. In one embodiment, the HAP sequence is capable of extending half-life of a moiety fused to or linked to the HAP sequence. Non-limiting examples of the HAP sequence includes, but are not limited to (Gly)$_n$, (Gly$_4$Ser)$_n$, or S(Gly$_4$Ser)$_n$, wherein n is 1, 2, 3, 4, 5, 6, 7, 8, 9, 10, 11, 12, 13, 14, 15, 16, 17, 18, 19, or 20. In one embodiment, n is 20, 21, 22, 23, 24, 25, 26, 26, 28, 29, 30, 31, 32, 33, 34, 35, 36, 37, 38, 39, or 40. In another embodiment, n is 50, 60, 70, 80, 90, 100, 110, 120, 130, 140, 150, 160, 170, 180, 190, or 200.

B.3.i. Transferrin or Fragment Thereof

In certain embodiments, the heterologous moiety is transferrin or a fragment thereof. Any transferrin can be used to make the FVIII proteins of the disclosure. As an example, wild-type human TF (TF) is a 679 amino acid protein, of approximately 75 KDa (not accounting for glycosylation), with two main domains, N (about 330 amino acids) and C (about 340 amino acids), which appear to originate from a gene duplication. See GenBank accession numbers NM001063, XM002793, M12530, XM039845, XM 039847 and S95936 (www.ncbi.nlm.nih.gov/), all of which are herein incorporated by reference in their entirety. Transferrin comprises two domains, N domain and C domain. N domain comprises two subdomains, N1 domain and N2 domain, and C domain comprises two subdomains, C1 domain and C2 domain.

In one embodiment, the transferrin heterologous moiety includes a transferrin splice variant. In one example, a transferrin splice variant can be a splice variant of human transferrin, e.g., Genbank Accession AAA61140. In another embodiment, the transferrin portion of the chimeric protein includes one or more domains of the transferrin sequence, e.g., N domain, C domain, N1 domain, N2 domain, C1 domain, C2 domain or any combinations thereof.

B.3.j. Clearance Receptors

In certain embodiments, the heterologous moiety is a clearance receptor, fragment, variant, or derivative thereof. LRP1 is a 600 kDa integral membrane protein that is implicated in the receptor-mediate clearance of a variety of proteins, such as Factor X. See, e.g., Narita et al., *Blood* 91:555-560 (1998).

B.3.k. von Willebrand Factor or Fragments Thereof

In certain embodiments, the heterologous moiety is von Willebrand Factor (VWF) or one or more fragments thereof.

VWF (also known as F8VWF) is a large multimeric glycoprotein present in blood plasma and produced constitutively in endothelium (in the Weibel-Palade bodies), megakaryocytes (α-granules of platelets), and subendothelian connective tissue. The basic VWF monomer is a 2813 amino acid protein. Every monomer contains a number of specific domains with a specific function, the D' and D3 domains (which together bind to Factor VIII), the A1 domain (which binds to platelet GPIb-receptor, heparin, and/or possibly collagen), the A3 domain (which binds to collagen), the C1 domain (in which the RGD domain binds to platelet integrin αIIbβ3 when this is activated), and the "cysteine knot" domain at the C-terminal end of the protein (which VWF shares with platelet-derived growth factor (PDGF), transforming growth factor-β (TGFβ) and -human chorionic gonadotropin (PHCG)).

The 2813 monomer amino acid sequence for human VWF is reported as Accession Number NP000543.2 in Genbank. The nucleotide sequence encoding the human VWF is reported as Accession Number NM000552.3 in Genbank. SEQ ID NO:62 is the amino acid sequence reported in Genbank Accession Number NM000552.3. The D' domain includes amino acids 764 to 866 of SEQ ID NO:62. The D3 domain includes amino acids 867 to 1240 of SEQ ID NO:62.

In plasma, 95-98% of FVIII circulates in a tight non-covalent complex with full-length VWF. The formation of this complex is important for the maintenance of appropriate plasma levels of FVIIII in vivo. Lenting et al., *Blood.* 92(11): 3983-96 (1998); Lenting et al., *J. Thromb. Haemost.* 5(7): 1353-60 (2007). When FVIII is activated due to proteolysis at positions 372 and 740 in the heavy chain and at position 1689 in the light chain, the VWF bound to FVIII is removed from the activated FVIII.

In certain embodiments, the heterologous moiety is full length von Willebrand Factor. In other embodiments, the heterologous moiety is a von Willebrand Factor fragment.

As used herein, the term "VWF fragment" or "VWF fragments" used herein means any VWF fragments that interact with FVIII and retain at least one or more properties that are normally provided to FVIII by full-length VWF, e.g., preventing premature activation to FVIIIa, preventing premature proteolysis, preventing association with phospholipid membranes that could lead to premature clearance, preventing binding to FVIII clearance receptors that can bind naked FVIII but not VWF-bound FVIII, and/or stabilizing the FVIII heavy chain and light chain interactions. In a specific embodiment, the heterologous moiety is a (VWF) fragment comprising a D' domain and a D3 domain of VWF. The VWF fragment comprising the D' domain and the D3 domain can further comprise a VWF domain selected from the group consisting of an A1 domain, an A2 domain, an A3 domain, a D1 domain, a D2 domain, a D4 domain, a B1 domain, a B2 domain, a B3 domain, a C1 domain, a C2 domain, a CK domain, one or more fragments thereof, and any combinations thereof. Additional examples of the polypeptide having FVIII activity fused to the VWF fragment are disclosed in U.S. provisional patent application No. 61/667,901, filed Jul. 3, 2012, and U.S. Publication No. 2015/0023959 A1, which are both incorporated herein by reference in its entirety.

B.3.l. Linker Moieties

In certain embodiments, the heterologous moiety is a peptide linker.

As used herein, the terms "peptide linkers" or "linker moieties" refer to a peptide or polypeptide sequence (e.g., a synthetic peptide or polypeptide sequence) which connects two domains in a linear amino acid sequence of a polypeptide chain.

In some embodiments, heterologous nucleotide sequences encoding peptide linkers can be inserted between the optimized FVIII polynucleotide sequences of the disclosure and a heterologous nucleotide sequence encoding, for example, one of the heterologous moieties described above, such as albumin. Peptide linkers can provide flexibility to the chimeric polypeptide molecule. Linkers are not typically cleaved, however such cleavage can be desirable. In one embodiment, these linkers are not removed during processing.

A type of linker which can be present in a chimeric protein of the disclosure is a protease cleavable linker which comprises a cleavage site (i.e., a protease cleavage site substrate, e.g., a factor XIa, Xa, or thrombin cleavage site) and which can include additional linkers on either the N-terminal of C-terminal or both sides of the cleavage site. These cleavable linkers when incorporated into a construct of the disclosure result in a chimeric molecule having a heterologous cleavage site.

In one embodiment, an FVIII polypeptide encoded by a nucleic acid molecule of the instant disclosure comprises two or more Fc domains or moieties linked via a cscFc linker to form an Fc region comprised in a single polypeptide chain. The cscFc linker is flanked by at least one intracellular processing site, i.e., a site cleaved by an intracellular enzyme. Cleavage of the polypeptide at the at least one intracellular processing site results in a polypeptide which comprises at least two polypeptide chains.

Other peptide linkers can optionally be used in a construct of the disclosure, e.g., to connect an FVIII protein to an Fc region. Some exemplary linkers that can be used in connection with the disclosure include, e.g., polypeptides comprising GlySer amino acids described in more detail below.

In one embodiment, the peptide linker is synthetic, i.e., non-naturally occurring. In one embodiment, a peptide linker includes peptides (or polypeptides) (which can or cannot be naturally occurring) which comprise an amino acid sequence that links or genetically fuses a first linear sequence of amino acids to a second linear sequence of amino acids to which it is not naturally linked or genetically fused in nature. For example, in one embodiment the peptide linker can comprise non-naturally occurring polypeptides which are modified forms of naturally occurring polypeptides (e.g., comprising a mutation such as an addition, substitution or deletion). In another embodiment, the peptide linker can comprise non-naturally occurring amino acids. In another embodiment, the peptide linker can comprise naturally occurring amino acids occurring in a linear sequence that does not occur in nature. In still another embodiment, the peptide linker can comprise a naturally occurring polypeptide sequence.

For example, in certain embodiments, a peptide linker can be used to fuse identical Fc moieties, thereby forming a homodimeric scFc region. In other embodiments, a peptide linker can be used to fuse different Fc moieties (e.g. a wild-type Fc moiety and an Fc moiety variant), thereby forming a heterodimeric scFc region.

In another embodiment, a peptide linker comprises or consists of a gly-ser linker. In one embodiment, a scFc or cscFc linker comprises at least a portion of an immunoglobulin hinge and a gly-ser linker. As used herein, the term "gly-ser linker" refers to a peptide that consists of glycine and serine residues. In certain embodiments, said gly-ser linker can be inserted between two other sequences of the peptide linker. In other embodiments, a gly-ser linker is attached at one or both ends of another sequence of the peptide linker. In yet other embodiments, two or more gly-ser linker are incorporated in series in a peptide linker. In one embodiment, a peptide linker of the disclosure comprises at least a portion of an upper hinge region (e.g., derived from an IgG1, IgG2, IgG3, or IgG4 molecule), at least a portion of a middle hinge region (e.g., derived from an IgG1, IgG2, IgG3, or IgG4 molecule) and a series of gly/ser amino acid residues.

Peptide linkers of the disclosure are at least one amino acid in length and can be of varying lengths. In one embodiment, a peptide linker of the disclosure is from about 1 to about 50 amino acids in length. As used in this context, the term "about" indicates+/−two amino acid residues. Since linker length must be a positive integer, the length of from about 1 to about 50 amino acids in length, means a length of from 1-3 to 48-52 amino acids in length. In another embodiment, a peptide linker of the disclosure is from about 10 to about 20 amino acids in length. In another embodiment, a peptide linker of the disclosure is from about 15 to about 50 amino acids in length. In another embodiment, a peptide linker of the disclosure is from about 20 to about 45 amino acids in length. In another embodiment, a peptide linker of the disclosure is from about 15 to about 35 or about 20 to about 30 amino acids in length. In another embodiment, a peptide linker of the disclosure is from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 500, 1000, or 2000 amino acids in length. In one embodiment, a peptide linker of the disclosure is 20 or 30 amino acids in length.

In some embodiments, the peptide linker can comprise at least two, at least three, at least four, at least five, at least 10, at least 20, at least 30, at least 40, at least 50, at least 60, at least 70, at least 80, at least 90, or at least 100 amino acids. In other embodiments, the peptide linker can comprise at least 200, at least 300, at least 400, at least 500, at least 600, at least 700, at least 800, at least 900, or at least 1,000 amino acids. In some embodiments, the peptide linker can comprise at least about 10, 20, 30, 40, 50, 60, 70, 80, 90, 100, 150, 200, 300, 400, 500, 600, 700, 800, 900, 1000, 1100, 1200, 1300, 1400, 1500, 1600, 1700, 1800, 1900, or 2000 amino acids. The peptide linker can comprise 1-5 amino acids, 1-10 amino acids, 1-20 amino acids, 10-50 amino acids, 50-100 amino acids, 100-200 amino acids, 200-300 amino acids, 300-400 amino acids, 400-500 amino acids, 500-600 amino acids, 600-700 amino acids, 700-800 amino acids, 800-900 amino acids, or 900-1000 amino acids.

Peptide linkers can be introduced into polypeptide sequences using techniques known in the art. Modifications can be confirmed by DNA sequence analysis. Plasmid DNA can be used to transform host cells for stable production of the polypeptides produced.

B.3.m. Monomer-Dimer Hybrids

In some embodiments, the isolated nucleic acid molecules of the disclosure which further comprise a heterologous nucleotide sequence encode a monomer-dimer hybrid molecule comprising FVIII.

The term "monomer-dimer hybrid" used herein refers to a chimeric protein comprising a first polypeptide chain and a second polypeptide chain, which are associated with each other by a disulfide bond, wherein, e.g., the first chain comprises Factor VIII and a first Fc region and the second chain comprises, consists essentially of, or consists of a second Fc region without the FVIII. The monomer-dimer hybrid construct thus is a hybrid comprising a monomer aspect having only one clotting factor and a dimer aspect having two Fc regions.

B.3.n. Expression Control Element

In some embodiments, the nucleic acid molecule or vector of the disclosure further comprises at least one expression control sequence. A expression control sequences as used herein is any regulatory nucleotide sequence, such as a promoter sequence or promoter-enhancer combination, which facilitates the efficient transcription and translation of the coding nucleic acid to which it is operably linked. For example, the isolated nucleic acid molecule of the disclosure can be operably linked to at least one transcription control sequence.

The gene expression control sequence can, for example, be a mammalian or viral promoter, such as a constitutive or inducible promoter. Constitutive mammalian promoters include, but are not limited to, the promoters for the following genes: hypoxanthine phosphoribosyl transferase (HPRT), adenosine deaminase, pyruvate kinase, beta-actin promoter, and other constitutive promoters. Exemplary viral promoters which function constitutively in eukaryotic cells include, for example, promoters from the cytomegalovirus (CMV), simian virus (e.g., SV40), papilloma virus, adenovirus, human immunodeficiency virus (HIV), Rous sarcoma virus, cytomegalovirus, the long terminal repeats (LTR) of Moloney leukemia virus, and other retroviruses, and the thymidine kinase promoter of herpes simplex virus.

Other constitutive promoters are known to those of ordinary skill in the art. The promoters useful as gene expression sequences of the disclosure also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

In one embodiment, the disclosure includes expression of a transgene under the control of a tissue specific promoter and/or enhancer. In another embodiment, the promoter or other expression control sequence selectively enhances expression of the transgene in liver cells. Examples of liver specific promoters include, but are not limited to, a mouse thyretin promoter (mTTR), an endogenous human factor VIII (F8) promoter, an endogenous human factor IX (F9) promoter, human alpha-1-antitrypsin promoter (hAAT), human albumin minimal promoter, and mouse albumin promoter. In a particular embodiment, the promoter comprises a mTTR promoter. The mTTR promoter is described in R. H. Costa et al., 1986, *Mol. Cell. Biol.* 6:4697. The F8 promoter is described in Figueiredo and Brownlee, 1995, *J. Biol. Chem.* 270:11828-11838. In certain embodiments, the promoter comprises any of the mTTR promoters (e.g., mTTR202 promoter, mTTR202opt promoter, mTTR482 promoter) as disclosed in U.S. patent publication no. US2019/0048362, which is incorporated by reference herein in its entirety.

Expression levels can be further enhanced to achieve therapeutic efficacy using one or more enhancers. One or more enhancers can be provided either alone or together with one or more promoter elements. Typically, the expression control sequence comprises a plurality of enhancer elements and a tissue specific promoter. In one embodiment, an enhancer comprises one or more copies of the α-1-microglobulin/bikunin enhancer (Rouet et al., 1992, *J. Biol. Chem.* 267:20765-20773; Rouet et al., 1995, *Nucleic Acids Res.* 23:395-404; Rouet et al., 1998, *Biochem. J.* 334:577-584; Ill et al., 1997, *Blood Coagulation Fibrinolysis* 8:S23-S30). In another embodiment, an enhancer is derived from liver specific transcription factor binding sites, such as EBP, DBP, HNF1, HNF3, HNF4, HNF6, with Enh1, comprising HNF1, (sense)-HNF3, (sense)-HNF4, (antisense)-HNF1, (antisense)-HNF6, (sense)-EBP, (antisense)-HNF4 (antisense).

In a particular example, a promoter useful for the disclosure comprises SEQ ID NO:63 (i.e., ET promoter), which is also known as GenBank No. AY661265. See also Vigna et al., *Molecular Therapy* 11(5):763 (2005). Examples of other suitable vectors and gene regulatory elements are described in WO 02/092134, EP1395293, or U.S. Pat. Nos. 6,808,905, 7,745,179, or 7,179,903, which are incorporated by reference herein in their entireties.

In general, the expression control sequences shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined coding nucleic acid. The gene expression sequences optionally include enhancer sequences or upstream activator sequences as desired.

EXAMPLES

Example 1—Recombinant Lentiviral Vector (LV) Preparation

Lentiviral vector drug product stability was assessed by exposure of vector to various stress conditions (e.g. freezing and thawing (F/T), elevated temperature (37° C.), agitation) and monitoring changes over time. Methods of determining stability included: ddPCR for functional titer, p24 ELISA for p24 concentration, and NanoSight for particle size distribution and particle concentration. Functional titer is a cell-based assay (HEK293) whereby LV is incubated with cells, allowed to integrate into cellular genome, extracted, and DNA is measured with ddPCR. The ELISA based p24 method is a kit-based method (Invitrogen) where the viral capsid protein, p24, is measured and related to a total particle concentration. NanoSight is a method that uses Brownian motion of the particles to evaluate size and concentration of LV particles in solution.

Functional titer is a dose defining parameter and is a key metric. It provides information about whether LVs are stable and can therefore integrate their payload into cells (related to the efficacy of the drug and mechanism of action). Functional titer is a dose defining criterion.

Vector Production and Measurement

VSV-pseudotyped third-generation lentiviral vectors (LVs) were produced by transient four-plasmid cotransfection into HEK293T cells and purified by anion-exchange as described in OXB patent (U.S. Pat. No. 9,169,491 B2). Vector particles were initially analyzed by functional titer and HIV-I gag p24 antigen immunocapture (NEN Life Science Products) to ensure proper transfection, production, and purification yields. Concentrated vector expression titer, or functional titer ranged from 1-10E8 TU/mL transducing units$^{293T}$(TU)/ml for all vectors.

Cell Cultures

Functional titer was measured by transducing adherent HEK293T cells with lentivector. Cells were split three times and then harvested for genomic DNA isolation. LV integration was measured in the genomic DNA by droplet digital PCR (ddPCR) using lentivector specific primers and probes. HEK293T adherent cells were maintained in Iscove's modified Dulbecco's medium (IMDM; Gibco) supplemented with 10% fetal bovine serum (FBS; Gibco) and a combination of penicillin-streptomycin and glutamine.

Processing LVs into Vehicle (Formulation)

After purification the LV material (drug substance—DS) was pooled and buffer exchanged into respective formulation buffers using a hollow fiber membrane. The DS was first concentrated roughly ten-fold and then exchanged with the respective formulation buffer six times the volume of the concentrated DS (e.g. 6 mL buffer for every 1 mL of concentrated DS). The final formulated LV was considered Drug Product (DP) and was tested for stability. FIG. 7A-7B and FIGS. 8A-8B show characterization of the formulation upon re-processing into the vehicle Phosphate (Formulation 1) (10 mM phosphate, 100 mM NaCl, 3% (w/v) sucrose, 0.05% (w/v) P188, pH 7.3) from the vehicle TSSM (20 mM Tris, 100 mM NaCl, 1% (w/v) sucrose, 1% (w/v) mannitol, pH 7.3). In addition to TSSM, there were four alternative formulations tested herein: Formulation 2 (Phosphate HigherSalt). 10 mM Phosphate, 130 mM NaCl, 1% (w/v) sucrose, 0.05% (w/v) P188, pH 7.3; Formulation 3 (Histidine). 20 mM Histidine, 100 mM NaCl, 3% (w/v) sucrose, 0.05% (w/v) P188, pH 6.5; Formulation 4 (Phosphate pH 7.0). 10 mM Phosphate, 100 mM NaCl, 3% (w/v) sucrose, 0.05% (w/v) P188, pH 7.0; Formulation 5 (Histidine pH 7.0). 20 mM Histidine, 100 mM NaCl, 3% (w/v) sucrose, 0.05% (w/v) P188, pH 7.0.

Example 2—In Vivo Administration of Lentiviral Vector (LV) Preparation 5-week old CD-1 and C57BL6 mice were purchased from Charles Rivers Laboratories and maintained in specific-pathogen-free conditions. 6 male HemA mice were obtained from our colony housed at Charles River. Administration of vector plus vehicle or vehicle alone was carried out by tail vein injection or temporal vein injection in mice. All animal procedures were performed according to protocols approved by Bioverativ/Sanofi IACUC (Animal Protocol 547). Three different formulations were tested: (1) 20 mM Tris, 100 mM NaCl, 1% (w/v) sucrose, 1% (w/v) mannitol, pH 7.3 (TSSM); (2) 10 mM phosphate, 100 mM NaCl, 3% (w/v) sucrose, 0.05% (w/v) P188, pH 7.3 (Phosphate); and (3) 20 mM histidine, 100 mM NaCl, 3% (w/v) sucrose, 0.05% (w/v) P188, pH 6.5 (Histidine) (Table 4).

TABLE 4

In vivo administration of LV preparations

| Formulation | Treatment | Fatality | Observation | No Response |
|---|---|---|---|---|
| TSSM | Vector + Vehicle | x (n = 1) | x [rough coat, excessive grooming, hunched posture] (n = 5) | |
| TSSM | Vehicle alone | | x [rough coat, excessive grooming, hunched posture] (n = 4) | |
| Phosphate | Vector + Vehicle | | | x (n = 3) |
| Phosphate | Vehicle alone | | | x (n = 3) |
| Histidine | Vector + Vehicle | | | x (n = 3) |
| Histidine | Vehicle alone | | | x (n = 3) |

Formulation: Vehicle (TSSM) Alone and Vehicle (TSSM) with LV

A dose response study was conducted using LV-coFIX in C57BL6 and CD-1 adult mice after a single intravenous administration. 11 male C57BL6 mice (5 weeks old) and 11 male CD-1 mice (5 weeks old) were used. The doses administered were as follows: 6E10 (n=3), 2E10 (n=4), and 7.5E9 (n=4) TU/kg. The formulation vehicle was TSSM buffer.

C57BL6 and CD-1 mice were dosed with LV-FIX vector formulated in TSSM Buffer. The 6E10 TU/kg dose was given straight, no dilution at 13.3-15 ml/kg. The other two lower doses were diluted in PBS prior to administration. Three mice of each strain were given the high dose. Immediately upon injection of the 6E10 TU/kg dose, one C57BL6 mouse went into cardiac arrest and died. The other mice in the group exhibited adverse effects approximately a half hour later. We observed excessive grooming, then rough coat, listlessness, and inactivity. These mice seemed to recover after an hour post injection. Only the mice in the high dose (6E10 TU/kg) group showed an adverse effect. The mice that received a diluted dose showed no adverse effects at all. Later, 2 CD-1 and 2 C57BL6 mice were given just TSSM vehicle formulation buffer alone at 10-15 ml/kg. These mice also exhibited adverse effects post injection (excessive grooming, then rough coat, listlessness, and inactivity) that normalized after about an hour. The results are summarized in Table 4.

Formulation: Vehicle (Phosphate) Alone

A dose response study was conducted using HemA mice. 3 male HemA mice (9 weeks old) were used. The dose administered was 15 ml/kg. The formulation vehicle was Phosphate buffer.

Three HemA mice were dosed with 15 ml/kg Phosphate formulation buffer to test for any adverse in-vivo effects. Mice were closely observed for the next 2 days. No adverse effects were noted including the excessive grooming, rough coat, listlessness, and inactivity seen with the TSSM formulation buffer.

Formulation: Vehicle (Phosphate) with LV

A dose response study was conducted using LV-coFVIII-6XTEN in HemA mice pups by temporal vein injection. 22 male and female HemA pups (2 days old) were used. The doses administered were as follows: 3E9 and 1.5E9 TU/kg. The formulation vehicle was Phosphate buffer.

Two day old mice were administered LV-FVIIIXTEN formulated in Phosphate Buffer at 3E9 or 1.5E9 TU/kg by temporal vein injection. The high dose (3E9) was given with no dilution. No adverse effects were seen in these mice post injection.

(FIGS. 3A-3B, FIG. 4, FIGS. 5A-5B, Table 5). Stability of the vector was measured by determining the functional titer, p24 concentration, and particle size and distribution (Nano-Sight). As shown in FIGS. 3A-3B, FIG. 4, FIGS. 5A-5B, and Table 5, there was no significant change in vector stability under the different conditions for the formulation with or without P188. Vector integrity was determined by particle size measurements using NanoSight.

TABLE 5

Testing of Formulation Using the Vehicle TSSM

| Formulation | Stress | ddPCR TU/mL | NanoSight particles/mL | p24 particles/mL | NanoSight/ddPCR Inf. Ratio | p24/ddPCR Inf. Ratio |
|---|---|---|---|---|---|---|
| TSSM | T0 | 1.33E+08 | 6.08E+11 | 9.46E+11 | 4571 | 7109 |
| TSSM + P188 | T0 | 1.27E+08 | 6.74E+11 | 1.00E+12 | 5292 | 7876 |
| TSSM | Agitation | 1.45E+08 | 6.50E+11 | 1.03E+12 | 4471 | 7101 |
| TSSM + P188 | Agitation | 1.45E+08 | 6.46E+11 | 1.21E+12 | 4443 | 8339 |
| TSSM | RT-6 h | 1.29E+08 | NT | 1.04E+12 | NT | 8047 |
| TSSM + P188 | RT-6 h | 1.34E+08 | NT | 1.13E+12 | NT | 8461 |
| TSSM | F/T | 1.49E+08 | 6.18E+11 | 8.81E+11 | 4153 | 5919 |
| TSSM + P188 | F/T | 1.72E+08 | 6.78E+11 | 9.66E+11 | 3945 | 5620 |

*assuming 1 ng/mL p24 = 1.25E7 particles/mL (NT = Not Tested)

Formulation: Vehicle (Histidine) Alone

A dose response study was conducted using HemA mice. 3 male HemA mice (19 weeks old) were used. The dose administered was 15 ml/kg. The formulation vehicle was Histidine buffer.

Three HemA mice were dosed with 15 ml/kg Histidine formulation buffer to test for any adverse in-vivo effects. Mice were closely observed for the next 2 days. No adverse effects were noted including the excessive grooming, rough coat, listlessness, and inactivity seen with the TSSM formulation buffer.

Formulation: Vehicle (Histidine) with LV

A dose response study was conducted using LV-coFVIII-6XTEN in tolerized adult HemA mice by tail vein injection. 4 male HF8 mice (12 weeks old) were used. The dose administered was 15 ml/kg. The formulation vehicle was Histidine buffer.

Four tolerized HemA mice (HF8) were dosed with 15 ml/kg LV-FVIIIXTEN vector formulated in Histidine formulation buffer. No adverse effects were noted including the excessive grooming, rough coat, listlessness, and inactivity seen with the TSSM formulation.

In summary, mice were injected with vector plus vehicle or vehicle alone for each of the formulations. Table 4 shows that TSSM injection, both vector plus vehicle and vehicle alone, had adverse toxic effects on mice, including one fatality. Conversely, Phosphate and Histidine formulations, vector plus vehicle or vehicle alone, resulted in no response (no toxic effects) in the mice.

Example 3—Testing of Formulation Using the Vehicle TSSM

Agitation, Freeze-Thaw, and Temperature Conditions

Figure 6A:
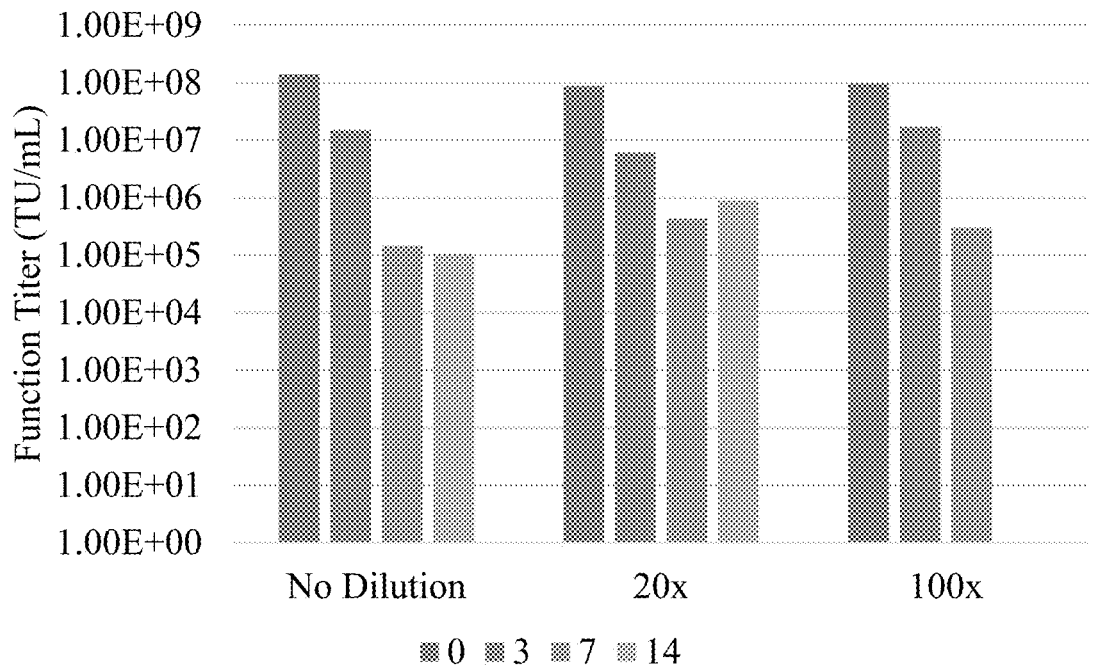
FIGS. 6A-6B depict stability of lentiviral vectors (LVs) in the vehicle TSSM (20 mM TRIS, 100 mM NaCl, 1% (w/v) Sucrose, 1% (w/v) Mannitol, pH 7.3) at 37° C. over 0, 3, 7, and 14 days, as measured by functional titer in TU/ml (FIG. 6A) and % of TO (FIG. 6B) using ddPCR.
Figure 6B:
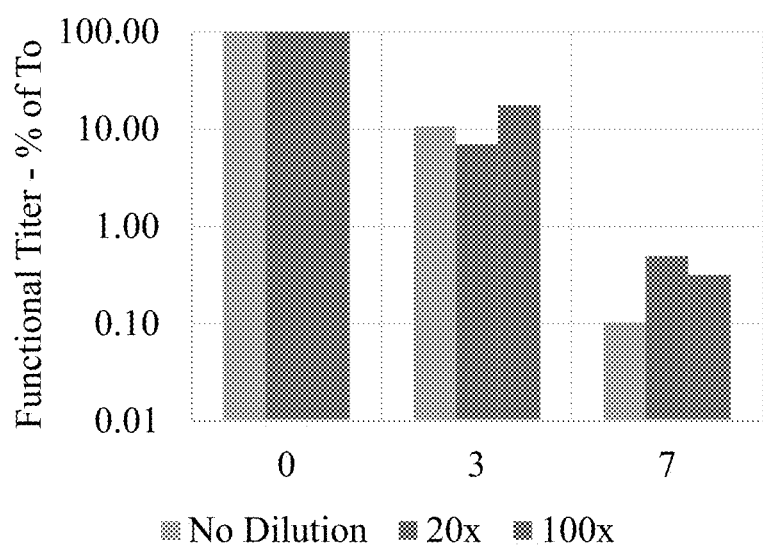
Figure 7A:
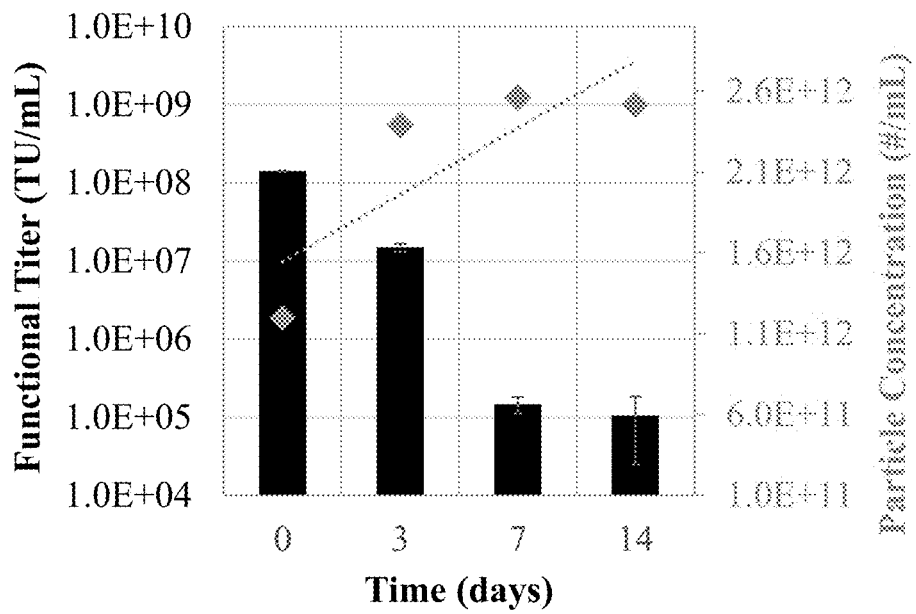
FIGS. 7A-7B depict stability of lentiviral vectors (LVs) in the vehicle TSSM (20 mM TRIS, 100 mM NaCl, 1% (w/v) Sucrose, 1% (w/v) Mannitol, pH 7.3) at 37° C. over 0, 3, 7, and 14 days, as measured by functional titer in TU/ml using ddPCR and particle concentration using NanoSight (FIG. 7A) or functional titer overlaid with p24 data (FIG. 7B).
Figure 7B:
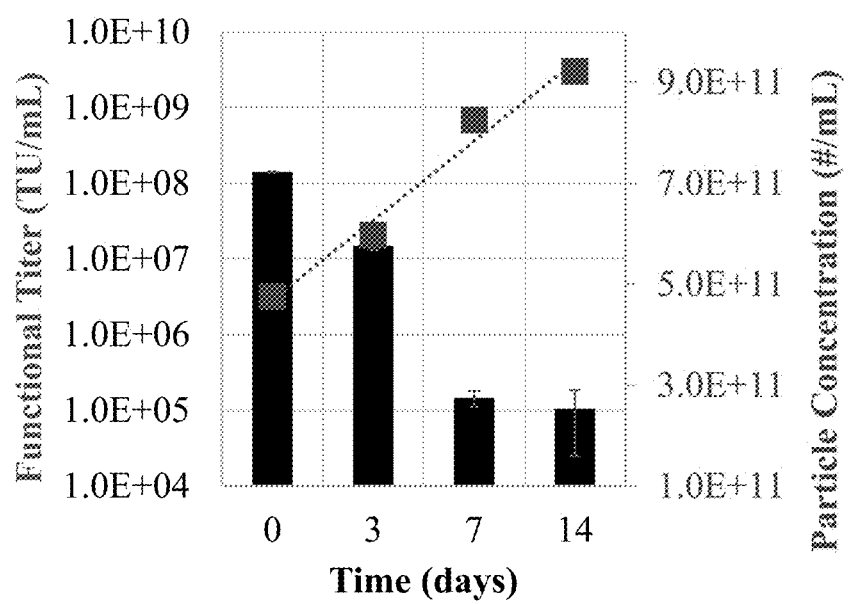
Figure 8A:
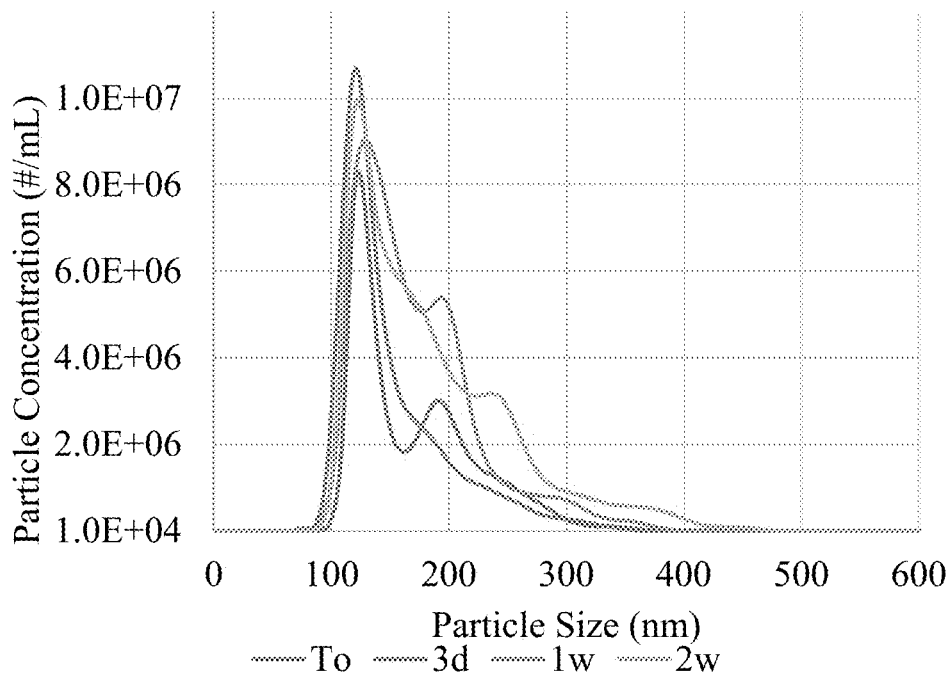
FIGS. 8A-8B.
Figure 8B:
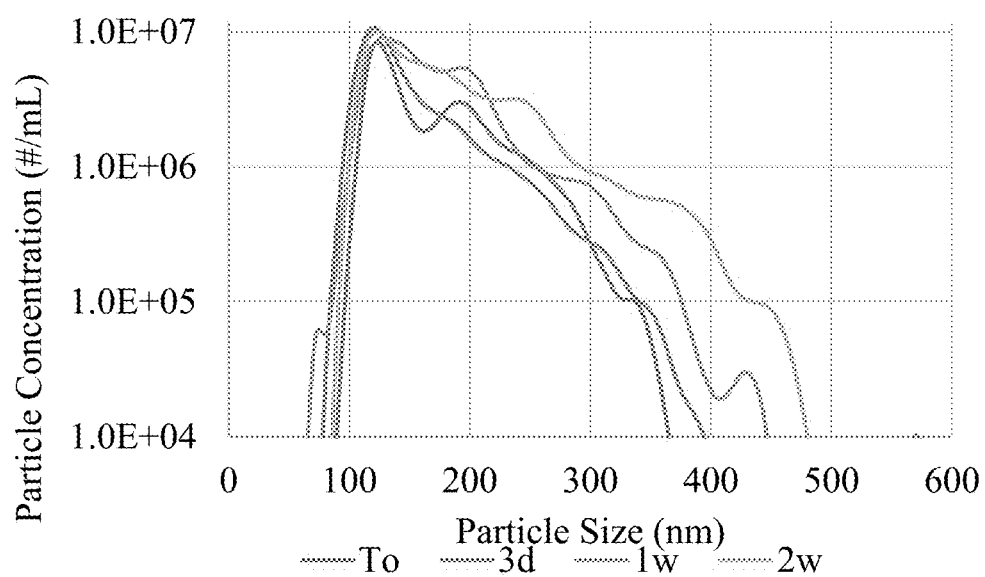

The stability of the TSSM formulation (vector plus vehicle) with and without the addition of 1% (w/v) P188, for a final concentration of 1% (w/v) P188, was tested by subjecting the formulation to agitation, freeze-thaw (F/T) cycles (5 and 10), and 6 hour room temperature incubation Dilution Conditions The TSSM formulation (vector plus vehicle) was diluted 1×, 20×, and 100×, incubated at 37° C., and stability determined through measurement of functional titer via ddPCR on days 0, 3, 7, and 14. FIG. 6A and FIG. 6B show that dilution had no effect on stability over two weeks at elevated temperature.

Incubation for Different Time Periods

The TSSM formulation (vector plus vehicle) was incubated at 37° C. for 0, 3, 7, or 14 days. Stability was measured through determination of functional titer via ddPCR, while particle integrity (particle concentration) was measured using Nanosight or p24 ELISA. Stability and vector integrity (particle concentration) as a function of incubation time were determined, as shown in FIGS. 7A-7B and FIGS. 8A-8B. Vector stability decreased as incubation time increased, while particle concentration increased.

Extended Incubation at 37° C.

The TSSM formulation (vector plus vehicle) was incubated at 37° C. for 0 days, 3 days, 1 week, or 2 weeks. Particle size distribution was measured using Nanosight. As shown in FIGS. 7A-7B and FIGS. 8A-8B, with extended incubation time, particle size distribution broadened, while particle concentration increased. The results may be explained as follows. The total particle concentration is increasing while infectivity is decreasing, because prolonged exposure to 37° C. temperature is causing the capsid to break apart, resulting in more apparent p24 measured in ELISA. Furthermore, the virus breaking apart leads to an increase in smaller sized species.

Example 4—Testing Formulations Using the Vehicles Phosphate and Histidine

Phosphate Formulation

Figure 2A:
FIGS. 2A-2B depict effects of sterile filtration on lentiviral vectors (LVs) in the vehicle Phosphate (10 mM Phosphate, 100 mM NaCl, 3% (w/v) sucrose, 0.05% (w/v) P188, pH 7.3) post tangential flow filtration (TFF) (FIG. 2A) and in the final drug substance (DS) pool (FIG. 2B).
Figure 2B:
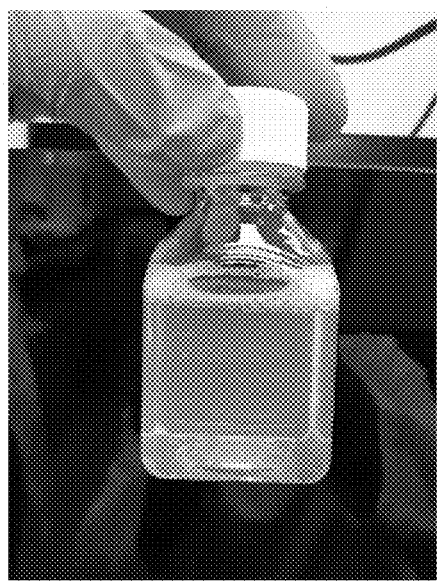
Figure 3A:
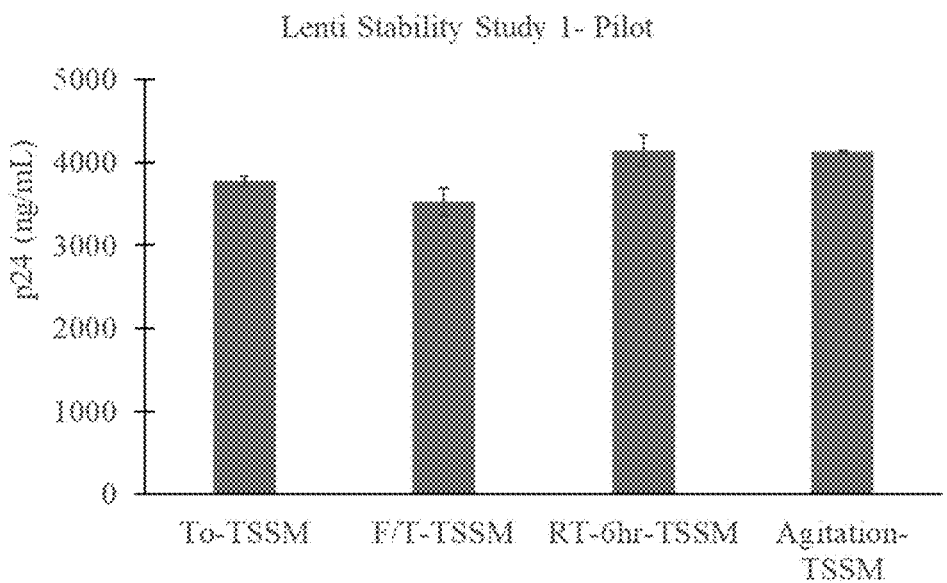
FIGS. 3A-3B depict stability of lentiviral vectors (LVs) in the vehicle TSSM (20 mM TRIS, 100 mM NaCl, 1% (w/v) Sucrose, 1% (w/v) Mannitol, pH 7.3), without the addition of 1% (w/v) P188 (FIG. 3A) and with the addition of 1% (w/v) P188 (FIG. 3B), as measured by p24 concentration using p24 ELISA.
Figure 3B:
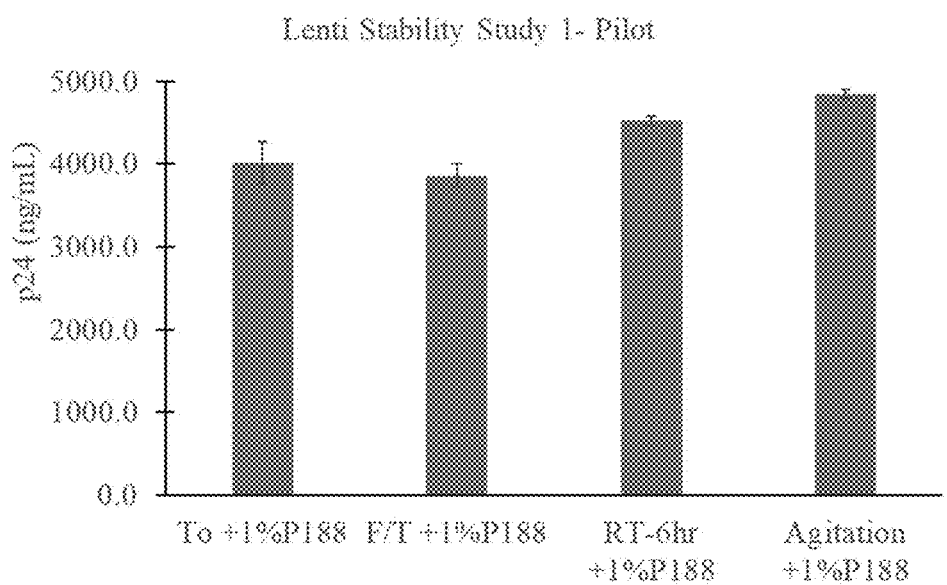
Figure 4:
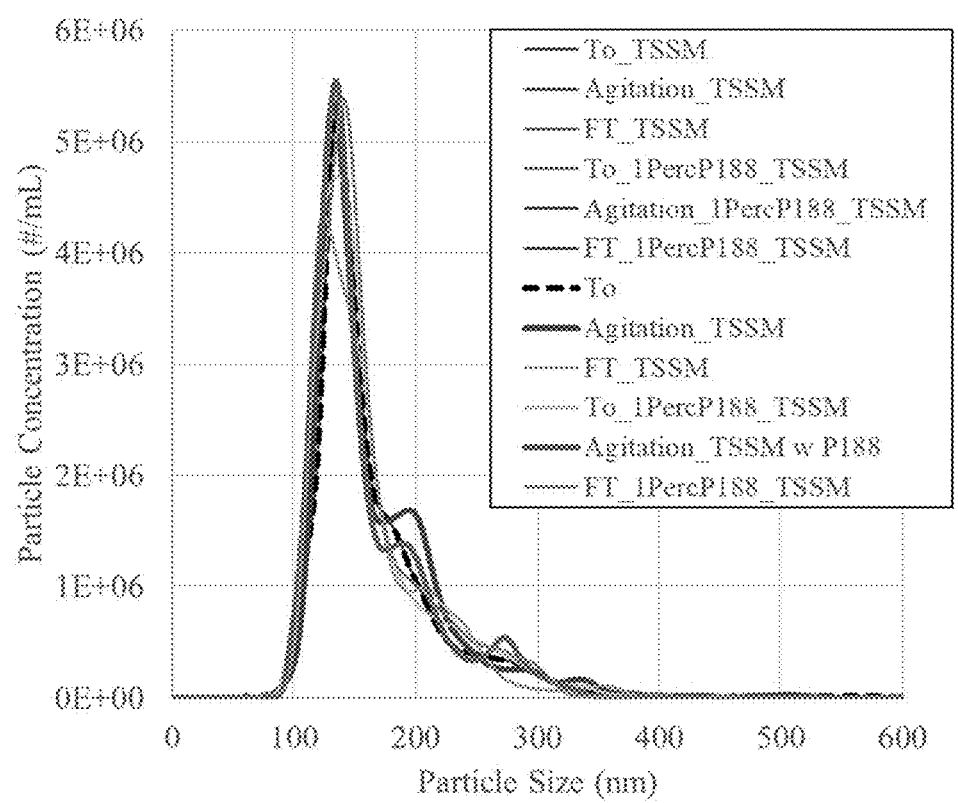
FIG. 4 depicts stability of lentiviral vectors (LVs) in the vehicle TSSM (20 mM TRIS, 100 mM NaCl, 1% (w/v) Sucrose, 1% (w/v) Mannitol, pH 7.3) upon agitation, as measured by particle concentration and particle size using NanoSight. Stability study using TSSM formulation: 20 mM Tris, 100 mM NaCl, 1% (w/v) Sucrose, 1% (w/v) Mannitol, pH 7.3, as indicated with and without Poloxomer 188 (P188). Measurements were made using NanoSight.
Figure 5A:
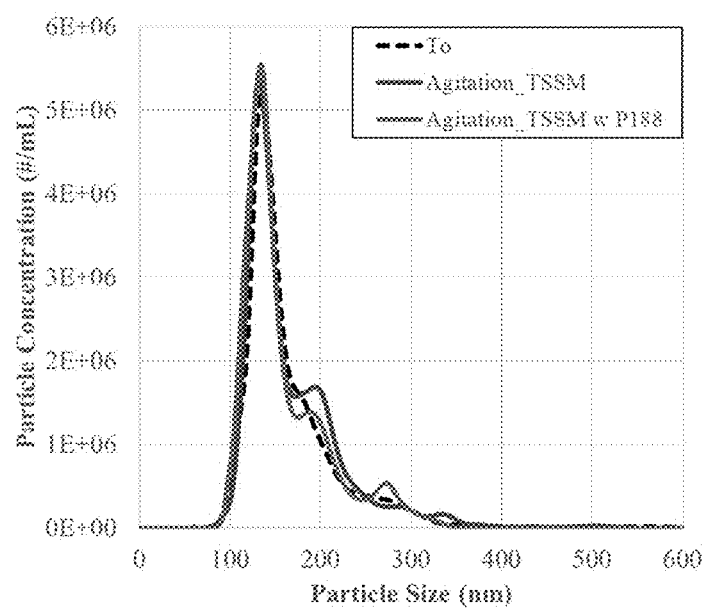
FIGS. 5A-5B depict stability of lentiviral vectors (LVs) in the vehicle TSSM (20 mM TRIS, 100 mM NaCl, 1% (w/v) Sucrose, 1% (w/v) Mannitol, pH 7.3) upon agitation, as measured by particle concentration and particle size using NanoSight.
Figure 5B:
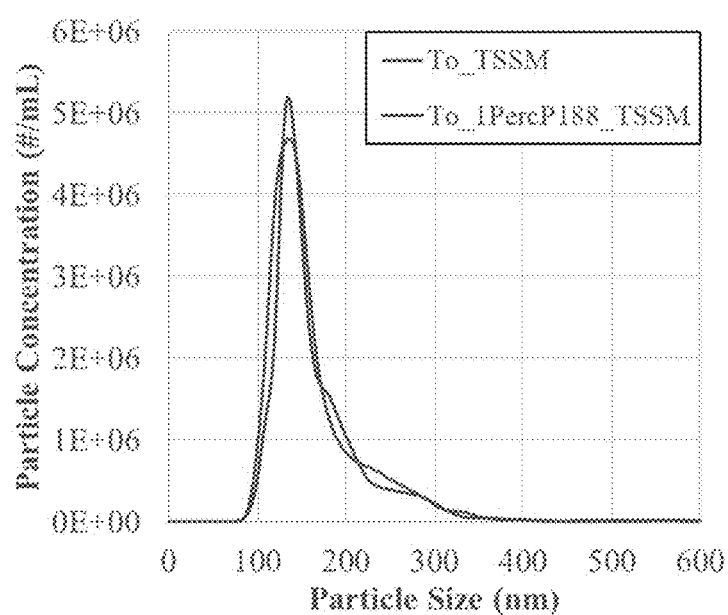

The lentiviral vector (LV) formulation was characterized upon processing into the vehicle Phosphate (10 mM Phosphate, 100 mM NaCl, 3% (w/v) sucrose, 0.05% (w/v) P188, pH 7.3). Particle size and distribution was measured using Nanosight (FIG. 1). FIG. 1 is a plot showing results from Nanosight showing a clean monomeric peak for the drug substance (DS) pool, which after ultrafiltration/diafiltration into the final vehicle buffer (post tangential flow filtration—TFF) shifts slightly to a larger particle size with the appearance of the presence of some larger particles. Without being bound to theory, this may be due to physical degradation of the particle during the stress of processing the material. The final drug product (DP) when filtered through a 0.22 μm sized filter membrane results in a particle size and distribution profile that returns back in line with the DS pool at the start of processing. TFF stress is visually shown in the photographs in FIGS. 2A-2B.

Figure 9:
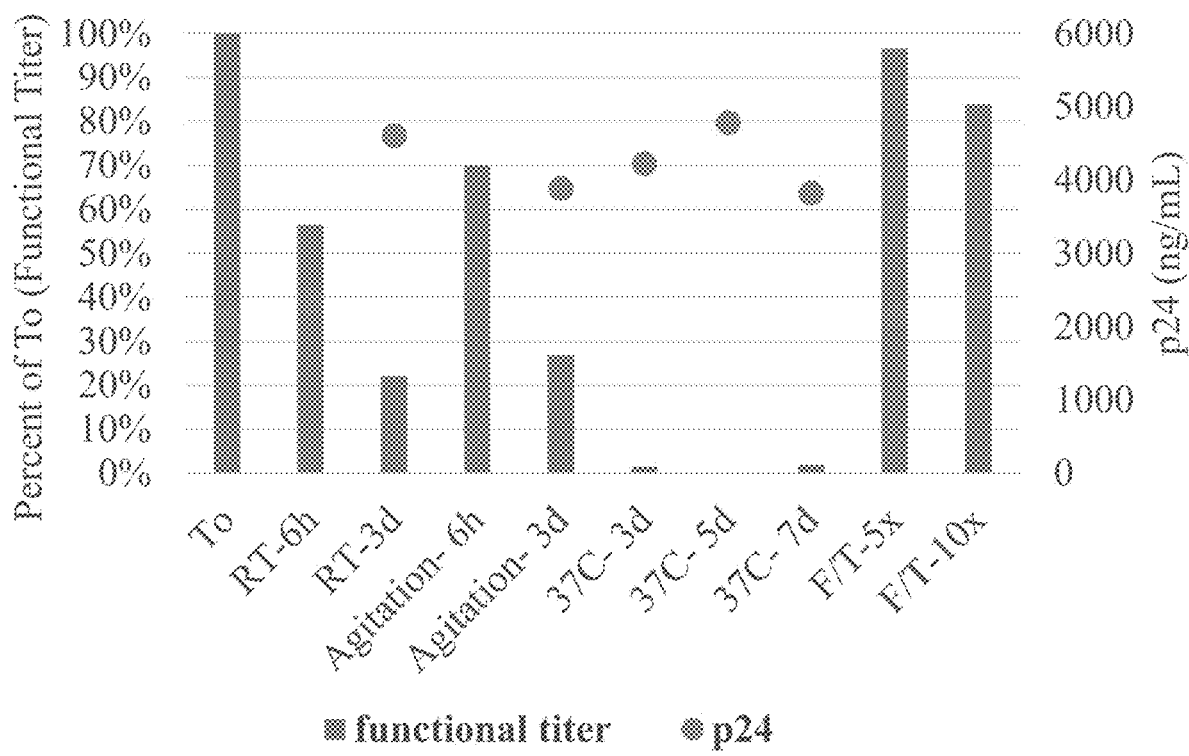
FIG. 9 depicts stability of lentiviral vectors (LVs) in the vehicle Phosphate Formulation (10 mM Phosphate, 100 mM NaCl, 3% (w/v) sucrose, 0.05% (w/v) P188, pH 7.3) as a function of incubation time, incubation temperature, agitation, and freeze/thaw (F/T) cycles in days, as measured by functional titer in % of TO using ddPCR and p24 concentration using p24 ELISA.
Figure 10A:
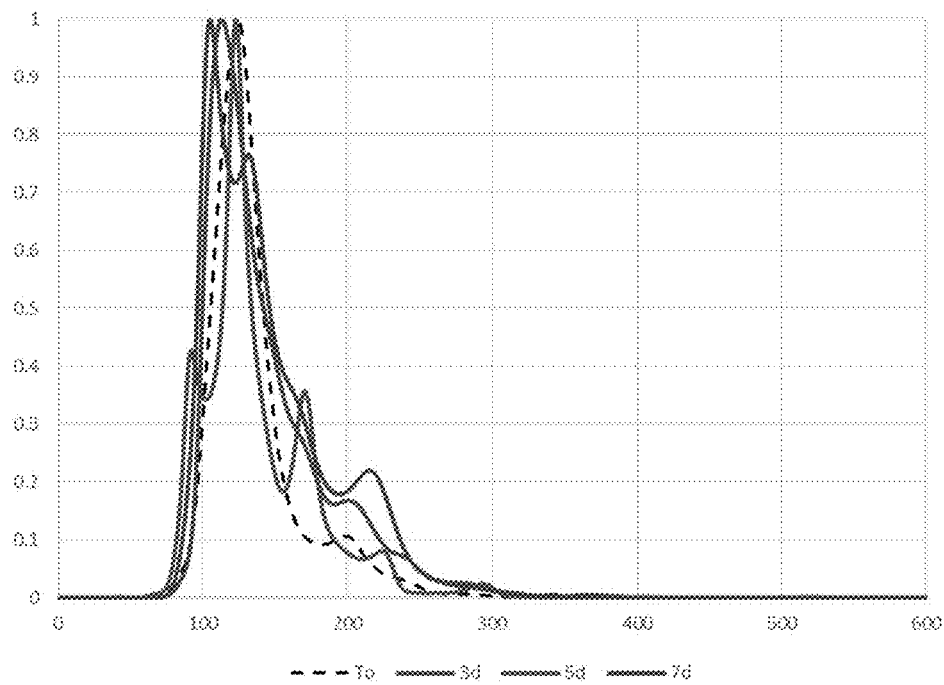
FIGS. 10A-10B depict stability of lentiviral vectors (LVs) at 37° C. using Phosphate formulation (10 mM Phosphate, 100 mM NaCl, 3% (w/v) sucrose, 0.05% (w/v) P188, pH 7.3) as a function of time in days, as measured by particle concentration and particle size distribution using NanoSight.
Figure 10B:
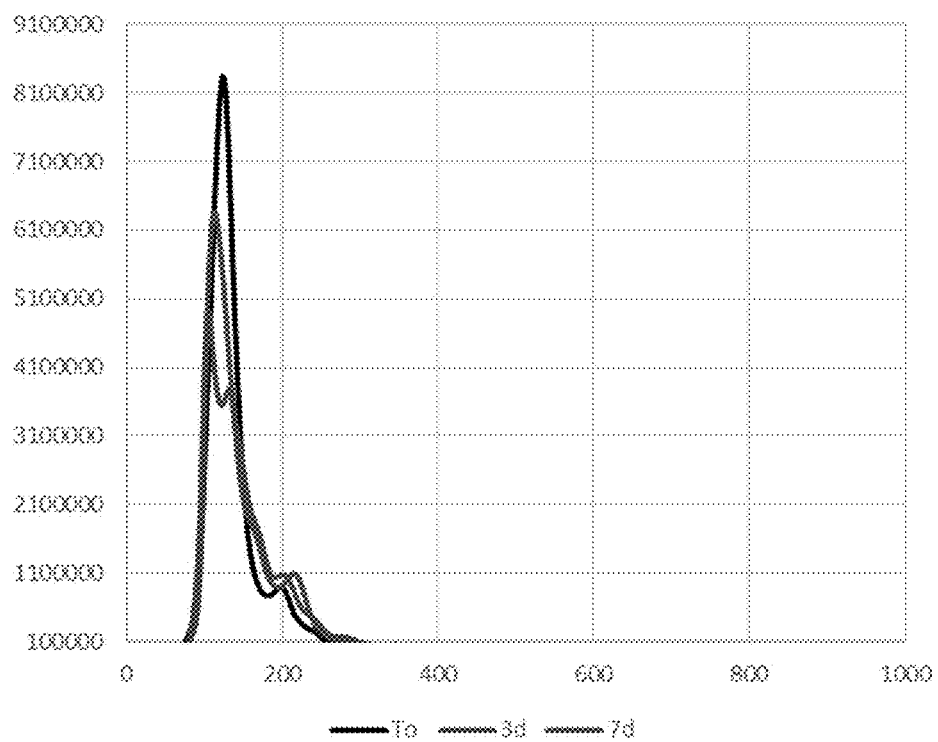

Vector stability was tested for the phosphate formulation (vector plus vehicle) under different conditions, including agitation, incubation at 37° C., duration, and dilution (FIG. 9 and FIGS. 10A-10B).

FIGS. 10A-10B shows the NanoSight size data for the phosphate buffer over one week at 37° C. There is a slight increase in higher molecular weight species as well as an overall drop in total particles over incubation time. The data suggests the loss in function titer shown in FIG. 9 over the course of stability at RT or 37° C. may correspond to the physical loss of particles observed in FIGS. 10A-10B.

Figure 13:
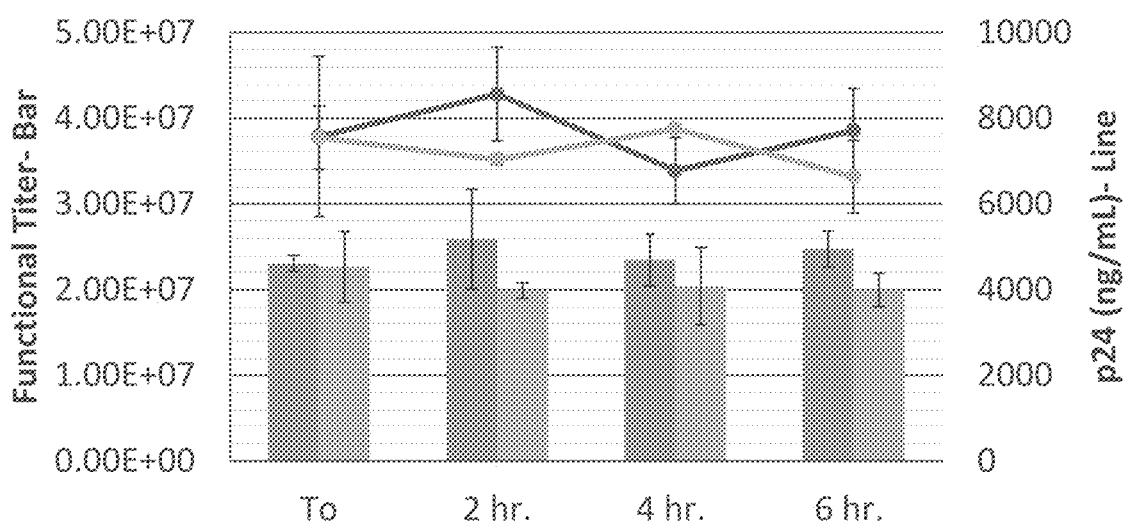
FIG. 13 depicts a mock in-use stability study with one formulation over 6 hours at room temperature exposed to an IV bag: Formulation 1 (Phosphate Buffer): 10 mM Phosphate, 100 mM NaCl, 3% (w/v) sucrose, 0.05% (w/v) P188, pH 7.3.
Figure 14:
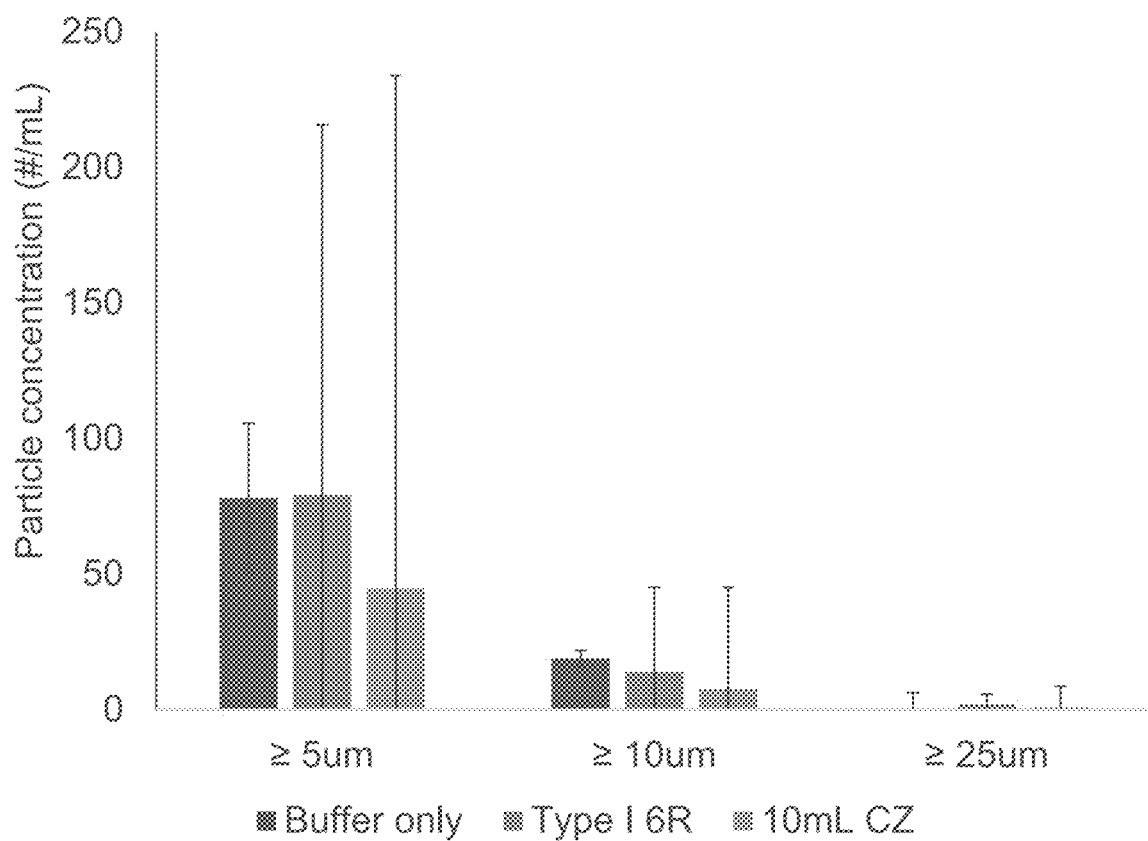
FIG. 14 depicts a formulation buffer stability study comparing container closure (Schott Type 1 glass vials and West CZ COP vials) performance over one freezing and thawing cycle (−80° C. overnight, thaw in 37° C. water bath): Formulation 1 (Phosphate Buffer): 10 mM Phosphate, 100 mM NaCl, 3% (w/v) sucrose, 0.05% (w/v) P188, pH 7.3. Particle concentration was obtained using Microflow Imaging (MFI).
Figure 15:
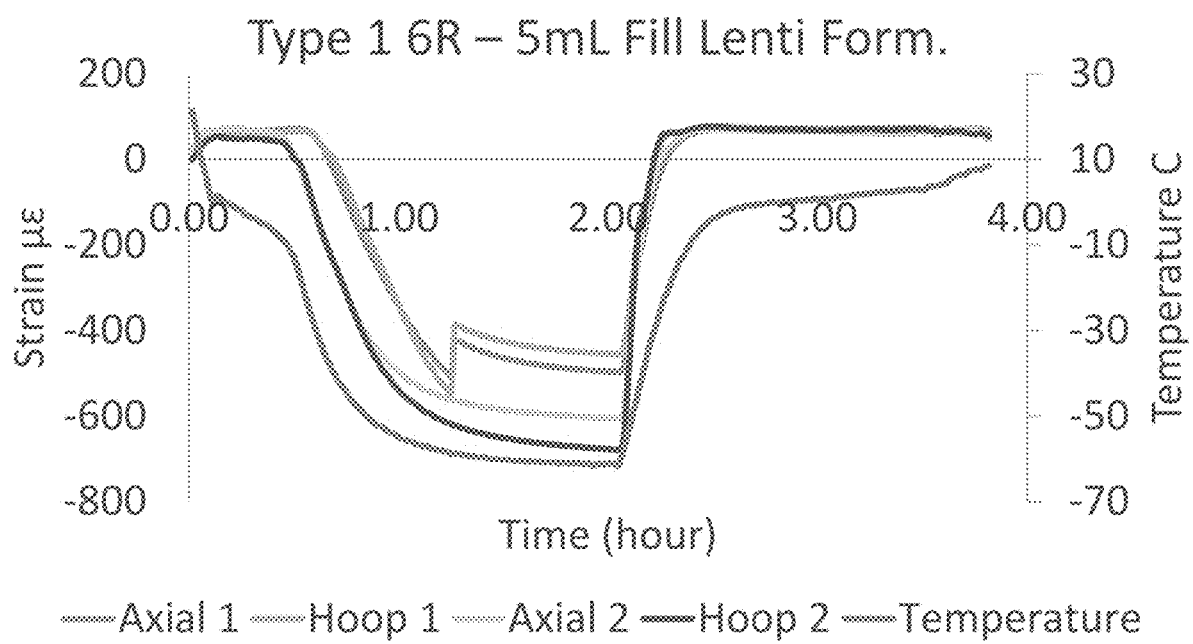
FIG. 15 depicts a vial strain study using Schott Type 1 glass vials over one freezing and thawing cycle (−80 C, thaw in 37° C. water bath): Formulation 1 (Phosphate Buffer Only): 10 mM Phosphate, 100 mM NaCl, 3% (w/v) sucrose, 0.05% (w/v) P188, pH 7.3. Data was collected using a strain gauge and thermocouple.
Figure 16A:
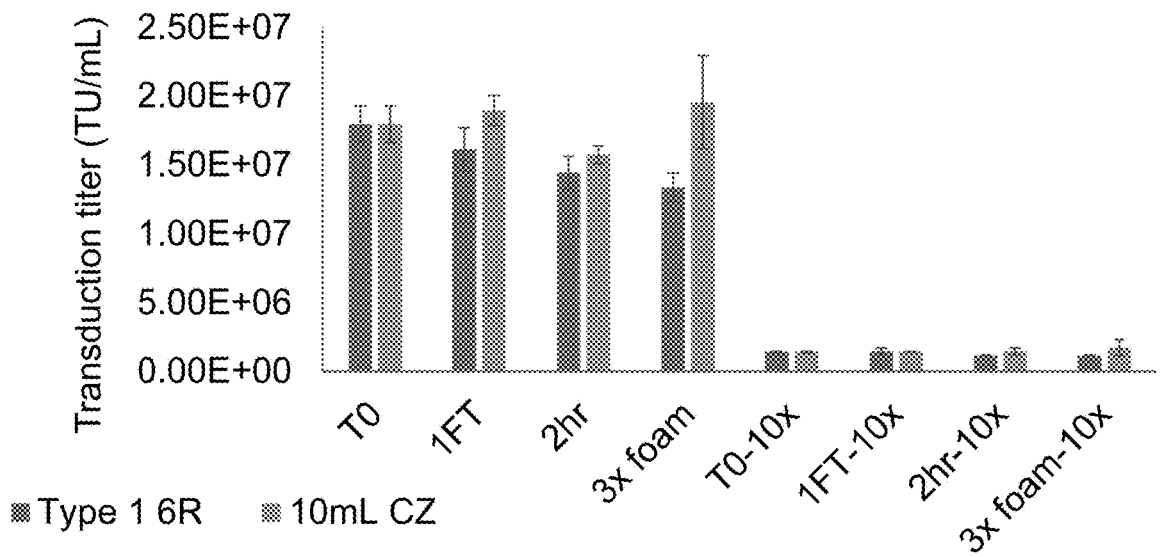
FIGS. 16A-FIG. 16C depict LVV material compatibility comparing container closure (Schott Type 1 glass vials and West CZ vials) performance over various stability conditions, 1 FT=1 cycle of freezing and thawing; 2 hr=2 hr exposure to room temperature; 3× foam is aggressive aspiration and dispensing from a pipette generating visible foam in the container; 10× is the same stability parameters at a 10 fold dilution. LVV was in Formulation 1 (Phosphate Buffer): 10 mM Phosphate, 100 mM NaCl, 3% (w/v) sucrose, 0.05% (w/v) P188, pH 7.3.; as measured by functional titer (FIG. 16A), p24 concentration (FIG. 16B), and particle concentration (FIG. 16C). Data was collected using a strain gauge and thermocouple. Particle concentration was obtained using NanoSight.
Figure 16B:
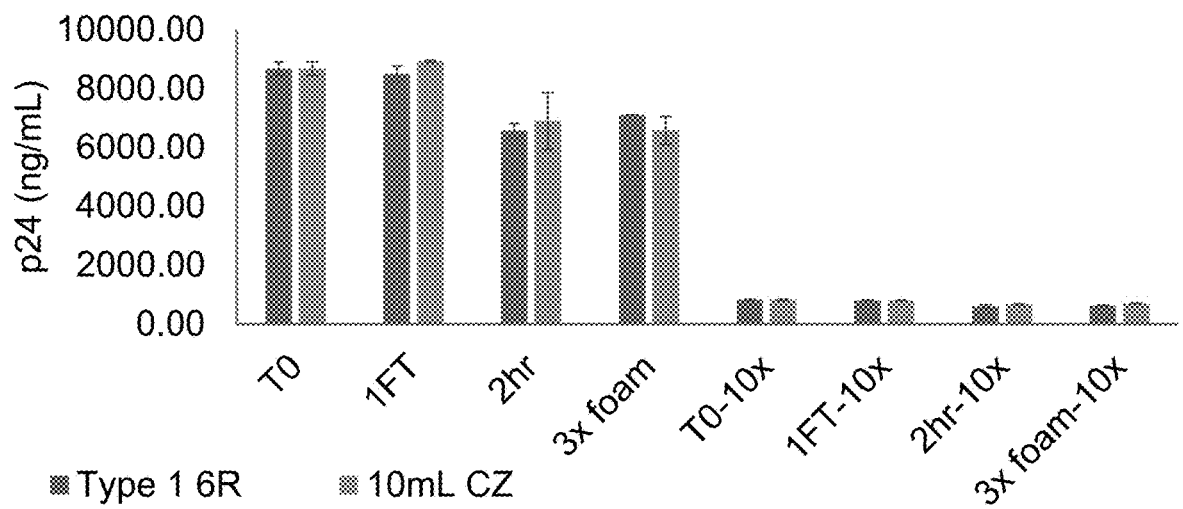
Figure 16C:
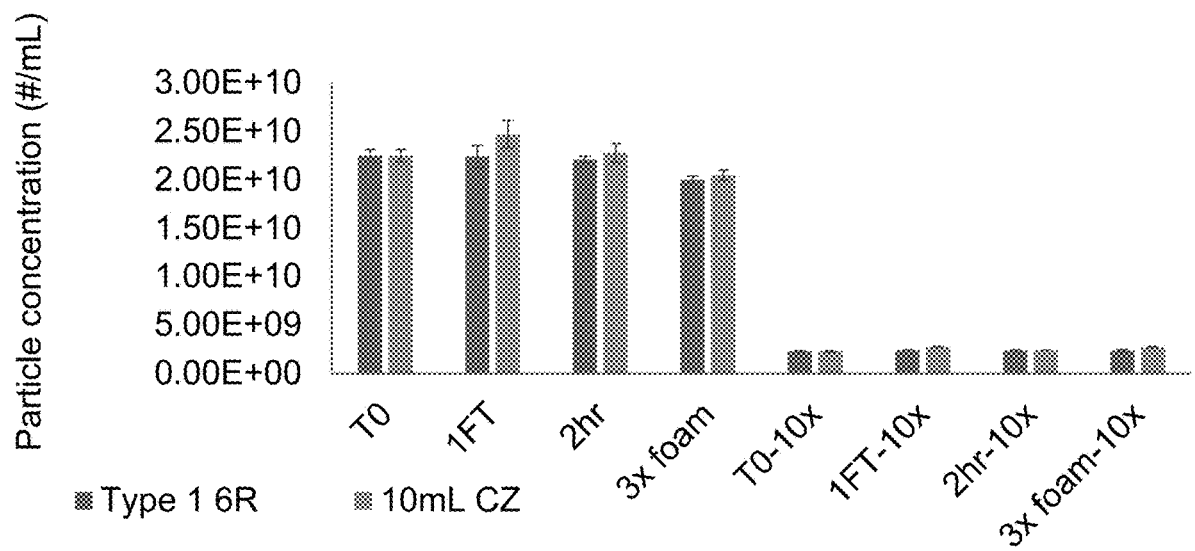

A mock in-use study was performed in order to assess the stability of the phosphate formulation over the course of a typical infusion scenario during clinical administration. The LVV material was diluted with the phosphate vehicle and injected into an empty IV bag. Data was collected over six hours at room temperature, FIG. 13. The stability study shows no signs of loss by functional titer or p24 indicating the vector was stable over the duration of the study.

In order to test compatibility with a prospective container closure system, a study was performed in order to examine the stability of the vector and phosphate vehicle in Schott Type 1 glass vials as well as West CZ COP vials (FIG. 14, FIG. 15, and FIGS. 16A-16C). The data indicates that there were no significant particles produced when treated with the vehicle only in either the Type 1 or CZ vial, FIG. 14. In order to assess strain on the vial during freezing and thawing, a strain gauge was glued to the glass vial and placed in a −80° C. freezer for a period of two hours, followed by rapid warming in a 37° C. water bath, FIG. 15. The study indicates no appreciable positive strain on the vial, which would suggest that at this relatively high fill volume of 5 mL, the phosphate formulation does not impose high stress on the container, which has been shown in literature to damage certain vials. LVV material was also tested for compatibility with the respective containers, shown in FIGS. 16A-16C. Through each test, transduction titer (FIG. 16A), p24 (FIG. 16B), and particle concentration (FIG. 16C), there was comparability stability and integrity of the vector indicating compatibility with both container closure formats, glass and plastic vials.

Phosphate and Histidine Formulation Comparisons

Vector stability was tested for the phosphate (Formulation 1 and Formulation 2) and histidine (Formulation 3) formulations (vector plus vehicle) under different stress conditions (FIGS. 11A-11B, FIGS. 12A-12B). In the freeze-thaw cycling study both phosphate formulations were observed to decrease in functional titer as a function of cycling. By contrast, the histidine formulation did not show a functional loss and remained stable. During the room temperature hold as well as the agitation stress condition, the phosphate formulation showed a high level of functional loss (down to the limit of quantitation). Surprisingly, the Histidine formulation remained unaffected by the incubation at room temperature for 3 days or the agitation for 3 days. Additionally, the addition of more sodium chloride and the drop in sucrose for the phosphate formulation (comparing Formulation 1 and Formulation 2) did not affect vector stability.

Figure 11A:
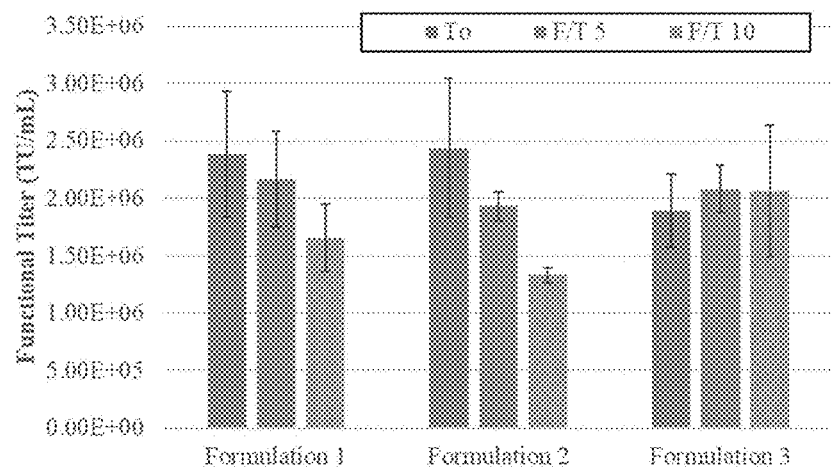
FIGS. 11A-11B depict stability of lentiviral vectors (LVs) comparing three formulations: Formulation 1. Phosphate formulation: 10 mM Phosphate, 100 mM NaCl, 3% (w/v) sucrose, 0.05% (w/v) P188, pH 7.3; Formulation 2. 10 mM Phosphate, 130 mM NaCl, 1% (w/v) sucrose, 0.05% (w/v) P188, pH 7.3; Formulation 3. 20 mM Histidine, 100 mM NaCl, 3% (w/v) sucrose, 0.05% (w/v) P188, pH 6.5; over 5 and 10 cycles of Freezing and Thawing (F/T) (FIG. 11A) and comparing 3 days at room temperature (RT) and RT with agitation (orbital shaker, 350 rpm) (FIG. 11B), as measured by functional titer using ddPCR.
Figure 11B:
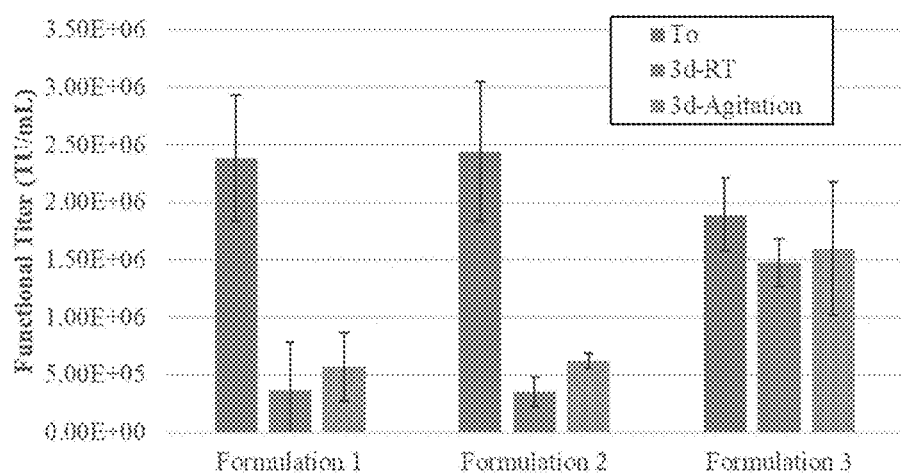
Figure 12A:
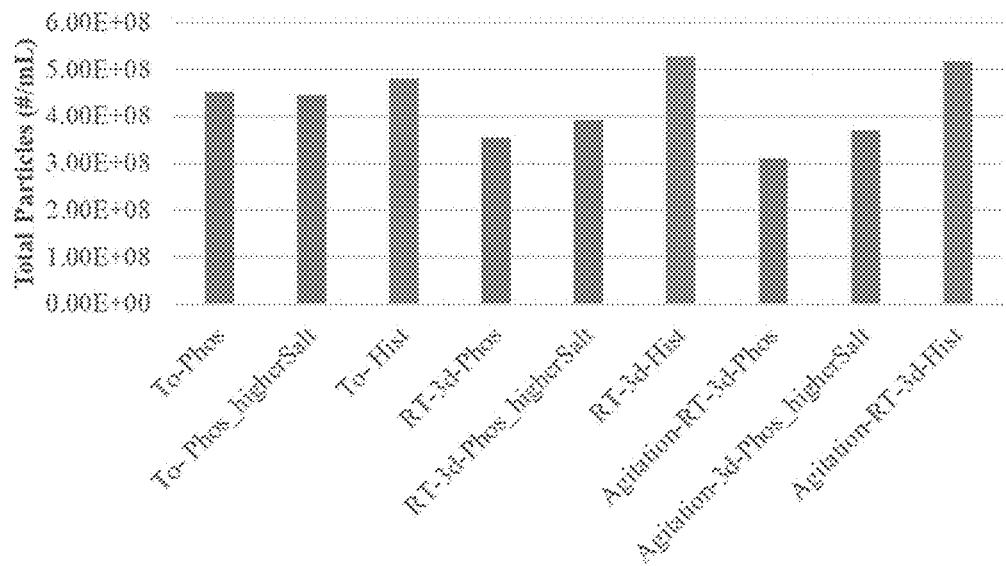
FIGS. 12A-12B depict stability of lentiviral vectors (LVs) comparing three formulations): Formulation 1 (Phos). Phosphate formulation: 10 mM Phosphate, 100 mM NaCl, 3% (w/v) sucrose, 0.05% (w/v) P188, pH 7.3; Formulation 2 (Phos. higherSalt). 10 mM Phosphate, 130 mM NaCl, 1% (w/v) sucrose, 0.05% (w/v) P188, pH 7.3; Formulation 3 (Hist). 20 mM Histidine, 100 mM NaCl, 3% (w/v) sucrose, 0.05% (w/v) P188, pH 6.5, as measured by number of particles using NanoSight.
Figure 12B:
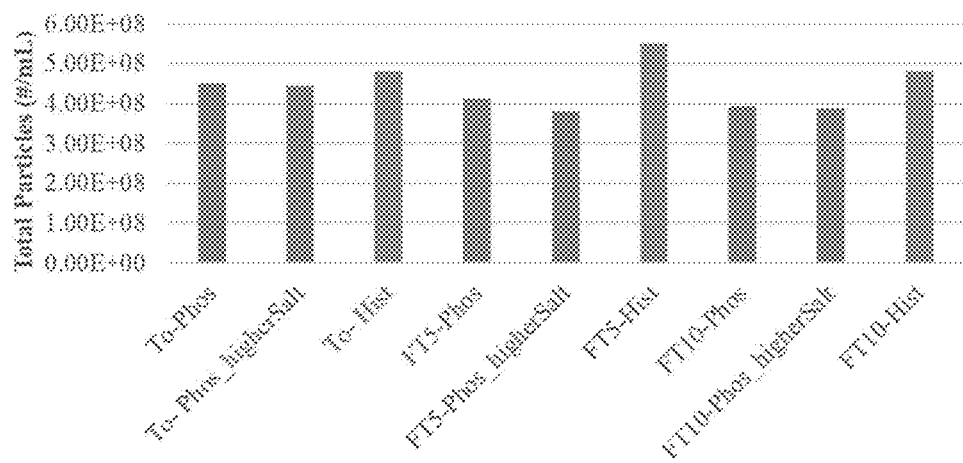
Figure 17:
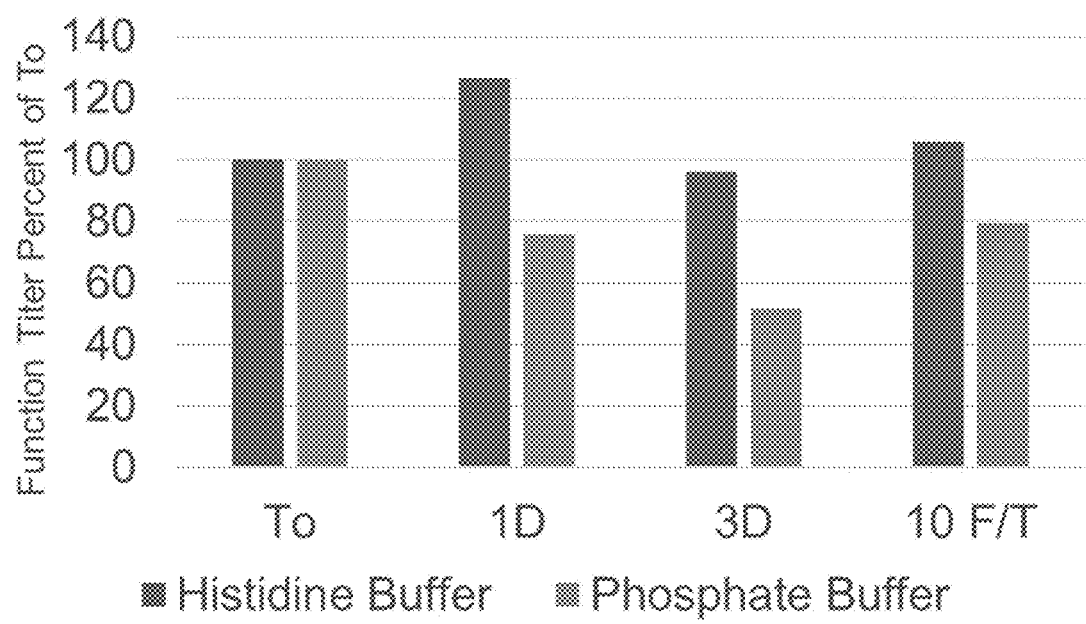
FIG. 17 depicts a stability study comparing two formulations over 10 cycles of Freezing and Thawing (F/T) and comparing 1 and 3 days at room temperature (RT): Formulation 1 (Phosphate Buffer): 10 mM Phosphate, 100 mM NaCl, 3% (w/v) sucrose, 0.05% (w/v) P188, pH 7.3; Formulation 3 (Histidine Buffer). 20 mM Histidine, 100 mM NaCl, 3% (w/v) sucrose, 0.05% (w/v) P188, pH 6.5.

In a separate preparation of material, re-testing of the stability study demonstrated in FIGS. 11A-11B was repeated and reported in FIG. 17. Losses in functional titer were not as drastic for the phosphate formulation, but the trends are consistent between histidine and phosphate formulations.

Figure 18:
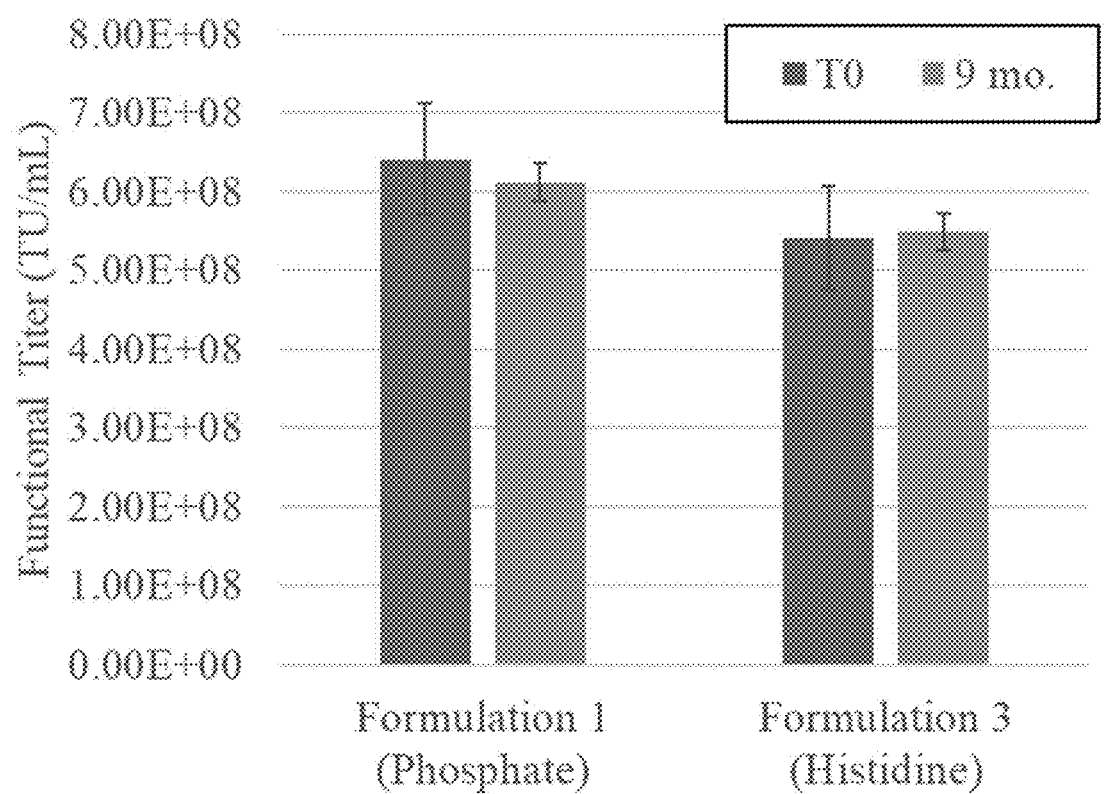
FIG. 18 depicts a long-term stability (9 month timepoint (9 mo.) stored frozen at −80° C.) data for the Phosphate and Histidine formulations: Formulation 1 (Phosphate): 10 mM Phosphate, 100 mM NaCl, 3% (w/v) sucrose, 0.05% (w/v) P188, pH 7.3; Formulation 3 (Histidine). 20 mM Histidine, 100 mM NaCl, 3% (w/v) sucrose, 0.05% (w/v) P188, pH 6.5.
Figure 19A:
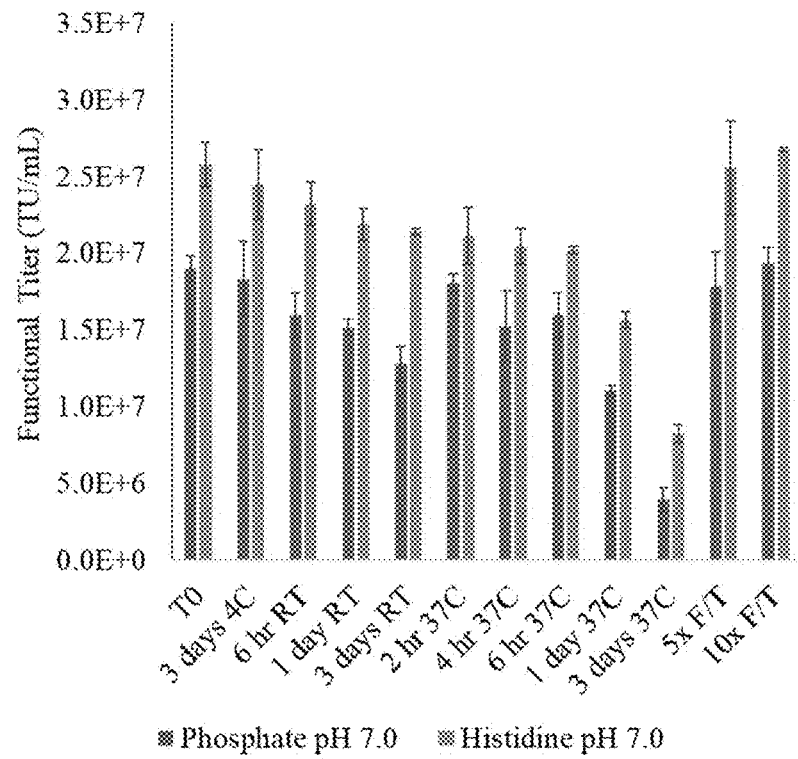
FIGS. 19A-19D depict stability studies comparing the Phosphate and Histidine buffers at the same pH, 7.0: Formulation 4 (Phosphate): 10 mM Phosphate, 100 mM NaCl, 3% (w/v) sucrose, 0.05% (w/v) P188, pH 7.0; Formulation 5 (Histidine). 20 mM Histidine, 100 mM NaCl, 3% (w/v) sucrose, 0.05% (w/v) P188, pH 7.0; as measured by functional titer (FIG. 19A), normalized functional titer (FIG. 19B), p24 concentration (FIG. 19C), and particle concentration (FIG. 19D). Results are shown in units of functional titer and normalized as a percentage of the starting material (TO). Particle concentration was obtained using the NanoSight.
Figure 19B:
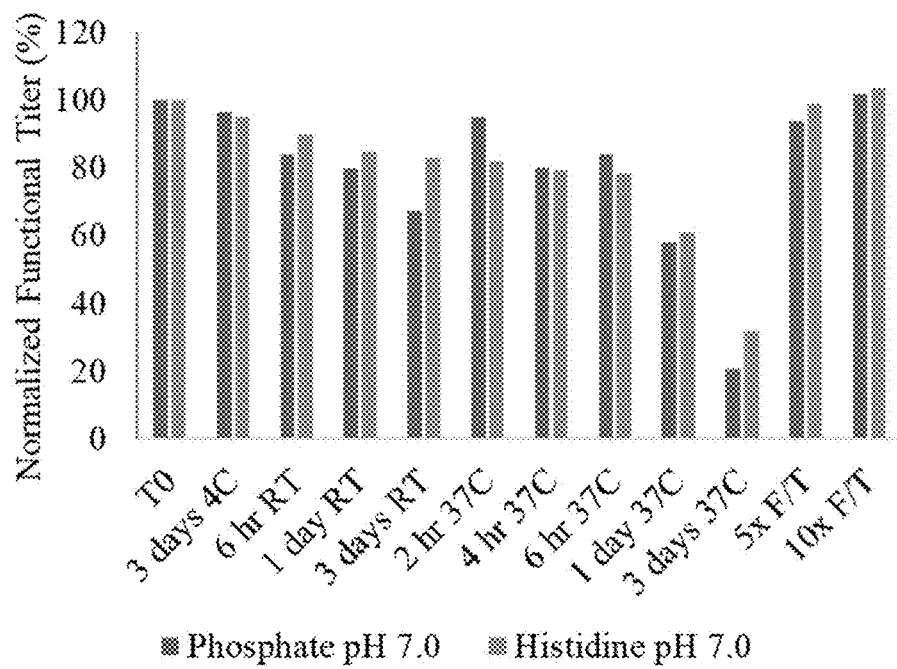
Figure 19C:
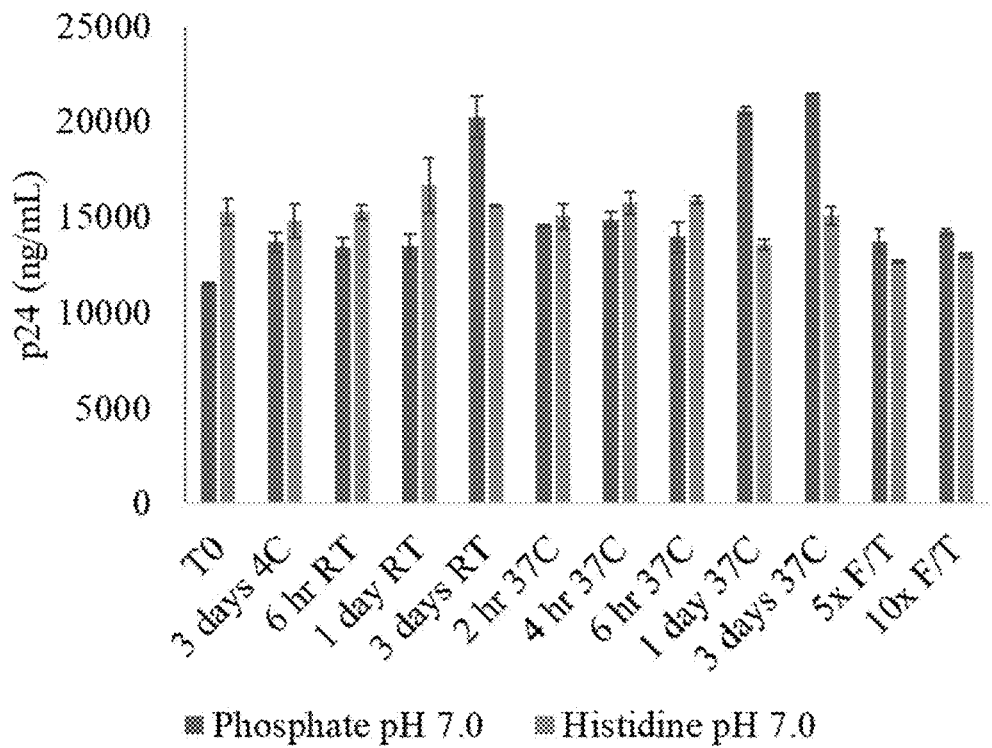
Figure 19D:
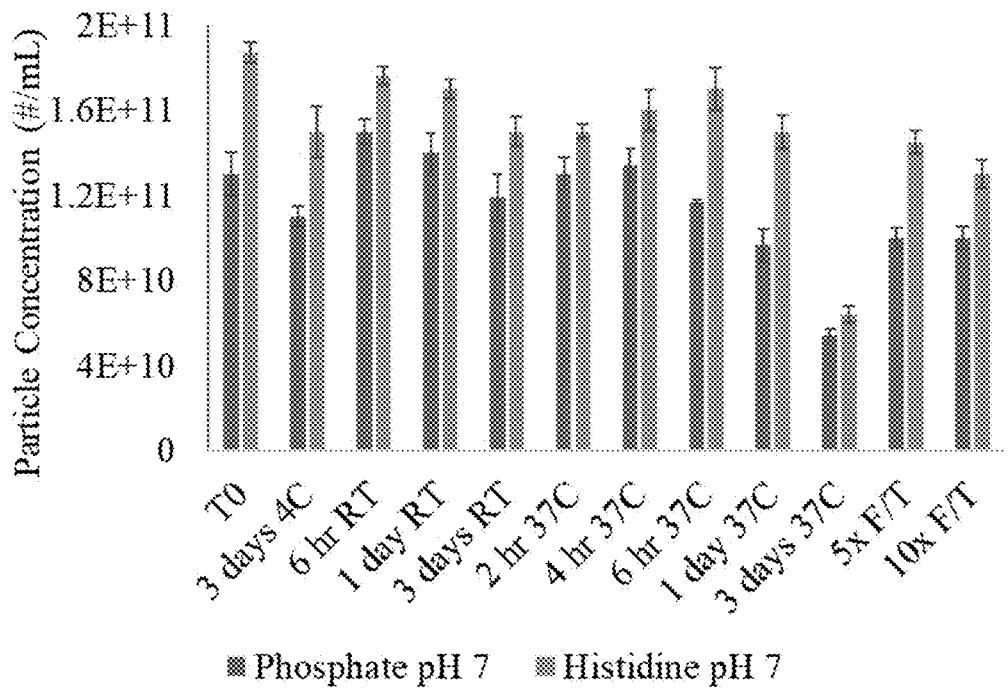

Over the course of a 9 month, frozen (−80° C.), stability study both the Phosphate Formulation 1 and the Histidine Formulation 3 buffers seemed to enable stable LVV DP, FIG. 18. Based on functional titer, the data suggests there was not any loss of material over storage at −80° C., within assay variability.

Lastly, in order to evaluate the effect of the buffers only (phosphate and histidine), the two formulations were prepared identically, at the same pH, 7.0. That is, the only difference between Formulation 4 and Formulation 5 was the buffer component (either phosphate or histidine). In the context of the manufacturing process, both formulations seem to behave similarly across ultrafiltration and diafiltration (TFF) as well as terminal sterile filtration, Table 6.

TABLE 6

Preparation of Formulation 4 (Phosphate) and Formulation 5 (Histidine) using Tangential Flow Filtration. The samples were diafiltered against respective formulations six times by volume and then ultrafiltered (concentrated) several fold, by volume.

| Formulation | Process Step | Volume (mL) | NanoSight (particles/mL) | Total Particles |
|---|---|---|---|---|
| Phosphate | Pre TFF | 165.2 | 1.28E+11 | 2.11E+13 |
| Phosphate | Post 0.2 um filtration | 88.5 | 2.11E+11 | 1.87E+13 |
| Histidine | Pre TFF | 155.8 | 9.64E+10 | 1.50E+13 |
| Histidine | Post 0.2 um filtration | 65.2 | 2.54E+11 | 1.66E+13 |

Upon preparing the respective formulations, a stability study was conducted in order to compare the buffer components. FIGS. 19A-19D summarizes the findings, shown as a function of stability condition across functional and normalized functional titer, p24 and particle concentration that there were only minor differences between the LVV stability of either formulation. This seems to suggest that results presented in FIGS. 11A-11B, FIGS. 12A-12B, and FIG. 13 seem to reflect varying levels of stability due to the differences in pH (7.3 and 6.5) and not the buffer composition (phosphate or histidine).

What is claimed:

1. A reduced in-vivo toxicity recombinant lentiviral particle preparation comprising:
   (a) a therapeutically effective dose of a lentiviral particle comprising a recombinant lentiviral vector;
   (b) a TRIS-free buffer system comprising a phosphate buffer;
   (c) a salt;
   (d) a poloxamer 188 (P188);
   (e) a carbohydrate;
   wherein the lentiviral particle further comprises an envelope comprising a vesicular stomatitis virus G (VSV-G) protein or a fragment thereof;
   wherein the recombinant lentiviral vector comprises a nucleic acid comprising a nucleotide sequence that is at least 80% identical to a Factor VIII (FVIII) coding sequence set forth in SEQ ID NO: 1 or SEQ ID NO: 2;
   wherein the recombinant lentiviral particle preparation is suitable for systemic administration to a human patient; and
   wherein systemic administration of the recombinant lentiviral particle preparation to the patient has reduced in-vivo toxicity relative to a recombinant lentiviral particle preparation comprising a TRIS buffer.

2. The preparation of claim 1, wherein the pH of the buffer system or of the preparation is from about from about 7.0 to about 8.0.

3. The preparation of claim 1, wherein the concentration of the phosphate buffer is from about 5 mM to about 30 mM.

4. The preparation of claim 1, wherein the concentration of the phosphate buffer is from about 10 mM to about 20 mM.

5. The preparation of claim 1, wherein the concentration of the salt is from about 80 mM to about 150 mM.

6. The preparation of claim 1, wherein the concentration of the poloxamer 188 is from about 0.01% (w/v) to about 0.1% (w/v), about 0.03% (w/v), about 0.05% (w/v), about 0.07% (w/v), or about 0.09% (w/v).

7. The preparation of claim 1, wherein the concentration of the carbohydrate is from about 0.5% (w/v) to about 5% (w/v), about 1% (w/v), about 2% (w/v), about 3% (w/v), or about 4% (w/v), optionally wherein the carbohydrate is sucrose.

8. The preparation of claim 1, comprising:
   (a) a therapeutically effective dose of a recombinant lentiviral vector;
   (b) about 10 mM phosphate buffer;
   (c) about 100 mM salt, wherein the salt is sodium chloride;
   (d) about 0.05% (w/v) P188; and
   (e) about 3% (w/v) carbohydrate, wherein the carbohydrate is sucrose,
   wherein the pH of the preparation is about 7.3, and wherein the preparation is suitable for systemic administration to a human patient.

9. The preparation of claim 1, comprising:
   (a) a therapeutically effective dose of a recombinant lentiviral vector;
   (b) about 10 mM phosphate buffer;
   (c) about 130 mM salt, wherein the salt is sodium chloride;
   (d) about 0.05% (w/v) P188; and
   (e) about 1% (w/v) carbohydrate, wherein the carbohydrate is sucrose,
   wherein the pH of the preparation is about 7.3, and wherein the preparation is suitable for systemic administration to a human patient.

10. The preparation of claim 1, comprising:
    (a) a therapeutically effective dose of a recombinant lentiviral vector;
    (b) about 10 mM phosphate buffer;
    (c) about 100 mM salt, wherein the salt is sodium chloride;
    (d) about 0.05% (w/v) P188; and
    (e) about 3% (w/v) carbohydrate, wherein the carbohydrate is sucrose,
    wherein the pH of the preparation is about 7.0, and wherein the preparation is suitable for systemic administration to a human patient.

11. The preparation of claim 1, wherein the recombinant lentiviral vector comprises:
an enhanced transthyretin (ET) promoter; and/or
a nucleotide sequence at least 90% identical to the target sequence for miR-142 set forth in SEQ ID NO: 7.

12. The preparation of claim 1, wherein the recombinant lentiviral vector is isolated from a transfected host cell selected from the group consisting of a CHO cell, a HEK293 cell, a BHK21 cell, a PER.C6 cell, an NSO cell, and a CAP cell.

13. The preparation of claim 1, wherein the recombinant lentiviral vector comprises a nucleic acid comprising the Factor VIII (FVIII) coding sequence set forth in SEQ ID NO: 1 or SEQ ID NO: 2.

14. A reduced in-vivo toxicity recombinant lentiviral particle preparation, comprising:
(a) a therapeutically effective dose of a lentiviral particle comprising a recombinant lentiviral vector;
(b) a TRIS-free buffer system comprising about 10 mM phosphate buffer;
(c) about 100 mM or about 130 mM sodium chloride;
(d) about 0.05% (w/v) P188;
(e) about 3% (w/v) sucrose;
wherein the pH of the preparation is about 7.3; wherein the lentiviral particle preparation is suitable for systemic administration to a human patient
wherein the recombinant lentiviral particle further comprises an envelope comprising a vesicular stomatitis virus G (VSV-G) protein or a fragment thereof;
wherein the recombinant lentiviral vector comprises a nucleic acid comprising a nucleotide sequence that is at least 80% identical to a Factor VIII (FVIII) coding sequence set forth in SEQ ID NO: 1 or SEQ ID NO: 2; and
wherein administration of the lentiviral particle preparation to a patient has reduced in-vivo toxicity relative to a recombinant lentiviral particle preparation comprising a TRIS buffer.

15. A reduced in-vivo toxicity recombinant lentiviral particle preparation, comprising:
(a) a therapeutically effective dose of a lentiviral particle comprising a recombinant lentiviral vector;
(b) a TRIS-free buffer system comprising about 10 mM phosphate buffer;
(c) about 100 mM or about 130 mM sodium chloride;
(d) about 0.05% (w/v) P188;
(e) about 3% (w/v) sucrose;
wherein the pH of the preparation is about 7.0; and
wherein the lentiviral particle preparation is suitable for systemic administration to a human patient;
wherein the recombinant lentiviral particle further comprises an envelope comprising a vesicular stomatitis virus G (VSV-G) protein or a fragment thereof;
wherein the recombinant lentiviral vector comprises a nucleic acid comprising a nucleotide sequence that is at least 80% identical to a Factor VIII (FVIII) coding sequence set forth in SEQ ID NO: 1 or SEQ ID NO: 2; and
wherein administration of the lentiviral particle preparation to a patient has reduced in-vivo toxicity relative to a recombinant lentiviral particle preparation comprising a TRIS buffer.

* * * * *